(12) United States Patent
Goto et al.

(10) Patent No.: US 8,288,396 B2
(45) Date of Patent: Oct. 16, 2012

(54) PYRIMIDOPYRIMIDOINDAZOLE DERIVATIVE

(75) Inventors: Yasuhiro Goto, Tachikawa (JP); Kenji Niiyama, Tsuchiura (JP); Satoshi Sunami, Toride (JP); Keiji Takahashi, Yachiyo (JP)

(73) Assignee: MSDKK, Tokyo (JP)

( * ) Notice: Subject to any disclaimer, the term of this patent is extended or adjusted under 35 U.S.C. 154(b) by 0 days.

(21) Appl. No.: 13/202,773

(22) PCT Filed: Feb. 18, 2010

(86) PCT No.: PCT/JP2010/052910
§ 371 (c)(1),
(2), (4) Date: Aug. 23, 2011

(87) PCT Pub. No.: WO2010/098367
PCT Pub. Date: Sep. 2, 2010

(65) Prior Publication Data
US 2012/0134955 A1    May 31, 2012

(30) Foreign Application Priority Data
Feb. 25, 2009    (JP) .................. 2009-042873

(51) Int. Cl.
A61K 31/519    (2006.01)
C07D 487/14    (2006.01)

(52) U.S. Cl. ...................... 514/257; 544/247

(58) Field of Classification Search ............ 544/247; 514/257
See application file for complete search history.

(56) References Cited

U.S. PATENT DOCUMENTS

| | | | |
|---|---|---|---|
| 4,604,463 A | 8/1986 | Miyasaka et al. | |
| 5,162,532 A | 11/1992 | Comins et al. | |
| 5,191,082 A | 3/1993 | Comins et al. | |
| 5,200,524 A | 4/1993 | Comins et al. | |
| 5,223,608 A | 6/1993 | Chou et al. | |
| 5,243,050 A | 9/1993 | Comins et al. | |
| 5,247,089 A | 9/1993 | Comins et al. | |
| 5,321,140 A | 6/1994 | Comins et al. | |
| 5,420,319 A | 5/1995 | Okamoto et al. | |
| 5,434,254 A | 7/1995 | Chou et al. | |
| 5,734,056 A | 3/1998 | Burk et al. | |
| 5,770,599 A | 6/1998 | Gibson | |
| 5,959,133 A | 9/1999 | Ohnishi | |
| 7,094,798 B1 | 8/2006 | Booth et al. | |
| 2004/0044012 A1 | 3/2004 | Dobrusin et al. | |
| 2005/0250836 A1 | 11/2005 | Booth et al. | |
| 2007/0254892 A1 | 11/2007 | Sagara et al. | |
| 2011/0135601 A1 | 6/2011 | Bamba | |

FOREIGN PATENT DOCUMENTS

| | | | |
|---|---|---|---|
| WO | WO9410202 A1 | 5/1994 | |
| WO | WO9640210 A1 | 12/1996 | |
| WO | WO03091255 A1 | 11/2003 | |
| WO | WO2007126128 A1 | 7/2007 | |
| WO | WO2008153207 A1 | 12/2008 | |

OTHER PUBLICATIONS

Donkor, 1995, Journal of Pharmaceutical Sciences, vol. 84, No. 5, p. 661-664.*
Molinari, Cell cycle checkpoints and their inactivation in human cancer, Cell Proliferation, 2000, 261-274, vol. 33.
Wang et al., Knockdown of Chk1, Wee 1 and Myt1 by RNA Interference Abrogates G2 Checkpoint and Induces Apoptosis, Cancer Biology & Therapy, 2004, 305-313, vol. 3, No. 3.
Palmer et al., "Structure-activity relationships for 2-anilino-6-phenylpyrido[2,3-d]pyrimidin-7(8H)-ones as inhibitors of the cellular checkpoint kinase Wee1", Bioorganic & Medicinal Chemistry Letters 15, 2005, 1931-1935.
Wang et al., "Radiosensitization of p53 Mutant Cells by PD0166285, a Novel G2 Checkpoint Abrogator", Cancer Research, 2001, 8211-8217, vol. 61.
Nitta et al., "Antitumor activity of new derivatives of camptothecin", Gan to Kagaku Ryoho Cancer & Chemotherapy, 1987, 850-857, vol. 14, No. 3 (Abstract—1 page).
McGowan et al., "Huamn Wee1 kinase inhibits cell division by phosphorylating p34cdc2 exclusively on Tyr15",The EMBO Journal, 1993, 75-87, vol. 12, No. 1.

* cited by examiner

*Primary Examiner* — Golam M M Shameem
*Assistant Examiner* — Karen Cheng
(74) *Attorney, Agent, or Firm* — Joan E. Switzer; David A. Muthard

(57) ABSTRACT

The invention is to provide a novel anticancer agent or sensitizer for cancer chemotherapy or radiotherapy. A compound of a general formula (I): wherein A means an aryl group or a heteroaryl group, or a group of a formula (a): $R^1$ means a $-(C=O)_aO_b(C1-C6)$alkyl group, a $-(C=O)_aO_b(C2-C6)$alkenyl group, a $-(C=O)_aO_b(C3-C6)$cycloalkyl group, an aryl group or a heteroaryl group; $R^2$ and $R^3$ each mean a hydrogen atom, a halogen atom, a hydroxyl group, a carboxyl group, a $-(C=O)_aO_b(C1-C6)$alkyl group or a group of $-(C=O)_aN(R^{1e})R^{2e}$; $R^4$ means a hydrogen atom or a (C1-C6)alkyl group, and the like have an excellent Wee1-kinase-inhibitory effect, and are therefore useful in the field of medicine, especially in the field of various cancer treatments.

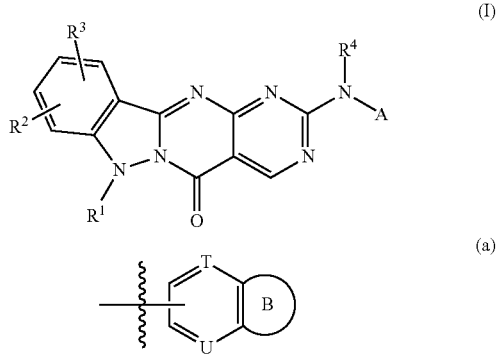

16 Claims, No Drawings

PYRIMIDOPYRIMIDOINDAZOLE DERIVATIVE

TECHNICAL FIELD

The present invention is useful in the field of medicine. More precisely, the pyrimidopyrimidoindazole derivative of the invention is useful in the field of various cancer treatments, as a kinase inhibitor, especially as a Wee1 kinase inhibitor.

BACKGROUND ART

Cells have a checkpoint mechanism of such that, when the DNA therein is damaged, then the cells temporarily stop the cell cycle and repair the damaged DNA (Cell Proliferation, Vol. 33, pp. 261-274). In about a half of human cancers, a cancer-suppressor gene, p53 is mutated or depleted and the cells thereby have lost the G1 checkpoint function thereof. However, such cancer cells still keep the G2 checkpoint function remaining therein, which is considered to be one factor of lowering the sensitivity of the cells to DNA-active anticancer agents and to radiations.

A Wee1 kinase is a tyrosine kinase that participates in the G2 checkpoint of a cell cycle. Wee1 phosphorylates Cdc2 (Cdk1) tyrosine 15 that participates in the progress to the M stage from the G2 stage in a cell cycle, thereby inactivating Cdc2 and temporarily stopping the cell cycle at the G2 stage (The EMBO Journal, Vol. 12, pp. 75-85). Accordingly, in cancer cells having lost the p53 function therein, it is considered that the G2 checkpoint function by Wee1 is important for repairing the damaged DNA so as to evade the cell death. Heretofore, it has been reported that the Wee1 expression reduction by RNA interference or the Wee1 inhibition by compounds may increase the sensitivity of cancer cells to adriamycin, X ray and gamma ray (Cancer Biology & Therapy, Vol. 3, pp. 305-313; Cancer Research, Vol. 61, pp. 8211-8217). From the above, it is considered that a Wee1 inhibitor may inhibit the G2 checkpoint function of p53-depleted cancer cells, thereby enhancing the sensitivity of the cells to DNA-active anticancer agents and to radiations.

As a low-molecular Wee1 kinase inhibitor, for example, known are compounds described in US Application 2005/0250836 (Patent Reference 1), WO2003/091255 (Patent Reference 2), WO2007/126128 (Patent Reference 3), WO2008/153207 (Patent Reference 4), Cancer Research, Vol. 61, pp. 8211-8217 (Non-Patent Reference 1), or Bioorg & Med. Chem. Lett., Vol. 15, pp. 1931-1935 (Non-Patent Reference 2). However, the compounds described in these references quite differ from the compounds of the invention in point of their structures.

SUMMARY OF THE INVENTION

An object of the invention is to provide a novel anticancer agent having a kinase-inhibitory effect, especially a Wee1 kinase-inhibitory effect, or a sensitizer for cancer chemotherapy or radiotherapy.

As a result of assiduous studies, the present inventors have found that compounds of the following general formula (I) have an excellent kinase-inhibitory effect, especially an excellent Wee1 kinase-inhibitory effect, and have completed the present invention:

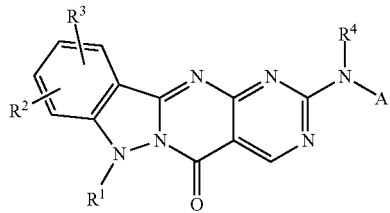

(I)

wherein,
a and b each independently mean 0 or 1;
A means an aryl or heteroaryl group, which may have a substituent selected from the group consisting of a halogen atom, a hydroxyl group, $-(C=O)_aO_b(C1-C6)$alkyl group and a group of $-Q^{1a}-R^{1a}$, wherein the alkyl group of the substituent may be substituted with a halogen atom or a hydroxyl group, or A means a group of a formula (a):

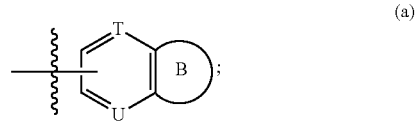

(a)

the ring B means a 5-membered to 7-membered aliphatic ring condensed with the ring of a formula (b):

(b)

wherein one or two or more methylene groups constituting the ring B may be each independently replaced by an oxygen atom, a sulfur atom, a sulfinyl group, a sulfonyl group, a carbonyl group or a group of $-N(R^{1b})-$, and one or two or more methylene groups constituting the ring B may be each independently substituted with a halogen atom, a hydroxyl group, a $-(C=O)_aO_b(C1-C6)$alkyl group or a group of $-Q^{1b}-N(R^{2b})R^{3b}$, wherein the alkyl group of the substituent may be substituted with a halogen atom or a hydroxyl group;
$Q^{1a}$, $Q^{1b}$, $Q^{2a}$ and $Q^{3a}$ each independently mean a single bond or a (C1-C6)alkylene group, wherein one or two or more methylene groups constituting the (C1-C6)alkylene group may be each independently replaced by an oxygen atom, a sulfur atom, a sulfinyl group, a sulfonyl group, a carbonyl group or a group of $-N(R^{2a})-$, and may be each independently substituted with a halogen atom, a hydroxyl group, a cyano group or a $-(C=O)_aO_b(C1-C6)$alkyl group;
$R^1$ means a $-(C=O)_aO_b(C1-C6)$alkyl group, a $-(C=O)_aO_b(C2-C6)$alkenyl group, a $-(C=O)_aO_b(C3-C6)$cycloalkyl group, an aryl or heteroaryl group, wherein the alkyl, alkenyl and cycloalkyl group may be each independently substituted with $R^{1c}$, and the aryl and heteroaryl group may be each independently substituted with $R^{1d}$;
$R^{1a}$ means a hydrogen atom, a hydroxyl group, a formyl group, a $-(C=O)_aO_b(C1-C6)$alkyl group or a group of $-(C=O)_aN(R^{3a})R^{4a}$, wherein the alkyl group may be substituted with a halogen atom or a hydroxyl group, or $R^{1a}$ means a heterocyclic group optionally having a substituent selected from the group consisting of a halogen atom, a hydroxyl group, an oxo group, a —(C=O)$_a$O$_b$(C1-C6)alkyl group, a —(C=O)$_a$O$_b$(C3-C6)cycloalkyl group and a group of -Q$^{2a}$-R$^{5a}$, wherein the alkyl and cycloalkyl group of the substituent may be each independently substituted with a halogen atom, a hydroxyl group, a —(C=O)$_a$O$_b$(C1-C6) alkyl group or a group of —(C=O)$_a$N(R$^{3a}$)R$^{4a}$;

R$^{1b}$ means a hydrogen atom or a —(C=O)$_a$O$_b$(C1-C6) alkyl group, wherein the alkyl group may be substituted with a halogen atom, a hydroxyl group or a group of —(C=O)$_a$N(R$^{4b}$)R$^{5b}$;

R$^{1c}$ means a halogen atom, a hydroxyl group, a cyano group, a —(C=O)$_a$O$_b$(C1-C6)alkyl group, a —(C=O)$_a$O$_b$(C3-C6)cycloalkyl group, an aryl group or a heteroaryl group, wherein the alkyl and cycloalkyl group may be each independently substituted with a halogen atom or a hydroxyl group, and the aryl and heteroaryl group may be each independently substituted with a substituent selected from the group consisting of a nitro group, a hydroxyamino group, a —(C=O)$_a$O$_b$(C1-C6)alkyl group and a group of —(C=O)$_a$N(R$^{2c}$)R$^{3c}$, and the alkyl group of the substituent may be substituted with a halogen atom or a hydroxyl group;

R$^{1d}$ means a nitro group, a hydroxyamino group, a —(C=O)$_a$O$_b$(C1-C6)alkyl group or a group of —(C=O)$_a$N(R$^{2d}$)R$^{3d}$, wherein the alkyl group may be substituted with a halogen atom or a hydroxyl group;

R$^{1e}$, R$^{2a}$, R$^{2b}$, R$^{2c}$, R$^{2d}$, R$^{2e}$, R$^{3a}$, R$^{3b}$, R$^{3c}$, R$^{3d}$, R$^{3e}$, R$^{4a}$, R$^{4b}$, R$^{4e}$ and R$^{5b}$ each independently mean a hydrogen atom or a —(C=O)$_a$O$_b$(C1-C6)alkyl group, wherein the alkyl group may be substituted with a halogen atom or a hydroxyl group;

R$^2$ and R$^3$ each independently mean a hydrogen atom, a halogen atom, a hydroxyl group, a carboxyl group, a —(C=O)$_a$O$_b$(C1-C6)alkyl group or a group of —(C=O)$_a$N(R$^{1e}$)R$^{2e}$, wherein the alkyl group may be substituted with a substituent selected from the group consisting of a halogen atom, a hydroxyl group, a carboxyl group, a —(C=O)$_a$O$_b$(C1-C6)alkyl group and a group of —(C=O)$_a$N(R$^{3e}$)R$^{4e}$;

R$^4$ means a hydrogen atom or a (C1-C6)alkyl group;

R$^{5a}$ means a hydrogen atom, a hydroxyl group, a formyl group, a —(C=O)$_a$O$_b$(C1-C6)alkyl group or a group of —(C=O)$_a$N(R$^{3a}$)R$^{4a}$, wherein the alkyl group may be substituted with a halogen atom or a hydroxyl group, or R$^{5a}$ means a heterocyclic group optionally having a substituent selected from the group consisting of a halogen atom, a hydroxyl group, an oxo group, a —(C=O)$_a$O$_b$(C1-C6)alkyl group and a group of -Q$^{3a}$-R$^{6a}$, and the alkyl group of the substituent may be substituted with a halogen atom, a hydroxyl group or a —(C=O)$_a$O$_b$(C1-C6)alkyl group;

R$^{6a}$ means a hydrogen atom, a halogen atom, a hydroxyl group or a —(C=O)$_a$O$_b$(C1-C6)alkyl group, wherein the alkyl group may be substituted with a halogen atom or a hydroxyl group; and T and U each independently mean a nitrogen atom, or mean a methine group optionally substituted with a halogen atom, a hydroxyl group, a cyano group or a —(C=O)$_a$O$_b$(C1-C6) alkyl group, wherein the alkyl group of the substituent may be substituted with a halogen atom or a hydroxyl group.

The compounds (I) of the invention have a kinase-inhibitory effect, especially a Wee1 kinase-inhibitory effect, and they are useful as remedies for various cancers such as brain cancer, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, Hodgkin's lymphoma, or as sensitizers for chemotherapy or radiotherapy of those cancers.

In particular, the compounds (I) of the invention are useful as remedies, for example, for breast cancer, lung cancer, pancreatic cancer, colon cancer, ovarian cancer, acute leukemia, chronic lymphatic leukemia, chronic myelocytic leukemia, Hodgkin's lymphoma, or as sensitizers for chemotherapy or radiotherapy of those cancers.

The invention relates to the compounds of formula (I), their pharmaceutically-acceptable salts, esters or N-oxide derivatives, as well as to their production methods and their use.

The meanings of the terms used in this description are described below, and the invention is described in more detail hereinunder.

"Halogen atom" means a fluorine atom, a chlorine atom, a bromine atom, an iodine atom.

"(C1-C6)alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isopentyl group, a hexyl group, an isohexyl group.

"—(C=O)$_a$O$_b$(C1-C6)alkyl group" means the above-mentioned (C1-C6)alkyl group attached to any other group via: —(C=O)$_a$O$_b$—.

"Aryl group" means an aromatic hydrocarbon cyclic group, and includes, for example, a phenyl group, a naphthyl group.

"Heteroaryl group" means a 5-membered or 6-membered monocyclic heteroaryl group having one or two or more, preferably from 1 to 3, the same or different hetero atoms selected from the group consisting of an oxygen atom, a nitrogen atom and a sulfur atom; or a condensed cyclic heteroaryl group formed through condensation of that monocyclic heteroaryl group and the above-mentioned aryl group, or through condensation of the same or different such monocyclic heteroaryl groups; and it includes, for example, a pyrrolyl group, a furyl group, a thienyl group, an imidazolyl group, a pyrazolyl group, a thiazolyl group, an isothiazolyl group, an oxazolyl group, an isoxazolyl group, a triazolyl group, a tetrazolyl group, an oxadiazolyl group, a 1,2,3-thiadiazolyl group, a 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group, a pyrido[3,2-b]pyridyl group, a [1,2,4]triazolo[1,5-a]pyridyl group, a [1,2,4]triazolo[4,3-a]pyridyl group.

"5-Membered to 7-membered aliphatic ring" means a structure comprising from 5 to 7 atoms attached to each other in a ring, and it may be a monocyclic saturated structure by itself, or may be an unsaturated bond-containing ring except an aromatic ring. For example, it includes cyclopentane, cyclopentene, cyclohexane, cyclohexene, cycloheptane, cycloheptene. The methylene group constituting the aliphatic ring may be "replaced by" or "substituted with" a predetermined atom or group, as described hereinunder.

"5-Membered to 7-membered aliphatic ring condensed with the ring of formula (b)" means a bicyclic condensed ring of the above-mentioned 5-membered to 7-membered aliphatic ring ortho-condensed with the ring of formula (b), including, for example, groups of a formula (a'-1):

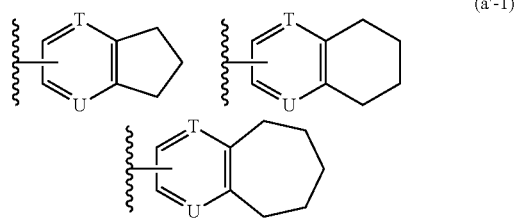

"(C1-C6)alkylene group" means an alkylene group having from 1 to 6 carbon atoms, including a methylene group, an ethylene group, a trimethylene group, a tetramethylene group, a pentamethylene group, a hexamethylene group.

"(C2-C6)alkenyl group" means a linear or branched alkenyl group having from 2 to 6 carbon atoms, including, for example, a vinyl group, a 1-propenyl group, an allyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, a 3-methyl-2-butenyl group, a 4-pentenyl group.

"—(C=O)$_a$O$_b$(C2-C6)alkenyl group" means the above-mentioned (C2-C6)alkenyl group attached to any other group via —(C=O)$_a$O$_b$—.

"(C3-C6)cycloalkyl group" means a cycloalkyl group having from 3 to 6 carbon atoms, including a cyclopropyl group, a cyclobutyl group, a cyclopentyl group, a cyclohexyl group.

"—(C=O)$_a$O$_b$(C3-C6)cycloalkyl group" means the above-mentioned (C3-C6)cycloalkyl group attached to any other group via —(C=O)$_a$O$_b$—.

In "(C=O)$_a$O$_b$", when "a" or "b" is 0, then it means the absence of —(C=O)— or —O—. Specifically, for example, "—(C=O)$_a$O$_b$(C1-C6)alkyl group" is meant to include a (C1-C6)alkyl group, an —O—(C1-C6)alkyl group, a —(C=O)—(C1-C6)alkyl group and a —(C=O)—O—(C1-C6)alkyl group.

"Heterocyclic group" means a 3-membered to 7-membered monocyclic heterocyclic group having one or two or more, preferably from 1 to 3, the same or different hetero atoms selected from the group consisting of an oxygen atom, a nitrogen atom and a sulfur atom; or a condensed cyclic heterocyclic group formed through condensation of that monocyclic heterocyclic group and a 3-membered to 7-membered carbocyclic group, or through condensation of the same or different such monocyclic heterocyclic groups; and it includes the above-mentioned heteroaryl group. Its concrete examples are those mentioned hereinabove for the heteroaryl group, and in addition, an azetidinyl group, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a dihydro-1,2,3,5-oxathiadiazolyl group, a dihydropyridyl group, a piperidyl group, a piperazinyl group, a morpholinyl group, a thiomorpholinyl group, a perhydro-1,4-diazepinyl group.

"Pharmaceutically-acceptable salts" of the compounds of the invention mean ordinary, pharmaceutically-acceptable salts. For example, when the compounds have a carboxyl group or a hydroxyl group, then they may form base-addition salts at the carboxyl group or the hydroxyl group; or when the compounds have an amino group or a basic nitrogen-containing heterocyclic group or any other heterocyclic group, they may form acid-addition salts at the amino group or the basic nitrogen-containing heterocyclic group or the other heterocyclic group.

The base-addition salts include, for example, alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid-addition salts include, for example, salts derived from inorganic acids (e.g., hydrochloric acid, hydrobromic acid, sulfuric acid, sulfamic aid, phosphoric acid, nitric acid), as well as salts prepared with organic acids (e.g., acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxy-benzoic acid, fumaric acid, toluenesulfonic acid, methanesulfonic acid, ethanedisulfonic acid, oxalic acid, isethionic acid, trifluoroacetic acid).

"Pharmaceutically-acceptable esters" of the compounds of the compounds of the invention mean ordinary, pharmaceutically-acceptable esters thereof, for example, those having a carboxyl group, at the carboxyl group thereof. For example, they include esters with a lower alkyl group such as a methyl group, an ethyl group, a propyl group, an isopropyl group, a butyl group, a sec-butyl group, a tert-butyl group, a pentyl group, an isopentyl group, a neopentyl group, a cyclopropyl group, a cyclobutyl group, a cyclopentyl group; esters with an aralkyl group such as a benzyl group, a phenethyl group; esters with a lower alkenyl group such as an allyl group, a 2-butenyl group; esters with a lower alkoxy-lower alkyl group such as a methoxymethyl group, a 2-methoxyethyl group, a 2-ethoxyethyl group; esters with a lower alkanoyloxy-lower alkyl group such as an acetoxymethyl group, a pivaloyloxymethyl group, a 1-pivaloyloxyethyl group; esters with a lower alkoxycarbonyl-lower alkyl group such as a methoxycarbonylmethyl group, an isopropoxycarbonylmethyl group; esters with a carboxy-lower alkyl group such as a carboxymethyl group; esters with a lower alkoxycarbonyloxy-lower alkyl group such as 1-(ethoxycarbonyloxy)ethyl group, a 1-(cyclohexyloxycarbonyloxy)ethyl group, esters with a carbamoyloxy-lower alkyl group such as a carbamoyloxymethyl group; esters with a phthalidyl group; esters with a (5-substituted-2-oxo-1,3-dioxol-4-yl)methyl group such as a (5-methyl-2-oxo-1,3-dioxol-4-yl)methyl group.

"Pharmaceutically-acceptable N-oxide derivatives" of the compounds of the invention are those in which one or two or more N-oxide forming nitrogen atoms existing in the compound are oxidized to form an N-oxide and which are pharmaceutically-acceptable ones. For example, they include compounds of the invention in which the ring-forming nitrogen atom of the pyrimido[4',5':4,5]pyrimido[1,2-b]indazole skeleton is oxidized, or those in which the ring-forming nitrogen atom of the group of a formula (a):

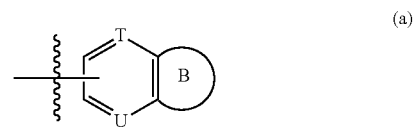

is oxidized.

For illustrating the compounds of the invention more concretely, preferred examples of the symbols used in this description are described below in more detail.

A means an aryl or heteroaryl group, which may have a substituent selected from the group consisting of a halogen atom, a hydroxyl group, —(C=O)$_a$O$_b$(C1-C6)alkyl group and a group of -Q$^{1a}$-R$^{1a}$, or A means a group of a formula (a):

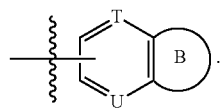

(a)

"An aryl or heteroaryl group, which may have a substituent selected from the group consisting of a halogen atom, a hydroxyl group, —(C=O)$_a$O$_b$(C1-C6)alkyl group and a group of -Q$^{1a}$-R$^{1a}$" means the above-mentioned unsubstituted aryl or heteroaryl group, or the above-mentioned aryl or heteroaryl group having a substituent at any substitutable position thereof, and for the substituent, one or two or more of, preferably one or two of, the same or different groups are selected from a halogen atom, a hydroxyl group, —(C=O)$_a$O$_b$(C1-C6)alkyl group and a group of -Q$^{1a}$-R$^{1a}$.

Preferably, the halogen atom for the substituent includes, for example, a fluorine atom, a chlorine atom.

The alkyl group itself of the substituent "—(C=O)$_a$O$_b$(C1-C6)alkyl group" is preferably a methyl group, an ethyl group. a and b each independently mean 0 or 1. Preferably, a and b are both 0, or a is 0 and b is 1. The alkyl group may be substituted with a halogen atom or a hydroxyl group. More concretely, the alkyl group means the above-mentioned unsubstituted alkyl group, or the above-mentioned alkyl group substituted at any substitutable position thereof with the same or different substituents selected from one or two or more, preferably from 1 to 3 halogen atoms and one or two or more, preferably one or two hydroxyl groups. Examples of the substituted group include a fluoromethyl group, a difluoromethyl group, a trifluoromethyl group, a hydroxymethyl group, a 1-hydroxyethyl group.

The substituent, —(C=O)$_a$O$_b$(C1-C6)alkyl group (where the alkyl group may be substituted) is preferably a methyl group, an ethyl group, a methoxy group, a hydroxymethyl group, a 1-hydroxyethyl group.

In the group of -Q$^{1a}$-R$^{1a}$ of the substituent, Q$^{1a}$ means a single bond or a (C1-C6)alkylene group, wherein one or two or more methylene groups constituting the (C1-C6)alkylene group may be each independently replaced by an oxygen atom, a sulfur atom, a sulfinyl group, a sulfonyl group, a carbonyl group or a group of —N(R$^{2a}$)—, and may be each independently substituted with a halogen atom, a hydroxyl group, a cyano group or a —(C=O)$_a$O$_b$(C1-C6)alkyl group; R$^{1a}$ means a hydrogen atom, a hydroxyl group, a formyl group, a —(C=O)$_a$O$_b$(C1-C6)alkyl group or a group of —(C=O)$_a$N(R$^{3a}$)R$^{4a}$, or means a heterocyclic group optionally having a substituent selected from the group consisting of a halogen atom, a hydroxyl group, an oxo group, a —(C=O)$_a$O$_b$(C1-C6)alkyl group, a —(C=O)$_a$O$_b$(C3-C6)cycloalkyl group and a group of -Q$^{2a}$-R$^{5a}$.

Preferably, the (C1-C6)alkylene group of Q$^{1a}$ is, for example, a methylene group, an ethylene group, a trimethylene group, a tetramethylene group.

One or more methylene groups constituting the (C1-6)alkylene group of Q$^{1a}$ may be each independently replaced by an oxygen atom, a sulfur atom, a sulfinyl group, a sulfonyl group, a carbonyl group or a group of —N(R$^{2a}$)—. R$^{2a}$ means a hydrogen atom or a —(C=O)$_a$O$_b$(C1-C6)alkyl group. The alkyl group itself of R$^{2a}$ is preferably a methyl group, an ethyl group; and preferably, a and b are both 0.

Preferably, the (C1-C6)alkylene group of Q$^{1a}$, in which the methylene group is replaced by the above-mentioned atom or group is selected from, for example, groups of a formula (aa1):

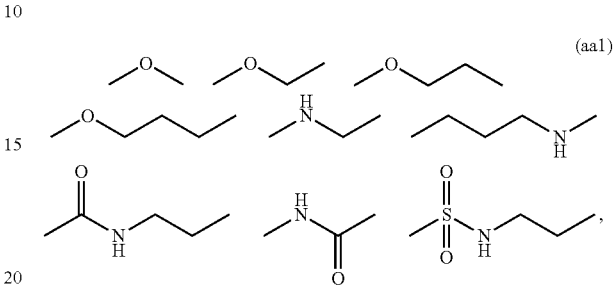

(aa1)

more preferably, those of a formula (aa2):

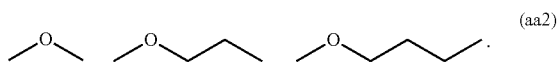

(aa2)

In the groups of the above-mentioned formula (aa1) or (aa2) where the methylene group constituting the (C1-C6)alkylene group of Q$^{1a}$ is replaced by the above-mentioned atom or group, any substitutable methylene group may be substituted with one or two or more of, preferably one or two of, the same or different substituents selected from the group consisting of a halogen atom, a hydroxyl group, a cyano group and a —(C=O)$_a$O$_b$(C1-C6)alkyl group.

The substituent is preferably a halogen atom such as a fluorine atom, a chlorine atom; a hydroxyl group; a —(C=O)$_a$O$_b$(C1-C6)alkyl group such as a methyl group.

The alkyl group itself of "—(C=O)$_a$O$_b$(C1-C6)alkyl group" of R$^{1a}$ is preferably a methyl group, an ethyl group. Preferably, a and b are both 1. The alkyl group may be substituted with a halogen atom or a hydroxyl group. More concretely, the alkyl group means the above-mentioned unsubstituted alkyl group, or means the above-mentioned alkyl group in which any substitutable position is substituted with the same or different substituents selected from one or two or more, preferably from 1 to 3 halogen atoms and one or two or more, preferably one or two hydroxyl groups.

The —(C=O)$_a$O$_b$(C1-C6)alkyl group (where the alkyl group may be substituted) of R$^{1a}$ is preferably a methoxycarbonyl group, an ethoxycarbonyl group.

In the group of —(C=O)$_a$N(R$^{3a}$)R$^{4a}$ of R$^{1a}$, a means 0 or 1, preferably 0; and R$^{3a}$ and R$^{4a}$ each independently mean a hydrogen atom or a —(C=O)$_a$O$_b$(C1-C6)alkyl group.

The alkyl group itself in "—(C=O)$_a$O$_b$(C1-C6)alkyl group" of R$^{3a}$ and R$^{4a}$ is preferably a methyl group, an ethyl group. Preferably, a and b are both 0. The alkyl group may be substituted with a halogen atom or a hydroxyl group. More concretely, the alkyl group means the above-mentioned unsubstituted alkyl group, or means the above-mentioned alkyl group in which any substitutable position is substituted with the same or different substituents selected from one or two or more, preferably from 1 to 3 halogen atoms and one or two or more, preferably one or two hydroxyl groups.

The —(C=O)$_a$O$_b$(C1-C6)alkyl group (where the alkyl group may be substituted) of R$^{3a}$ and R$^{4a}$ is preferably a methyl group, ethyl group.

The group of —(C=O)$_a$N(R$^{3a}$)R$^{4a}$ of R$^{1a}$ is preferably a dimethylamino group, a diethylamino group.

"Heterocyclic group optionally having a substituent selected from the group consisting of a halogen atom, a hydroxyl group, an oxo group, a —(C=O)$_a$O$_b$(C1-C6)alkyl group, a —(C=O)$_a$O$_b$(C3-C6)cycloalkyl group and a group of -Q$^{2a}$-R$^{5a}$" of R$^{1a}$ means the above-mentioned unsubstituted heterocyclic group, or the above-mentioned heterocyclic group having a substituent at any substitutable position, in which one or two or more of, preferably one or two of, the same or different groups may be selected from a halogen atom, a hydroxyl group, an oxo group, a —(C=O)$_a$O$_b$(C1-C6)alkyl group, a —(C=O)$_a$O$_b$(C3-C6)cycloalkyl group and a group of -Q$^{2a}$-R$^{5a}$, for the substituent.

Preferably, the halogen atom of the substituent includes, for example, a fluorine atom, a chlorine atom.

The alkyl group itself of the substituent "—(C=O)$_a$O$_b$(C1-C6)alkyl group" is preferably a methyl group, an ethyl group, an isopropyl group, a tert-butyl group. Preferably, a and b are both 0, or a is 1 and b is 0, or a and b are both 1. The alkyl group may be substituted with a halogen atom, a hydroxyl group, a —(C=O)$_a$O$_b$(C1-C6)alkyl group or a group of —(C=O)$_a$N(R$^{3a}$)R$^{4a}$. More concretely, the alkyl group means the above-mentioned unsubstituted alkyl group, or means the above-mentioned alkyl group in which any substitutable position is substituted with the same or different substituents selected from one or two or more, preferably from 1 to 3 halogen atoms, and one or two or more, preferably one or two hydroxyl groups, —(C=O)$_a$O$_b$(C1-C6)alkyl and —(C=O)$_a$N(R$^{3a}$)R$^{4a}$ groups.

The —(C=O)$_a$O$_b$(C1-C6)alkyl group of the substituent for the alkyl group is preferably a methoxy group, an ethoxy group.

Preferred examples of the group of —(C=O)$_a$N(R$^{3a}$)R$^{4a}$, the substituent for the alkyl group are the same as those mentioned hereinabove as preferred examples of the group of —(C=O)$_a$N(R$^{3a}$)R$^{4a}$ groups of R$^{1a}$.

Examples of the substituted alkyl group include a fluoromethyl group, a difluoromethyl group, a trifluoromethyl group, a hydroxymethyl group, a 1-hydroxy-1-methylethyl group, a 2-hydroxyethyl group, a methoxymethyl group, a 2-methoxyethyl group, a dimethylaminomethyl group.

The substituent, —(C=O)$_a$O$_b$(C1-C6)alkyl group (where the alkyl group may be substituted) for the heterocyclic group of R$^{1a}$ is preferably a methyl group, an ethyl group, an isopropyl group, a hydroxymethyl group, a 2-hydroxyethyl group, an acetyl group, an isobutyryl group, a pivaloyl group, a hydroxyacetyl group, a 2-methoxyacetyl group, a 2-hydroxy-2-methylpropanoyl group, a tert-butoxycarbonyl group, a 2-dimethylaminoacetyl group.

The cycloalkyl group itself of the substituent "—(C=O)$_a$O$_b$(C3-C6)cycloalkyl group" for the heterocyclic group of R$^{1a}$ is preferably a cyclopropyl group, a cyclobutyl group. Preferably, a and b are both 0, or a is 1 and b is 0. The cycloalkyl group may be substituted with a halogen atom or a hydroxyl group. More concretely, the cycloalkyl group means the above-mentioned unsubstituted cycloalkyl group, or means the above-mentioned cycloalkyl group in which any substitutable position is substituted with the same or different substituents selected from one or two or more, preferably from 1 to 3 halogen atoms and one or two or more, preferably one or two hydroxyl groups.

The substituent, —(C=O)$_a$O$_b$(C3-C6)cycloalkyl group (where the cycloalkyl group may be substituted) for the heterocyclic group of R$^{1a}$ is preferably a cyclopropyl group, a cyclopropylcarbonyl group, a cyclobutyl group, a cyclobutylcarbonyl group.

In the substituent, -Q$^{2a}$-R$^{5a}$ for the heterocyclic group of R$^{1a}$, Q$^{2a}$ has the same meaning as that of the above-mentioned Q$^{1a}$; and R$^{5a}$ means a hydrogen atom, a formyl group, a —(C=O)$_a$O$_b$(C1-C6)alkyl group or a group of —(C=O)$_a$N(R$^{3a}$)R$^{4a}$, wherein the alkyl group may be substituted with a halogen torn or a hydroxyl group; or R$^{5a}$ means a heterocyclic group optionally having a substituent selected from the group consisting of a halogen atom, a hydroxyl group, an oxo group, a —(C=O)$_a$O$_b$(C1-C6)alkyl group and a group of -Q$^{3a}$-R$^{6a}$, and the alkyl group of the substituent may be substituted with a halogen atom, a hydroxyl group or a —(C=O)$_a$O$_b$(C1-C6)alkyl group.

Q$^{2a}$ is preferably a single bond.

The —(C=O)$_a$O$_b$(C1-C6)alkyl group and the group of —(C=O)$_a$N(R$^{3a}$)R$^{4a}$ of R$^{5a}$ have the same meanings as those of the —(C=O)$_a$O$_b$(C1-C6)alkyl group and the group of —(C=O)$_a$N(R$^{3a}$)R$^{4a}$ of R$^{1a}$; and their preferred examples are also the same. Especially preferred are a methoxy group, a dimethylamino group, a dimethylcarbamoyl group.

"Heterocyclic group optionally having a substituent selected from the group consisting of a halogen atom, a hydroxyl group, an oxo group, a —(C=O)$_a$O$_b$(C1-C6)alkyl group and a group of -Q$^{3a}$-R$^{6a}$" of R$^{5a}$ means the above-mentioned unsubstituted heterocyclic group, or the above-mentioned heterocyclic group having a substituent at any substitutable position thereof, in which one or two or more of, preferably one or two of, the same or different groups may be selected from the above for the substituent.

In the group of -Q$^{3a}$-R$^{6a}$ as the substituent, Q$^{3a}$ has the same meaning as that of the above-mentioned Q$^{1a}$; R$^{6a}$ means a hydrogen atom, a halogen atom, a hydroxyl group or a —(C=O)$_a$O$_b$(C1-C6)alkyl group, and the alkyl group may be substituted with a halogen atom or a hydroxyl group.

Q$^{3a}$ is preferably a single bond. R$^{6a}$ is preferably a hydrogen atom; a halogen atom such as a fluorine atom, a chlorine atom; a hydroxyl group; or a —(C=O)$_a$O$_b$(C1-C6)alkyl group such as a methyl group, an ethyl group, a methoxy group, an acetyl group.

"Heterocyclic group" itself of R$^{5a}$ includes an azetidinyl group, a pyrrolidinyl group, a piperidinyl group, a piperazinyl group.

The heterocyclic group itself of the above-mentioned "heterocyclic group optionally having a substituent" of R$^{1a}$ includes an azetidinyl group, a pyrrolidinyl group, a piperidinyl group, a piperazinyl group, a morpholinyl group, a perhydro-1,4-diazepinyl group, a 1,2,4-oxadiazolyl group. Above all, preferred are an azetidinyl group, a piperidinyl group, a piperazinyl group, a perhydro-1,4-diazepinyl group; more preferred are a piperidinyl group, a piperazinyl group.

The substituent of the above-mentioned "heterocyclic group optionally having a substituent" of R$^{1a}$ preferably includes a hydroxyl group, an oxo group, a —(C=O)$_a$O$_b$(C1-C6)alkyl group (where the alkyl group may be substituted), a group of -Q$^{2a}$-R$^{5a}$.

More concretely, the above-mentioned "heterocyclic group optionally having a substituent" of R$^{1a}$ preferably includes, for example, a 1-azetidinyl group, a 3-hydroxyazetidin-1-yl group, a 3-dimethylaminoazetidin-1-yl group, a 1-pyrrolidinyl group, a 3-hydroxypyrrolidin-1-yl group, a 3-dimethylaminopyrrolidin-1-yl group, a 1-piperidinyl group, a 2-piperidinyl group, a 4-piperidinyl group, a 4-hydroxypiperidin-1-yl group, a 1-methylpiperidin-4-yl group, a 1,4-dimethylpiperidin-4-yl group, a 1-tert-butoxycarbonylpiperidin-2-yl group, a 1-piperazinyl group, a 4-methylpiperazin-1-yl group, a 4-methylpiperazin-2-yl group, a 2,4-dimethylpiperazin-1-yl group, a 3,4-dimethylpiperazin-1-yl group, a 4-isopropylpiperazin-1-yl group, a 3-isopropyl-4-methylpiperazin-1-yl group, a 4-(2-hydroxyethyl)piperazin-1-yl group, a 2-hydroxymethyl-4-methylpiperazin-1-yl group, a 3-hydroxymethyl-4-methylpiperazin-1-yl group, a 4-(2-methoxyethyl)piperazin-1-yl group, a 2-methoxymethyl-4-methylpiperazin-1-yl group, a 4-acetylpiperazin-1-yl group, a 4-isobutyrylpiperazin-1-yl group, a 4-pivaloylpiperazin-1-yl group, a 4-(2-hydroxyacetyl)piperazin-1-yl group, a 4-(2-methoxyacetyl)piperazin-1-yl group, a 4-(2-hydroxy-2-methylpropanoyl)piperazin-1-yl group, a 4-(2-dimethylaminoacetyl)piperazin-1-yl group, a 4-cyclopropylpiperazin-1-yl group, a 4-cyclopropylcarbonylpiperazin-1-yl group, a 4-cyclobutylcarbonylpiperazin-1-yl group, a 3-dimethylcarbamoyl-4-methylpiperazin-1-yl group, a 4-morpholinyl group, a perhydro-1,4-diazepin-1-yl group, a 4-methyl-perhydro-1,4-diazepin-1-yl group, a 4-methyl-5-oxo-perhydro-1,4-diazepin-1-yl group, a 1,2,4-oxadiazol-3-yl group, a 5-dimethylaminomethyl-1,2,4-oxadiazol-3-yl group; and above all, more preferred are a 3-hydroxyazetidin-1-yl group, a 4-hydroxypiperizin-1-yl group, a 1-methylpiperizin-4-yl group, a 4-methylpiperazin-1-yl group, a 4-isopropylpiperazin-1-yl group, a 3-hydroxymethyl-4-methylpiperazin-1-yl group, a 4-(2-methoxyacetyl)piperazin-1-yl group, a 4-(2-dimethylaminoacetyl)piperazin-1-yl group.

One embodiment of the group of $-Q^{1a}-R^{1a}$ is, (i) $Q^{1a}$ is a (C1-C6)alkylene group, in which one methylene group constituting the (C1-C6)alkylene group may be replaced by an oxygen atom, and said one or two methylene groups may be substituted with a hydroxyl group or a $—(C=O)_aO_b(C1-C6)$alkyl group; and $R^{1a}$ is a group of $—(C=O)_aN(R^{3a})R^{4a}$.

More concretely, for example, the embodiment includes a dimethylaminomethyl group, a diethylaminomethyl group, a 2-dimethylaminoethyl group, a 3-dimethylaminopropyl group, a 3-dimethylamino-1-hydroxypropyl group, a 2-dimethylaminoethoxy group, a 2-diethylaminoethoxy group, a 2-dimethylamino-1-methylethoxy group, a 2-[isopropyl(methyl)amino]ethoxy group, a 2-dimethylaminopropoxy group, a 3-dimethylaminopropoxy group, a 3-dimethylamino-2-hydroxypropoxy group, a 3-dimethylamino-2-methylpropoxy group. Above all, more preferred are a 3-dimethylamino-1-hydroxypropyl group, a 2-dimethylamino-1-methylethoxy group, a 2-[isopropyl(methyl)amino]ethoxy group, a 2-dimethylaminopropoxy group, a 3-dimethylaminopropoxy group, a 3-dimethylamino-2-hydroxypropoxy group.

Another embodiment of the group of $-Q^{1a}-R^{1a}$ is, (ii) $Q^{1a}$ is a (C1-C6)alkylene group, in which one methylene group constituting the (C1-C6)alkylene group may be replaced by an oxygen atom, and said one or two methylene groups may be substituted with a hydroxyl group or a $—(C=O)_aO_b(C1-C6)$alkyl group; and $R^{1a}$ is a heterocyclic group optionally substituted with a $—(C=O)_aO_b(C1-C6)$alkyl group, wherein the alkyl group of the substituent may be substituted with a hydroxyl group or a $—(C=O)_aO_b(C1-C6)$alkyl group.

More concretely, for example, the embodiment includes a 2-(1-pyrrolidinyl)ethyl group, a 1-methylpyrrolidin-3-yloxy group, a hydroxy(1-methylpiperidin-4-yl)methyl group, a 1-methylpiperidin-4-yloxy group, a 4-methylpiperazin-1-ylmethyl group, a 4-isobutyrylpiperazin-1-ylmethyl group, a 4-pivaloylpiperazin-1-ylmethyl group. Above all, more preferred are a hydroxy(1-methylpiperidin-4-yl)methyl group, a 1-methylpiperidin-4-yloxy group.

Still another embodiment of the group of $-Q^{1a}-R^{1a}$ is, (iii) $Q^{1a}$ is a single bond; and $R^{1a}$ is a heterocyclic group optionally having a substituent selected from the group consisting of a hydroxyl group, an oxo group and a $—(C=O)_aO_b(C1-C6)$alkyl group, wherein the alkyl group of the substituent may be substituted with a hydroxyl group, a $—(C=O)_aO_b(C1-C6)$alkyl group or a group of $—(C=O)_aN(R^{3a})R^{4a}$.

More concretely, for example, the embodiment is preferably a 1-azetidinyl group, a 3-hydroxyazetidin-1-yl group, a 1-pyrrolidinyl group, a 3-hydroxypyrrolidin-1-yl group, a 1-piperidinyl group, a 2-piperidinyl group, a 4-piperidinyl group, a 4-hydroxypiperidin-1-yl group, a 1-methylpiperidin-4-yl group, a 1,4-dimethylpiperidin-4-yl group, a 1-tert-butoxycarbonylpiperidin-2-yl group, a 1-piperazinyl group, a 4-methylpiperazin-1-yl group, a 4-methylpiperazin-2-yl group, a 2,4-dimethylpiperazin-1-yl group, a 3,4-dimethylpiperazin-1-yl group, a 4-isopropylpiperazin-1-yl group, a 3-isopropyl-4-methylpiperazin-1-yl group, a 4-(2-hydroxyethyl)piperazin-1-yl group, a 2-hydroxymethyl-4-methylpiperazin-1-yl group, a 3-hydroxymethyl-4-methylpiperazin-1-yl group, a 4-(2-methoxyethyl)piperazin-1-yl group, a 2-methoxymethyl-4-methylpiperazin-1-yl group, a 4-acetylpiperazin-1-yl group, a 4-isobutyrylpiperazin-1-yl group, 4-pivaloylpiperazin-1-yl group, a 4-(2-hydroxyacetyl)piperazin-1-yl group, a 4-(2-methoxyacetyl)piperazin-1-yl group, a 4-(2-hydroxy-2-methylpropanoyl)piperazin-1-yl group, a 4-(2-dimethylaminoacetyl)piperazin-1-yl group, a 4-morpholinyl group, a perhydro-1,4-diazepin-1-yl group, a 4-methyl-perhydro-1,4-diazepin-1-yl group, a 4-methyl-5-oxo-perhydro-1,4-diazepin-1-yl group, a 1,2,4-oxadiazol-3-yl group, a 5-dimethylaminomethyl-1,2,4-oxadiazol-3-yl group. Above all, more preferred are a 3-hydroxyazetidin-1-yl group, a 4-hydroxypiperidin-1-yl group, a 1-methylpiperidin-4-yl group, a 4-methylpiperazin-1-yl group, a 3,4-dimethylpiperazin-1-yl group, a 4-isopropylpiperazin-1-yl group, a 3-hydroxymethyl-4-methylpiperazin-1-yl group, a 4-(2-methoxyacetyl)piperazin-1-yl group, a 4-(2-dimethylaminoacetyl)piperazin-1-yl group.

The aryl group itself of the above-mentioned "aryl or heteroaryl group optionally having a substituent" of A is preferably a phenyl group; and the heteroaryl group itself includes a pyrazolyl group, an indolyl group, an indazolyl group. The substituent is preferably selected from the group consisting of a halogen atom, a hydroxyl group, a $—(C=O)_aO_b(C1-C6)$alkyl group (where the alkyl group may be substituted with a halogen atom or a hydroxyl group) and a group of $-Q^{1a}-R^{1a}$. Also preferably, at least one substituent is the group of $-Q^{1a}-R^{1a}$.

More concretely, the above-mentioned "aryl or heteroaryl group optionally having a substituent" of A includes preferably a phenyl group, a 4-diethylaminophenyl group, a 4-(3-ethoxycarbonylpropoxy)phenyl group, a 4-dimethylaminomethylphenyl group, a 4-diethylaminomethylphenyl group, a 4-(2-dimethylaminoethyl)phenyl group, a 4-(3-dimethylaminopropyl)phenyl group, a 4-(3-dimethylamino-1-hydroxypropyl)phenyl group, a 4-(2-dimethylaminoethoxy)phenyl group, a 4-(2-dimethylaminoethoxy)-3-methylphenyl group, a 4-(2-diethylaminoethoxy)phenyl group, a 4-(2-dimethylamino-1-methylethoxy)phenyl group, a 4-[2-[isopropyl(methyl)amino]ethoxy]phenyl group, a 4-(2-dimethylaminopropoxy)phenyl group, a 3-(3-dimethylaminopropoxy)phenyl group, a 4-(3-dimethylaminopropoxy)phenyl group, a 3-(3-dimethylaminopropoxy)-4-methylphenyl group, a 3-methoxy-4-(3-dimethylaminopropoxy)phenyl group, a 4-methoxy-3-(3-dimethylaminopropoxy)phenyl group, a 4-(3-dimethylamino-2-hydroxypropoxy)phenyl group, a 4-(3-dimethylamino-2-hydroxypropoxy)-3-methylphenyl group, a 3-(3-dimethylamino-2-methylpropoxy)phenyl group, a 4-(3-hydroxypyrrolidin-1-ylmethyl)phenyl group, a 4-(1-methylpyrrolidin-3-yloxy)phenyl group, a 4-[hydroxy(1-methylpiperidin-4-yl)methyl]phenyl group, a 4-(1-methylpiperidin-4-yloxy)phenyl group, a 4-(4-(methylpiperazin-1-ylmethyl)phenyl group, a 4-(4-isobutyrylpiperazin-1-ylmethyl)phenyl group, a 4-(4-pivaloylpiperazin-1-ylmethyl)phenyl group, a 4-(1-azetidinyl)phenyl group, a 4-(3-hydroxyazetidin-1-yl)-3-methylphenyl group, a 4-(3-dimethylaminoazetidin-1-yl)phenyl group, a 4-(3-dimethylaminoazetidin-1-yl)-3-fluorophenyl group, a 4-(1-pyrrolidinyl)phenyl group, a 4-(3-dimethylaminopyrrolidin-1-yl)phenyl group, a 4-(1-piperidinyl)phenyl group, a 4-(2-piperidinyl)phenyl group, a 4-(4-piperidinyl)phenyl group, a 4-(4-hydroxypiperidin-1-yl)-3-methylphenyl group, a 4-(1-methylpiperidin-4-yl)phenyl group, a 4-(1,4-dimethylpiperidin-4-yl)phenyl group, a 4-(1-tert-butoxycarbonylpiperidin-2-yl)phenyl group, a 4-(1-piperazinyl)phenyl group, a 4-(4-methylpiperazin-1-yl)phenyl group, a 4-(4-methylpiperazin-2-yl)phenyl group, a 3-fluoro-4-(4-methylpiperazin-1-yl)phenyl group, a 3-methyl-4-(4-methylpiperazin-1-yl)phenyl group, a 3-methoxy-4-(4-methylpiperazin-1-yl)phenyl group, a 3-hydroxymethyl-4-(4-methylpiperazin-1-yl)phenyl group, a 3-(1-hydroxyethyl)-4-(4-methylpiperazin-1-yl) phenyl group, a 3-dimethylcarbamoyl-4-(4-methylpiperazin-1-yl)phenyl group, a 4-(2,4-dimethylpiperazin-1-yl)phenyl group, a 4-(3,4-dimethylpiperazin-1-yl)phenyl group, a 4-(4-isopropylpiperazin-1-yl)phenyl group, a 4-(3-isopropyl-4-methylpiperazin-1-yl)phenyl group, a 4-(4-(2-hydroxyethyl)piperazin-1-yl)phenyl group, a 4-(4-(2-hydroxyethyl)piperazin-1-yl)-3-methylphenyl group, a 4-(2-hydroxymethyl-4-methylpiperazin-1-yl)phenyl group, a 4-(3-hydroxymethyl-4-methylpiperazin-1-yl)phenyl group, a 4-[4-(2-methoxyethyl)piperazin-1-yl]-3-methylphenyl group, a 4-(2-methoxymethyl-4-methylpiperazin-1-yl)phenyl group, a 4-(4-acetylpiperazin-1-yl)phenyl group, a 4-(4-acetylpiperazin-1-yl)-3-methylphenyl group, a 4-(4-isobutyrylpiperazin-1-yl)phenyl group, a 4-(4-pivaloylpiperazin-1-yl)phenyl group, a 4-[4-(2-hydroxyacetyl)piperazin-1-yl] phenyl group, a 3-fluoro-4-[4-(2-methoxyacetyl)piperazin-1-yl]phenyl group, a 3-chloro-4-[4-(2-methoxyacetyl)piperazin-1-yl]phenyl group, a 4-[4-(2-methoxyacetyl)piperazin-1-yl]-3-methylphenyl group, a 3-hydroxymethyl-4-[4-(2-methoxyacetyl)piperazin-1-yl]phenyl group, a 4-[4-(2-hydroxy-2-methylpropanoyl)piperazin-1-yl]phenyl group, a 4-[4-(2-dimethylaminoacetyl)piperazin-1-yl]phenyl group, a 4-(4-cyclopropylpiperazin-1-yl)-3-methylphenyl group, a 4-(4-cyclopropylcarbonylpiperazin-1-yl)phenyl group, a 4-(4-cyclobutylcarbonylpiperazin-1-yl)phenyl group, a 4-(3-dimethylcarbamoyl-4-methylpiperazin-1-yl)phenyl group, a 4-(3-dimethylcarbamoyl-4-methylpiperazin-1-yl)-3-methylphenyl group, a 3-hydroxymethyl-4-(4-morpholinyl)phenyl group, a 4-(perhydro-1,4-diazepin-1-yl)phenyl group, a 4-(4-methyl-perhydro-1,4-diazepin-1-yl)phenyl group, a 4-(4-methyl-5-oxo-perhydro-1,4-azepin-1-yl)phenyl group, a 1-(1-methylpiperidin-4-yl)pyrazol-4-yl group, a 5-dimethylaminomethyl-1,2,4-oxadiazol-3-yl group, a 1-ethylindol-5-yl group, a 1-(2-dimethylaminoethyl)indol-5-yl group, a 1-[2-(1-pyrrolidinyl)ethyl]indol-5-yl group, a 1-ethylindazol-5-hl group, a 1-ethylindazol-6-yl group, a 2-ethylindazol-5-yl group, a 2-ethylindazol-6-yl group. Above all, more preferred are a 4-(3-dimethylamino-1-hydroxypropyl)phenyl group, a 4-(2-dimethylamino-1-methylethoxy)phenyl group, a 4-[2-[isopropyl(methyl) amino]ethoxy]phenyl group, a 4-(2-dimethylaminopropoxy) phenyl group, a 4-(3-dimethylamino-2-hydroxypropoxy)-3-methylphenyl group, a 4-[hydroxy(1-methylpiperidin-4-yl) methyl] group, a 4-(3-hydroxyazetidin-1-yl)-3-methylphenyl group, a 4-(4-hydroxypiperidin-1-yl)-3-methylphenyl group, a 4-(4-methylpiperazin-1-yl)phenyl group, a 3-methyl-4-(4-methylpiperazin-1-yl)phenyl group, a 3-hydroxymethyl-4-(4-methylpiperazin-1-yl)phenyl group, a 4-(3,4-dimethylpiperazin-1-yl)phenyl group, a 4-(4-isopropylpiperazin-1-yl)phenyl group, a 4-(4-(2-hydroxyethyl)piperazin-1-yl) phenyl group, a 4-(3-hydroxymethyl-4-methylpiperazin-1-yl)phenyl group, a 3-chloro-4-[4-(2-methoxyacetyl)piperazin-1-yl]phenyl group, a 4-[4-(2-dimethylaminoacetyl)piperazin-1-yl]phenyl group.

In the group of a formula (a):

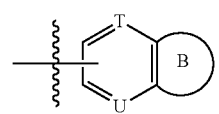

(a)

of A,
the ring B means a 5-membered to 7-membered aliphatic ring condensed with the ring of a formula (b):

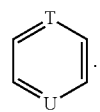

(b)

T and U each independently mean a nitrogen atom, or mean a methine group optionally substituted with a halogen atom, a hydroxyl group, a cyano group or a —(C═O)$_a$O$_b$(C1-C6) alkyl group.

"Methine group optionally substituted with a halogen atom, a hydroxyl group, a cyano group or a —(C═O)$_a$O$_b$ (C1-C6)alkyl group" means an unsubstituted methine group, or a methine group substituted with a substituent selected from the group consisting of a halogen atom, a hydroxyl group, a cyano group and a —(C═O)$_a$O$_b$(C1-C6)alkyl group.

The halogen atom as the substituent is preferably a fluorine atom, a chlorine atom.

The alkyl group itself of "—(C═O)$_a$O$_b$(C1-C6)alkyl group" as the substituent is preferably a methyl group, an ethyl group. Preferably, a and b are both 0. The alkyl group may be substituted with a halogen atom or a hydroxyl group. More concretely, the alkyl group means the above-mentioned unsubstituted alkyl group, or means the above-mentioned alkyl group in which any substitutable position is substituted with the same or different substituents selected from one or two or more, preferably from 1 to 3 halogen atoms and one or two or more, preferably one or two hydroxyl groups. Examples of the substituted group include a fluoromethyl group, a difluoromethyl group, a trifluoromethyl group, a hydroxymethyl group, a 1-hydroxyethyl group.

The substituent —(C═O)$_a$O$_b$(C1-C6)alkyl group (where the alkyl group may be substituted) is preferably a methyl group, an ethyl group, a methoxy group, a hydroxymethyl group, a 1-hydroxyethyl group.

The substituent is preferably a halogen atom, a hydroxyl group, a —(C═O)$_a$O$_b$(C1-C6)alkyl group (where the alkyl group may be substituted).

Preferred embodiments of T and U include: T and U are both unsubstituted methine groups; or any one of T and U is a nitrogen atom, and the other is a methine group optionally substituted with a halogen atom, a hydroxyl group, a cyano group or a —(C=O)$_a$O$_b$(C1-C6)alkyl group, more preferably an unsubstituted methine group. More preferably, T and U are both unsubstituted methine groups.

The 5-membered to 7-membered aliphatic ring to condense with the ring of formula (b) includes rings of a formula (b'-1):

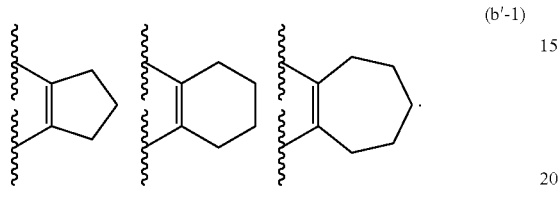

(b'-1)

One or two or more methylene groups constituting the ring B may be each independently replaced by an oxygen atom, a sulfur atom a sulfinyl group, a sulfonyl group, a carbonyl group or a group of —N(R$^{1b}$)—.

"One or two or more methylene groups constituting the ring B may be each independently replaced by an oxygen atom, a sulfur atom a sulfinyl group, a sulfonyl group, a carbonyl group or a group of —N(R$^{1b}$)—" as referred to herein means that one or two or more methylene groups constituting the ring B are replaced, or are not replaced by themselves by one or two or more, preferably from 1 to 3, the same or different groups or atoms selected the group consisting of an oxygen atom, a sulfur atom, a sulfinyl group, a sulfonyl group, a carbonyl group and a group of —N(R$^{1b}$)—; and as a result of such "replacement", the group represented by a formula (ab-1):

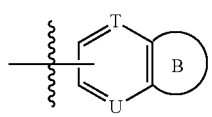

(a)

is a group selected from groups of a formula (a-0):

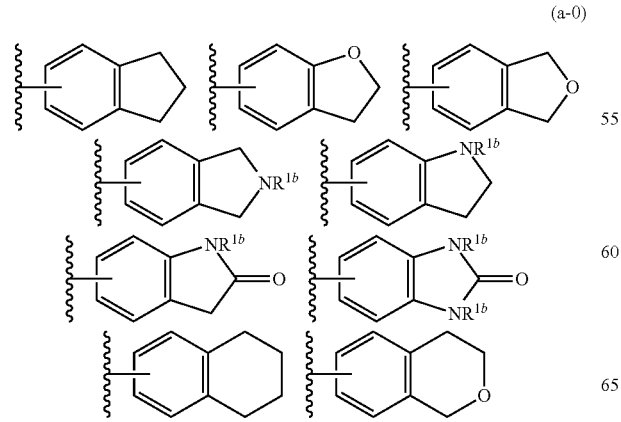

(a-0)

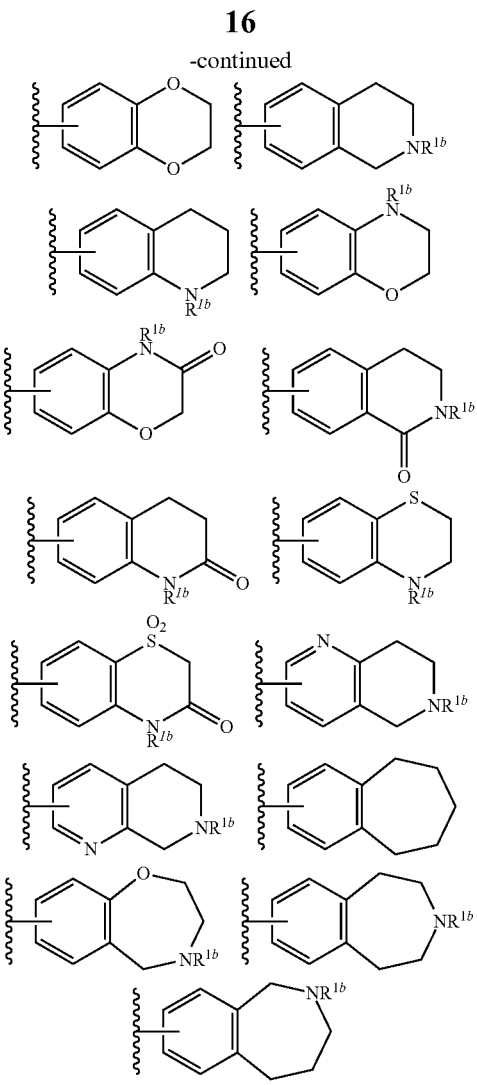

Of the groups of formula (a-0), preferred embodiments are groups selected from those of a formula (a-1):

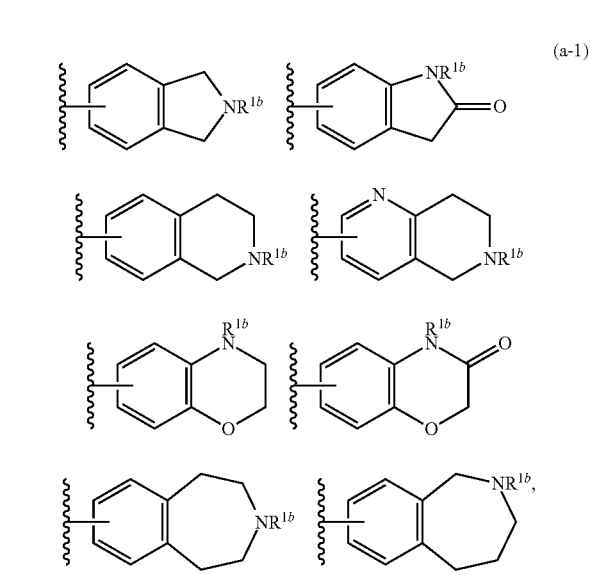

(a-1)

more preferred are groups selected from those of a formula (a-2):

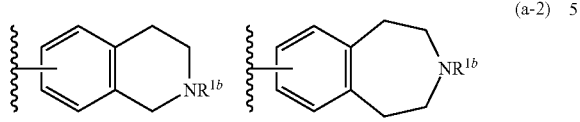

(a-2)

In the above formulae, $R^{1b}$ each independently means a hydrogen atom or a $—(C=O)_aO_b(C1-C6)$alkyl group.

The alkyl group itself of "$—(C=O)_aO_b(C1-C6)$alkyl group" of $R^{1b}$ is preferably a methyl group, an ethyl group. Preferably, a and b are both 0. The alkyl group may be substituted with a halogen atom, a hydroxyl group or a group of $—(C=O)_aN(R^{3e})R^{4e}$. More concretely, the alkyl group means the above-mentioned unsubstituted alkyl group, or means the above-mentioned alkyl group in which any substitutable position is substituted with the same or different substituents selected from one or two or more, preferably from 1 to 3 halogen atoms and one or two or more, preferably one or two hydroxyl groups and groups of $—(C=O)_aN(R^{3e})R^{4e}$.

Preferred examples of the group of $—(C=O)_aN(R^{4b})R^{5b}$ as the substituent are the same as those mentioned hereinabove as preferred examples of the group of $—(C=O)_aN(R^{3a})R^{4a}$ of $R^{1a}$.

The $—(C=O)_aO_b(C1-C6)$alkyl group of $R^{1b}$ (where the alkyl group may be substituted) is preferably a methyl group, an ethyl group, a hydroxymethyl group, a 2-hydroxyethyl group, a 2-dimethylaminoethyl group.

$R^{1b}$ is preferably a $—(C=O)_aO_b(C1-C6)$alkyl group (where the alkyl group may be substituted).

One or two or more methylene groups constituting the aliphatic ring corresponding to the ring B may be each independently substituted, at the hydrogen atom thereof, with a halogen atom, a hydroxyl group, a $—(C=O)_aO_b(C1-C6)$alkyl group or a group of $-Q^{1b}-N(R^{2b})R^{3b}$.

The halogen atom as the substituent is preferably a fluorine atom, a chlorine atom.

The alkyl group itself of "$—(C=O)_aO_b(C1-C6)$alkyl group" as the substituent is preferably a methyl group, an ethyl group. Preferably, a and b are both 0. The alkyl group may be substituted with a halogen atom or a hydroxyl group. More concretely, the alkyl group means the above-mentioned unsubstituted alkyl group, or means the above-mentioned alkyl group in which any substitutable position is substituted with the same or different substituents selected from one or two or more, preferably from 1 to 3 halogen atoms and one or two or more, preferably one or two hydroxyl groups.

The above-mentioned $—(C=O)_aO_b(C1-C6)$alkyl group (where the alkyl group may be substituted) is more preferably a methyl group, an ethyl group, a hydroxymethyl group, a 2-hydroxyethyl group, and even more preferably a methyl group.

In the substituent $-Q^{1b}-N(R^{2b})R^{3b}$, $Q^{1b}$ has the same meaning as that of $Q^{1a}$ in the above-mentioned $-Q^{1a}-R^{1a}$, and its preferred examples are also the same as those of the latter. $R^{2b}$ and $R^{3b}$ have the same meanings as those of $R^{3a}$ and $R^{4a}$ in $—(C=O)_aN(R^{3a})R^{4a}$ of the above-mentioned $R^{1a}$, and their preferred examples are also the same as those of the latter.

The substituent on one or two or more methylene groups constituting the aliphatic ring corresponding to the above-mentioned ring B is preferably a $—(C=O)_aO_b(C1-C6)$alkyl group (where the alkyl group may be substituted).

Preferred embodiments of the group of a formula (a):

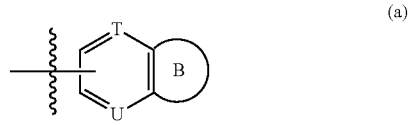

(a)

includes the groups mentioned below.
A preferred embodiment of the group of:

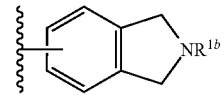

which may be substituted with the above-mentioned substituent, is a 2-methyl-2,3-dihydro-1H-isoindol-5-yl group.
A preferred embodiment of the group of:

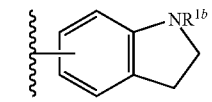

which may be substituted with the above-mentioned substituent, is a 1-(2-dimethylaminoethyl)-2,3-dihydro-1H-indol-5-yl group.
A preferred embodiment of the group of:

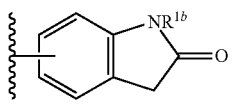

which may be substituted with the above-mentioned substituent, is a 1-(2-dimethylaminoethyl)-2-oxo-2,3-dihydro-1H-indol-5-yl group.
Preferred embodiments of the group of:

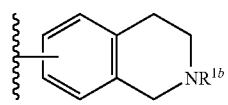

which may be substituted with the above-mentioned substituent, include a 2-methyl-1,2,3,4-tetrahydroisoquinolin-6-yl group, a 2-methyl-1,2,3,4-tetrahydroisoquinolin-7-yl group, a 1,1,2-trimethyl-1,2,3,4-tetrahydroisoquinolin-6-yl group, a 2-(2-hydroxyethyl)-1,2,3,4-tetrahydroisoquinolin-7-yl group.
A preferred embodiment of the group of:

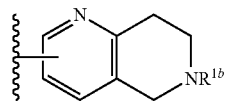

which may be substituted with the above-mentioned substituent, is a 6-methyl-5,6,7,8-tetrahydro-1,6-naphthyridin-3-yl group.

A preferred embodiment of the group of:

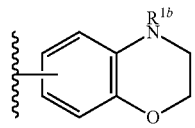

which may be substituted with the above-mentioned substituent, is a 4-(2-dimethylaminoethyl)-3,4-dihydro-2H-1,4-benzoxazin-7-yl group.

A preferred embodiment of the group of:

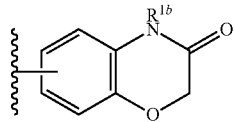

which may be substituted with the above-mentioned substituent, is a 4-(2-dimethylaminoethyl)-3-oxo-3,4-dihydro-2H-1,4-benzoxazin-7-yl group.

A preferred embodiment of the group of:

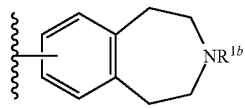

which may be substituted with the above-mentioned substituent, is a 3-methyl-2,3,4,5-tetrahydro-1H-3-benzazepin-7-yl group.

Preferred embodiments of the group of:

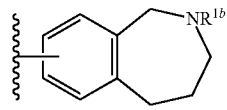

which may be substituted with the above-mentioned substituent, include a 2-methyl-2,3,4,5-tetrahydro-1H-2-benzazepin-7-yl group, a 2-methyl-2,3,4,5-tetrahydro-1H-2-benzazepin-8-yl group.

$R^1$ means a $—(C=O)_aO_b(C1-C6)$alkyl group, a $—(C=O)_aO_b(C2-C6)$alkenyl group, a $—(C=O)_aO_b(C3-C6)$cycloalkyl group, an aryl group or a heteroaryl group.

The alkyl group itself of "$—(C=O)_aO_b(C1-C6)$alkyl group" of $R^1$ is preferably a methyl group, an ethyl group, a propyl group, an isopropyl group. Preferably, a and b are both 0.

The alkenyl group itself of "$—(C=O)_aO_b(C2-C6)$alkenyl group" of $R^1$ is preferably a vinyl group, a 1-propenyl group, a 2-propenyl group, more preferably a 2-propenyl group. Preferably, a and b are both 0.

The cycloalkyl group itself of "$—(C=O)_aO_b(C3-C6)$cycloalkyl group" of $R^1$ is preferably a cyclopropyl group. Preferably, a and b are both 0.

The alkyl, alkenyl or cycloalkyl group of $R^1$ may be each independently substituted with $R^{1c}$. More concretely, the alkyl, alkenyl or cycloalkyl group means the above-mentioned, unsubstituted alkyl, alkenyl or cycloalkyl group, or means the above-mentioned alkyl, alkenyl or cycloalkyl group in which any substitutable position is substituted with one or two or more of, preferably one or two of, the same or different $R^{1c}$'s.

$R^{1c}$ means a halogen atom, a hydroxyl group, a cyano group, a $—(C=O)_aO_b(C1-C6)$alkyl group, a $—(C=O)_aO_b(C3-C6)$cycloalkyl group, an aryl group or a heteroaryl group.

The halogen atom of $R^{1c}$ is preferably a fluorine atom, a chlorine atom.

The alkyl group itself of "$—(C=O)_aO_b(C1-C6)$alkyl group" of $R^{1c}$ is preferably a methyl group, an ethyl group. Preferably, a is 0 and b is 1.

The cycloalkyl group itself of "$—(C=O)_aO_b(C3-C6)$cycloalkyl group" of $R^{1c}$ is preferably a cyclopropyl group. Preferably, a and b are both 0.

The alkyl or cycloalkyl group of the above $R^{1c}$ may be each independently substituted with a halogen atom or a hydroxyl group. More concretely, the alkyl or cycloalkyl group means the above-mentioned, unsubstituted alkyl or cycloalkyl group, or means the above-mentioned alkyl or cycloalkyl group in which any substitutable position is substituted with the same or different substituents selected from one or two or more, preferably from 1 to 3 halogen atoms and one or two or more, preferably one or two hydroxyl groups.

The aryl group of $R^{1c}$ includes a phenyl group, and the heteroaryl group includes a furyl group, a thienyl group, a thiazolyl group, a pyridyl group, a pyrimidinyl group. Preferred is a phenyl group.

The aryl or heteroaryl group of $R^{1c}$ may be each independently substituted with a substituent selected from the group consisting of a nitro group, a hydroxyamino group, a $—(C=O)_aO_b(C1-C6)$alkyl group and a group of $—(C=O)_aN(R^{2c})R^{3c}$.

The $—(C=O)_aO_b(C1-C6)$alkyl group as the substituent is preferably a methyl group, an ethyl group, a methoxy group. The alkyl group may be substituted with a halogen atom or a hydroxyl group. More concretely, it may be substituted with one or two or more, preferably from 1 to 3 halogen atoms and/or one or two or more, preferably one or two hydroxyl groups.

Preferred examples of the group of $—(C=O)_aN(R^{2c})R^{3c}$ of the substituent are the same as those of the group of $—(C=O)_aN(R^{3a})R^{4a}$ of the above-mentioned $R^{1a}$.

The aryl group of $R^1$ is preferably a phenyl group. The heteroaryl group of $R^1$ is preferably a furyl group, a thienyl group, an imidazolyl group, a thiazolyl group, a pyridyl group, a pyrazinyl group, a pyrimidinyl group, more preferably a furyl group, a thiazolyl group, a pyridyl group, a pyrimidinyl group.

The aryl or heteroaryl group of $R^1$ may be each independently substituted with $R^{1d}$. More concretely, the aryl or heteroaryl group means an unsubstituted aryl or heteroaryl group, or means an aryl or heteroaryl group in which any substitutable position is substituted with the same or different substituents, one or two or more, preferably one or two $R^{1d}$'s.

$R^{1d}$ means a nitro group, a hydroxyamino group, a $—(C=O)_aO_b(C1-C6)$alkyl group or a group of $—(C=O)_aN(R^{2d})R^{3d}$, and the alkyl group may be substituted with a halogen atom or a hydroxyl group.

The alkyl group itself of "$—(C=O)_aO_b(C1-C6)$alkyl group" of $R^{1d}$ is preferably a methyl group, an ethyl group. Preferably a and b are both 0, or a is 0 and b is 1. The alkyl group may be substituted with a halogen atom or a hydroxyl group. More concretely, the alkyl group means the above-mentioned, unsubstituted alkyl group, or means the above-mentioned alkyl group in which any substitutable position is substituted with the same or different substituents selected from one or two or more, preferably from 1 to 3 halogen atoms and one or two or more, preferably one or two hydroxyl groups. Examples of the substituted group include a fluoromethyl group, a difluoromethyl group, a trifluoromethyl group, a hydroxymethyl group, a 1-hydroxyethyl group.

The $-(C=O)_aO_b$(C1-C6)alkyl group of $R^{1d}$ (in which the alkyl group may be substituted) is preferably a methyl group, an ethyl group, a methoxy group, a hydroxymethyl group.

In the group of $-(C=O)_aN(R^{2d})R^{3d}$ of $R^{1d}$, a is preferably 1. $R^{2d}$ and $R^{3d}$ have the same meanings as those of $R^{3a}$ and $R^{4a}$ in the above-mentioned group of $-(C=O)_aN(R^{3a})R^{4a}$ of $R^{1a}$, and their preferred examples are also the same as those of the latter.

A specific example of the group of $-(C=O)_aN(R^{2d})R^{3d}$ of $R^{1d}$ is a dimethylcarbamoyl group.

$R^1$ is preferably an aryl or heteroaryl group optionally substituted with $R^{1d}$, more preferably a phenyl, furyl, thienyl, imidazolyl, thiazolyl, pyridyl, pyrazinyl or pyrimidinyl group optionally substituted with $R^{1d}$.

More concretely, $R^1$ includes a methyl group, an ethyl group, a propyl group, an isopropyl group, a 2,2-difluoroethyl group, a 2-hydroxyethyl group, a 3-hydroxypropyl group, a 1-cyanoethyl group, a 2-methoxyethyl group, a cyclopropylmethyl group, a benzyl group, a 2-propenyl group, a cyclopropyl group, a phenyl group, a 4-hydroxymethylphenyl group, a 3-furyl group, a 3-thienyl group, a 1-methyl-2-imidazolyl group, a 2-thiazolyl group, a 4-thiazolyl group, a 2-pyridyl group, a 3-pyridyl group, a 4-pyridyl group, a 3-nitro-2-pyridyl group, a 3-hydroxyamino-2-pyridyl group, a 3-methyl-2-pyridyl group, a 4-methyl-2-pyridyl group, a 5-methyl-2-pyridyl group, a 6-methyl-2-pyridyl group, a 6-methoxy-2-pyridyl group, a 5-dimethylcarbamoyl-2-pyridyl group, a 6-dimethylcarbamoyl-2-pyridyl group, a 2-pyrazinyl group, a 2-pyrimidinyl group, a 5-pyrimidinyl group. Above all, preferred are a 3-furyl group, a 3-thienyl group, a 2-thiazolyl group, a 2-pyridyl group, a 2-pyrimidinyl group.

$R^2$ and $R^3$ each independently mean a hydrogen atom, a halogen atom, a hydroxyl group, a carboxyl group, a $-(C=O)_aO_b$(C1-C6)alkyl group or a group of $-(C=O)_aN(R^{1e})R^{2e}$.

The halogen atom of $R^2$ and $R^3$ is preferably a fluorine atom, a chlorine atom.

The alkyl group itself of the "$-(C=O)_aO_b$(C1-C6)alkyl group" of $R^2$ and $R^3$ is preferably a methyl group, an ethyl group. Preferably, a is 0 and b is 1, or a and b are both 1. The alkyl group may be substituted with a substituent selected from the group consisting of a halogen atom, a hydroxyl group, a carboxyl group, a $-(C=O)_aO_b$(C1-C6)alkyl group and a group of $-(C=O)_aN(R^{3e})R^{4e}$. More concretely, the alkyl group means the above-mentioned unsubstituted alkyl group, or means the above-mentioned alkyl group in which any substitutable position is substituted with the same or different substituents selected from one or two or more, preferably from 1 to 3 halogen atoms and one or two or more, preferably one or two hydroxyl groups, carboxyl groups, $-(C=O)_aO_b$(C1-C6)alkyl groups and groups of $-(C=O)_aN(R^{3e})R^{4e}$.

In the $-(C=O)_aO_b$(C1-C6)alkyl group as the substituent of the alkyl group, preferably, a and b are both 1. Preferably, the group is a methoxycarbonyl group, an ethoxycarbonyl group, a tert-butoxycarbonyl group.

In the group of $(C=O)_aN(R^{3e})R^{4e}$ as the substituent of the alkyl group, a is preferably 1. $R^{3e}$ and $R^{4e}$ have the same meanings as those of $R^{3a}$ and $R^{4a}$ in the group of $-(C=O)_aN(R^{3a})R^{4a}$ of the above-mentioned $R^{1a}$, and they are preferably both hydrogen atoms. The group is preferably a carbamoyl group.

The $-(C=O)_aO_b$(C1-C6)alkyl group of $R^2$ and $R^3$ (where the alkyl group may be substituted) is preferably a fluoromethyl group, a difluoromethyl group, a trifluoromethyl group, a methoxy group, an ethoxy group, a methoxycarbonyl group, a 2-hydroxyethoxy group, a carboxymethoxy group, a methoxycarbonylmethoxy group, a tert-butoxycarbonylmethoxy group, a carbamoylmethoxy group.

In the group of $-(C=O)_aN(R^{1e})R^{2e}$ of $R^2$ and $R^3$, a is preferably 1. $R^{1e}$ and $R^{2e}$ have the same meanings as those of $R^{3a}$ and $R^{4a}$ in $-(C=O)_aN(R^{3a})R^{4a}$ of the above-mentioned $R^{1a}$, and preferred are a carbamoyl group, a dimethylcarbamoyl group, a diethylcarbamoyl group.

Preferably, $R^2$ and $R^3$ each are independently a hydrogen atom or a hydroxyl group.

Preferred embodiments of $R^2$ and $R^3$ are that they are both hydrogen atoms or one of them is a hydroxyl group and the other is a hydrogen atom.

$R^4$ means a hydrogen atom or a (C1-C6)alkyl group, and is preferably a hydrogen atom.

One embodiment of the invention includes a compound of a formula (I-1):

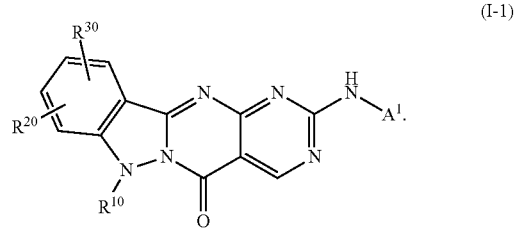

(I-1)

$A^1$ means a phenyl, pyrazolyl, indolyl or indazolyl group, which may have a substituent selected from the group consisting of a halogen atom, a hydroxyl group, a $-(C=O)_aO_b$(C1-C6)alkyl group and a group of $-Q^{1a}-R^{1a}$, wherein the alkyl group of the substituent may be substituted with a halogen atom or a hydroxyl group, or $A^1$ means a group selected from those of a formula (a-1):

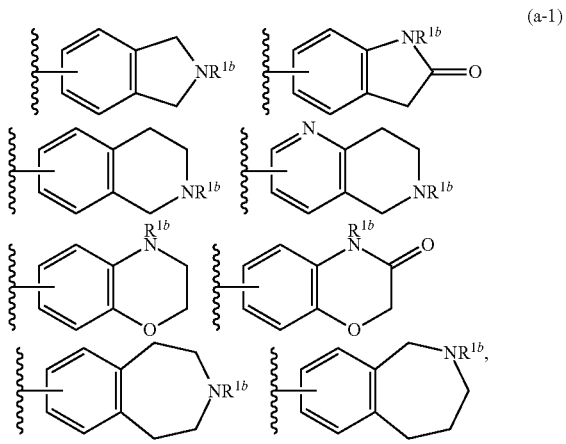

(a-1)

one or two or more methylene groups constituting the aliphatic ring of the group may be each independently substituted with a halogen atom, a hydroxyl group, a $-(C=O)_aO_b$(C1-C6)alkyl group or a group of $-Q^{1b}-N(R^{2b})R^{3b}$, wherein the alkyl group of the substituent may be substituted with a halogen atom or a hydroxyl group.

"A phenyl, pyrazolyl, indolyl or indazolyl group, which may have a substituent selected from the group consisting of a halogen atom, a hydroxyl group, a —$(C=O)_aO_b$(C1-C6) alkyl group and a group of -$Q^{1a}$-$R^{1a}$" means an unsubstituted phenyl, pyrazolyl, indolyl or indazolyl group, or means a phenyl, pyrazolyl, indolyl or indazolyl group having a substituent at the substitutable position thereof; and the substituent may be selected from one or two or more, preferably one or two, the same or different substituents of the group consisting of a halogen atom, a hydroxyl group, a —$(C=O)_aO_b$(C1-C6)alkyl group and a group of -$Q^{1a}$-$R^{1a}$.

The halogen atom, the —$(C=O)_aO_b$(C1-C6)alkyl group and the group of -$Q^{1a}$-$R^{1a}$ as the substituent may have the same meanings as the halogen atom, the —$(C=O)_aO_b$(C1-C6)alkyl group and the group of -$Q^{1a}$-$R^{1a}$ as the substituent for the aryl or heteroaryl group of the above-mentioned A, and their preferred examples are also the same as those of the latter. Preferably, the group has at least one substituent of -$Q^{1a}$-$R^{1a}$.

Specific examples of the above-mentioned "phenyl, pyrazolyl, indolyl or indazolyl group optionally having a substituent" of $A^1$ are the same as those of the optionally-substituted phenyl, pyrazolyl, indolyl or indazolyl group of the above-mentioned "aryl or heteroaryl optionally having a substituent" of A, and their preferred examples are also the same as those of the latter.

In case where $A^1$ is a group of formula (a-1), the meanings of the variables ($R^{1b}$ and others) therein are the same as those of the variables in the group of formula (a-1) indicating the above-mentioned A. Specific examples and preferred examples of $A^1$ are also the same as those of A of formula (a-1).

$R^{10}$ means an aryl or heteroaryl group optionally substituted with $R^{1d}$.

"An aryl or heteroaryl group optionally substituted with $R^{1d}$" means an unsubstituted aryl or heteroaryl group, or means an aryl or heteroaryl group in which any substitutable position is substituted with one or two or more, preferably one or two, the same or different $R^{1d}$'s.

$R^{1d}$ in $R^{10}$ has the same meaning as that of $R^{1d}$ in the above-mentioned $R^1$.

$R^{20}$ and $R^{30}$ each independently mean a hydrogen atom or a hydroxyl group. Their preferred embodiments are that they are both hydrogen atoms, or one of them is a hydroxyl group and the other is a hydrogen atom.

In case where any variables (e.g., a, b, $R^{3a}$, etc.) occurs more than one time in any constituent, its definition on each occurrence is independent at every other occurrence. The combinations of the substituent and the variable are acceptable only when they provide stable compounds. The line from one substituent to the skeletal ring means that the indicated bond is applicable to any substitutable ring-constitutive atom.

The term "substitutable position" as referred to herein is meant to indicate the position of a hydrogen atom substitutable on the carbon, nitrogen, oxygen and/or sulfur atoms of the compound, and the substitution at the hydrogen atom is chemically acceptable and, as a result, the substitution gives a stable compound.

In the compounds of the invention, the replacement of the methylene group constituting the C1-C6 alkylene group, for example, by oxygen, sulfur, sulfonyl, sulfonyl, carbonyl, vinylene, substituted or unsubstituted imine or the like is acceptable only when the replacement is chemically acceptable and as a result, the replacement provides a stable compound.

Depending on the type of the substituent therein and on the salt form thereof, the compound of the invention may include stereoisomers such as optical isomers, diastereomers and geometric isomers, or tautomers; and the compound of the invention encompasses all such stereoisomers, tautomers and their mixtures.

The invention includes various crystals, amorphous substances, salts, hydrates and solvates of the compounds of the invention.

Further, prodrugs of the compounds of the invention are within the scope of the invention. In general, such prodrugs are functional derivatives of the compounds of the invention that can be readily converted into compounds that are needed by living bodies. Accordingly, in the method of treatment of various diseases in the invention, the term "administration" includes not only the administration of a specific compound but also the administration of a compound which, after administered to patients, can be converted into the specific compound in the living bodies. Conventional methods for selection and production of suitable prodrug derivatives are described, for example, in "Design of Prodrugs", ed. H. Bundgaard, Elsevier, 1985, which is entirely incorporated herein by reference. Metabolites of these compounds include active compounds that are produced by putting the compounds of the invention in a biological environment, and are within the scope of the invention.

Examples of the compounds of formula (I) and their salts and N-oxide derivatives are, for example, the compounds described in examples and their salts and N-oxide derivatives. Preferred examples of the compounds are mentioned below.

2-{[3-methyl-4-(4-methylpiperazin-1-yl)phenyl]amino}-7-(pyridin-2-yl)pyrimido[4',5':4,5]pyrimido[1,2-b]indazol-5(7H)-one;

2-{[4-(4-methylpiperazin-1-yl)phenyl]amino}-7-(pyridin-2-yl)pyrimido[4',5':4,5]pyrimido[1,2-b]indazol-5(7H)-one;

2-[(2-methyl-1,2,3,4-tetrahydroisoquinolin-6-yl)amino]-7-(pyridin-2-yl)pyrimido[4',5':4,5]pyrimido[1,2-b]indazol-5(7H)-one;

2-[(2-methyl-1,2,3,4-tetrahydroisoquinolin-7-yl)amino]-7-(pyridin-2-yl)pyrimido[4',5':4,5]pyrimido[1,2-b]indazol-5(7H)-one;

2-{[3-methyl-4-(4-methylpiperazin-1-yl)phenyl]amino}-7-(3-thienyl)pyrimido[4',5':4,5]pyrimido[1,2-b]indazol-5(7H)-one;

2-{[3-methyl-4-(4-methylpiperazin-1-yl)phenyl]amino}-7-(pyrimidin-2-yl)pyrimido[4',5':4,5]pyrimido[1,2-b]indazol-5(7H)-one;

2-{[4-(4-methylpiperazin-1-yl)phenyl]amino}-7-(pyrimidin-2-yl)pyrimido[4',5':4,5]pyrimido[1,2-b]indazol-5(7H)-one;

2-({4-[(3S)-3-(dimethylamino)pyrrolidin-1-yl]phenyl}amino)-7-(pyrimidin-2-yl)pyrimido[4',5':4,5]pyrimido[1,2-b]indazol-5(7H)-one;

2-{[4-(1,4-dimethylpiperidin-4-yl)phenyl]amino}-7-(pyrimidin-2-yl)pyrimido[4',5':4,5]pyrimido[1,2-b]indazol-5(7H)-one;

2-({4-[2-(dimethylamino)ethoxy]-3-methylphenyl}amino)-7-(pyrimidin-2-yl)pyrimido[4',5':4,5]pyrimido[1,2-b]indazol-5(7H)-one;

2-({4-[(dimethylamino)methyl]phenyl}amino)-7-(pyrimidin-2-yl)pyrimido[4',5':4,5]pyrimido[1,2-b]indazol-5(7H)-one;

2-({4-[2-(dimethylamino)ethyl]phenyl}amino)-7-(pyrimidin-2-yl)pyrimido[4',5':4,5]pyrimido[1,2-b]indazol-5(7H)-one;

2-[(2-methyl-1,2,3,4-tetrahydroisoquinolin-6-yl)amino]-7-(pyrimidin-2-yl)pyrimido[4',5':4,5]pyrimido[1,2-b]indazol-5(7H)-one;

2-[(2-methyl-1,2,3,4-tetrahydroisoquinolin-7-yl)-amino]-7-(pyrimidin-2-yl)pyrimido[4',5':4,5]pyrimido[1,2-b]indazol-5(7H)-one;

2-[(2-methyl-2,3-dihydro-1H-isoindol-5-yl)amino]-7-(pyrimidin-2-yl)pyrimido[4',5':4,5]pyrimido[1,2-b]indazol-5(7H)-one;

7-(pyrimidin-2-yl)-2-[(1,1,2-trimethyl-1,2,3,4-tetrahydroisoquinolin-6-yl)amino]pyrimido[4',5':4,5]pyrimido[1,2-b]indazol-5(7H)-one;

2-{[4-(4-methylpiperazin-1-yl)phenyl]amino}-7-(1,3-thiazol-2-yl)pyrimido[4',5':4,5]pyrimido[1,2-b]indazol-5(7H)-one;

2-({4-[3-(dimethylamino)propoxy]phenyl}amino)-7-(1,3-thiazol-2-yl)pyrimido[4',5':4,5]pyrimido[1,2-b]indazol-5(7H)-one;

2-[(2-methyl-1,2,3,4-tetrahydroisoquinolin-6-yl)amino]-7-(1,3-thiazol-2-yl)pyrimido[4',5':4,5]pyrimido[1,2-b]indazol-5(7H)-one;

2-[(2-methyl-1,2,3,4-tetrahydroisoquinolin-7-yl)amino]-7-(1,3-thiazol-2-yl)pyrimido[4',5':4,5]pyrimido[1,2-b]indazol-5(7H)-one;

2-({4-[2-(dimethylamino)ethyl]-3,4-dihydro-2H-1,4-benzoxazin-7-yl}amino)-7-(1,3-thiazol-2-yl)pyrimido[4',5':4,5]pyrimido[1,2-b]indazol-5(7H)-one;

2-({1-[2-(dimethylamino)ethyl]-2,3-dihydro-1H-indol-5-yl}amino)-7-(1,3-thiazol-2-yl)pyrimido[4',5':4,5]pyrimido[1,2-b]indazol-5(7H)-one;

2-{[4-(4-methylpiperazin-1-yl)phenyl]amino}-7-(1,3-thiazol-4-yl)pyrimido[4',5':4,5]pyrimido[1,2-b]indazol-5(7H)-one;

7-(furan-3-yl)-2-{[4-(4-methylpiperazin-1-yl)phenyl]amino}pyrimido[4',5':4,5]pyrimido[1,2-b]indazol-5(7H)-one;

9-hydroxy-2-{[4-(4-methylpiperazin-1-yl)phenyl]amino}-7-(pyridin-2-yl)pyrimido[4',5':4,5]pyrimido[1,2-b]indazol-5(7H)-one; or their pharmaceutically-acceptable salts.

Methods for producing the compounds of the invention are described below.

Compounds (I) of the invention can be produced, for example, according to the production methods mentioned below, or according to the methods shown in Examples and Production Examples given hereinunder. However, the production methods of the compounds (I) of the invention should not be limited to these reaction examples.

Production Method 1

A compound of formula (I) or its N-oxide derivative can be produced by reacting a compound of a general formula (II):

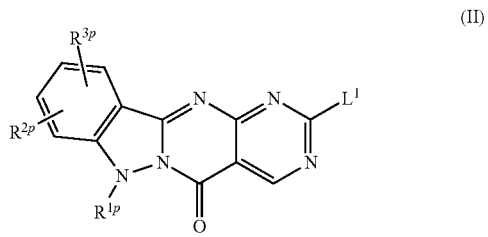

wherein $L^1$ means a leaving group;

$R^{1p}$ means a —(C=O)$_a$O$_b$(C1-C6)alkyl group, a —(C=O)$_a$O$_b$(C2-C6)alkenyl group, a —(C=O)$_a$O$_b$(C3-C6)cycloalkyl group, an aryl group or a heteroaryl group, wherein the alkyl, alkenyl and cycloalkyl group may be each independently substituted with $R^{1cp}$, and the aryl and heteroaryl group may be each independently substituted with $R^{1dp}$;

$R^{1cp}$ means a halogen atom, an optionally-protected hydroxyl group, a cyano group, a —(C=O)$_a$O$_b$(C1-C6)alkyl group, a —(C=O)$_a$O$_b$(C3-C6)cycloalkyl group, an aryl group or a heteroaryl group, wherein the alkyl and cycloalkyl group may be each independently substituted with a halogen atom or an optionally-protected hydroxyl group, the aryl and heteroaryl group may be each independently substituted with a substituent selected from the group consisting of a nitro group, a hydroxyamino group, a —(C=O)$_a$O$_b$(C1-C6)alkyl group and a group of —(C=O)$_a$N(R$^{2cp}$)R$^{3cp}$, and the alkyl group of the substituent may be substituted with a halogen atom or an optionally-protected hydroxyl group;

$R^{1dp}$ means a nitro group, a hydroxyamino group, a —(C=O)$_a$O$_b$(C1-C6)alkyl group or a group of —(C=O)$_a$N(R$^{2dp}$)R$^{3dp}$, wherein the alkyl group may be substituted with a halogen atom or an optionally-protected hydroxyl group;

$R^{1ep}$, $R^{2cp}$, $R^{2dp}$, $R^{2ep}$, $R^{3cp}$, $R^{3dp}$, $R^{3ep}$ and $R^{4ep}$ each independently mean an amino or imino-protective group, a hydrogen atom or —(C=O)$_a$O$_b$(C1-C6)alkyl group, wherein the alkyl group may be substituted with a halogen atom or an optionally-protected hydroxyl group;

$R^{2p}$ and $R^{3p}$ each independently mean a hydrogen atom, a halogen atom, an optionally-protected hydroxyl group, an optionally-protected carboxyl group, a —(C=O)$_a$O$_b$(C1-C6)alkyl group or a group of —(C=O)$_a$N(R$^{1ep}$)R$^{2ep}$, wherein the alkyl group may be substituted with a substituent selected from the group consisting of a halogen atom, an optionally-protected hydroxyl group, an optionally-protected carboxyl group, a —(C=O)$_a$O$_b$(C1-C6)alkyl group and a group of —(C=O)$_a$N(R$^{3ep}$)R$^{4ep}$; and a and b have the same meanings as above, and a compound of a general formula (III):

wherein

AP means an aryl or heteroaryl group, which may have a substituent selected from the group consisting of a halogen atom, an optionally-protected hydroxyl group, —(C=O)$_a$O$_b$(C1-C6)alkyl group and a group of -Q$^{1ap}$-R$^{1ap}$, wherein the alkyl group of the substituent may be substituted with a halogen atom or an optionally-protected hydroxyl group, or AP means a group of a formula (ap):

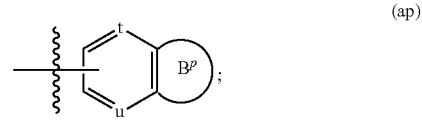

the ring BP means a 5-membered to 7-membered aliphatic ring condensed with the ring of a formula (bp):

wherein one or two or more methylene groups constituting the ring BP may be each independently replaced by an oxygen atom, a sulfur atom, a sulfinyl group, a sulfonyl group, an optionally-protected carbonyl group or a group of —N($R^{1bp}$)—, and one or more methylene groups constituting the ring BP may be each independently substituted with a halogen atom, an optionally-protected hydroxyl group, a —(C=O)$_a$O$_b$(C1-C6)alkyl group or a group of -Q$^{1bp}$-N($R^{2bp}$)$R^{3bp}$, wherein the alkyl group of the substituent may be substituted with a halogen atom or an optionally-protected hydroxyl group;

$Q^{1ap}$, $Q^{1bp}$, $Q^{2ap}$ and $Q^{3ap}$ each independently mean a single bond or a (C1-C6)alkylene group, wherein one or two or more methylene groups constituting the (C1-C6)alkylene group may be each independently replaced by an oxygen atom, a sulfur atom, a sulfinyl group, a sulfonyl group, an optionally-protected carbonyl group or a group of —N($R^{2ap}$)—, and may be each independently substituted with a halogen atom, an optionally-protected hydroxyl group, a cyano group or a —(C=O)$_a$O$_b$(C1-C6)alkyl group;

$R^{1ap}$ means a hydrogen atom, an optionally-protected hydroxyl group, a formyl group, a —(C=O)$_a$O$_b$(C1-C6)alkyl group or a group of —(C=O)$_a$N($R^{3ap}$)$R^{4ap}$, wherein the alkyl group may be substituted with a halogen atom or an optionally-protected hydroxyl group, or $R^{1ap}$ means a heterocyclic group optionally having a substituent selected from the group consisting of a halogen atom, an optionally-protected hydroxyl group, an optionally-protected oxo group, a —(C=O)$_a$O$_b$(C1-C6)alkyl group, a —(C=O)$_a$O$_b$(C3-C6)cycloalkyl group and a group of -Q$^{2ap}$-$R^{5ap}$, wherein the alkyl and cycloalkyl group of the substituent may be each independently substituted with a halogen atom, an optionally-protected hydroxyl group, a —(C=O)$_a$O$_b$(C1-C6)alkyl group or a group of —(C=O)$_a$N($R^{3ap}$)$R^{4ap}$;

$R^{1bp}$ means an imino-protective group, a hydrogen atom or a —(C=O)$_a$O$_b$(C1-C6)alkyl group, wherein the alkyl group may be substituted with a halogen atom, an optionally-protected hydroxyl group or a group of —(C=O)$_a$N($R^{4bp}$)$R^{5bp}$;

$R^{2ap}$, $R^{2bp}$, $R^{3ap}$, $R^{3bp}$, $R^{4ap}$, $R^{4bp}$ and $R^{5bp}$ each independently mean an amino or imino-protective group, a hydrogen atom or —(C=O)$_a$O$_b$(C1-C6)alkyl group, wherein the alkyl group may be substituted with a halogen atom or an optionally-protected hydroxyl group;

$R^4$ means a hydrogen atom or a (C1-C6)alkyl group;

$R^{5ap}$ means a hydrogen atom, an optionally-protected hydroxyl group, a formyl group, a —(C=O)$_a$O$_b$(C1-C6)alkyl group or a group of —(C=O)$_a$N($R^{3ap}$)$R^{4ap}$, wherein the alkyl group may be substituted with a halogen atom or an optionally-protected hydroxyl group, or $R^{5ap}$ means a heterocyclic group optionally having a substituent selected from the group consisting of a halogen atom, an optionally-protected hydroxyl group, an optionally-protected oxo group, a —(C=O)$_a$O$_b$(C1-C6)alkyl group and a group of -Q$^{3ap}$-$R^{6ap}$, wherein the alkyl group of the substituent may be substituted with a halogen atom, an optionally-protected hydroxyl group or a —(C=O)$_a$O$_b$(C1-C6)alkyl group;

$R^{6ap}$ means a hydrogen atom, a halogen atom, an optionally-protected hydroxyl group or a —(C=O)$_a$O$_b$(C1-C6)alkyl group, wherein the alkyl group may be substituted with a halogen atom or an optionally-protected hydroxyl group; and t and u each independently mean a nitrogen atom, or mean a methine group optionally substituted with a halogen atom, an optionally-protected hydroxyl group, a cyano group or —(C=O)$_a$O$_b$(C1-C6)alkyl group, wherein the alkyl group of the substituent may be substituted with a halogen atom or an optionally-protected hydroxyl group; and a and b have the same meanings as above, or its salt to thereby give a compound of a general formula (IV):

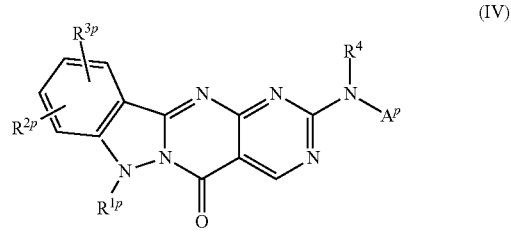

(IV)

wherein

AP, $R^{1p}$, $R^{2p}$, $R^{3p}$ and $R^4$ have the same meanings as above, followed by any of the following:

(1) when the compound (IV) has a protective group of the amino, imino, hydroxyl, carboxyl or carbonyl group, a step of removing the protective group;

(2) when the intended product is an N-oxide derivative, a step of oxidizing the nitrogen atom in the compound; and/or (3) when the compound (IV) has a functional group, a step of converting the functional group into any other functional group;

thereby producing a compound of formula (I) or its N-oxide derivative.

In case where the compound of formula (IV) does not have a protective group of the amino, imino, hydroxyl, carboxyl or carbonyl group, the compound (IV) is a compound of formula (I).

The leaving group of $L^1$ includes, for example, a halogen atom such as a chlorine atom, a bromine atom or an iodine atom; an organic sulfonyl group such as a methylsulfinyl group, a methylsulfonyl group, an ethylsulfonyl group, a phenylsulfonyl group; and an organic sulfonyloxy group such as a methylsulfonyloxy group, a trifluoromethylsulfonyloxy group, a p-tolylsulfonyloxy group; and of those, preferred are a chlorine atom, a methylsulfinyl group, a methylsulfonyl group.

The above production method is a general production method for the compounds of formula (I).

In the above reaction, when the reactants have an amino group, an imino group, a hydroxyl group, a carboxyl group, a carbonyl group or the like not participating in the reaction, then the amino group, the imino group, the hydroxyl group, the carboxyl group and the carbonyl group may be suitably protected with a protective group for the amino or imino group, a protective group for the hydroxyl group, a protective group for the carboxyl group, or a protective group for the carbonyl group prior to the reaction, and the protective group may be removed after the reaction.

Not specifically defined, "amino or imino-protective group" may be any one having its function. For example, it includes an aralkyl group such as a benzyl group, a p-methoxybenzyl group, a 3,4-dimethoxybenzyl group, an o-nitrobenzyl group, a p-nitrobenzyl group, a benzhydryl group, a trityl group; a lower alkanoyl group such as a formyl group, an acetyl group, a propionyl group, a butyryl group, a pivaloyl group; a benzoyl group; an arylalkanoyl group such as a phenylacetyl group, a phenoxyacetyl group; a lower alkoxycarbonyl group such as a methoxycarbonyl group, an ethoxycarbonyl group, a propyloxycarbonyl group, a tert-butoxycarbonyl group; an aralkyloxycarbonyl group such as a benzyloxycarbonyl group, a p-nitrobenzyloxycarbonyl group, a phenethyloxycarbonyl group; a lower alkylsilyl group such as a trimethylsilyl group, a tert-butyldimethylsilyl group; a tetrahydropyranyl group; a trimethylsilylethoxymethyl group; a lower alkylsulfonyl group such as a methylsulfonyl group, an ethylsulfonyl group; an arylsulfonyl group such as benzenesulfonyl group, a toluenesulfonyl group; a phthalimidoyl group; and is especially preferably an acetyl group, a benzoyl group, a tert-butoxycarbonyl group, a trimethylsilylethoxymethyl group, a methylsulfonyl group, a phthalimidoyl group.

Not specifically defined, "hydroxyl-protective group" may be any one having its function. For example, it includes a lower alkyl group such as a methyl group, an ethyl group, a propyl group, an isopropyl group, a tert-butyl group; a lower alkylsilyl group such as a trimethylsilyl group, a tert-butyldimethylsilyl group; a lower alkoxymethyl group such as a methoxymethyl group, a 2-methoxyethoxymethyl group; a tetrahydropyranyl group; a trimethylsilylethoxymethyl group; an aralkyl group such as a benzyl group, a p-methoxybenzyl group, a 2,3-dimethoxybenzyl group, an o-nitrobenzyl group, a p-nitrobenzyl group, a trityl group; an acyl group such as a formyl group, an acetyl group; and is especially preferably a methyl group, a methoxymethyl group, a tetrahydropyranyl group, a trityl group, a trimethylsilylethoxymethyl group, a tert-butyldimethylsilyl group, an acetyl group.

Not specifically defined, "carboxyl-protective group" may be any one having its function. For example, it includes a lower alkyl group such as a methyl group, an ethyl group, a propyl group, an isopropyl group, a tert-butyl group; a halo-lower alkyl group such as a 2,2,2-trichloroethyl group; a lower alkenyl group such as an alkyl group; an aralkyl group such as a benzyl group, a p-methoxybenzyl group, a p-nitrobenzyl group, a benzhydryl group, a trityl group; and is especially preferably a methyl group, an ethyl group, a tert-butyl group, an alkyl group, a benzyl group, a p-methoxybenzyl group, a benzhydryl group.

Not specifically defined, "carbonyl-protective group" may be any one having its function. For example, it includes acetals and ketals such as ethylene ketal, trimethylene ketal, dimethyl ketal.

For the reaction of the compound of formula (II) and the compound of formula (III), in general, an equimolar or excessive molar amount, preferably from an equimolar amount to 1.5 mols of the compound (III) is used relative to one mol of the compound (II).

The reaction is attained generally in an inert solvent. The inert solvent is, for example, preferably toluene, benzene, methylene chloride, chloroform, tetrahydrofuran, dioxane, dimethylformamide, N-methylpyrrolidone, dimethyl sulfoxide, or their mixed solvent.

Preferably, the reaction is attained in the presence of a base. The base includes, for example, organic bases such as triethylamine, diisopropylethylamine, pyridine, 4-dimethylaminopyridine; and inorganic bases such as sodium hydrogencarbonate, sodium carbonate, potassium carbonate, cesium carbonate, sodium hydroxide, potassium hydroxide.

The amount of the base to be used may be generally from an equimolar amount to an excessive molar amount, preferably from 1 to 3 mols relative to one mol of the compound of formula (II).

The reaction temperature may be generally from 0° C. to 200° C., preferably from 20° C. to 150° C.

The reaction time may be generally from 5 minutes to 7 days, preferably from 30 minutes to 24 hours.

After the reaction, the system may be processed in an ordinary manner to obtain a crude product of the compound of formula (IV). Thus obtained, the compound of formula (IV) is purified in an ordinary manner, or not purified, it may be processed according to any of the following:

(1) when the compound (IV) has an amino, imino, hydroxyl, carboxyl or carbonyl-protective group, a step of removing the protective group;

(2) when the intended product is an N-oxide derivative, a step of oxidizing the nitrogen atom in the compound; and/or (3) when the compound (IV) has a functional group, optionally a step of converting the functional group into any other functional group;

thereby producing a compound of formula (I) or its N-oxide derivative.

The method of removing the protective group varies, depending on the type of the protective group and on the stability of the intended compound (I), and may be attained according to methods described in references [see Protective Groups in Organic Synthesis, 3rd. Ed., by T. W. Greene, John Wiley & Sons (1999)] or according to methods similar thereto. For example, herein employable are a method of solvolysis with an acid or a base, which comprises processing the protected compound with from 0.01 mols to a large excessive amount of an acid, preferably trifluoroacetic acid, formic acid or hydrochloric acid, or with from an equimolar amount to a large excessive amount of a base, preferably potassium hydroxide or calcium hydroxide; and a method of chemical reduction with a metal hydride complex, or catalytic reduction with a palladium-carbon catalyst or a Raney nickel catalyst.

In the step of oxidizing the nitrogen atom to produce an N-oxide derivative, for example, used is an oxidizing agent such as m-chloroperbenzoic acid, dioxirane, sodium periodate, hydrogen peroxide.

The amount of the oxidizing agent to be used may be generally from 0.5 mols to an excessive molar amount, preferably from 1 to 5 mols relative to 1 mol of the compound of formula (IV).

The reaction may be carried out generally in a solvent suitably selected in accordance with the oxidizing agent used for the reaction. For example, when m-chloroperbenzoic acid is used as the oxidizing agent, then a solvent such as methylene chloride or chloroform is preferred; and when dioxirane is used as the oxidizing agent, then a solvent such as acetone or water is preferred.

The reaction temperature may be generally from −50° C. to 100° C., preferably from −20° C. to 50° C.

The reaction time may be generally from 15 minutes to 7 days, preferably from 30 minutes to 24 hours.

The step of optionally converting the functional group in the compound of formula (IV) into any other functional group may be attained in a per-se ordinary manner generally employed in the field of organic chemistry. The functional group as referred to herein has an ordinary meaning in the field of organic chemistry. In the invention, it includes a hydroxyl group, a carbonyl group, a nitro group, a carboxyl group, an alkoxycarbonyl group, a carbamoyl group and the like in AP, $R^{1p}$, $R^{2p}$, $R^{3p}$, etc. In case where the intended product is a compound having any other functional group, then the functional group may be converted to the other functional group. For example, when the compound has a hydroxyl group, then the hydroxyl group may be converted into an alkoxy group, a hydroxyalkoxy group or an alkoxyalkoxy group; when the compound has a carboxyl group, then the carboxyl group may be converted into a substituted or unsubstituted carbamoyl group; when the compound has an alkoxycarbonyl group, then the alkoxycarbonyl group may be converted into a carboxyl group; when the compound has a nitro group, then the nitro group may be converted into a hydroxyamino group.

The compound of formula (I) or its N-oxide derivative may be readily isolated and purified in any ordinary separation method. Examples of the method are, for example, solvent extraction, recrystallization, column chromatography, preparative thin-layer chromatography.

The compounds may be converted into their pharmaceutically-acceptable salts or esters in an ordinary manner; and on the contrary, their salts or esters may also be converted into free compounds in an ordinary manner.

"Salts" of the compound of formula (III) mean ordinary salts used in the field of organic chemistry. For example, when the compound has an amino group or a basic heterocyclic group, then its salts are acid-addition salts at the amino group or the basic heterocyclic group.

The acid-addition salts include, for example, inorganic acid salts such as hydrochlorides, sulfates, nitrates, phosphates, perchlorates; organic acid salts such as maleates, fumarates, tartrates, citrates, ascorbates, trifluoroacetates; sulfonates such as methanesulfonates, isethionates, benzenesulfonates, p-toluenesulfonates.

The compounds of the general formulae (II) and (III) may be commercially available, or may be produced according to known methods or according to methods similar to them, or according to the methods described below, or according to the methods described in Examples and Production Examples, optionally as suitably combined.

Production Method A

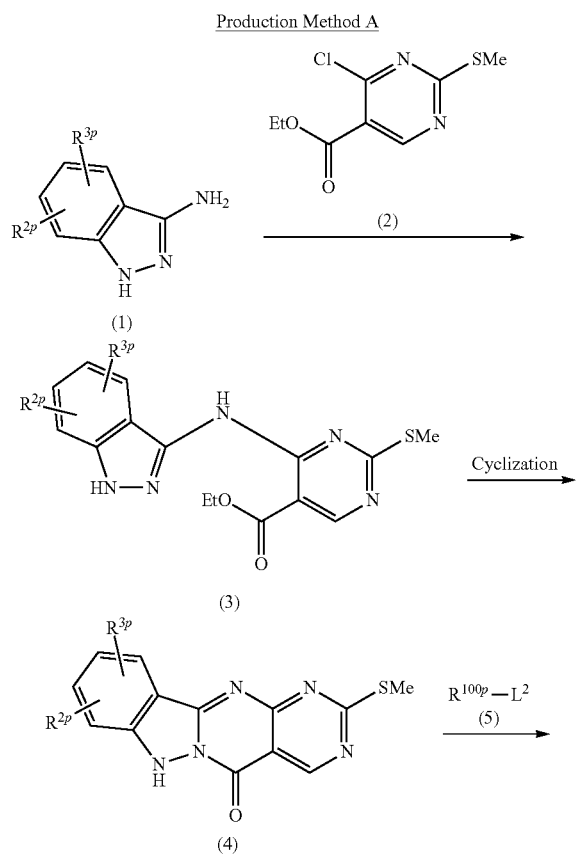

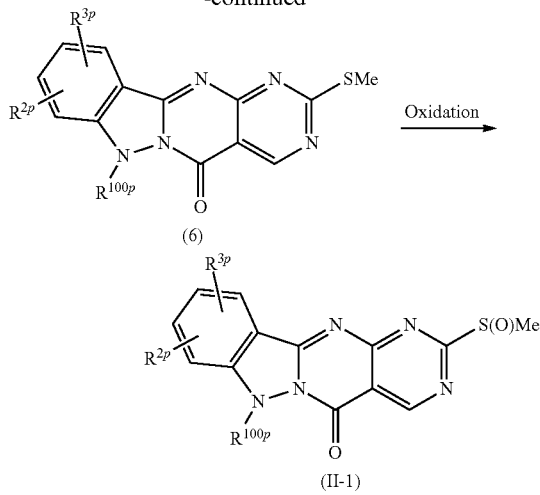

wherein Et means an ethyl group; $L^2$ means a leaving group; Me means a methyl group; $R^{100p}$ means a —(C=O)$_a$O$_b$(C1-C6)alkyl group, a —(C=O)$_a$O$_b$(C2-C6)alkenyl group or a —(C=O)$_a$O$_b$(C3-C6)cycloalkyl group, wherein the alkyl, alkenyl or cycloalkyl group may be each independently substituted with $R^{1cp}$; and a, b, $R^{1cp}$, $R^{2p}$ and $R^{3p}$ have the same meanings as above.

The production method A is a production method for compounds of formula (II) where the leaving group of $L^1$ is a methylsulfinyl group, and $R^{1p}$ is a —(C=O)$_a$O$_b$(C1-C6) alkyl group, a —(C=O)$_a$O$_b$(C2-C6)alkenyl group or a —(C=O)$_a$O$_b$(C3-C6)cycloalkyl group optionally substituted with a predetermined group, or that is, the production method for compounds of formula (II-1).

According to the production method, the compound of formula (II-1) can be produced by reacting a compound of formula (1) and a compound of formula (2) in the presence of a base to give a compound of formula (3), then hydrolyzing and cyclizing the resulting compound (3) to give a compound (4), introducing $R^{100p}$ into the 7-position imino group in the compound (4) to give a compound (6), and finally oxidizing the compound (6) to thereby convert the methylthio group therein into a methylsulfinyl group.

In the step of reacting the compound of formula (1) with a compound of formula (2) in the presence of a base to produce a compound of formula (3), in general, from 0.5 mols to an excessive molar amount, preferably from an equimolar amount to 3.0 mols of the compound (1) is reacted with one mol of the compound (2).

The reaction is generally attained in an inert solvent, and the inert solvent is, for example, preferably methylene chloride, chloroform, tetrahydrofuran, ethyl ether, benzene, toluene, dimethylformamide, or their mixed solvent.

Preferably, the reaction is attained in the presence of a base. As the base, usable is an organic base such as triethylamine, diisopropylethylamine, pyridine, 4-dimethylaminopyridine, or an inorganic base such as sodium hydroxide, potassium hydroxide, sodium carbonate, potassium carbonate, sodium hydrogencarbonate.

Preferably, the base is used generally in an amount of from an equimolar amount to an excessive molar amount relative to 1 mol of the compound (2). In case where the base is a liquid, the base may serve also as a solvent.

The reaction temperature may be generally from −78° C. to 100° C., preferably from 20° C. to 80° C.

The reaction time may be generally from 5 minutes to 7 days, preferably from 30 minutes to 24 hours.

To the step of hydrolyzing the compound (3), applicable is carboxylate hydrolysis per-se well known in the field of organic chemistry. In general, the hydrolysis may be attained in a solvent such as methanol, ethanol, tetrahydrofuran, dioxane, water or their mixed solvent, for example, using an acid such as hydrochloric acid or sulfuric acid, or a base such as sodium hydroxide, potassium hydroxide or calcium hydroxide.

The reaction temperature is, in general, preferably from 50° C. to the boiling point of the solvent used in the reaction, and the reaction time is, in general, preferably from 1 hour to 48 hours.

After the hydrolysis, the step of producing the compound (4) through cyclization of the resulting compound may be attained as follows: After the hydrolysis, the reaction liquid is acidified with hydrochloric acid or the like and then directly subjected to cyclization as it is, or when the cyclization could not go on, the hydrolyzed compound is reacted with acetic anhydride, thionyl chloride, 1-hydroxybenzotriazole or the like to thereby activate the carboxyl group prior to the cyclization.

The cyclization with acetic anhydride may be attained generally under reflux by heating, and the amount of acetic anhydride to be sued is preferably an excessive molar amount, and the reaction time may be generally from 1 hour to 48 hours.

In case of reaction with thionyl chloride, the amount of thionyl chloride to be used is preferably an excessive molar amount, and the reaction time is, in general, preferably from 1 hour to 48 hours.

The reaction with 1-hydroxybenzotriazole may be attained generally in the presence of a condensing agent, for example, N,N'-dicyclohexylcarbodiimide, 1-(3-dimethylaminopropyl)-3-ethylcarbodiimide.

The cyclization with carboxyl activation may be attained generally in an inert solvent. The inert solvent is, for example, preferably methylene chloride, chloroform, tetrahydrofuran, dimethylformamide, pyridine, or their mixed solvent.

The reaction may go on in the absence of a base, but is preferably in the presence of a base for more smoothly attaining the reaction.

As the base, usable is an organic base such as triethylamine, diisopropylethylamine, pyridine, 4-dimethylaminopyridine, or an inorganic base such as sodium hydroxide, potassium hydroxide, sodium carbonate, potassium carbonate, sodium hydrogencarbonate.

Preferably, in general, the base is used in an amount of from 1 mol to an excessive molar amount relative to 1 mol of the hydrolyzed compound of the compound (3). In case where the base is a liquid, the base may serve also as a solvent.

The reaction temperature may be generally from −50° C. to 100° C., preferably from −20° C. to 50° C.

The reaction time may be generally from 5 minutes to 7 days, preferably from 30 minutes to 24 hours.

In the step of reacting the compound (4) with a compound (5) to produce a compound (6), in general, the compound (5) is used in an amount of from 0.5 mols to an excessive molar amount, preferably from 2.0 mols to 5.0 mols relative to 1 mol of the compound (4).

The leaving group of $L^2$ is preferably a halogen atom such as a chlorine atom, a bromine atom, an iodine atom.

The reaction may be attained generally, for example, in an inert solvent such as tetrahydrofuran, benzene, toluene, acetonitrile, dimethylformamide and in the presence of a base such as sodium hydride, sodium amide, sodium alkoxide, or in a solvent such as methanol, ethanol, acetonitrile and in the presence of a base such as sodium hydroxide, potassium hydroxide, potassium carbonate.

The reaction temperature is, in general, preferably from 0° C. to the boiling point of the solvent used in the reaction, and the reaction time is, in general, preferably from 1 hour to 48 hours.

To the step of oxidizing the methylthio group of the compound (6) to produce a compound (II-1), applicable is a method of oxidizing a methylthio group into a methylsulfinyl group or a methylsulfonyl group well known in the field of organic chemistry. In general, in an inert solvent such as benzene, toluene, methylene chloride, chloroform, tetrahydrofuran, acetonitrile or dimethylformamide, an oxidizing agent such as metachloroperbenzoic acid or ozone is used in an amount of from 0.5 mols to an excessive molar amount, preferably from an equimolar amount to 1.5 mols relative to 1 mol of the compound (6).

The reaction temperature is, in general, preferably from 0° C. to the boiling point of the solvent used in the reaction, and the reaction time is, in general, preferably from 30 minutes to 8 hours.

The compounds of formulae (1), (2) and (5) may be commercial products, or may be produced according to known methods, or according to the methods described in Production Examples and Examples, or according to methods similar to them, optionally as combined in any desired manner.

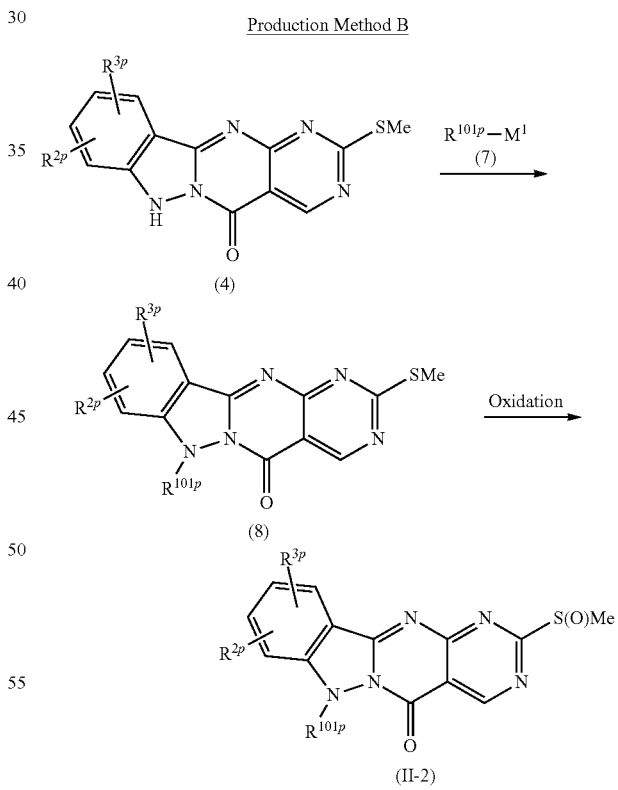

Production Method B wherein $M^1$ means an ordinary organic metal atom; $R^{101p}$ means an aryl group or a heteroaryl group, wherein the aryl and heteroaryl group may be each independently substituted with $R^{1dp}$; and Me, $R^{1dp}$, $R^{2p}$ and $R^{3p}$ have the same meanings as above.

The production method B is a production method for compounds of formula (II) where the leaving group of $L^1$ is a methylsulfinyl group, and $R^{1p}$ is an aryl or heteroaryl group optionally substituted with a predetermined group, or that is, the production method for compounds of formula (II-2).

According to the production method, the compound of formula (II-2) can be produced by reacting the compound of formula (4) produced in the above-mentioned production method A, with an organic metal compound of formula (7) in the presence of a metal salt catalyst or a metal salt reagent to thereby produce a compound of formula (8), followed by oxidizing the compound (8) at the methylthio group therein into a methylsulfinyl group.

In the step of reacting the compound (4) and the compound (7) to give the compound (8), in general, the compound (7) is used in an amount of from 0.5 mols to 5 mols, preferably from 0.7 mols to 3 mols relative to 1 mol of the compound (4) in the presence of a metal salt catalyst or a metal salt reagent.

For the metal salt catalyst or the metal salt reagent to be used in the reaction, for example, there may be mentioned transition metals generally used in cross-coupling reaction, such as copper, nickel, palladium. For example, preferred are copper(II) acetate, copper trifluoromethanesulfonate, copper iodide.

$M^1$ may be an ordinary organic metal atom generally used in cross-coupling reaction, including, for example, lithium, boron, silicon, magnesium, aluminium, zinc, tin, preferably boron, zinc, tin. Regarding the compound in practical use, concretely, boron may be in the form of boric acid or borate; zinc may be in the form of zinc chloride, zinc bromide or zinc iodide; and tin may be in the form of tri-lower alkyl-tin.

The reaction may be attained generally in an inert solvent. The inert solvent is, for example, preferably water, benzene, toluene, xylene, methylene chloride, chloroform, dimethoxyethane, tetrahydrofuran, dioxane, dimethylformamide, or their mixed solvent.

The reaction temperature may be generally from room temperature to the boiling point of the solvent used in the reaction, preferably from 20° C. to 200° C.

The reaction time may be generally from 30 minutes to 7 days, preferably from 24 hours to 3 days.

The reaction is preferably in the presence of a base. The base includes, for example, an inorganic base such as potassium phosphate, sodium hydrogencarbonate, sodium carbonate, potassium carbonate, cesium carbonate; an organic base such as triethylamine, diisopropylamine.

The amount of the base to be used may be generally from 0.5 mols to 5 mols, preferably from an equimolar amount to 3 mols relative to 1 mol of the compound (4).

In the above-mentioned step, a halide compound having a group of $R^{101p}$ may be used in place of the organic metal compound of formula (7). In case where the halide compound is used, the catalyst is preferably copper(I) iodide/diamine complex.

The step of oxidizing the methylthio group of the compound (8) to produce the compound (II-2) may be attained in the same manner as that for the step of oxidizing the methylthio group of the compound (6) to produce the compound (II-1) in the above-mentioned production method A.

The compounds of formula (7) may be commercial products, or may be produced according to known methods, or according to the methods described in Production Examples and Examples, or according to methods similar to them, optionally as combined in any desired manner.

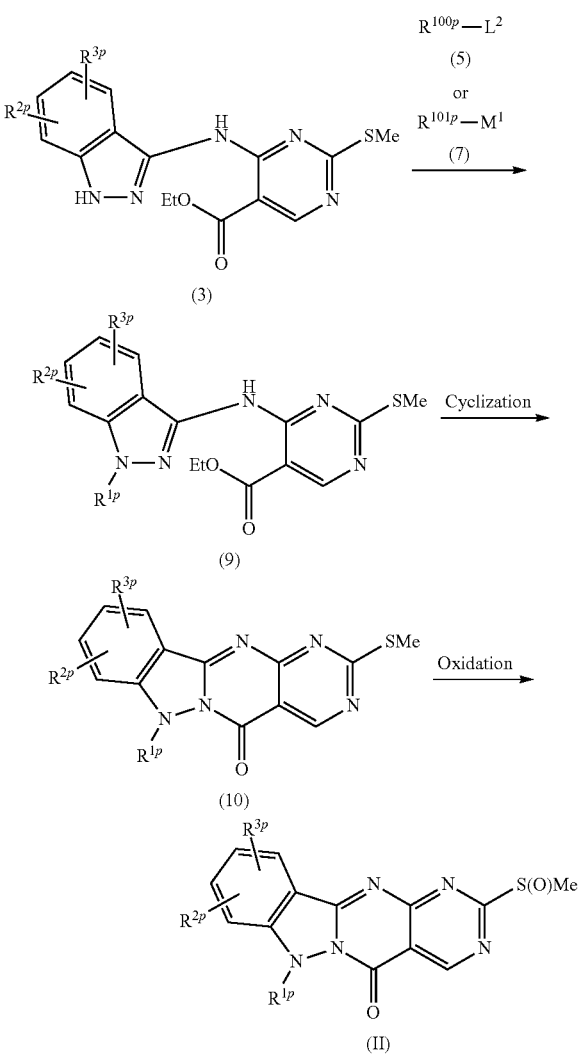

wherein Et, $L^2$, $M^1$, Me, $R^{1p}$, $R^{2p}$, $R^{3p}$, $R^{100p}$ and $R^{101p}$ have the same meanings as above.

The production method C is a production method for compounds of formula (II).

According to the production method, the compound of formula (II) can be produced by reacting the compound of formula (3) produced in the above-mentioned production method A, with a compound (5) or a compound (7) thereby giving a compound (9) through introduction of $R^{100p}$ or $R^{101p}$ to the corresponding $R^{1p}$ in the compound (9), and thereafter hydrolyzing and cyclizing the compound (9) to give a compound (10), and finally oxidizing the methylthio group of the compound (10) into a methylsulfinyl group.

The step of reacting the compound (3) with the compound (5) or the compound (7) may be attained in the same manner as in the step of reacting the compound (4) with the compound (5) in the production method A, or in the step of reacting the compound (4) with the compound (7) in the production method B.

The step of hydrolyzing and cyclizing the compound (9) to give the compound (10) may be attained in the same manner as in the step of hydrolyzing and cyclizing the compound (3) to give the compound (4) in the production method A.

The step of oxidizing the methylthio group of the compound (10) to give the compound (II) may be attained in the same manner as in the step of oxidizing the methylthio group of the compound (6) to give the compound (II-1) in the production method A.

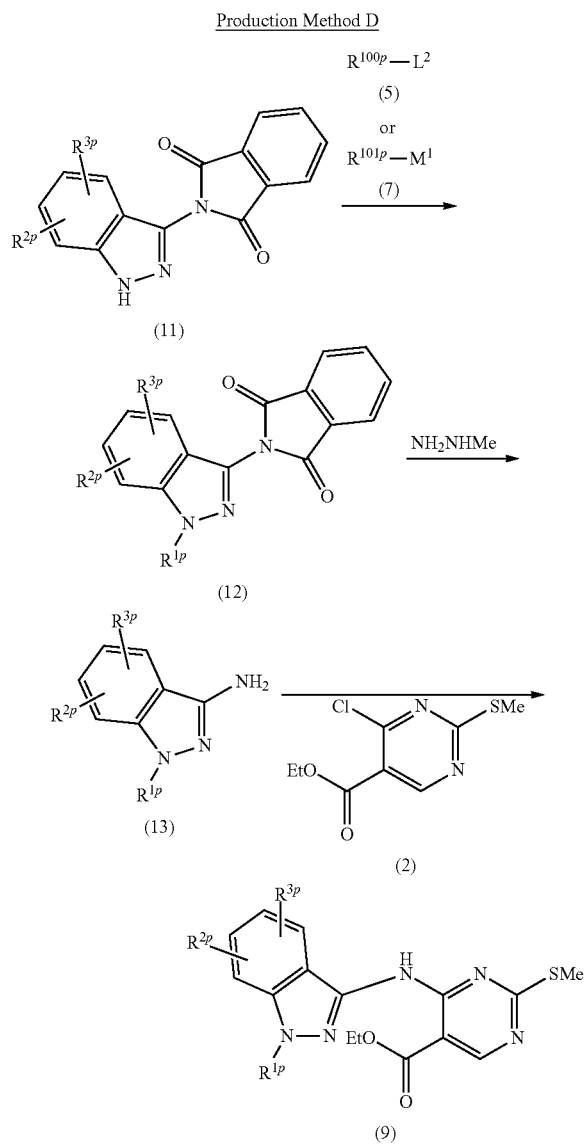

wherein Et, $L^2$, $M^1$, Me, $R^{1p}$, $R^{2p}$, $R^{3p}$, $R^{100p}$ and $R^{101p}$ have the same meanings as above.

The production method D is an alternative production method for producing the compound (9).

According to this production method, the compound (9) is produced by reacting a compound of formula (11) with a compound (5) or a compound (7) to give a compound (12) through introduction of $R^{100p}$ or $R^{101p}$ to the corresponding $R^{1p}$ in the compound (12), and thereafter reacting the compound (12) with methylhydrazine to thereby a compound (13) through conversion of the phthalimidoyl group in the compound (12) into an amino group, and then further reacting the compound (13) with a compound (2).

The step of reacting the compound (11) with the compound (5) or the compound (7) may be attained in the same manner as in the step of reacting the compound (4) with the compound (5) in the production method A, or in the step of reacting the compound (4) with the compound (7) in the production method B.

The step of reacting the compound (12) with methylhydrazine to give the compound (13) is deprotection of phthalimide with methylhydrazine per-se generally employed in the filed of organic chemistry.

In general, the reaction is attained, for example, in an inert solvent such as tetrahydrofuran, benzene, toluene, acetonitrile or dimethylformamide, using methylhydrazine in an amount of from 0.5 mols to an excessive molar amount, preferably from 1 mol to 5 mols relative to 1 mol of the compound (12), at a reaction temperature of from 0° C. to the boiling point of the solvent used in the reaction, preferably for 1 hour to 48 hours.

The step of reacting the compound (13) with the compound (2) to give the compound (9) may be attained in the same manner as in the step of reacting the compound (1) with the compound (2) to give the compound (3) in the production method A.

The compounds of formula (11) may be commercial products, or may be produced according to known methods, or according to the methods described in Production Examples and Examples, or according to methods similar to them, optionally as combined in any desired manner.

In the production methods A to D where the compounds have a functional group not participating in the reaction steps, the functional group may be converted into any other desired functional group according to methods per se known and generally employed in the field of organic chemistry. For example, the conversion includes a reductive conversion from an alkenyl group into an alkyl group; a conversion from a hydroxyl group into an alkoxy group, a hydroxyalkoxy group or an alkoxyalkoxy group; a conversion from a carboxyl group into a substituted or unsubstituted carbamoyl group; a conversion from an alkoxycarbonyl group into a carboxyl group; a conversion from a nitro group into a hydroxyamino group. The converted functional group may be optionally protected with a suitable protective group. Not having any negative influence on the production of the intended products in the production methods A to D, the conversion step may be inserted in any step of the production methods A to D.

Pharmacological Test Examples of the compounds of the invention are shown below.

Pharmacological Test 1 (Wee1 Kinase Inhibitory Effect)

(1) Purification of Wee1 Kinase

A cDNA of Wee1 kinase with glutathione-5-transferase (GST) fused at the amino terminal thereof was inserted into a baculovirus expression vector to construct a recombinant baculovirus, with which cells of an insect cell line Sf9 were infected to overexpress the target protein. The infected cells were collected and lysed, and then the GST-tagged Wee1 kinase protein was adsorbed to a glutathione column and eluted from the column with glutathione, and the active fraction was desalted in a desalting column to give a purified enzyme.

(2) Measurement of Wee1 Kinase Activity

In measurement of the Wee1 kinase activity, a synthetic peptide, Poly(Lys, Tyr) hydrobromide (Lys:Tyr (4:1)) purchased from Sigma was used as the substrate.

The amount of the reaction mixture was 21.1 μL; and the composition of the reaction buffer was 50 mM Tris-HCl buffer (pH 7.4)/10 mM magnesium chloride/1 mM dithiothreitol. The purified Wee1 kinase, 2.5 μg of the substrate peptide, 10 μM of non-labeled adenosine triphosphate (ATP) and 1 μCi of [γ-$^{33}$P]-labeled ATP (2500 Ci/mmol or more)

were added to the reaction buffer, and the resulting mixture was incubated at 30° C. for 30 minutes. Thereafter, 10 µL of 350 mM phosphate buffer was added to the reaction system to stop the reaction. The substrate peptide was adsorbed on a P81 paper filter 96-well plate and the plate was washed several times with 130 mM phosphate buffer, and the radioactivity thereof was counted using a liquid scintillation counter. The [γ-$^{33}$P]-labeled ATP was purchased from Amersham Bioscience, Ltd.

The addition of a test compound to the reaction system was carried out by preparing a series of dilutions of the compound with dimethyl sulfoxide (DMSO) and adding 1.1 µL of each dilution to the reaction system. As a control, 1.1 µL of DMSO was added to the reaction system.

As shown in Table 1, the compounds according to the invention exhibit an excellent Wee1 inhibitory effect.

TABLE 1

|  | Wee1-Inhibitory Effect (IC50, nM) |
| --- | --- |
| Example 21 | 32 |
| Example 23 | 30 |
| Example 43 | 4.9 |
| Example 44 | 3.9 |
| Example 55 | 13 |
| Example 61 | 12 |
| Example 62 | 38 |
| Example 79 | 24 |
| Example 88 | 26 |
| Example 90 | 30 |
| Example 91 | 34 |
| Example 92 | 46 |
| Example 100 | 5.1 |
| Example 101 | 3.8 |
| Example 102 | 19 |
| Example 103 | 6.8 |
| Example 105 | 9.1 |
| Example 121 | 23 |
| Example 136 | 5.3 |
| Example 137 | 6.1 |
| Example 143 | 15 |
| Example 144 | 15 |
| Example 146 | 13 |
| Example 147 | 5.8 |
| Example 150 | 8.6 |

Subsequently, an inhibitory effect of the compound of the general formula (I) according to the invention on Cdc2 tyrosine-15 phosphorylation in cells will be described below.
Pharmacological Test 2 (Method for Determining Drug Effect Using Cells (Inhibitory Effect on Cdc2 (Cdk1) Tyrosine-15 Phosphorylation))
a) Reagents Fetal bovine serum (FBS) was purchased from Morgate, Inc.; an RPMI-1640 medium and a DMEM medium were purchased from Invitrogen, Inc.; camptothecin was purchased from Sigma Co.; gemcitabine was purchased from Eli Lilly Japan K.K.; nocodazole and protease inhibitor cocktail were purchased from Sigma Co.; a rabbit anti-Cdc2 antibody and a mouse anti-Cdc2 antibody were purchased from Santa Cruz Biotechnology, Inc.; a rabbit anti-tyrosine-15-phosphorylated Cdc2 antibody and a horseradish peroxidase-labeled anti-mouse IgG antibody were purchased from Cell Signaling Technology, Inc.; and Sure Blue Reserve TMB peroxidase substrate was purchased from Kirkegaard & Perry Laboratories, Inc.
b) Cells A human non-small cell lung cancer cell line (NCI-H1299) and a human colon cancer cell line (WiDr) can be obtained from American Type Culture Collection (ATCC).

c) Method for Determining Effect

In the method using NCI-H1299 cells, the cells were suspended in an RPMI-1640 medium supplemented with 10% FBS, and 100 µL of the resulting cell suspension was dispensed in a Nunclon Delta treated 96-well plastic plate purchased from Nunc, Inc. at a density of 2000 cells per well, and the plate was incubated overnight at 37° C. under an atmosphere of 5% $CO_2$ and 95% air. Camptothecin was dissolved in dimethyl sulfoxide (DMSO) and further the resulting solution was diluted with an RPMI-1640 medium supplemented with 10% FBS. Then, 50 µL of the diluted solution was added to each well of the plate in which the cells were seeded in advance such that the final concentration of camptothecin was 200 nM, and the plate was incubated at 37° C. under an atmosphere of 5% $CO_2$ and 95% air for 16 hours. A test compound was serially diluted with DMSO, and further diluted with an RPMI-1640 medium supplemented with 10% FBS containing 4000 nM nocodazole. Then, 50 µL of the test compound solution was added to each well of the plate in which the cells treated with camptothecin were seeded, and the plate was incubated at 37° C. under an atmosphere of 5% $CO_2$ and 95% air for 8 hours. Then, the culture medium was removed from each well and 100 µL of a cell lysis buffer was added to each well, and the plate was shaken at 4° C. for 2 hours, and thereafter the liquid in the plate was frozen at −80° C. and then thawed, which was used as a lysed cell solution. Cdc2 and tyrosine-15-phosphorylated Cdc2 in this lysed cell solution were measured by an enzyme-linked immunosorbent assay (ELISA method), and a ratio of tyrosine-15-phosphorylated Cdc2 to Cdc2 was calculated to determine a 50% effective concentration ($EC_{50}$, nM) of the test compound for inhibition of phosphorylation in cells. The cell lysis buffer as used herein is an aqueous solution containing 20 mM HEPES (pH 7.5), 150 mM sodium chloride, 1 mM disodium ethylenediamine tetraacetate, 0.1% polyoxyethylene (10) octylphenyl ether, 1% protease inhibitor cocktail, 1 mM dithiothreitol, 2 mM sodium orthovanadate, 10 mM sodium fluoride and 10 mM glycerol diphosphate. The measurement of Cdc2 by the ELISA method was carried out as follows. 50 µL of a solution of a rabbit anti-Cdc2 antibody obtained by diluting the antibody to 200 times with 50 mM carbonate-bicarbonate buffer (pH 9.6) was dispensed into each well of a 96-well Maxisorb immunoplate purchased from Nunc, Inc., and the immunoplate was let stand overnight at 4° C. to immobilize the antibody thereto. Subsequently, each well was washed three times with phosphate buffered saline (PBS), and 300 µL of PBS containing 5% bovine serum albumin (5% BSA/PBS) was added to each well, and then, the immunoplate was let stand at room temperature for 2 hours. Thereafter, each well was washed again three times with PBS, and 50 µL of a solution of a mouse anti-Cdc2 antibody obtained by diluting the antibody to 100 times with Tris-HCl buffered saline containing 0.05% polyoxyethylene sorbitan monolaurate and 1% BSA (1% BSA/TBS-T) was added to each well and also 5 µL of the lysed cell solution was added thereto, and then, the immunoplate was let stand overnight at 4° C. Subsequently, each well was washed three times with Tris-HCl buffered saline containing 0.05% polyoxyethylene sorbitan monolaurate and 0.1% BSA (0.1% BSA/TBS-T), and 70 µL of a solution of a horseradish peroxidase-labeled anti-mouse IgG antibody obtained by diluting the antibody to 2000 times with 1% BSA/TBS-T was added to each well, and then, the immunoplate was let stand at room temperature for 3 hours. Finally, each well was washed five times with 0.1% BSA/TBS-T, and 100 µL of Sure Blue Reserve TMB peroxidase substrate was added to each well, and a chromogenic reaction was allowed to proceed for 15 minutes in a dark place at room temperature. Thereafter, 100 μl of 1 M hydrochloric acid was added to each well to stop the reaction, and measurement was carried out by the colorimetric method. The measurement of tyrosine-15-phosphorylated Cdc2 by the ELISA method was carried out as follows. 50 μL of a solution of a rabbit anti-tyrosine-15-phosphorylated Cdc2 antibody obtained by diluting the antibody to 100 times with 50 mM carbonate-bicarbonate buffer (pH 9.6) was dispensed into each well of a 96-well Maxisorb immunoplate, and the immunoplate was let stand overnight at 4° C. to immobilize the antibody thereto. Subsequently, each well was washed three times with PBS, and 300 μL of 5% BSA/PBS was added to each well, and then, the immunoplate was let stand at room temperature for 2 hours. Thereafter, each well was washed again three times with PBS, and 50 μL of a solution of a mouse anti-Cdc2 antibody obtained by diluting the antibody to 100 times with 1% BSA/TBS-T was added to each well and also 5 μL of the lysed cell solution was added thereto, and then, the immunoplate was let stand overnight at 4° C. Subsequently, each well was washed three times with 0.1% BSA/TBS-T, and 70 μL of a solution of a horseradish peroxidase-labeled anti-mouse IgG antibody obtained by diluting the antibody to 2000 times with 1% BSA/TBS-T was added to each well, and then, the immunoplate was let stand at room temperature for 3 hours. Finally, each well was washed five times with 0.1% BSA/TBS-T, and 100 μL of Sure Blue Reserve TMB peroxidase substrate was added to each well, and a chromogenic reaction was allowed to proceed for 5 minutes in a dark place at room temperature. Thereafter, 100 μL of 1 M hydrochloric acid was added to each well to stop the reaction, and measurement was carried out by the colorimetric method. The results are shown in Table 2.

In the method using WiDr cells, the cells are suspended in a DMEM medium supplemented with 10% FBS, and 100 μL of the resulting cell suspension is dispensed in a Nunclon Delta treated 96-well plastic plate at a density of 2000 cells per well, and the plate is incubated overnight at 37° C. under an atmosphere of 5% $CO_2$ and 95% air. Gemcitabine is dissolved in PBS and further the resulting solution is diluted with a DMEM medium supplemented with 10% FBS. Then, 50 μL of the diluted solution is added to each well of the plate in which the cells have been seeded in advance such that the final concentration of gemcitabine is 100 nM, and the plate is incubated at 37° C. under an atmosphere of 5% $CO_2$ and 95% air for 24 hours. A test compound is serially diluted with DMSO, and further diluted with a DMEM medium supplemented with 10% FBS containing 1200 nM nocodazole. Then, 50 μL of the test compound solution is added to each well of the plate in which the cells treated with gemcitabine have been seeded, and the plate is incubated at 37° C. under an atmosphere of 5% $CO_2$ and 95% air for 8 hours. Then, the culture medium is removed from each well and 100 μL of a cell lysis buffer is added to each well, and the plate is shaken at 4° C. for 2 hours, and thereafter the liquid in the plate is frozen at −80° C. and then thawed, which is used as a lysed cell solution. Cdc2 and tyrosine-15-phosphorylated Cdc2 in this lysed cell solution are measured by the ELISA method, and a ratio of tyrosine-15-phosphorylated Cdc2 to Cdc2 is calculated to determine a 50% effective concentration ($EC_{50}$, nM) of the test compound for inhibition of phosphorylation in cells. The measurement of Cdc2 by the ELISA method is carried out as follows. 50 μL of a solution of a rabbit anti-Cdc2 antibody obtained by diluting the antibody to 200 times with 50 mM carbonate-bicarbonate buffer (pH 9.6) is dispensed into each well of a 96-well Maxisorb plastic plate, and the plate is let stand overnight at 4° C. to immobilize the antibody thereto. Thereafter, each well is washed three times with PBS, and 300 μL of 5% BSA/PBS is added to each well, and then, the plate is let stand at room temperature for 2 hours. Thereafter, each well is washed again three times with PBS, and 50 μL of a solution of a mouse anti-Cdc2 antibody obtained by diluting the antibody to 100 times with 1% BSA/TBS-T is added to each well and also 10 μL of the lysed cell solution is added thereto, and then, the plate is let stand overnight at 4° C. Subsequently, each well is washed three times with 0.1% BSA/TBS-T, and 70 μL of a solution of a horseradish peroxidase-labeled anti-mouse IgG antibody obtained by diluting the antibody to 2000 times with 1% BSA/TBS-T is added to each well, and then, the plate is let stand at room temperature for 3 hours. Finally, each well is washed five times with 0.1% BSA/TBS-T, and 100 μL of Sure Blue Reserve TMB peroxidase substrate is added to each well, and a chromogenic reaction is allowed to proceed for 15 minutes in a dark place at room temperature. Thereafter, 100 μL of 1 M hydrochloric acid is added to each well to stop the reaction, and measurement is carried out by the colorimetric method. The measurement of tyrosine-15-phosphorylated Cdc2 by the ELISA method is carried out as follows. 50 μL of a solution of a rabbit anti-tyrosine-15-phosphorylated Cdc2 antibody obtained by diluting the antibody to 100 times with 50 mM carbonate-bicarbonate buffer (pH 9.6) is dispensed into each well of a 96-well Maxisorb plastic plate, and the plate is let stand overnight at 4° C. to immobilize the antibody thereto. Thereafter, each well is washed three times with PBS, and 300 μL of 5% BSA/PBS is added to each well, and then, the plate is let stand at room temperature for 2 hours. Thereafter, each well is washed again three times with PBS, and 50 μL of a solution of a mouse anti-Cdc2 antibody obtained by diluting the antibody to 100 times with 1% BSA/TBS-T is added to each well and also 10 μL of the lysed cell solution is added thereto, and then, the plate is let stand overnight at 4° C. Subsequently, each well is washed three times with 0.1% BSA/TBS-T, and 70 μL of a solution of a horseradish peroxidase-labeled anti-mouse IgG antibody obtained by diluting the antibody to 2000 times with 1% BSA/TBS-T is added to each well, and then, the plate is let stand at room temperature for 3 hours. Finally, each well is washed five times with 0.1% BSA/TBS-T, and 100 μL of Sure Blue Reserve TMB peroxidase substrate is added to each well, and a chromogenic reaction is allowed to proceed for 10 minutes in a dark place at room temperature. Thereafter, 100 μL of 1 M hydrochloric acid is added to each well to stop the reaction, and measurement is carried out by the colorimetric method.

As shown in Table 2, the compounds according to the invention exhibit an excellent inhibitory effect on Cdc2 tyrosine-15 phosphorylation against human-derived cancer cell lines.

TABLE 2

| | Cdc2-Y15 Phosphorylation-Inhibitory Effect (H1299, +camptothecin) ($EC_{50}$, nM) |
|---|---|
| Example 21 | 111 |
| Example 43 | 31 |
| Example 44 | 38 |
| Example 61 | 130 |
| Example 79 | 370 |
| Example 90 | 250 |
| Example 100 | 52 |
| Example 101 | 43 |
| Example 103 | 31 |
| Example 105 | 69 |
| Example 136 | 11 |
| Example 137 | 17 |
| Example 143 | 190 |

TABLE 2-continued

| | Cdc2-Y15 Phosphorylation-Inhibitory Effect (H1299, +camptothecin) (EC50, nM) |
|---|---|
| Example 144 | 190 |
| Example 147 | 170 |

The compound represented by the general formula (I) can be administered orally or parenterally, and by formulating the compound into a preparation suitable for such an administration route, the compound can be used as a pharmaceutical composition or an anticancer agent.

The term "cancer" as used herein includes various sarcomas and carcinomas and includes solid cancers and hematopoietic cancers. Here, the solid cancers include, for example, brain tumor, head and neck cancer, esophageal cancer, thyroid cancer, small cell cancer, non-small cell cancer, breast cancer, lung cancer, stomach cancer, gallbladder and bile duct cancer, liver cancer, pancreatic cancer, colon cancer, rectal cancer, ovarian cancer, chorioepithelioma, endometrial cancer, cervical cancer, renal pelvic and ureteral cancer, bladder cancer, prostate cancer, penile cancer, testicular cancer, embryonal carcinoma, Wilms' tumor, skin cancer, malignant melanoma, neuroblastoma, osteosarcoma, Ewing's tumor, soft tissue sarcoma and the like. On the other hand, the hematopoietic cancers include, for example, acute leukemia, chronic lymphocytic leukemia, chronic myeloid leukemia, polycythemia vera, malignant lymphoma, multiple myeloma, Hodgkin's lymphoma, non-Hodgkin's lymphoma and the like.

The term "treatment of cancer" as used herein means that an anticancer agent is administered to a cancer patient so as to inhibit the growth of the cancer cells. Preferably, the treatment enables the regression of cancer growth, i.e., the reduction of the size of detectable cancer. More preferably, the treatment eradicates cancer completely.

Preferred examples of the cancer on which the therapeutic effect of the compound according to the invention is expected include human solid cancers. Examples of the human solid cancers include brain tumor, head and neck cancer, esophageal cancer, thyroid cancer, small cell cancer, non-small cell cancer, breast cancer, lung cancer, stomach cancer, gallbladder and bile duct cancer, liver cancer, pancreatic cancer, colon cancer, rectal cancer, ovarian cancer, chorioepithelioma, endometrial cancer, cervical cancer, renal pelvic and ureteral cancer, bladder cancer, prostate cancer, penile cancer, testicular cancer, embryonal carcinoma, Wilms' tumor, skin cancer, malignant melanoma, neuroblastoma, osteosarcoma, Ewing's tumor, soft tissue sarcoma, acute leukemia, chronic lymphocytic leukemia, chronic myeloid leukemia and Hodgkin's lymphoma.

The pharmaceutical composition or anticancer agent according to the invention may contain a pharmaceutically acceptable carrier or diluent. Here, the "pharmaceutically acceptable carrier or diluent" means an excipient (for example, a fat, beeswax, a semi-solid or liquid polyol, a natural or hydrogenated oil, etc.); water (for example, distilled water, particularly distilled water for injection, etc.), physiological saline, an alcohol (for example, ethanol), glycerol, a polyol, an aqueous glucose solution, mannitol, a vegetable oil, etc.; an additive (for example, an expander, a disintegrant, a binder, a lubricant, a wetting agent, a stabilizer, an emulsifier, a dispersant, a preservative, a sweetener, a colorant, a seasoning agent or a flavor, a thickening agent, a diluent, a buffer substance, a solvent or a solubilizing agent, a chemical for providing a storage effect, a salt for changing osmotic pressure, a coating agent or an antioxidant) or the like.

The preparation related to the pharmaceutical composition or anticancer agent of the invention can have any of various dosage forms, and examples thereof include oral preparations such as tablets, capsules, powders, granules and liquids, sterilized liquid parenteral preparations such as solutions and suspensions, suppositories and ointments.

A solid preparation can be prepared in the form of a tablet, a capsule, a granule or a powder as such, or can be prepared using an appropriate carrier (additive). Examples of such carrier (additive) include saccharides such as lactose and glucose; starches of corn, wheat and rice; fatty acids such as stearic acid; inorganic salts such as magnesium metasilicate aluminate and anhydrous calcium phosphate; synthetic polymers such as polyvinylpyrrolidone and polyalkylene glycol; fatty acid salts such as calcium stearate and magnesium stearate; alcohols such as stearyl alcohol and benzyl alcohol; synthetic cellulose derivatives such as methyl cellulose, carboxymethyl cellulose, ethyl cellulose and hydroxypropyl methyl cellulose; and other conventionally used additives such as gelatin, talc, vegetable oils and gum arabic.

These solid preparations such as tablets, capsules, granules and powders may generally contain, as an active ingredient, for example, 0.1 to 100% by weight, preferably 5 to 98% by weight of the compound represented by the above-mentioned formula (I) based on the total weight of the preparation.

A liquid preparation is produced in the form of a suspension, a syrup, an injection or a drip infusion (intravenous infusion) using an appropriate additive which is conventionally used in a liquid preparation such as water, an alcohol or a plant-derived oil such as soybean oil, peanut oil or sesame oil.

In particular, as an appropriate solvent or diluent when the preparation is administered parenterally in the form of an intramuscular injection, an intravenous injection or a subcutaneous injection, distilled water for injection, an aqueous solution of lidocaine hydrochloride (for intramuscular injection), physiological saline, an aqueous glucose solution, ethanol, polyethylene glycol, propylene glycol, a liquid for intravenous injection (for example, an aqueous solution of citric acid, sodium citrate or the like) or an electrolytic solution (for intravenous drip infusion or intravenous injection), or a mixed solution thereof can be exemplified.

Such an injection may be also in the form of a preliminarily dissolved solution, or in the form of a powder per se or a powder with the addition of a suitable carrier (additive) which is dissolved at the time of use. The injection liquid can contain, for example, 0.1 to 10% by weight of an active ingredient based on the total weight of the preparation.

The liquid preparation such as a suspension or a syrup for oral administration can contain, for example, 0.1 to 10% by weight of an active ingredient based on the total weight of the preparation.

Such a preparation can be easily produced by a person skilled in the art according to a common procedure or a conventional technique. For example, in the case of an oral preparation, it can be produced by, for example, mixing an appropriate amount of the compound of the invention with an appropriate amount of lactose and filling this mixture into a hard gelatin capsule suitable for oral administration. On the other hand, in the case where the preparation containing the compound of the invention is an injection, it can be produced by; for example, mixing an appropriate amount of the compound of the invention with an appropriate amount of 0.9% physiological saline and filling this mixture in a vial for injection.

The compound of the invention can be used by combining it with any other agent useful for treatment of various cancers or with radiotherapy. The individual ingredients in the case of such a combination can be administered at different times or at the same time as divided preparations or a single preparation during the period of treatment. Accordingly, the invention should be so interpreted that it includes all modes of administration at the same time or at different times, and the administration in the invention should be interpreted so. The scope of the combination of the compound of the invention with any other agent useful for the treatment of the above-mentioned diseases should include, in principle, every combination thereof with every pharmaceutical preparation useful for the treatment of the above-mentioned diseases.

The radiation therapy itself means an ordinary method in the field of treatment of cancer. In the radiation therapy, any of various radiations such as an X-ray, a γ-ray, a neutron ray, an electron beam and a proton beam, and radiation sources is used. The most common radiation therapy is one which is carried out by external radiation using a linear accelerator, and in which a γ-ray is irradiated.

The compound of the invention can potentiate the therapeutic effect of the radiation therapy by combining the compound of the invention with the radiation therapy and therefore can be useful as a radiation sensitizer in the field of treatment of cancer.

Another aspect of the compound of the invention is that the compound of the invention is also useful as a sensitizer for any other anticancer agents in the field of treatment of cancer.

The compound of the invention can be used by combining it with radiation therapy and/or any other anticancer agents described below.

The "sensitizer" of radiation or for an anticancer agent as used herein means a medicinal agent which, when it is used by combining it with radiation therapy and/or chemotherapy using an anticancer agent, additively or synergistically potentiates the therapeutic effect of the radiation therapy and/or chemotherapy in the field of treatment of cancer.

The respective preparations in the combined preparation according to the invention can have any form, and they can be produced in the same manner as that for the above-mentioned preparation. A drug combination containing the compound of the invention and any other anticancer agents can also be easily produced by a person skilled in the art according to a common procedure or a conventional technique.

The above-mentioned combination includes a combination of the composition of the invention not only with one other active substance but also with two or more other active substances. There are a lot of examples of the combination of the composition of the invention with one or two or more active substances selected from the therapeutic agents for the above-mentioned diseases.

The agents to be combined with the compositions include, for example, an anticancer agent selected from the group consisting of anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, interferons, biological response modifiers and other anticancer agents as well as pharmaceutically acceptable salt(s) or ester(s) thereof.

The term "anticancer alkylating agent" as used in the present specification refers to an alkylating agent having anticancer activity, and the term "alkylating agent" herein generally refers to an agent giving an alkyl group in the alkylation reaction in which a hydrogen atom of an organic compound is substituted with an alkyl group. The term "anticancer alkylating agent" may be exemplified by nitrogen mustard N-oxide, cyclophosphamide, ifosfamide, melphalan, busulfan, mitobronitol, carboquone, thiotepa, ranimustine, nimustine, temozolomide or carmustine.

The term "anticancer antimetabolite" as used in the specification refers to an antimetabolite having anticancer activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). The term "anticancer antimetabolites" may be exemplified methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine or pemetrexed disodium, and preferred are cytarabine, gemcitabine and the like.

The term "anticancer antibiotic" as used in the specification refers to an antibiotic having anticancer activity, and the "antibiotic" herein includes substances that are produced by microorganisms and inhibit cell growth and other functions of microorganisms and of other living organisms. The term "anticancer antibiotic" may be exemplified by actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin, and preferred are doxorubicin, mitomycin C and the like.

The term "plant-derived anticancer agent" as used in the specification includes compounds having anticancer activities which originate from plants, or compounds prepared by applying chemical modification to the foregoing compounds. The term "plant-derived anticancer agent" may be exemplified by vincristine, vinblastine, vindesine, etoposide, sobuzoxane, docetaxel, paclitaxel and vinorelbine, and preferred are etoposide and the like.

The term "anticancer camptothecin derivative" as used in the specification refers to compounds that are structurally related to camptothecin and inhibit cancer cell growth, including camptothecin per se. The term "anticancer camptothecin derivative" is not particularly limited to, but may be exemplified by, camptothecin, 10-hydroxycamptothecin, topotecan, irinotecan or 9-aminocamptothecin, with camptothecin being preferred. Further, irinotecan is metabolized in vivo and exhibits anticancer effect as SN-38. The action mechanism and the activity of the camptothecin derivatives are believed to be virtually the same as those of camptothecin (e.g., Nitta, et al., *Gan to Kagaku Ryoho,* 14, 850-857 (1987)).

The term "anticancer platinum coordination compound" as used in the specification refers to a platinum coordination compound having anticancer activity, and the term "platinum coordination compound" herein refers to a platinum coordination compound which provides platinum in ion form. Preferred platinum compounds include cisplatin; cis-diamminediaquoplatinum (II)-ion; chloro(diethylenetriamine)-platinum (II) chloride; dichloro(ethylenediamine)-platinum (II); diammine(1,1-cyclobutanedicarboxylato)platinum (II) (carboplatin); spiroplatin; iproplatin; diammine(2-ethylmalonato)platinum (II); ethylenediaminemalonatoplatinum (II); aqua(1,2-diaminodicyclohexane)sulfatoplatinum (II); aqua (1,2-diaminodicyclohexane)malonatoplatinum (II); (1,2-diaminocyclohexane)malonatoplatinum (II); (4-carboxyphthalato)(1,2-diaminocyclohexane) platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin, and preferred is carboplatin or cisplatin. Further, other anticancer platinum coordination compounds mentioned in the specification are known and are commercially available and/or producible by a person having ordinary skill in the art by conventional techniques.

The term "anticancer tyrosine kinase inhibitor" as used in the specification refers to a tyrosine kinase inhibitor having anticancer activity, and the term "tyrosine kinase inhibitor" herein refers to a chemical substance inhibiting "tyrosine kinase" which transfers a γ-phosphate group of ATP to a hydroxyl group of a specific tyrosine in protein. The term "anticancer tyrosine kinase inhibitor" may be exemplified by gefitinib, imatinib or erlotinib.

The term "monoclonal antibody" as used in the specification, which is also known as single clonal antibody, refers to an antibody produced by a monoclonal antibody-producing cell, and examples thereof include cetuximab, bevacizumab, rituximab, alemtuzumab and trastuzumab.

The term "interferon" as used in the specification refers to an interferon having anticancer activity, and it is a glycoprotein having a molecular weight of about 20,000 which is produced and secreted by most animal cells upon viral infection. It has not only the effect of inhibiting viral growth but also various immune effector mechanisms including inhibition of growth of cells (in particular, tumor cells) and enhancement of the natural killer cell activity, thus being designated as one type of cytokine. Examples of "interferon" include interferon α, interferon α-2a, interferon α-2b, interferon β, interferon γ-1a and interferon γ-n1.

The term "biological response modifier" as used in the specification is the so-called biological response modifier or BRM and is generally the generic term for substances or drugs for modifying the defense mechanisms of living organisms or biological responses such as survival, growth or differentiation of tissue cells in order to direct them to be useful for an individual against tumor, infection or other diseases. Examples of the "biological response modifier" include krestin, lentinan, sizofuran, picibanil and ubenimex.

The term "other anticancer agent" as used in the specification refers to an anticancer agent which does not belong to any of the above-described agents having anticancer activities. Examples of the "other anticancer agent" include mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

The above-described terms "anticancer alkylating agent", "anticancer antimetabolite", "anticancer antibiotic", "plant-derived anticancer agent", "anticancer platinum coordination compound", "anticancer camptothecin derivative", "anticancer tyrosine kinase inhibitor", "monoclonal antibody", "interferon", "biological response modifier" and "other anticancer agent" are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. Nos. 5,420,319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; and the process for preparation of rituximab is described, for example, in JP-W No. 2-503143.

The above-mentioned anticancer alkylating agents are commercially available, as exemplified by the following: nitrogen mustard N-oxide from Mitsubishi Pharma Corp. as Nitromin (tradename); cyclophosphamide from Shionogi & Co., Ltd. as Endoxan (tradename); ifosfamide from Shionogi & Co., Ltd. as Ifomide (tradename); melphalan from GlaxoSmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned anticancer antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co., Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); carmofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned anticancer antibiotics are commercially available, as exemplified by the following: actinomycin D from Banyu Pharmaceutical Co., Ltd. as Cosmegen (tradename); doxorubicin from Kyowa Hakko Kogyo Co., Ltd. as Adriacin (tradename); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorubicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from Wyeth Corp. as Rapamune (tradename); and valrubicin from Anthra Pharmaceuticals Inc. as Valstar (tradename).

The above-mentioned plant-derived anticancer agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., Ltd. as Lastet (tradename); sobuzoxane from Zenyaku Kogyo Co., Ltd. as Perazolin (tradename); docetaxel from Aventis Corp. as Taxsotere (tradename); paclitaxel from Bristol-Myers Squibb Co. as Taxol (tradename); and vinorelbine from Kyowa Hakko Kogyo Co., Ltd. as Navelbine (tradename).

The above-mentioned anticancer platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned anticancer camptothecin derivatives are commercially available, as exemplified by the following: irinotecan from Yakult Honsha Co., Ltd. as Campto (tradename); topotecan from GlaxoSmithKline Corp. as Hycamtin (tradename); and camptothecin from Aldrich Chemical Co., Inc., U.S.A.

The above-mentioned anticancer tyrosine kinase inhibitors are commercially available, as exemplified by the following: gefitinib from AstraZeneca Corp. as Iressa (tradename); imatinib from Novartis AG as Gleevec (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idec Inc. as Rittman (tradename); alemtuzumab from Berlex Inc. as Campath (tradename); and trastuzumab from Chugai Pharmaceutical Co., Ltd. as Herceptin (tradename).

The above-mentioned interferons are commercially available, as exemplified by the following: interferon α from Sumitomo Pharmaceutical Co., Ltd. as Sumiferon (tradename); interferon α-2a from Takeda Pharmaceutical Co., Ltd. as Canferon-A (tradename); interferon α-2b from Schering-Plough Corp. as Intron A (tradename); interferon β from Mochida Pharmaceutical Co., Ltd. as IFNβ (tradename); interferon γ-1a from Shionogi & Co., Ltd. as Immunomax-γ (tradename); and interferon γ-n1 from Otsuka Pharmaceutical Co., Ltd. as Ogamma (tradename).

The above-mentioned biological response modifiers are commercially available, as exemplified by the following: krestin from Sankyo Co., Ltd. as Krestin (tradename); lentinan from Aventis Corp. as Lentinan (tradename); sizofuran from Kaken Seiyaku Co., Ltd. as Sonifuran (tradename); picibanil from Chugai Pharmaceutical Co., Ltd. as Picibanil (tradename); and ubenimex from Nippon Kayaku Co., Ltd. as Bestatin (tradename).

The above-mentioned other anticancer agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idec Inc. as Amevive (tradename); darbepoetin alfa from Amgen Inc. as Aranesp (tradename); anastrozole from AstraZeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co., Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goserelin from AstraZeneca Corp. as Zoladex (tradename).

The invention also relates to a method for the treatment of cancer, which comprises administering to a subject in need thereof a therapeutically-effective amount of the compound of the invention or a pharmaceutically acceptable salt or ester thereof.

In the process according to the invention, preferred therapeutic unit may vary in accordance with, for example, the administration route of the compound of the invention, the type of the compound of the invention used, and the dosage form of the compound of the invention used; the type, administration route and dosage form of the other anticancer agent used in combination; and the type of cells to be treated, the condition of patient, and the like. The optimal treatment under the given conditions can be determined by a person skilled in the art, based on the set conventional therapeutic unit and/or based on the content of the present specification.

In the process according to the invention, the therapeutic unit for the compound of the invention may vary in accordance with, specifically, the type of compound used, the type of compounded composition, application frequency and the specific site to be treated, seriousness of the disease, age of the patient, doctor's diagnosis, the type of cancer, or the like. However, as an exemplary reference, the daily dose for an adult may be within a range of, for example, 1 to 1,000 mg in the case of oral administration. In the case of parenteral administration, preferably intravenous administration, and more preferably intravenous drip infusion, the daily dose may be within a range of, for example, 1 to 100 mg/m$^2$ (body surface area). Here, in the case of intravenous drip infusion, administration may be continuously carried out for, for example, 1 to 48 hours. Moreover, the administration frequency may vary depending on the administering method and symptoms, but it is, for example, once to five times a day. Alternatively, periodically intermittent administration such as administration every other day, administration every two days or the like may be employed as well in the administering method. The period of withdraw from medication in the case of parenteral administration is, for example, 1 to 6 weeks.

Although the therapeutic unit for the other anticancer agent used in combination with the compound of the invention is not particularly limited, it can be determined, if needed, by those skilled in the art according to known literatures. Examples may be as follows.

The therapeutic unit of 5-fluorouracil (5-FU) is such that, in the case of oral administration, for example, 200 to 300 mg per day is administered in once to three times consecutively, and in the case of injection, for example, 5 to 15 mg/kg per day is administered once a day for the first 5 consecutive days by intravenous injection or intravenous drip infusion, and then 5 to 7.5 mg/kg is administered once a day every other day by intravenous injection or intravenous drip infusion (the dose may be appropriately increased or decreased).

The therapeutic unit of S-1 (Tegafur, Gimestat and Ostat potassium) is such that, for example, the initial dose (singe dose) is set to the following standard amount in accordance with the body surface area, and it is orally administered twice a day, after breakfast and after dinner, for 28 consecutive days, followed by withdrawal from medication for 14 days. This is set as one course of administration, which is repeated. The initial standard amount per unit body surface area (Tegafur equivalent) is 40 mg in one administration for an area less than 1.25 m$^2$; 50 mg in one administration for an area of 1.25 m$^2$ to less than 1.5 m$^2$; 60 mg in one administration for an area of 1.5 m$^2$ or more. This dose is appropriately increased or decreased depending on the condition of the patient.

The therapeutic unit for gemcitabine is, for example, 1 g as gemcitabine/m$^2$ in one administration, which is administered by intravenous drip infusion over a period of 30 minutes, and one administration per week is continued for 3 weeks, followed by withdrawal from medication on the fourth week. This is set as one course of administration, which is repeated. The dose is appropriately decreased in accordance with age, symptom or development of side-effects.

The therapeutic unit for doxorubicin (e.g., doxorubicin hydrochloride) is such that, for example, in the case of intravenous injection, 10 mg (0.2 mg/kg) (titer) is administered once a day by intravenous one-shot administration for 4 to 6 consecutive days, followed by withdrawal from medication for 7 to 10 days. This is set as one course of administration, which is repeated two or three times. Here, the total dose is preferably 500 mg (titer)/m$^2$ (body surface area) or less, and it may be appropriately increased or decreased within the range.

The therapeutic unit for etoposide is such that, for example, in the case of intravenous injection, 60 to 100 mg/m$^2$ (body surface area) per day is administered for 5 consecutive days, followed by withdrawal from medication for three weeks (the dose may be appropriately increased or decreased). This is set as one course of administration, which is repeated. Meanwhile, in the case of oral administration, for example, 175 to 200 mg per day is administered for 5 consecutive days, followed by withdrawal from medication for three weeks (the dose may be appropriately increased or decreased). This is set as one course of administration, which is repeated.

The therapeutic unit for docetaxel (docetaxel hydrate) is such that, for example, 60 mg as docetaxel/m$^2$ (body surface area) is administered once a day by intravenous drip infusion over a period of 1 hour or longer at an interval of 3 to 4 weeks (the dose may be appropriately increased or decreased).

The therapeutic unit of paclitaxel is such that, for example, 210 mg/m$^2$ (body surface area) is administered once a day by intravenous drip infusion over a period of 3 hours, followed by withdrawal from medication for at least 3 weeks. This is set as one course of administration, which is repeated. The dose may be appropriately increased or decreased.

The therapeutic unit for cisplatin is such that, for example, in the case of intravenous injection, 50 to 70 mg/m$^2$ (body surface area) is administered once a day, followed by withdrawal from medication for 3 weeks or longer (the dose may be appropriately increased or decreased). This is set as one course of administration, which is repeated.

The therapeutic unit for carboplatin is such that, for example, 300 to 400 mg/m$^2$ is administered once a day by intravenous drip infusion over a period of 30 minutes or longer, followed by withdrawal from medication for at least 4 weeks (the dose may be appropriately increased or decreased). This is set as one course of administration, which is repeated.

The therapeutic unit for oxaliplatin is such that 85 mg/m$^2$ is administered once a day by intravenous injection, followed by withdrawal from medication for two weeks. This is set as one course of administration, which is repeated.

The therapeutic unit for irinotecan (e.g., irinotecan hydrochloride) is such that, for example, 100 mg/m$^2$ is administered once a day by intravenous drip infusion for 3 or 4 times at an interval of one week, followed by withdrawal from medication for at least two weeks.

The therapeutic unit for topotecan is such that, for example, 1.5 mg/m$^2$ is administered once a day by intravenous drip infusion for 5 days, followed by withdrawal from medication for at least 3 weeks.

The therapeutic unit for cyclophosphamide is such that, for example, in the case of intravenous injection, 100 mg is administered once a day by intravenous injection for consecutive days. If the patient can tolerate, the daily dose may be increased to 200 mg. The total dose is 3,000 to 8,000 mg, which may be appropriately increased or decreased. If necessary, it may be injected or infused intramuscularly, intrathoracically or intratumorally. On the other hand, in the case of oral administration, for example, 100 to 200 mg is administered a day.

The therapeutic unit for gefitinib is such that 250 mg is orally administered once a day.

The therapeutic unit for cetuximab is such that, for example, 400 mg/m$^2$ is administered on the first day by intravenous drip infusion, and then 250 mg/m$^2$ is administered every week by intravenous drip infusion.

The therapeutic unit for bevacizumab is such that, for example, 3 mg/kg is administered every week by intravenous drip infusion.

The therapeutic unit for trastuzumab is such that, for example, typically for an adult, once a day, 4 mg as trastuzumab/kg (body weight) is administered initially, followed by intravenous drip infusion of 2 mg/kg over a period of 90 minutes or longer every week from the second administration.

The therapeutic unit for exemestane is such that, for example, typically for an adult, 25 mg is orally administered once a day after meal.

The therapeutic unit for leuprorelin (e.g., leuprorelin acetate) is such that, for example, typically for an adult, 11.25 mg is subcutaneously administered once in 12 weeks.

The therapeutic unit for imatinib is such that, for example, typically for an adult in the chronic phase of chronic myelogenous leukemia, 400 mg is orally administered once a day after meal.

The therapeutic unit for a combination of 5-FU and leucovorin is such that, for example, 425 mg/m$^2$ of 5-FU and 200 mg/m$^2$ of leucovorin are administered from the first day to the fifth day by intravenous drip infusion, and this course is repeated at an interval of 4 weeks.

The compounds of the invention have an excellent Wee1 kinase inhibitory effect, and therefore are useful in the field of medicine, especially in the field of treatment of various cancers.

The invention is described more concretely with reference to the following Examples and Production Examples, which, however, are not intended to restrict the scope of the invention.

EXAMPLES

In thin-layer chromatography in Examples and Production Examples, Silica Gel$_{60}$F$_{254}$ (Merck) was used for the plate, and a UV detector was used for detection. Wakogel™ C-300 or C-200 (Wako Pure Chemical Industries) or NH (Fuji Silysia Chemical) was used for column silica gel. In MS spectrometry, used was JMS-SX102A (JEOL) or QUATTROII (Micromass). In NMR spectrometry, dimethyl sulfoxide was used as the internal standard in a heavy dimethyl sulfoxide solution; a spectrometer of JNM-AL 400 (400 MHz; JEOL), Mercury 400 (400 MHz; Varian) or Inova 400 (400 MHz; Varian) was used; and all δ values are by ppm.

The meanings of the abbreviations in Production Examples and Examples are mentioned below.

s: singlet
d: doublet
dd: double doublet
ddd: double double doublet
t: triplet
dt: double triplet
ddt: double double triplet
q: quartet
m: multiplet
br: broad
J: coupling constant
Hz: hertz
DMSO-$d_6$: deuteriated dimethyl sulfoxide
CDCl$_3$: deuteriated chloroform
CD$_3$OD: deuteriated methanol
mCPBA: 3-chlorobenzoic acid
Me: methyl group
TFA: trifluoroacetic acid
TsOH: p-toluenesulfonic acid Production Example 1

Production of 2-(methylthio)pyrimido[4',5':4,5]pyrimido[1,2-b]indazol-5(7H)-one

1) Production of ethyl 4-(1H-indazol-3-ylamino)-2-(methylthio)pyrimidine-5-carboxylate N,N-diisopropylethylamine (19.4 g) and 3-aminoindazole (6.66 g) were added to a tetrahydrofuran (0.2 L) solution of ethyl 4-chloro-2-(methylthio)pyrimidine-5-carboxylate (12.22 g), and stirred with heating under reflux for 15 hours. After cooled to room temperature, the reaction solution was evaporated under reduced pressure, water (50 mL) was added to the residue and the precipitated solid was collected through filtration, washed with distilled water and ethyl acetate in that order, and dried to give the title compound as a white solid (14.3 g).

$^1$H-NMR (400 MHz, DMSO-$d_6$) δ: 12.89 (1H, s), 10.17 (1H, s), 8.75 (1H, s), 7.59 (1H, d, J=8.0 Hz), 7.49 (1H, d, J=8.5 Hz), 7.36 (1H, t, J=8.5 Hz), 7.08 (1H, t, J=8.0 Hz), 4.37 (2H, q, J=7.1 Hz), 2.13 (3H, s), 1.34 (3H, t, J=7.1 Hz).

ESI-MS Found: m/z [M+H]+ 330.

2) Production of 2-(methylthio)pyrimido[4',5':4,5]pyrimido[1,2-b]indazol-5(7H)-one Aqueous 5 N sodium hydroxide solution (20 mL) was added to a methanol (100 mL) solution of the above compound (7.9 g), and stirred for 1 hour. Methanol was evaporated away under reduced pressure, the residue was made to have a pH of about 2 with aqueous 5 N hydrochloric acid solution added thereto, and stirred for 3.5 hours. Water (50 mL) was added to the reaction solution, and the precipitated solid was collected through filtration, washed with distilled water and ethyl acetate in that order, and dried to give the title compound as a yellow solid (6.4 g).

$^1$H-NMR (400 MHz, DMSO-$d_6$) δ: 14.24 (1H, s), 9.30 (1H, s), 8.09 (1H, d, J=8.3 Hz), 7.60 (1H, d, J=8.0 Hz), 7.48 (1H, t, J=8.0 Hz), 7.10 (1H, t, J=8.3 Hz), 2.65 (3H, s).

ESI-MS Found: m/z [M+H]+ 284.

Production Example 2

Production of 7-methyl-2-(methylthio)pyrimido[4',5':4,5]pyrimido[1,2-b]indazol-5(7H)-one Methyl iodide (0.3 mL) and potassium carbonate (400 mg) were added to an N,N-dimethylformamide (10 mL) solution of the compound (500 mg) obtained in Production Example 1-2, and stirred at 60° C. for 3 hours. After cooled to room temperature, the reaction solution was evaporated under reduced pressure, water (5 mL) was added to the residue, and the precipitated solid was collected through filtration, washed with distilled water, and dried to give the title compound as a white solid (400 mg).

ESI-MS Found: m/z [M+H]+ 298.

Production Example 3

Production of 7-ethyl-2-(methylthio)pyrimido[4',5':4,5]pyrimido[1,2-b]indazol-5(7H)-one The title compound (240 mg) was produced as a yellow solid in the same manner as in Production Example 2, for which, however, ethyl iodide was used in place of methyl iodide used in Production Example 2.

$^1$H-NMR (400 MHz, CDCl$_3$) δ: 9.45 (1H, s), 7.81 (1H, d, J=8.8 Hz), 7.76 (1H, d, J=9.0 Hz), 7.42 (1H, ddd, J=9.0, 6.6, 1.0 Hz), 7.14 (1H, ddd, J=8.8, 6.6, 1.0 Hz), 4.94 (2H, q, J=7.2 Hz), 2.71 (3H, s), 1.63 (1H, t, J=7.2 Hz).

ESI-MS Found: m/z [M+H]+ 312.

Production Example 4

Production of 7-isopropyl-2-(methylthio)pyrimido[4',5':4,5]pyrimido[1,2-b]indazol-5(7H)-one The title compound (240 mg) was produced as a yellow solid in the same manner as in Production Example 2, for which, however, isopropyl iodide was used in place of methyl iodide used in Production Example 2.

$^1$H-NMR (400 MHz, CDCl$_3$) δ: 9.42 (1H, s), 8.39 (1H, dt, J=8.5, 1.3 Hz), 7.79-7.74 (1H, m), 7.61 (1H, d, J=8.5 Hz), 7.45 (1H, d, J=7.6 Hz), 5.59-5.48 (1H, m), 2.74 (3H, s), 1.41 (1H, d, J=7.1 Hz).

ESI-MS Found: m/z [M+H]+ 326.

Production Example 5

Production of 7-allyl-2-(methylthio)pyrimido[4',5':4,5]pyrimido[1,2-b]indazol-5(7H)-one The title compound (536 mg) was produced as a yellow solid in the same manner as in Production Example 2, for which, however, allyl bromide was used in place of methyl iodide used in Production Example 2.

ESI-MS Found: m/z [M+H]+ 324.

Production Example 6

Production of 2-(methylthio)-7-propylpyrimido[4',5':4,5]pyrimido[1,2-b]indazol-5(7H)-one 10% palladium-carbon (20 mg) was added to a methanol (20 mL) solution of the compound obtained in Production Example 5, and stirred in a one-atmospheric hydrogen atmosphere at room temperature for 4 hours. Palladium-carbon was removed through filtration, and the filtrate was concentrated to give the title compound (276 mg).

ESI-MS Found: m/z [M+H]+ 326.

Production Example 7

Production of 2-[2-(methylthio)-5-oxopyrimido[4',5':4,5]pyrimido[1,2-b]indazol-7(5H)-yl]propanenitrile The title compound (56 mg) was produced as a yellow solid in the same manner as in Production Example 2, for which, however, 3-bromo-2-methylpropanenitrile was used in place of methyl iodide used in Production Example 2.
ESI-MS Found: m/z [M+H]+ 337.

Production Example 8

Production of 7-(cyclopropylmethyl)-2-(methylthio)pyrimido[4',5':4,5]pyrimido[1,2-b]indazol-5(7H)-one The title compound (121 mg) was produced as a yellow solid in the same manner as in Production Example 2, for which, however, cyclopropylmethyl bromide was used in place of methyl iodide used in Production Example 2.
ESI-MS Found: m/z [M+H]+ 338.

Production Example 9

Production of 7-(2,2-difluoroethyl)-2-(methylthio)pyrimido[4',5':4,5]pyrimido[1,2-b]indazol-5(7H)-one The title compound (15 mg) was produced as a yellow solid in the same manner as in Production Example 2, for which, however, 2,2-difluoroethyl bromide was used in place of methyl iodide used in Production Example 2.
ESI-MS Found: m/z [M+H]+ 348.

Production Example 10

Production of 7-benzyl-2-(methylthio)pyrimido[4',5':4,5]pyrimido[1,2-b]indazol-5(7H)-one The title compound (224 mg) was produced as a yellow solid in the same manner as in Production Example 2, for which, however, benzyl bromide was used in place of methyl iodide used in Production Example 2.
$^1$H-NMR (400 MHz, CDCl$_3$) δ: 9.43 (1H, s), 8.31 (1H, d, J=8.0 Hz), 7.87-7.82 (1H, m), 7.61 (1H, d, J=8.5 Hz), 7.44 (1H, t, J=8.5 Hz), 7.19-7.08 (3H, m), 7.02-6.99 (2H, m), 5.75 (2H, s), 2.70 (3H, s).
ESI-MS Found: m/z [M+H]+ 374.

Production Example 11

Production of 7-(2-{[tert-butyl(dimethyl)silyl]oxy}ethyl)-2-(methylthio)pyrimido[4',5':4,5]pyrimido[1,2-b]indazol-5(7H)-one The title compound (261 mg) was produced as a yellow solid in the same manner as in Production Example 2, for which, however, (2-bromoethoxy)(tert-butyl)dimethylsilane was used in place of methyl iodide used in Production Example 2.
ESI-MS Found: m/z [M+H]+ 442.

Production Example 12

Production of 7-(3-{[tert-butyl(dimethyl)silyl]oxy}propyl)-2-(methylthio)pyrimido[4',5':4,5]pyrimido[1,2-b]indazol-5(7H)-one The title compound (91 mg) was produced as a yellow solid in the same manner as in Production Example 2, for which, however, (3-bromopropoxy)(tert-butyl)dimethylsilane was used in place of methyl iodide used in Production Example 2.
ESI-MS Found: m/z [M+H]+ 456.

Production Example 13

Production of 7-(2-methoxyethyl)-2-(methylthio)pyrimido[4',5':4,5]pyrimido[1,2-b]indazol-5(7H)-one The title compound (266 mg) was produced as a yellow solid in the same manner as in Production Example 2, for which, however, (2-methoxyethyl)bromide was used in place of methyl iodide used in Production Example 2.
ESI-MS Found: m/z [M+H]+ 341.

Production Example 14

Production of 2-(methylthio)-7-pyridin-2-ylpyrimido[4',5':4,5]pyrimido[1,2-b]indazol-5(7H)-one N,N'-dimethylethylenediamine (2.1 mL) was added to a 1,4-dioxane (50 mL) solution of the compound (2.38 g) obtained in Production Example 1-2, copper(I) iodide (1.90 g), 2-bromopyridine (1.91 mL) and potassium carbonate (2.76 g), and stirred at 100° C. for 7 hours. The reaction liquid was cooled, then aqueous ammonia was added thereto, and extracted with a mixed solution of chloroform/methanol (90/10), then washed with saturated saline water, and dried with anhydrous magnesium sulfate. The solvent was evaporated away, and the residue was purified through basic silica gel chromatography (chloroform/methanol=90/10) to give the title compound as a yellow crystal (3.26 g).
$^1$H-NMR (400 MHz, DMSO-d$_6$) δ: 9.26 (1H, s), 8.50 (1H, d, J=5.1 Hz), 8.34 (1H, d, J=8.0 Hz), 8.04 (1H, td, J=7.1, 1.9 Hz), 7.88 (1H, t, J=8.0 Hz), 7.77 (1H, d, J=8.0 Hz), 7.71 (1H, d, J=7.1 Hz), 7.59 (1H, t, J=8.0 Hz), 7.46 (1H, dd, J=7.1, 5.1 Hz), 2.64 (3H, s).
ESI-MS Found: m/z [M+H]+ 361.

Production Example 15

Production of 7-(6-methylpyridin-2-yl)-2-(methylthio)pyrimido[4',5':4,5]pyrimido[1,2-b]indazol-5(7H)-one The title compound (41 mg) was produced as a yellow solid in the same manner as in Production Example 2, for which, however, 6-bromo-2-picoline was used in place of 2-bromopyridine used in Production Example 14.
$^1$H-NMR (400 MHz, DMSO-d$_6$) δ: 9.35 (1H, s), 8.43 (1H, d, J=8.0 Hz), 8.82 (1H, t, J=8.0 Hz), 7.75 (1H, t, J=7.8 Hz), 7.54 (1H, d, J=8.0 Hz), 7.50 (1H, t, J=8.0 Hz), 7.31 (1H, d, J=7.8 Hz), 7.21 (1H, d, J=7.8 Hz), 2.75 (3H, s), 2.49 (3H, s).
ESI-MS Found: m/z [M+H]+ 375.

Production Example 16

Production of 7-(5-methylpyridin-2-yl)-2-(methylthio)pyrimido[4',5':4,5]pyrimido[1,2-b]indazol-5(7H)-one The title compound (88 mg) was produced as a yellow solid in the same manner as in Production Example 2, for which, however, 6-bromo-3-picoline was used in place of 2-bromopyridine used in Production Example 14.
$^1$H-NMR (400 MHz, DMSO-d$_6$) δ: 9.24 (1H, s), 8.33 (1H, d, J=7.8 Hz), 8.30 (1H, d, J=2.4 Hz), 7.89-7.84 (2H, m), 7.69

(1H, d, J=8.5 Hz), 7.63 (1H, d, J=8.5 Hz), 7.58 (1H, t, J=7.8 Hz), 2.64 (3H, s), 2.35 (3H, s).
ESI-MS Found: m/z [M+H]+ 375.

Production Example 17

Production of 7-(4-methylpyridin-2-yl)-2-(methylthio)pyrimido[4',5':4,5]pyrimido[1,2-b]indazol-5(7H)-one The title compound (69 mg) was produced as a yellow solid in the same manner as in Production Example 2, for which, however, 6-bromo-4-picoline was used in place of 2-bromopyridine used in Production Example 14.
$^1$H-NMR (400 MHz, DMSO-$d_6$) δ: 9.26 (1H, s), 8.35-8.30 (2H, m), 7.90-7.85 (2H, m), 7.76 (1H, d, J=8.5 Hz), 7.61-7.57 (2H, m), 7.29 (1H, d, J=8.5 Hz), 2.64 (3H, s), 2.42 (3H, s).
ESI-MS Found: m/z [M+H]+ 375.

Production Example 18

Production of N,N-dimethyl-6-[2-(methylthio)-5-oxopyrimido[4',5':4,5]pyrimido[1,2-b]indazol-7(5H)-yl]pyridine-2-carboxamide The title compound (48 mg) was produced as a yellow solid in the same manner as in Production Example 2, for which, however, 6-bromo-N,N-dimethylpyridine-2-carboxamide was used in place of 2-bromopyridine used in Production Example 14.
ESI-MS Found: m/z [M+H]+ 432.

Production Example 19

Production of N,N-dimethyl-6-[2-(methylthio)-5-oxopyrimido[4',5':4,5]pyrimido[1,2-b]indazol-7(5H)-yl]nicotinamide The title compound (51 mg) was produced as a yellow solid in the same manner as in Production Example 2, for which, however, 6-bromo-N,N-dimethylpyridine-3-carboxamide was used in place of 2-bromopyridine used in Production Example 14.
ESI-MS Found: m/z [M+H]+ 432.

Production Example 20

Production of 7-(6-methoxypyridin-2-yl)-2-(methylthio)pyrimido[4',5':4,5]pyrimido[1,2-b]indazol-5(7H)-one The title compound (66 mg) was produced as a yellow solid in the same manner as in Production Example 2, for which, however, 2-bromo-6-methoxypyridine was used in place of 2-bromopyridine used in Production Example 14.
ESI-MS Found: m/z [M+H]+ 391.

Production Example 21

Production of 7-(6-nitropyridin-2-yl)-2-(methylthio)pyrimido[4',5':4,5]pyrimido[1,2-b]indazol-5(7H)-one The title compound (159 mg) was produced as a yellow solid in the same manner as in Production Example 2, for which, however, 2-bromo-6-nitropyridine was used in place of 2-bromopyridine used in Production Example 14.
ESI-MS Found: m/z [M+H]+ 406.

Production Example 22

Production of 7-[6-(hydroxyamino)pyridin-2-yl]-2-(methylthio)pyrimido[4',5':4,5]pyrimido[1,2-b]indazol-5(7H)-one 10% palladium-carbon (20 mg) was added to a methanol (20 mL) solution of the compound obtained in Production Example 21, and stirred in a one-atmospheric hydrogen atmosphere at room temperature for 4 hours. Palladium-carbon was removed through filtration, and the filtrate was concentrated under reduced pressure to give the title compound (61 mg).
ESI-MS Found: m/z [M+H]+ 392.

Production Example 23

Production of 2-(methylthio)-7-(3-thienyl)pyrimido[4',5':4,5]pyrimido[1,2-b]indazol-5(7H)-one Pyridine (2 mL) was added to a chloroform solution of the compound (750 mg) obtained in Production Example 1-2, copper(II) acetate (610 mg) and 3-thienylboronic acid (1.0 g), and stirred at room temperature for 3 days. Aqueous 30% ammonia and saturated saline water were added in that order to the reaction liquid, and extracted with chloroform. The organic layer was washed with saturated saline water, dried with anhydrous magnesium sulfate, and the solvent was evaporated away. The crude product was purified through silica gel column chromatography (hexane/ethyl acetate) to give the title compound as a yellow solid (110 mg).
ESI-MS Found: m/z [M+H]+ 366.

Production Example 24

Production of 7-[4-(hydroxymethyl)phenyl]-2-(methylthio)pyrimido[4',5':4,5]pyrimido[1,2-b]indazol-5(7H)-one The title compound (21 mg) was produced as a yellow solid in the same manner as in Production Example 23, for which, however, 4-hydroxymethylphenylboronic acid was used in place of 3-thienylboronic acid used in Production Example 23.
ESI-MS Found: m/z [M+H]+ 390.

Production Example 25

Production of 7-(3-methylpyridin-2-yl)-2-(methylthio)pyrimido[4',5':4,5]pyrimido[1,2-b]indazol-5(7H)-one 1) Production of ethyl 4-{[1-(3-methylpyridin-2-yl)-1H-indazol-3-yl]amino}-2-(methylthio)pyrimidine-5-carboxylate N,N'-dimethylethylenediamine (270 mg) was added to a 1,4-dioxane (50 mL) solution of the compound (988 mg) obtained in Production Example 1-1, copper(I) iodide (286 mg), 2-bromo-3-methylpyridine (715 mg) and potassium carbonate (622 mg), and stirred at 100° C. for 18 hours. The reaction liquid was cooled, then aqueous ammonia was added thereto, extracted with chloroform, washed with saturated saline water, and dried with anhydrous magnesium sulfate. The solvent was evaporated away, and the residue was purified through basic silica gel column chromatography (chloroform) to give the title compound as a yellow crystal (449 mg).

$^1$H-NMR (400 MHz, CDCl$_3$) δ: 10.54 (1H, s), 8.84-8.81 (3H, m), 7.72 (1H, d, J=8.0 Hz), 7.60-7.56 (1H, m), 7.31 (1H, t, J=8.0 Hz), 7.17 (1H, t, J=4.8 Hz), 4.43 (2H, q, J=7.1 Hz), 2.17 (3H, s), 1.43 (3H, t, J=7.1 Hz).

ESI-MS Found: m/z [M+H]+ 408.

2) Production of 4-{[1-(3-methylpyridin-2-yl)-1H-indazol-3-yl]amino}-2-(methylthio)pyrimidine-5-carboxylic acid Aqueous 5 N sodium hydroxide solution (1 mL) was added to a methanol (2 mL) solution of the compound (114 mg) obtained in Production Example 25-1, and stirred for 1 hour. Methanol was evaporated away under reduced pressure, then the residue was made to have a pH of about 2 with aqueous 5 N hydrochloric acid solution added thereto, and stirred for 3.5 hours. Water (50 mL) was added to the reaction solution, and the precipitated solid was collected through filtration, washed with distilled water and ethyl acetate in that order, and dried to give the title compound.

3) Production of 7-(3-methylpyridin-2-yl)-2-(methylthio)pyrimido[4',5':4,5]pyrimido[1,2-b]indazol-5(7H)-one An N,N-dimethylformamide (3 mL) solution of the compound obtained in Production Example 25-2, 1-(3-dimethylaminopropyl)-3-ethylcarbodiimide hydrochloride (77.9 mg) and 1-hydroxybenzotriazole monohydrate (41.5 mg) was stirred for 6 hours. The reaction liquid was concentrated under reduced pressure, and the precipitated solid was collected through filtration, washed with distilled water and ethyl acetate in that order, and dried to give the title compound as a yellow solid (84 mg).

$^1$H-NMR (400 MHz, DMSO-d$_6$) δ: 9.26 (1H, s), 8.50 (1H, d, J=5.1 Hz), 8.34 (1H, d, J=8.0 Hz), 8.04 (1H, td, J=7.1, 1.9 Hz), 7.88 (1H, t, J=8.0 Hz), 7.77 (1H, d, J=8.0 Hz), 7.71 (1H, d, J=7.1 Hz), 7.59 (1H, t, J=8.0 Hz), 7.46 (1H, dd, J=7.1, 5.1 Hz), 2.64 (3H, s).

ESI-MS Found: m/z [M+H]+ 361.

Production Example 26

Production of 2-(methylthio)-7-pyridin-3-yl-pyrimido[4',5':4,5]pyrimido[1,2-b]indazol-5(7H)-one 1) Production of ethyl 2-(methylthio)-4-[(1-pyridin-3-yl-1H-indazol-3-yl)amino]pyrimidine-5-carboxylate The title compound was produced as a white solid in the same manner as in Production Example 25-1, for which, however, 3-bromopyridine was used in place of 2-bromo-3-methylpyridine used in Production Example 25-1.

ESI-MS Found: m/z [M+H]+ 407.

2) Production of 2-(methylthio)-4-[(1-pyridin-3-yl-1H-indazol-3-yl)amino]pyrimidine-5-carboxylic acid The title compound was produced as a white solid in the same manner as in Production Example 25-2, for which, however, ethyl 2-(methylthio)-4-[(1-pyridin-3-yl-1H-indazol-3-yl)amino]pyrimidine-5-carboxylate was used in place of ethyl 4-{[1-(3-methylpyridin-2-yl)-1H-indazol-3-yl]amino}-2-(methylthio)pyrimidine-5-carboxylate used in Production Example 25-2.

3) Production of 2-(methylthio)-7-pyridin-3-yl-pyrimido[4',5':4,5]pyrimido[1,2-b]indazol- The title compound was produced as a yellow solid in the same manner as in Production Example 25-3, for which, however, 2-(methylthio)-4-[(1-pyridin-3-yl-1H-indazol-3-yl)amino]pyrimidine-5-carboxylic acid was used in place of 4-{[1-(3-methylpyridin-2-yl)-1H-indazol-3-yl]amino}-2-(methylthio)pyrimidine-5-carboxylic acid used in Production Example 25-3.

ESI-MS Found: m/z [M+H]+ 361.

Production Example 27

Production of 2-(methylthio)-7-pyridin-4-yl-pyrimido[4',5':4,5]pyrimido[1,2-b]indazol-5(7H)-one 1) Production of ethyl 2-(methylthio)-4-[(1-pyridin-4-yl-1H-indazol-3-yl)amino]pyrimidine-5-carboxylate The title compound was produced as a white solid in the same manner as in Production Example 25-1, for which, however, 4-bromopyridine was used in place of 2-bromo-3-methylpyridine used in Production Example 25-1.

ESI-MS Found: m/z [M+H]+ 407.

2) Production of 2-(methylthio)-4-[(1-pyridin-4-yl-1H-indazol-3-yl)amino]pyrimidine-5-carboxylic acid The title compound was produced as a white solid in the same manner as in Production Example 25-2, for which, however, ethyl 2-(methylthio)-4-[(1-pyridin-4-yl-1H-indazol-3-yl)amino]pyrimidine-5-carboxylate was used in place of ethyl 4-{[1-(3-methylpyridin-2-yl)-1H-indazol-3-yl]amino}-2-(methylthio)pyrimidine-5-carboxylate used in Production Example 25-2.

3) Production of 2-(methylthio)-7-pyridin-4-yl-pyrimido[4',5':4,5]pyrimido[1,2-b]indazol-5(7H)-one The title compound was produced as a yellow solid in the same manner as in Production Example 25-3, for which, however, 2-(methylthio)-4-[(1-pyridin-4-yl-1H-indazol-3-yl)amino]pyrimidine-5-carboxylic acid was used in place of 4-{[1-(3-methylpyridin-2-yl)-1H-indazol-3-yl]amino}-2-(methylthio)pyrimidine-5-carboxylic acid used in Production Example 25-3.

ESI-MS Found: m/z [M+H]+ 361.

Production Example 28

Production of 2-(methylthio)-7-pyrimidin-5-yl-pyrimido[4',5':4,5]pyrimido[1,2-b]indazol-5(7H)-one 1) Production of ethyl 2-(methylthio)-4-[(1-pyrimidin-5-yl-1H-indazol-3-yl)amino]pyrimidine-5-carboxylate The title compound was produced as a white solid in the same manner as in Production Example 25-1, for which, however, 5-bromopyrimidine was used in place of 2-bromo-3-methylpyridine used in Production Example 25-1.

ESI-MS Found: m/z [M+H]+ 407.

2) Production of 2-(methylthio)-4-[(1-pyrimidin-5-yl-1H-indazol-3-yl)amino]pyrimidine-5-carboxylic acid The title compound was produced as a white solid in the same manner as in Production Example 25-2, for which, however, ethyl 2-(methylthio)-4-[(1-pyrimidin-5-yl-1H-indazol-3-yl)amino]pyrimidine-5-carboxylate was used in place of ethyl 4-{[1-(3-methylpyridin-2-yl)-1H-indazol-3-yl]amino}-2-(methylthio)pyrimidine-5-carboxylate used in Production Example 25-2.

3) Production of 2-(methylthio)-7-pyrimidin-5-yl-pyrimido[4',5':4,5]pyrimido[1,2-b]indazol-5(7H)-one The title compound was produced as a yellow solid in the same manner as in Production Example 25-3, for which, however, 2-(methylthio)-4[(1-pyrimidin-5-yl-1H-indazol-3-yl)amino]pyrimidine-5-carboxylic acid was used in place of 4-{[1-(3-methylpyridin-2-yl)-1H-indazol-3-yl]amino}-2-(methylthio)pyrimidine-5-carboxylic acid used in Production Example 25-3.

ESI-MS Found: m/z [M+H]+ 362.

Production Example 29

Production of 2-(methylthio)-7-pyrimidin-2-yl-pyrimido[4',5':4,5]pyrimido[1,2-b]indazol-5(7H)-one 1) Production of ethyl 2-(methylthio)-4-[(1-pyrimidin-2-yl-1H-indazol-3-yl)amino]pyrimidine-5-carboxylate The title compound was produced as a white solid in the same manner as in Production Example 25-1, for which, however, 2-bromopyrimidine was used in place of 2-bromo-3-methylpyridine used in Production Example 25-1.

ESI-MS Found: m/z [M+H]+ 407.

2) Production of 2-(methylthio)-4-[(1-pyrimidin-2-yl-1H-indazol-3-yl)amino]pyrimidine-5-carboxylic acid The title compound was produced as a white solid in the same manner as in Production Example 25-2, for which, however, ethyl 2-(methylthio)-4-[(1-pyrimidin-2-yl-1H-indazol-3-yl)amino]pyrimidine-5-carboxylate was used in place of ethyl 4-{[1-(3-methylpyridin-2-yl)-1H-indazol-3-yl]amino}-2-(methylthio)pyrimidine-5-carboxylate used in Production Example 25-2.

3) Production of 2-(methylthio)-7-pyrimidin-2-yl-pyrimido[4',5':4,5]pyrimido[1,2-b]indazol-5(7H)-one The title compound was produced as a yellow solid in the same manner as in Production Example 25-3, for which, however, 2-(methylthio)-4-[(1-pyrimidin-2-yl-1H-indazol-3-yl)amino]pyrimidine-5-carboxylic acid was used in place of 4-{[1-(3-methylpyridin-2-yl)-1H-indazol-3-yl]amino}-2-(methylthio)pyrimidine-5-carboxylic acid used in Production Example 25-3.

ESI-MS Found: m/z [M+H]+ 362.

Production Example 30

Production of 2-(methylthio)-7-pyrazin-2-yl-pyrimido[4',5':4,5]pyrimido[1,2-b]indazol-5(7H)-one 1) Production of ethyl 2-(methylthio)-4-[(1-pyrazin-2-yl-1H-indazol-3-yl)amino]pyrimidine-5-carboxylate The title compound was produced as a white solid in the same manner as in Production Example 25-1, for which, however, 2-iodopyrazine was used in place of 2-bromo-3-methylpyridine used in Production Example 25-1.

ESI-MS Found: m/z [M+H]+ 407.

2) Production of 2-(methylthio)-4-[(1-pyrazin-2-yl-1H-indazol-3-yl)amino]pyrimidine-5-carboxylic acid The title compound was produced as a white solid in the same manner as in Production Example 25-2, for which, however, ethyl 2-(methylthio)-4-[(1-pyrazin-2-yl-1H-indazol-3-yl)amino]pyrimidine-5-carboxylate was used in place of ethyl 4-{[1-(3-methylpyridin-2-yl)-1H-indazol-3-yl]amino}-2-(methylthio)pyrimidine-5-carboxylate used in Production Example 25-2.

3) Production of 2-(methylthio)-7-pyrazin-2-yl-pyrimido[4',5':4,5]pyrimido[1,2-b]indazol-5(7H)-one The title compound was produced as a yellow solid in the same manner as in Production Example 25-3, for which, however, 2-(methylthio)-4-[(1-pyrazin-2-yl-1H-indazol-3-yl)amino]pyrimidine-5-carboxylic acid was used in place of 4-{[1-(3-methylpyridin-2-yl)-1H-indazol-3-yl]amino}-2-(methylthio)pyrimidine-5-carboxylic acid used in Production Example 25-3.

ESI-MS Found: m/z [M+H]+ 362.

Production Example 31

Production of 2-(methylthio)-7-(1,3-thiazol-2-yl)pyrimido[4',5':4,5]pyrimido[1,2-b]indazol-5(7H)-one 1) Production of 2-(1H-indazol-3-yl)-1H-isoindole-1,3(2H)-dione A 1,4-dioxane (0.5 L) solution of 1H-indazol-3-amine (3.3 g) and phthalic anhydride (14.8 g) was stirred with heating under reflux for 15 hours. After cooled to room temperature, the reaction solution was evaporated under reduced pressure, water (50 mL) was added to the residue, and the precipitated solid was collected through filtration, washed with distilled water and ethyl acetate in that order, and dried to give the title compound as a white solid (26.0 g).

2) Production of 2-[1-(1,3-thiazol-2-yl)-1H-indazol-3-yl]-1H-isoindole-1,3(2H)-dione N,N'-dimethylcyclohexane-1,2-diamine (270 mg) was added to a 1,4-dioxane (10 mL) solution of the compound (260 mg) obtained in Production Example 31-1, copper(I) iodide (286 mg), 2-bromo-1,3-thiazole (715 mg) and potassium phosphate (622 mg), and stirred at 100° C. for 18 hours. The reaction liquid was cooled, then aqueous ammonia was added thereto, and extracted with chloroform, then washed with saturated saline water, and dried with anhydrous magnesium sulfate. The solvent was evaporated away, and the residue was purified through basic silica gel chromatography (hexane/ethyl acetate) to give the title compound as a white crystal (214 mg).

¹H-NMR (400 MHz, CDCl₃) δ: 8.70 (1H, dt, J=8.9, 0.8 Hz), 8.05 (1H, d, J=3.2 Hz), 8.04 (1H, d, J=2.9, 1.9 Hz), 7.87 (1H, d, J=3.2 Hz), 7.86 (1H, d, J=2.9 Hz), 7.66-7.61 (3H, m), 7.39-7.35 (1H, m), 7.09 (1H, d, J=3.7 Hz).

ESI-MS Found: m/z [M+H]+ 347.

3) Production of 1-(1,3-thiazol-2-yl)-1H-indazole-3-amine

A tetrahydrofuran (5 mL) solution of the compound (214 mg) obtained in Production Example 31-2 and methylhydrazine (150 mg) was stirred at room temperature for 18 hours. The solvent was evaporated away, and the residue was purified through basic silica gel chromatography (hexane/ethyl acetate) to give the title compound as a white crystal (104 mg).

¹H-NMR (400 MHz, CDCl₃) δ: 8.50 (1H, d, J=8.5 Hz), 7.57 (1H, d, J=8.5 Hz), 7.53 (1H, d, J=3.9 Hz), 7.26 (1H, dd, J=7.1, 0.7 Hz), 7.24 (1H, dd, J=7.1, 0.7 Hz), 6.92 (1H, d, J=3.9 Hz), 4.42 (2H, s).

ESI-MS Found: m/z [M+H]+ 217.

4) Production of ethyl 2-(methylthio)-4-{[1-(1,3-thiazol-2-yl)-1H-indazol-3-yl]amino}pyrimidine-5-carboxylate N,N-diisopropylethylamine (100 mg) was added to a 1,4-dioxane (10 mL) solution of the compound (104 mg) obtained in Production Example 31-3 and ethyl 4-chloro-2-(methylthio)pyrimidine-5-carboxylate (150 mg), and stirred with heating under reflux for 15 hours. After cooled to room temperature, the reaction solution was evaporated under reduced pressure, water (50 mL) was added to the residue, and the precipitated solid was collected through filtration, washed with distilled water and ethyl acetate in that order, and dried to give the title compound as a white solid (253 mg).

¹H-NMR (400 MHz, CDCl₃) δ: 10.72 (1H, s), 8.86 (1H, s), 8.63 (1H, d, J=8.0 Hz), 7.76 (1H, d, J=8.0 Hz), 7.62-7.57 (1H, m), 7.61 (1H, d, J=3.7 Hz), 7.30 (1H, dd, J=7.1, 1.0 Hz), 7.03 (1H, d, J=3.4 Hz), 4.45 (2H, q, J=7.2 Hz), 2.40 (2H, s), 1.45 (3H, t, J=7.2 Hz).

ESI-MS Found: m/z [M+H]+ 413.

5) Production of 2-(methylthio)-4-{[1-(1,3-thiazol-2-yl)-1H-indazol-3-yl]amino}pyrimidine-5-carboxylic acid Aqueous 5 N sodium hydroxide solution (1 mL) was added to a methanol (2 mL) solution of the compound (253 mg) obtained in Production Example 31-4, and stirred for 1 hour. Methanol was evaporated away under reduced pressure, and the residue was made to have a pH of about 2 with aqueous 5 N hydrochloric acid solution added thereto, and stirred for 3.5 hours. Water (50 mL) was added to the reaction solution, and the precipitated solid was collected through filtration, washed with distilled water and ethyl acetate in that order, and dried to give the title compound.

6) Production of 2-(methylthio)-7-(1,3-thiazol-2-yl)pyrimido[4',5':4,5]pyrimido[1,2-b]indazol-5(7H)-one An N,N-dimethylformamide (10 mL) solution of the compound obtained in Production Example 31-5, 1-(3-dimethylaminopropyl)-3-ethylcarbodiimide hydrochloride (192 mg) and 1-hydroxybenzotriazole monohydrate (78 mg) was stirred for 6 hours. The reaction liquid was concentrated under reduced pressure, and the precipitated solid was collected through filtration, washed with distilled water and ethyl acetate in that order, and dried to give the title compound as a yellow solid (144 mg).

¹H-NMR (400 MHz, CDCl₃) δ: 9.28 (1H, s), 8.36 (1H, d, J=7.8 Hz), 7.94 (1H, t, J=7.8 Hz), 7.85 (1H, d, J=3.4 Hz), 7.78 (1H, d, J=3.4 Hz), 7.70 (1H, d, J=7.6 Hz), 7.65 (1H, t, J=7.6 Hz), 2.64 (3H, s).

ESI-MS Found: m/z [M+H]+ 367.

Production Example 32

Production of 2-(methylthio)-7-(1,3-thiazol-4-yl)pyrimido[4',5':4,5]pyrimido[1,2-b]indazol-5(7H)-one 1) Production of 2-{1-[2-(trimethylsilyl)-1,3-thiazolyl-4-yl]-1H-indazol-3-yl}-1H-isoindole-1,3(2H)-dione The title compound was produced as a white solid in the same manner as in Production Example 31-2, for which, however, 4-bromo-2-(trimethylsilyl)-1,3-thiazole was used in place of 2-bromo-1,3-thiazole used in Production Example 31-2.

ESI-MS Found: m/z [M+H]+ 419.

2) Production of 1-[2-(trimethylsilyl)-1,3-thiazolyl-4-yl]-1H-indazol-3-amine

The title compound was produced as a white solid in the same manner as in Production Example 31-3, for which, however, 2-{1-[2-(trimethylsilyl)-1,3-thiazolyl-4-yl]-1H-indazol-3-yl}-1H-isoindole-1,3(2H)-dione was used in place of 2-[1-(1,3-thiazol-2-yl)-1H-indazol-3-yl]-1H-isoindole-1,3(2H)-dione used in Production Example 31-3.

ESI-MS Found: m/z [M+H]+ 289.

3) Production of ethyl 2-(methylthio)-4-({1-[2-(trimethylsilyl)-1,3-thiazol-4-yl]-1H-indazol-3-yl}amino)pyrimidine-5-carboxylate The title compound was produced as a white solid in the same manner as in Production Example 31-4, for which, however, 1-[2-(trimethylsilyl)-1,3-thiazol-4-yl]-1H-indazol-3-amine was used in place 1-(1,3-thiazol-2-yl)-1H-indazol-3-amine used in Production Example 31-4.

ESI-MS Found: m/z [M+H]+ 485.

4) Production of 2-(methylthio)-4-{[1-(1,3-thiazol-4-yl)-1H-indazol-3-yl]amino}pyrimidine-5-carboxylic acid The title compound was produced as a white solid in the same manner as in Production Example 31-5, for which, however, ethyl 2-(methylthio)-4-({1-[2-(trimethylsilyl)-1,3-thiazol-4-yl]-1H-indazol-3-yl}amino)pyrimidine-5-carboxylate was used in place ethyl 2-(methylthio)-4-{[1-(1,3-thiazol-2-yl)-1H-indazol-3-yl]amino}pyrimidine-5-carboxylate used in Production Example 31-5.

5) Production of 2-(methylthio)-7-(1,3-thiazol-4-yl)pyrimido[4',5':4,5]pyrimido[1,2-b]indazol-5(7H)-one The title compound was produced as a white solid in the same manner as in Production Example 31-6, for which, however, 2-(methylthio)-4-{[1-(1,3-thiazol-4-yl)-1H-indazol-3-yl]amino}pyrimidine-5-carboxylic acid was used in place of 2-(methylthio)-4-{[1-(1,3-thiazol-2-yl)-1H-indazol-3-yl]amino}pyrimidine-5-carboxylic acid used in Production Example 31-6.

ESI-MS Found: m/z [M+H]+ 367.

Production Example 33

Production of 7-(3-furyl)-2-(methylthio)pyrimido[4',5':4,5]pyrimido[1,2-b]indazol-5(7H)-one 1) Production of 2-[1-(3-furyl)-1H-indazol-3-yl]-1H-isoindole-1,3(2H)-dione The title compound was produced as a white solid in the same manner as in Production Example 31-2, for which, however, 3-bromofuran was used in place of 2-bromo-1,3-thiazole used in Production Example 31-2.

ESI-MS Found: m/z [M+H]+ 330.

2) Production of 1-(3-furyl)-1H-indazol-3-amine

The title compound was produced as a white solid in the same manner as in Production Example 31-3, for which, however, 2-[1-(3-furyl)-1H-indazol-3-yl]-1H-isoindole-1,3(2H)-dione was used in place of 2-[1-(1,3-thiazol-2-yl)-1H-indazol-3-yl]-1H-isoindole-1,3(2H)-dione used in Production Example 31-3.

ESI-MS Found: m/z [M+H]+ 200.

3) Production of ethyl 4-{[1-(3-furyl)-1H-indazol-3-yl]amino}-2-(methylthio)pyrimidine-5-carboxylate The title compound was produced as a white solid in the same manner as in Production Example 31-4, for which, however, 1-(3-furyl)-1H-indazol-3-amine was used in place 1-(1,3-thiazolyl-2-yl)-1H-indazol-3-amine used in Production Example 31-4.

ESI-MS Found: m/z [M+H]+ 396.

4) Production of 4-{[1-(3-furyl)-1H-indazol-3-yl]amino}-2-(methylthio)pyrimidine-5-carboxylic acid The title compound was produced as a white solid in the same manner as in Production Example 31-5, for which, however, ethyl 4-{[1-(3-furyl)-1H-indazol-3-yl]amino}-2-(methylthio)pyrimidine-5-carboxylate was used in place ethyl 2-(methylthio)-4-{[1-(1,3-thiazol-2-yl)-1H-indazol-3-yl]amino}pyrimidine-5-carboxylate used in Production Example 31-5.

5) Production of 7-(3-furyl)-2-(methylthio)pyrimido[4',5':4,5]pyrimido[1,2-b]indazol-5(7H)-one The title compound was produced as a white solid in the same manner as in Production Example 31-6, for which, however, 4-{[1-(3-furyl)-1H-indazol-3-yl]amino}-2-(methylthio)pyrimidine-5-carboxylic acid was used in place of 2-(methylthio)-4-{[1-(1,3-thiazol-2-yl)-1H-indazol-3-yl]amino}pyrimidine-5-carboxylic acid used in Production Example 31-6.

ESI-MS Found: m/z [M+H]+ 350.

Production Example 34

Production of 7-(1-methyl-1H-imidazol-2-yl)-2-(methylthio)pyrimido[4',5':4,5]pyrimido[1,2-b]indazol-5(7H)-one 1) Production of 2-[1-(1-methyl-1H-imidazol-2-yl)-1H-indazol-3-yl]-1H-isoindole-1,3(2H)-dione The title compound was produced as a white solid in the same manner as in Production Example 31-2, for which, however, 2-bromo-1-methyl-1H-imidazole was used in place of 2-bromo-1,3-thiazole used in Production Example 31-2.

ESI-MS Found: m/z [M+H]+ 344.

2) Production of 1-(1-methyl-1H-imidazol-2-yl)-1H-indazol-3-amine

The title compound was produced as a white solid in the same manner as in Production Example 31-3, for which, however, 2-[1-(1-methyl-1H-imidazol-2-yl)-1H-indazol-3-yl]-1H-isoindole-1,3(2H)-dione was used in place of 2-[1-(1,3-thiazol-2-yl)-1H-indazol-3-yl]-1H-isoindole-1,3(2H)-dione used in Production Example 31-3.

ESI-MS Found: m/z [M+H]+ 214.

3) Production of ethyl 4-{[1-(1-methyl-1H-imidazol-2-yl)-1H-indazol-3-yl]amino}-2-(methylthio)pyrimidine-5-carboxylate The title compound was produced as a white solid in the same manner as in Production Example 31-4, for which, however, 1-(1-methyl-1H-imidazol-2-yl)-1H-indazol-3-amine was used in place 1-(1,3-thiazol-2-yl)-1H-indazol-3-amine used in Production Example 31-4.

ESI-MS Found: m/z [M+H]+ 410.

4) Production of 4-{[1-(1-methyl-1H-imidazol-2-yl)-1H-indazol-3-yl]amino}-2-(methylthio)pyrimidine-5-carboxylic acid The title compound was produced as a white solid in the same manner as in Production Example 31-5, for which, however, ethyl 4-{[1-(1-methyl-1H-imidazol-2-yl)-1H-indazol-3-yl]amino}-2-(methylthio)pyrimidine-5-carboxylate was used in place ethyl 2-(methylthio)-4-{[1-(1,3-thiazol-2-yl)-1H-indazol-3-yl]amino}pyrimidine-5-carboxylate used in Production Example 31-5.

5) Production of 7-(1-methyl-1H-imidazol-2-yl)-2-(methylthio)pyrimido[4',5':4,5]pyrimido[1,2-b]indazol-5(7H)-one The title compound was produced as a white solid in the same manner as in Production Example 31-6, for which, however, 4-{[1-(1-methyl-1H-imidazol-2-yl)-1H-indazol-3-yl]amino}-2-(methylthio)pyrimidine-5-carboxylic acid was used in place of 2-(methylthio)-4-{[1-(1,3-thiazol-2-yl)-1H-indazol-3-yl]amino}pyrimidine-5-carboxylic acid used in Production Example 31-6.

ESI-MS Found: m/z [M+H]+ 364.

Production Example 35

Production of 7-cyclopropyl-2-(methylthio)pyrimido[4',5':4,5]pyrimido[1,2-b]indazol-5(7H)-one

1) Production of 2-(1-cyclopropyl-1H-indazol-3-yl)-1H-isoindole-1,3(2H)-dione A tetrahydrofuran solution (10 mL) of the compound (135 mg) obtained in Production Example 31-1, copper(II) acetate (127 mg) and cyclohexylboronic acid (80 mg) was stirred with heating under reflux for 15 hours. Aqueous 30% ammonia and saturated saline water were added in that order to the reaction liquid, and extracted with chloroform. The organic layer was washed with saturated saline water, dried with anhydrous magnesium sulfate, and the solvent was evaporated away. The crude product was purified through silica gel column chromatography (hexane/ethyl acetate) to give the title compound as a yellow solid (23.5 mg).

ESI-MS Found: m/z [M+H]+ 304.

2) Production of 1-cyclopropyl-1H-indazol-3-amine

The title compound was produced as a white solid in the same manner as in Production Example 31-3, for which, however, 2-(1-cyclopropyl-1H-indazol-3-yl)-1H-isoindole-1,3(2H)-dione was used in place of 2-[1-(1,3-thiazol-2-yl)-1H-indazol-3-yl]-1H-isoindole-1,3(2H)-dione used in Production Example 31-3.

ESI-MS Found: m/z [M+H]+ 174.

3) Production of ethyl 4-[(1-cyclopropyl-1H-indazol-3-yl)amino]-2-(methylthio)pyrimidine-5-carboxylate The title compound was produced as a white solid in the same manner as in Production Example 31-4, for which, however, 1-cyclopropyl-1H-indazol-3-amine was used in place 1-(1,3-thiazol-2-yl)-1H-indazol-3-amine used in Production Example 31-4.

ESI-MS Found: m/z [M+H]+ 370.

4) Production of 4-[(1-cyclopropyl-1H-indazol-3-yl)amino]-2-(methylthio)pyrimidine-5-carboxylic acid The title compound was produced as a white solid in the same manner as in Production Example 31-5, for which, however, ethyl 4-[(1-cyclopropyl-1H-indazol-3-yl)amino]-2-(methylthio)pyrimidine-5-carboxylate was used in place ethyl 2-(methylthio)-4-{[1-(1,3-thiazol-2-yl)-1H-indazol-3-yl]amino}pyrimidine-5-carboxylate used in Production Example 31-5.

5) Production of 7-cyclopropyl-2-(methylthio)pyrimido[4',5':4,5]pyrimido[1,2-b]indazol-5(7H)-one The title compound was produced as a white solid in the same manner as in Production Example 31-6, for which, however, 4-[(1-cyclopropyl-1H-indazol-3-yl)amino]-2-(methylthio)pyrimidine-5-carboxylic acid was used in place of 2-(methylthio)-4-{[1-(1,3-thiazol-2-yl)-1H-indazol-3-yl]amino}pyrimidine-5-carboxylic acid used in Production Example 31-6.

ESI-MS Found: m/z [M+H]+ 324.

Production Example 36

Production of 9-hydroxy-2-(methylthio)-7-pyridin-2-yl-pyrimido[4',5':4,5]pyrimido[1,2-b]indazol-5(7H)-one

1) Production of 2-fluoro-4-[(4-methoxybenzyl)oxy]benzonitrile

4-Methoxybenzyl chloride (5.0 g) and potassium carbonate (8.3 g) were added to an acetone (0.5 L) solution of 2-fluoro-4-hydroxybenzonitrile (4.1 g), and stirred with heating under reflux for 15 hours. After cooled to room temperature, the reaction solution was evaporated under reduced pressure, water (50 mL) was added to the residue, extracted with ethyl acetate, dried with sodium sulfate and concentrated under reduced pressure. The crude product was purified through silica gel column chromatography (hexane/ethyl acetate) to give the title compound as a white solid (7.2 g).

ESI-MS Found: m/z [M+H]+ 258.

2) Production of 6-[(4-methoxybenzyl)oxy]-1H-indazol-3-amine

Hydrazine monohydrate (2 g) was added to a butanol (0.5 L) solution of the compound (7.2 g) obtained in Production Example 36-1, and stirred with heating under reflux for 15 hours. After cooled to room temperature, the reaction solution was evaporated under reduced pressure, water (50 mL) was added to the residue, extracted with ethyl acetate, dried with sodium sulfate and concentrated under reduced pressure. The crude product was purified through silica gel column chromatography (hexane/ethyl acetate) to give the title compound as a white solid (6.6 g).

ESI-MS Found: m/z [M+H]+ 270.

3) Production of ethyl 4-({6-[(4-methoxybenzyl)oxy]-1H-indazol-3-yl}amino)-2-(methylthio)pyrimidine-5-carboxylate N,N-diisopropylethylamine (19.4 g) and the compound (6.6 g) obtained in Production Example 36-2 were added to a tetrahydrofuran (0.2 L) solution of ethyl 4-chloro-2-(methylthio)pyrimidine-5-carboxylate (12.22 g), and stirred with heating under reflux for 15 hours. After cooled to room temperature, the reaction solution was evaporated under reduced pressure, water (50 mL) was added to the residue, and the precipitated solid was collected through filtration, washed with distilled water and ethyl acetate in that order and dried to give the title compound as a white solid (8.7 g).

ESI-MS Found: m/z [M+H]+ 466.

4) Production of ethyl 4-({6-[(4-methoxybenzyl)oxy]-1-pyridin-2-yl-1H-indazol-3-yl}amino)-2-(methylthio)pyrimidine-5-carboxylate N,N'-dimethylethylenediamine (270 mg) was added to a 1,4-dioxane (50 mL) solution of the compound (1.0 g) obtained in Production Example 36-3, copper(I) iodide (286 mg), 2-bromopyridine (715 mg) and potassium carbonate (622 mg), and stirred at 100° C. for 18 hours. The reaction liquid was cooled, then aqueous ammonia was added thereto, extracted with chloroform, washed with saturated saline water, and dried with anhydrous magnesium sulfate. The solvent was evaporated away, and the residue was purified through basic silica gel chromatography (chloroform) to give the title compound as a white solid (830 mg).
ESI-MS Found: m/z [M+H]+ 543.

5) Production of 4-({6-[(4-methoxybenzyl)oxy]-1-pyridin-2-yl-1H-indazol-3-yl}amino)-2-(methylthio)pyrimidine-5-carboxylic acid Aqueous 5 N sodium hydroxide solution (3 mL) was added to a methanol (20 mL) solution of the compound (830 mg) obtained in Production Example 36-4, and stirred for 1 hour. Methanol was evaporated away under reduced pressure, and the residue was made to have a pH of about 2 with aqueous 5 N hydrochloric acid solution added thereto, and stirred for 3.5 hours. Water (50 mL) was added to the reaction solution, and the precipitated solid was collected through filtration, washed with distilled water and ethyl acetate in that order, and dried to give the title compound.

6) Production of 9-[(4-methoxybenzyl)oxy]-2-(methylthio)-7-pyridin-2-yl-pyrimido[4',5':4,5]pyrimido[1,2-b]indazol-5(7H)-one An N,N-dimethylformamide (20 mL) solution of the compound obtained in Production Example 36-5, 1-(3-dimethylaminopropyl)-3-ethylcarbodiimide hydrochloride (380 mg) and 1-hydroxybenzotriazole monohydrate (160 mg) was stirred for 6 hours. The reaction liquid was concentrated under reduced pressure, and the precipitated solid was collected through filtration, washed with distilled water and ethyl acetate in that order, and dried to give the title compound as a yellow solid (503 mg).
ESI-MS Found: m/z [M+H]+ 497.

7) Production of 9-hydroxy-2-(methylthio)-7-pyridin-2-yl-pyrimido[4',5':4,5]pyrimido[1,2-b]indazol-5(7H)-one A trifluoroacetic acid (5 mL) solution of the compound (200 mg) obtained in Production Example 36-5 was stirred at 60° C. for 5 hours. The reaction solution was evaporated under reduced pressure, and the residue was purified through silica gel column chromatography (hexane/ethyl acetate) to give the title compound as a white solid (103 mg).
ESI-MS Found: m/z [M+H]+ 377.

Production Example 37

Production of 10-hydroxy-2-(methylthio)-7-pyridin-2-yl-pyrimido[4',5':4,5]pyrimido[1,2-b]indazol-5(7H)-one 1) Production of 2-fluoro-5-[(4-methoxybenzyl)oxy]benzonitrile The title compound was produced as a white solid in the same manner as in Production Example 36-1, for which, however, 2-fluoro-5-hydroxybenzonitrile was used in place of 2-fluoro-4-hydroxybenzonitrile used in Production Example 36-1.
ESI-MS Found: m/z [M+H]+ 258.

2) Production of 5-[(4-methoxybenzyl)oxy]-1H-indazol-3-amine

The title compound was produced as a white solid in the same manner as in Production Example 36-2, for which, however, 2-fluoro-5-[(4-methoxybenzyl)oxy]benzonitrile was used in place of 2-fluoro-4-[(4-methoxybenzyl)oxy]benzonitrile used in Production Example 36-2.
ESI-MS Found: m/z [M+H]+ 270.

3) Production of ethyl 4-({5-[(4-methoxybenzyl)oxy]-1H-indazol-3-yl}amino)-2-(methylthio)pyrimidine-5-carboxylate The title compound was produced as a white solid in the same manner as in Production Example 36-3, for which, however, 5-[(4-methoxybenzyl)oxy]-1H-indazol-3-amine was used in place of 6-[(4-methoxybenzyl)oxy]-1H-indazol-3-amine used in Production Example 36-3.
ESI-MS Found: m/z [M+H]+ 466.

4) Production of ethyl 4-({5-[(4-methoxybenzyl)oxy]-1-pyridin-2-yl-1H-indazol-3-yl}amino)-2-(methylthio)pyrimidine-5-carboxylate The title compound was produced as a white solid in the same manner as in Production Example 36-4, for which, however, ethyl 4-({5-[(4-methoxybenzyl)oxy]-1H-indazol-3-yl}amino)-2-(methylthio)pyrimidine-5-carboxylate was used in place of ethyl 4-({6-[(4-methoxybenzyl)oxy]-1H-indazol-3-yl}amino)-2-(methylthio)pyrimidine-5-carboxylate used in Production Example 36-4.
ESI-MS Found: m/z [M+H]+ 543.

5) Production of 4-({5-[(4-methoxybenzyl)oxy]-1-pyridin-2-yl-1H-indazol-3-yl}amino)-2-(methylthio)pyrimidine-5-carboxylic acid The title compound was produced as a white solid in the same manner as in Production Example 36-5, for which, however, ethyl 4-({5-[(4-methoxybenzyl)oxy]-1-pyridin-2-yl-1H-indazol-3-yl}amino)-2-(methylthio)pyrimidine-5-carboxylate was used in place of ethyl 4-({6-[(4-methoxybenzyl)oxy]-1-pyridin-2-yl-1H-indazol-3-yl}amino)-2-(methylthio)pyrimidine-5-carboxylate used in Production Example 36-5.

6) Production of 10-[(4-methoxybenzyl)oxy]-2-(methylthio)-7-pyridin-2-yl-pyrimido[4',5':4,5]pyrimido[1,2-b]indazol-5(7H)-one The title compound was produced as a yellow solid in the same manner as in Production Example 36-6, for which, however, 4-({5-[(4-methoxybenzyl)oxy]-1-pyridin-2-yl-1H-indazol-3-yl}amino)-2-(methylthio)pyrimidine-5-carboxylic acid was used in place of 4-({6-[(4-methoxybenzyl)oxy]-1-pyridin-2-yl-1H-indazol-3-yl}amino)-2-(methylthio)pyrimidine-5-carboxylic acid used in Production Example 36-6.
ESI-MS Found: m/z [M+H]+ 497.

7) Production of 10-hydroxy-2-(methylthio)-7-pyridin-2-yl-pyrimido[4',5':4,5]pyrimido[1,2-b]indazol-5(7H)-one The title compound was produced as a yellow solid in the same manner as in Production Example 36-7, for which, however, 10-[(4-methoxybenzyl)oxy]-2-(methylthio)-7-pyridin-2-yl-pyrimido[4',5':4,5]pyrimido[1,2-b]indazol-5(7H)-one was used in place of 9-[(4-methoxybenzyl)oxy]-2-(methylthio)-7-pyridin-2-yl-pyrimido[4',5':4,5]pyrimido[1,2-b]indazol-5(7H)-one used in Production Example 36-7.
ESI-MS Found: m/z [M+H]+ 377.

Production Example 38

Production of 11-hydroxy-2-(methylthio)-7-pyridin-2-yl-pyrimido[4',5':4,5]pyrimido[1,2-b]indazol-5(7H)-one

1) Production of 2-fluoro-6-[(4-methoxybenzyl)oxy]benzonitrile

4-Methoxybenzyl alcohol (5.0 g) and cesium carbonate (8.3 g) were added to an N,N-dimethylformamide (0.5 L) solution of 2,6-difluorobenzonitrile (7.0 g), and stirred for 15 hours. The reaction solution was evaporated under reduced pressure, water (50 mL) was added to the residue, extracted with ethyl acetate, dried with sodium sulfate, and concentrated under reduced pressure. The crude product was purified through silica gel column chromatography (hexane/ethyl acetate) to give the title compound as a white solid (6.6 g).
ESI-MS Found: m/z [M+H]+ 258.

2) Production of 4-[(4-methoxybenzyl)oxy]-1H-indazol-3-amine

The title compound was produced as a white solid in the same manner as in Production Example 36-2, for which, however, 2-fluoro-6-[(4-methoxybenzyl)oxy]benzonitrile was used in place of 2-fluoro-4-[(4-methoxybenzyl)oxy]benzonitrile used in Production Example 36-2.
ESI-MS Found: m/z [M+H]+ 270.

3) Production of ethyl 4-({4-[(4-methoxybenzyl)oxy]-1H-indazol-3-yl}amino)-2-(methylthio)pyrimidine-5-carboxylate The title compound was produced as a white solid in the same manner as in Production Example 36-3, for which, however, 4-[(4-methoxybenzyl)oxy]-1H-indazol-3-amine was used in place of 5-[(4-methoxybenzyl)oxy]-1H-indazol-3-amine used in Production Example 36-3.
ESI-MS Found: m/z [M+H]+ 466.

4) Production of ethyl 4-({4-[(4-methoxybenzyl)oxy]-1-pyridin-2-yl-1H-indazol-3-yl}amino)-2-(methylthio)pyrimidine-5-carboxylate The title compound was produced as a white solid in the same manner as in Production Example 36-4, for which, however, ethyl 4-({4-[(4-methoxybenzyl)oxy]-1H-indazol-3-yl}amino)-2-(methylthio)pyrimidine-5-carboxylate was used in place of ethyl 4-({6-[(4-methoxybenzyl)oxy]-1H-indazol-3-yl}amino)-2-(methylthio)pyrimidine-5-carboxylate used in Production Example 36-4.
ESI-MS Found: m/z [M+H]+ 543.

5) Production of 4-({4-[(4-methoxybenzyl)oxy]-1-pyridin-2-yl-1H-indazol-3-yl}amino)-2-(methylthio)pyrimidine-5-carboxylic acid The title compound was produced as a white solid in the same manner as in Production Example 36-5, for which, however, ethyl 4-({4-[(4-methoxybenzyl)oxy]-1-pyridin-2-yl-1H-indazol-3-yl}amino)-2-(methylthio)pyrimidine-5-carboxylate was used in place of ethyl 4-({6-[(4-methoxybenzyl)oxy]-1-pyridin-2-yl-1H-indazol-3-yl}amino)-2-(methylthio)pyrimidine-5-carboxylate used in Production Example 36-5.

6) Production of 11-[(4-methoxybenzyl)oxy]-2-(methylthio)-7-pyridin-2-yl-pyrimido[4',5':4,5]pyrimido[1,2-b]indazol-5(7H)-one The title compound was produced as a yellow solid in the same manner as in Production Example 36-6, for which, however, 4-({4-[(4-methoxybenzyl)oxy]-1-pyridin-2-yl-1H-indazol-3-yl}amino)-2-(methylthio)pyrimidine-5-carboxylic acid was used in place of 4-({6-[(4-methoxybenzyl)oxy]-1-pyridin-2-yl-1H-indazol-3-yl}amino)-2-(methylthio)pyrimidine-5-carboxylic acid used in Production Example 36-6.
ESI-MS Found: m/z [M+H]+ 497.

7) Production of 11-hydroxy-2-(methylthio)-7-pyridin-2-yl-pyrimido[4',5':4,5]pyrimido[1,2-b]indazol-5(7H)-one The title compound was produced as a yellow solid in the same manner as in Production Example 36-7, for which, however, 11-[(4-methoxybenzyl)oxy]-2-(methylthio)-7-pyridin-2-yl-pyrimido[4',5':4,5]pyrimido[1,2-b]indazol-5(7H)-one was used in place of 9-[(4-methoxybenzyl)oxy]-2-(methylthio)-7-pyridin-2-yl-pyrimido[4',5':4,5]pyrimido[1,2-b]indazol-5(7H)-one used in Production Example 36-7.
ESI-MS Found: m/z [M+H]+ 377.

Production Example 39

Production of 2-(methylthio)-7-pyridin-2-yl-9-[2-(tetrahydro-2H-pyran-2-yloxy)ethoxy]pyrimido[4',5':4,5]pyrimido[1,2-b]indazol-5(7H)-one5(7H)-one 2-(2-Bromoethoxy)tetrahydro-2H-pyran (220 mg) and potassium carbonate (100 mg) were added to an N,N-dimethylformamide (0.5 L) solution of the compound (377 mg) obtained in Production Example 37-7, and stirred at 70° C. for 15 hours. The reaction solution was evaporated under reduced pressure, and the residue was purified through silica gel column chromatography (hexane/ethyl acetate) to give the title compound as a white solid (403 mg).
ESI-MS Found: m/z [M+H]+ 505.

Production Example 40

Production of 2-(methylthio)-7-pyridin-2-yl-10-[2-(tetrahydro-2H-pyran-2-yloxy)ethoxy]pyrimido[4',5':4,5]pyrimido[1,2-b]indazol-5(7H)-one The title compound was obtained as a yellow solid in the same manner as in Production Example 39, for which, however, 10-hydroxy-2-(methylthio)-7-pyridin-2-yl-pyrimido[4',5':4,5]pyrimido[1,2-b]indazol-5(7H)-one was used in place of 9-hydroxy-2-(methylthio)-7-pyridin-2-yl-pyrimido[4',5':4,5]pyrimido[1,2-b]indazol-5(7H)-one used in Production Example 39.
ESI-MS Found: m/z [M+H]+ 505.

Production Example 41

Production of 2-(methylthio)-7-pyridin-2-yl-11-[2-(tetrahydro-2H-pyran-2-yloxy)ethoxy]pyrimido[4',5':4,5]pyrimido[1,2-b]indazol-5(7H)-one The title compound was obtained as a yellow solid in the same manner as in Production Example 39, for which, however, 11-hydroxy-2-(methylthio)-7-pyridin-2-yl-pyrimido

[4',5':4,5]pyrimido[1,2-b]indazol-5(7H)-one was used in place of 9-hydroxy-2-(methylthio)-7-pyridin-2-yl-pyrimido[4',5':4,5]pyrimido[1,2-b]indazol-5(7H)-one used in Production Example 39.
ESI-MS Found: m/z [M+H]+ 505.

Production Example 42

Production of tert-butyl {[2-(methylthio)-5-oxo-7-pyridin-2-yl-5,7-dihydropyrimido[4',5':4,5]pyrimido[1,2-b]indazol-9-yl]oxy}acetate Tert-butyl bromoacetate (195 mg) and potassium carbonate (100 mg) were added to an N,N-dimethylformamide (0.5 mL) solution of the compound (377 mg) obtained in Production Example 37-7, and stirred at 80° C. for 15 hours. The reaction solution was evaporated under reduced pressure, and the residue was purified through silica gel column chromatography (hexane/ethyl acetate) to give the title compound as a white solid (294 mg).
ESI-MS Found: m/z [M+H]+ 491.

Production Example 43

Production of 9-methoxy-2-(methylthio)-7-pyridin-2-yl-pyrimido[4',5':4,5]pyrimido[1,2-b]indazol-5(7H)-one Potassium carbonate (50 mg) and iodomethane (25 mg) were added to an N,N-dimethylformamide solution (3 mL) of the compound (124 mg) obtained in Production Example 36-7, and stirred at room temperature for 15 hours. The reaction liquid was concentrated under reduced pressure, the precipitated solid was collected through filtration, washed with distilled water and ethyl acetate in that order, and dried to give the title compound as a yellow solid (110 mg).
ESI-MS Found: m/z [M+H]+ 391.

Production Example 44

Production of 9-fluoro-2-(methylthio)-7-pyridin-2-yl-pyrimido[4',5':4,5]pyrimido[1,2-b]indazol-5(7H)-one 1) Production of 6-fluoro-1H-indazol-3-amine The title compound was produced as a white solid in the same manner as in Production Example 36-2, for which, however, 2,4-difluorobenzonitrile was used in place of 2-fluoro-4-[(4-methoxybenzyl)oxy]benzonitrile used in Production Example 36-2.
ESI-MS Found: m/z [M+H]+ 152.

2) Production of ethyl 4-[(6-fluoro-1H-indazol-3-yl)amino]-2-(methylthio)pyrimidine-5-carboxylate The title compound was produced as a white solid in the same manner as in Production Example 36-3, for which, however, 6-fluoro-1H-indazol-3-amine was used in place of 6-[(4-methoxybenzyl)oxy]-1H-indazol-3-amine used in Production Example 36-3.
ESI-MS Found: m/z [M+H]+ 348.

3) Production of ethyl 4-[(6-fluoro-1-pyridin-2-yl-1H-indazol-3-yl)amino]-2-(methylthio)pyrimidine-5-carboxylate The title compound was produced as a white solid in the same manner as in Production Example 36-4, for which, however, ethyl 4-[(6-fluoro-1H-indazol-3-yl-amino]-2-(methylthio)pyrimidine-5-carboxylate was used in place of ethyl 4-({6-[(4-methoxybenzyl)oxy]-1H-indazol-3-yl}amino)-2-(methylthio)pyrimidine-5-carboxylate used in Production Example 36-4.
ESI-MS Found: m/z [M+H]+ 425.

4) Production of 4-[(6-fluoro-1-pyridin-2-yl-1H-indazol-3-yl)amino]-2-(methylthio)pyrimidine-5-carboxylic acid The title compound was produced as a white solid in the same manner as in Production Example 36-5, for which, however, ethyl 4-[(6-fluoro-1-pyridin-2-yl-1H-indazol-3-yl)amino]-2-(methylthio)pyrimidine-5-carboxylate was used in place of ethyl 4-({6-[(4-methoxybenzyl)oxy]-1-pyridin-2-yl-1H-indazol-3-yl}amino)-2-(methylthio)pyrimidine-5-carboxylate used in Production Example 36-5.

5) Production of 9-fluoro-2-(methylthio)-7-pyridin-2-yl-pyrimido[4',5':4,5]pyrimido[1,2-b]indazol-5(7H)-one The title compound was produced as a yellow solid in the same manner as in Production Example 36-6, for which, however, 4-[(6-fluoro-1-pyridin-2-yl-1H-indazol-3-yl)amino]-2-(methylthio)pyrimidine-5-carboxylic acid was used in place of 4-({6-[(4-methoxybenzyl)oxy]-1-pyridin-2-yl-1H-indazol-3-yl}amino)-2-(methylthio)pyrimidine-5-carboxylic acid used in Production Example 36-6.
ESI-MS Found: m/z [M+H]+ 379.

Production Example 45

Production of tert-butyl {[2-(methylthio)-5-oxo-7-(pyridin-2-yl)-5,7-dihydropyrimido[4',5':4,5]pyrimido[1,2-b]indazol-10-yl]oxy}acetate The title compound was obtained as a yellow solid in the same manner as in Production Example 42, for which, however, 10-hydroxy-2-(methylthio)-7-pyridin-2-yl-pyrimido[4',5':4,5]pyrimido[1,2-b]indazol-5(7H)-one was used in place of 9-hydroxy-2-(methylthio)-7-pyridin-2-yl-pyrimido[4',5':4,5]pyrimido[1,2-b]indazol-5(7H)-one used in Production Example 42.
ESI-MS Found: m/z [M+H]+ 491.

Production Example 46

Production of tert-butyl {[2-(methylthio)-5-oxo-7-(pyridin-2-yl)-5,7-dihydropyrimido[4',5':4,5]pyrimido[1,2-b]indazol-11-yl]oxy}acetate The title compound was obtained as a yellow solid in the same manner as in Production Example 42, for which, however, 11-hydroxy-2-(methylthio)-7-pyridin-2-yl-pyrimido[4',5':4,5]pyrimido[1,2-b]indazol-5(7H)-one was used in place of 9-hydroxy-2-(methylthio)-7-pyridin-2-yl-pyrimido[4',5':4,5]pyrimido[1,2-b]indazol-5(7H)-one used in Production Example 42.
ESI-MS Found: m/z [M+H]+ 491.

Production Example 47

Production of methyl 2-(methylthio)-5-oxo-7-(pyridin-2-yl)-5,7-dihydropyrimido[4',5':4,5]pyrimido[1,2-b]indazole-9-carboxylate 1) Production of 2-(methylthio)-5-oxo-7-(pyridin-2-yl)-5,7-dihydropyrimido[4',5':4,5]pyrimido[1,2-b]indazol-9-yl trifluoromethanesulfonate Trifluoromethanesulfonic anhydride (0.3 mL) was added to a chloroform (5 mL) solution of the compound (188 mg) obtained in Production Example 36-7, and stirred for 1 hour. Aqueous saturated sodium hydrogencarbonate solution (20 mL) was added to the reaction liquid, the organic layer was separated, dried with sodium sulfate, and concentrated under reduced pressure. The residue was purified through silica gel column chromatography (hexane/ethyl acetate) to give the title compound as a yellow solid (238 mg).

2) Production of methyl 2-(methylthio)-5-oxo-7-(pyridin-2-yl)-5,7-dihydropyrimido[4',5':4,5]pyrimido[1,2-b]indazole-9-carboxylate Palladium acetate (10 mg), diphenylphosphinoferrocene (20 mg) and methanol (1 mL) were added to an N,N-dimethylformamide (10 mL) solution of the compound obtained in Production Example 47-1, and stirred in a 1-atmospheric carbon monoxide atmosphere at 60° C. for 15 hours. The reaction liquid was concentrated under reduced pressure, and the residue was purified through silica gel column chromatography (hexane/ethyl acetate) to give the title compound as a yellow solid (174 mg).
ESI-MS Found: m/z [M+H]+ 419.

Production Example 48

Production of methyl 2-(methylthio)-5-oxo-7-(pyridin-2-yl)-5,7-dihydronyrimido[4',5':4,5]pyrimido[1,2-b]indazole-10-carboxylate 1) Production of 2-(methylthio)-5-oxo-7-pyridin-2-yl-5,7-dihydropyrimido[4',5':4,5]pyrimido[1,2-b]indazol-10-yl trifluoromethanesulfonate The title compound was produced as a yellow solid in the same manner as in Production Example 47-1, for which, however, 10-hydroxy-2-(methylthio)-7-pyridin-2-yl-pyrimido[4',5':4,5]pyrimido[1,2-b]indazol-5(7H)-one was used in place of 9-hydroxy-2-(methylthio)-7-pyridin-2-yl-pyrimido[4',5':4,5]pyrimido[1,2-b]indazol—used in Production Example 47-1.

2) Production of methyl 2-(methylthio)-5-oxo-7-(pyridin-2-yl)-5,7-dihydropyrimido[4',5':4,5]pyrimido[1,2-b]indazole-10-carboxylate The title compound was produced as a yellow solid in the same manner as in Production Example 47-2, for which, however, 2-(methylthio)-5-oxo-7-pyridin-2-yl-5,7-dihydropyrimido[4',5':4,5]pyrimido[1,2-b]indazol-10-yl trifluoromethanesulfonate was used in place of 2-(methylthio)-5-oxo-7-pyridin-2-yl-5,7-dihydropyrimido[4',5':4,5]pyrimido[1,2-b]indazol-9-yl trifluoromethanesulfonate used in Production Example 47-2.
ESI-MS Found: m/z [M+H]+ 419.

Production Example 49

Production of methyl 2-(methylthio)-5-oxo-7-(pyridin-2-yl)-5,7-dihydropyrimido[4',5':4,5]pyrimido[1,2-b]indazole-11-carboxylate 1) Production of 2-(methylthio)-5-oxo-7-pyridin-2-yl-5,7-dihydropyrimido[4',5':4,5]pyrimido[1,2-b]indazole-11-yl trifluoromethanesulfonate The title compound was produced as a yellow solid in the same manner as in Production Example 47-1, for which, however, 11-hydroxy-2-(methylthio)-7-pyridin-2-yl-pyrimido[4',5':4,5]pyrimido[1,2-b]indazol-5(7H)-one was used in place of 9-hydroxy-2-(methylthio)-7-pyridin-2-yl-pyrimido[4',5':4,5]pyrimido[1,2-b]indazol-5(7H)-one used in Production Example 47-1.

2) Production of methyl 2-(methylthio)-5-oxo-7-(pyridin-2-yl)-5,7-dihydropyrimido[4',5':4,5]pyrimido[1,2-b]indazole-11-carboxylate The title compound was produced as a yellow solid in the same manner as in Production Example 47-2, for which, however, 2-(methylthio)-5-oxo-7-pyridin-2-yl-5,7-dihydropyrimido[4',5':4,5]pyrimido[1,2-b]indazol-11-yl trifluoromethanesulfonate was used in place of 2-(methylthio)-5-oxo-7-pyridin-2-yl-5,7-dihydropyrimido[4',5':4,5]pyrimido[1,2-b]indazol-9-yl trifluoromethanesulfonate used in Production Example 47-2.
ESI-MS Found: m/z [M+H]+ 419.

Example 1

Production of 7-methyl-2-{[3-methyl-4-(4-methylpiperazin-1-yl)phenyl]amino}pyrimido[4',5':4,5]pyrimido[1,2-b]indazol-5(7H)-one

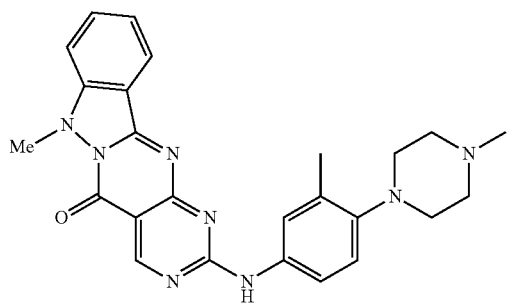

At 0° C., m-chloroperbenzoic acid (119 mg) was added to a toluene solution of the compound (50 mg) obtained in Production Example 2, and stirred for 30 minutes. 3-Methyl-4-(4-methyl-1-piperazinyl)aniline (15 mg) and N,N-diisopropylethylamine (0.1 mL) were added thereto, and stirred at 70° C. for 15 hours. The solvent was evaporated away, and the residue was purified through basic silica gel column chromatography (ethyl acetate) to give the title compound as a yellow solid (12 mg).
$^1$H-NMR (400 MHz, CDCl$_3$) δ: 9.38 (1H, s), 8.29 (1H, d, J=7.8 Hz), 7.78 (1H, ddd, J=8.3, 7.1, 1.0 Hz), 7.67-7.34 (5H, m), 7.09 (1H, d, J=8.3 Hz), 3.16 (3H, s), 3.00-2.93 (4H, m), 2.83-2.46 (4H, m), 2.40 (3H, s), 2.35 (3H, s).
ESI-MS Found: m/z [M+H]+ 455.

Example 2

Production of 2-{[3-(hydroxymethyl)-4-(4-methylpiperazin-1-yl)phenyl]amino}-7-methylpyrimido[4',5':4,5]pyrimido[1,2-b]indazol-5(7H)-one

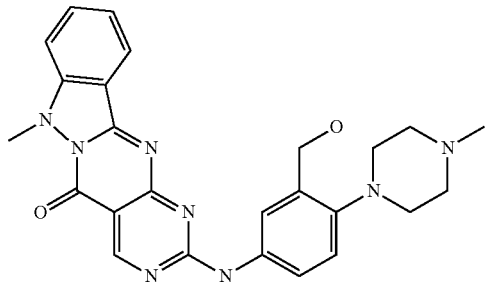

The title compound was produced as a yellow solid in the same manner as in Example 1, for which, however, [5-amino-2-(4-methyl-1-piperazin-1-yl)phenyl]methanol was used in place of 3-methyl-4-(4-methyl-1-piperazinyl)aniline used in Example 1.

$^1$H-NMR (400 MHz, DMSO-$d_6$) δ: 10.03 (1H, s), 9.11 (1H, s), 8.20 (1H, d, J=8.4 Hz), 7.87 (1H, t, J=7.8 Hz), 7.80 (1H, d, J=8.4 Hz), 7.72 (1H, s), 7.45 (1H, t, J=7.3 Hz), 6.92 (1H, d, J=8.8 Hz), 4.85 (2H, s), 3.91 (3H, s), 3.11 (4H, t, J=4.9 Hz), 2.46 (4H, t, J=4.9 Hz), 2.20 (3H, s).

ESI-MS Found: m/z [M+H]+ 471

Example 3

Production of 2-{[3-(hydroxymethyl)-4-morpholin-4-ylphenyl]amino}-7-methylpyrimido[4',5':4,5]pyrimido[1,2-b]indazol-5(7H)-one

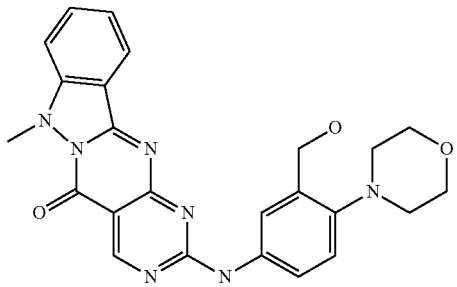

The title compound was produced as a yellow solid in the same manner as in Example 1, for which, however, (5-amino-2-morpholin-4-ylphenyl)methanol was used in place of 3-methyl-4-(4-methyl-1-piperazinyl)aniline used in Example 1.

$^1$H-NMR (400 MHz, DMSO-$d_6$) δ: 10.05 (1H, s), 9.11 (1H, s), 8.19 (1H, d, J=8.3 Hz), 7.87 (1H, t, J=7.8 Hz), 7.80 (1H, d, J=8.3 Hz), 7.72 (1H, s), 7.45 (1H, t, J=7.3 Hz), 6.95 (1H, d, J=8.6 Hz), 4.85 (2H, s), 3.10 (4H, t, J=4.5 Hz), 2.42 (4H, t, J=4.5 Hz), 2.22 (3H, s).

ESI-MS Found: m/z [M+H]+ 458.

Example 4

Production of 7-methyl-2-{[4-(4-methylpiperazin-1-yl)phenyl]amino}pyrimido[4',5':4,5]pyrimido[1,2-b]indazol-5(7H)-one

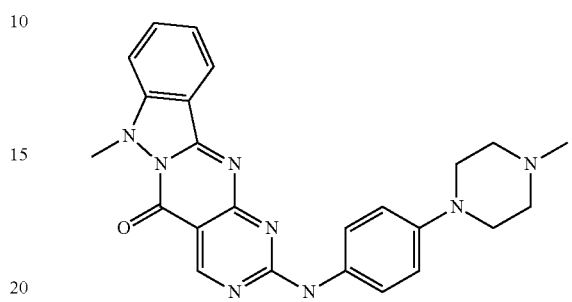

The title compound was produced as a yellow solid in the same manner as in Example 1, for which, however, 4-(4-methyl-1-piperazinyl)aniline was used in place of 3-methyl-4-(4-methyl-1-piperazinyl)aniline used in Example 1.

$^1$H-NMR (400 MHz, DMSO-$d_6$) δ: 10.04 (1H, s), 9.19 (1H, s), 8.19 (1H, d, J=8.3 Hz), 7.87 (1H, t, J=7.8 Hz), 7.80 (1H, d, J=8.3 Hz), 7.72 (1H, s), 7.45 (1H, t, J=7.3 Hz), 6.95 (2H, d, J=8.8 Hz), 3.90 (3H, s), 3.10 (4H, t, J=4.9 Hz), 2.46 (4H, t, J=4.9 Hz), 2.22 (3H, s).

ESI-MS Found: m/z [M+H]+ 441.

Example 5

Production of 2-anilino-7-methylpyrimido[4',5':4,5]pyrimido[1,2-b]indazol-5(7H)-one

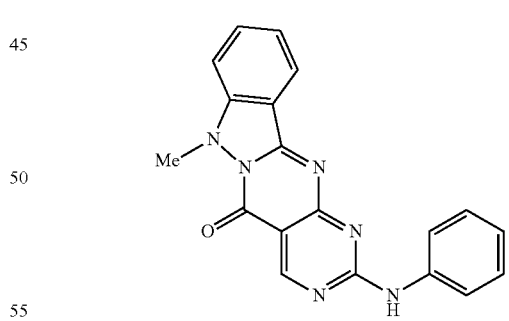

The title compound was produced as a yellow solid in the same manner as in Example 1, for which, however, aniline was used in place of 3-methyl-4-(4-methyl-1-piperazinyl)aniline used in Example 1.

$^1$H-NMR (400 MHz, DMSO-$d_6$) δ: 10.27 (1H, s), 9.27 (1H, s), 8.22 (1H, d, J=7.8 Hz), 7.92 (2H, d, J=7.8 Hz), 7.90-7.86 (1H, m), 7.81 (1H, d, J=8.3 Hz), 7.48-7.44 (1H, m), 7.37 (1H, t, J=8.0 Hz), 7.06 (1H, t, J=7.3 Hz), 3.92 (3H, s).

ESI-MS Found: m/z [M+H]+ 343.

Example 6

Production of 7-ethyl-2-{[3-methyl-4-(4-methylpiperazin-1-yl)phenyl]amino}pyrimido[4',5':4,5]pyrimido[1,2-b]indazol-5(7H)-one

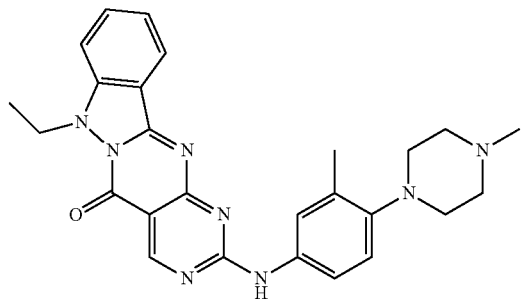

The title compound was produced as a yellow solid in the same manner as in Example 1, for which, however, 7-ethyl-2-(methylthio)pyrimido[4',5':4,5]pyrimido[1,2-b]indazol-5(7H)-one obtained in Production Example 3 was used in place of 7-methyl-2-(methylthio)pyrimido[4',5':4,5]pyrimido[1,2-b]indazol-5(7H)-one used in Example 1.

$^1$H-NMR (400 MHz, CDCl$_3$) δ: 9.38 (1H, s), 8.29 (1H, d, J=7.8 Hz), 7.78 (1H, ddd, J=8.3, 7.1, 1.0 Hz), 7.67-7.34 (5H, m), 7.09 (1H, d, J=8.3 Hz), 4.72 (2H, q, J=7.1 Hz), 3.00-2.93 (4H, m), 2.83-2.46 (4H, m), 2.40 (3H, s), 2.35 (3H, s), 0.94 (3H, t, J=7.1 Hz).

ESI-MS Found: m/z [M+H]+ 469.

Example 7

Production of 7-ethyl-2-[(2-methyl-1,2,3,4-tetrahydroisoquinolin-6-yl)amino]pyrimido[4',5':4,5]pyrimido[1,2-b]indazol-5(7H)-one

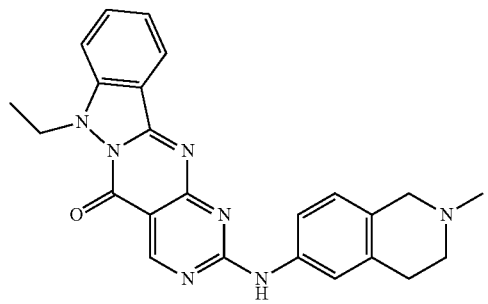

The title compound was produced as a yellow solid in the same manner as in Example 1, for which, however, 7-ethyl-2-(methylthio)pyrimido[4',5':4,5]pyrimido[1,2-b]indazol-5(7H)-one obtained in Production Example 3 was used in place of 7-methyl-2-(methylthio)pyrimido[4',5':4,5]pyrimido[1,2-b]indazol-5(7H)-one used in Example 1, and 2-methyl-1,2,3,4-tetrahydroisoquinolin-6-amine was used in place of 3-methyl-4-(4-methyl-1-piperazinyl)aniline.

$^1$H-NMR (400 MHz, CDCl$_3$) δ: 9.40 (1H, s), 8.31 (1H, d, J=8.3 Hz), 7.78 (1H, t, J=7.8 Hz), 7.57-7.44 (2H, m), 7.41 (2H, dd, J=8.3, 5.9 Hz), 7.06 (1H, d, J=8.3 Hz), 4.73 (2H, q, J=7.2 Hz), 3.59 (2H, s), 2.99 (4H, t, J=5.9 Hz), 2.71 (4H, t, J=5.9 Hz), 2.47 (3H, s), 0.94 (3H, t, J=7.2 Hz).

ESI-MS Found: m/z [M+H]+ 426.

Example 8

Production of 7-ethyl-2-[(2-methyl-1,2,3,4-tetrahydroisoquinolin-7-yl)amino]pyrimido[4',5':4,5]pyrimido[1,2-b]indazol-5(7H)-one

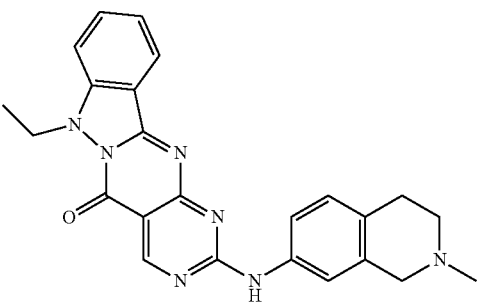

The title compound was produced as a yellow solid in the same manner as in Example 1, for which, however, 7-ethyl-2-(methylthio)pyrimido[4',5':4,5]pyrimido[1,2-b]indazol-5(7H)-one obtained in Production Example 3 was used in place of 7-methyl-2-(methylthio)pyrimido[4',5':4,5]pyrimido[1,2-b]indazol-5(7H)-one used in Example 1, and 2-methyl-1,2,3,4-tetrahydroisoquinolin-7-amine was used in place of 3-methyl-4-(4-methyl-1-piperazinyl)aniline.

$^1$H-NMR (400 MHz, CDCl$_3$) δ: 9.39 (1H, s), 8.31 (1H, d, J=7.8 Hz), 7.78 (1H, td, J=7.7, 1.3 Hz), 7.49 (2H, s), 7.41 (2H, dd, J=8.3, 5.9 Hz), 7.14 (1H, d, J=8.3 Hz), 4.73 (2H, q, J=7.1 Hz), 3.67 (2H, s), 2.93 (2H, t, J=6.1 Hz), 2.73 (2H, t, J=5.9 Hz), 2.49 (3H, s), 0.94 (3H, t, J=7.1 Hz).

ESI-MS Found: m/z [M+H]+ 426.

Example 9

Production of 2-{[3-methyl-4-(4-methylpiperazin-1-yl)phenyl]amino}-7-isopropylpyrimido[4',5':4,5]pyrimido[1,2-b]indazol-5(7H)-one

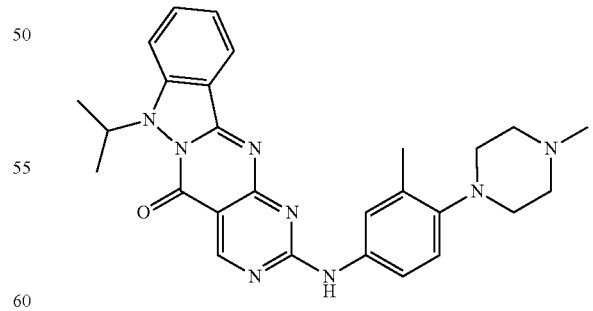

The title compound was produced as a yellow solid in the same manner as in Example 1, for which, however, 7-isopropyl-2-(methylthio)pyrimido[4',5':4,5]pyrimido[1,2-b]indazol-5(7H)-one obtained in Production Example 4 was used in place of 7-methyl-2-(methylthio)pyrimido[4',5':4,5]pyrimido[1,2-b]indazol-5(7H)-one used in Example 1.

¹H-NMR (400 MHz, CDCl₃) δ: 9.36 (1H, s), 8.29 (1H, d, J=7.6 Hz), 7.72 (1H, ddd, J=8.3, 7.3, 1.0 Hz), 7.65-7.32 (5H, m), 7.09 (1H, d, J=8.3 Hz), 5.55-5.43 (1H, m), 3.02-2.92 (4H, m), 2.78-2.50 (4H, m), 2.41 (3H, s), 2.35 (3H, s), 1.38 (6H, d, J=6.8 Hz).
ESI-MS Found: m/z [M+H]+ 483.

Example 10

Production of 2-{[3-methyl-4-(4-methylpiperazin-1-yl)phenyl]amino}-7-allylpyrimido[4',5':4,5]pyrimido[1,2-b]indazol-5(7H)-one

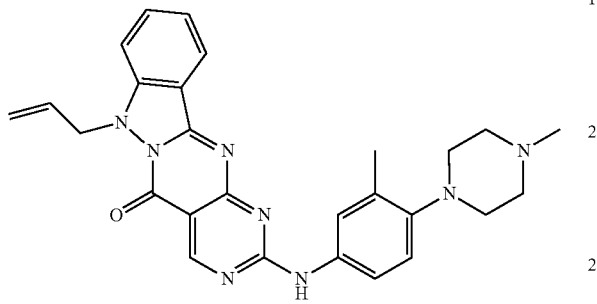

The title compound was produced as a yellow solid in the same manner as in Example 1, for which, however, 7-allyl-2-(methylthio)pyrimido[4',5':4,5]pyrimido[1,2-b]indazol-5(7H)-one obtained in Production Example 5 was used in place of 7-methyl-2-(methylthio)pyrimido[4',5':4,5]pyrimido[1,2-b]indazol-5(7H)-one used in Example 1.
¹H-NMR (400 MHz, CDCl₃) δ: 9.37 (1H, s), 8.29 (1H, d, J=8.0 Hz), 7.78 (1H, ddd, J=8.3, 7.1, 1.2 Hz), 7.70-7.33 (5H, m), 7.09 (1H, d, J=8.3 Hz), 5.45 (1H, ddt, J=17.1, 10.2, 6.5 Hz), 5.26 (1H, dd, J=17.1, 1.1 Hz), 5.18 (2H, d, J=6.5 Hz), 5.11 (1H, dd, J=10.2, 1.1 Hz), 3.02-2.94 (4H, m), 2.79-2.54 (4H, m), 2.42 (3H, s), 2.35 (3H, s).
ESI-MS Found: m/z [M+H]+ 481.

Example 11

Production of 2-{[3-methyl-4-(4-methylpiperazin-1-yl)phenyl]amino}-7-propylpyrimido[4',5':4,5]pyrimido[1,2-b]indazol-5(7H)-one

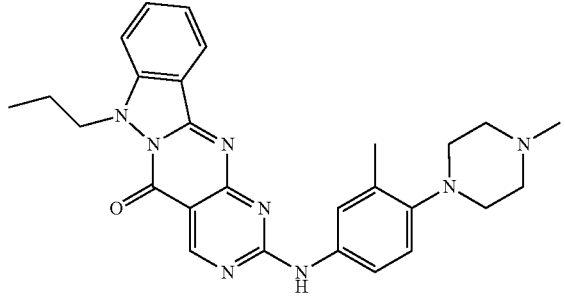

The title compound was produced as a yellow solid in the same manner as in Example 1, for which, however, 2-(methylthio)-7-propylpyrimido[4',5':4,5]pyrimido[1,2-b]indazol-5(7H)-one obtained in Production Example 6 was used in place of 7-methyl-2-(methylthio)pyrimido[4',5':4,5]pyrimido[1,2-b]indazol-5(7H)-one used in Example 1.

¹H-NMR (400 MHz, CDCl₃) δ: 9.38 (1H, s), 8.29 (1H, d, J=8.0 Hz), 7.76 (1H, ddd, J=8.5, 7.3, 1.2 Hz), 7.67-7.33 (5H, m), 7.09 (1H, d, J=8.5 Hz), 4.64-4.58 (2H, m), 3.01-2.95 (4H, m), 2.77-2.54 (4H, m), 2.42 (3H, s), 2.35 (3H, s), 1.45 (2H, ttd, J=7.4, 7.4, 7.4 Hz), 0.81 (3H, t, J=7.4 Hz).
ESI-MS Found: m/z [M+H]+ 483.

Example 12

Production of 2-[2-{[4-(4-methylpiperazin-1-yl)phenyl]amino}-5-oxopyrimido[4',5':4,5]pyrimido[1,2-b]indazol-7(5H)-yl]propionitrile

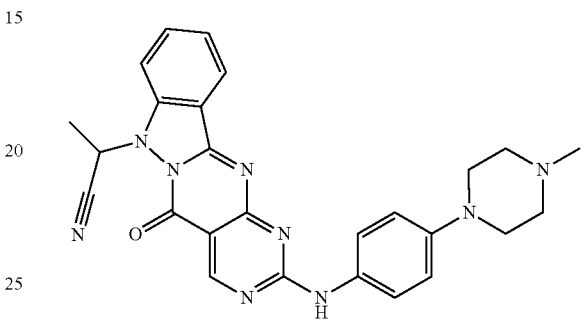

The title compound was produced as a yellow solid in the same manner as in Example 1, for which, however, 2-[(methylthio)-5-oxopyrimido[4',5':4,5]pyrimido[1,2-b]indazol-7(5H)-yl]propanenitrile obtained in Production Example 7 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.
¹H-NMR (400 MHz, CDCl₃) δ: 9.34 (1H, s), 8.85 (1H, s), 8.33 (1H, d, J=8.3 Hz), 7.87-7.48 (5H, m), 6.98 (1H, d, J=8.8 Hz), 6.48 (1H, d, J=7.3 Hz), 3.28-3.23 (4H, m), 2.70-2.63 (4H, m), 2.41 (3H, s), 1.73 (3H, d, J=7.3 Hz).
ESI-MS Found: m/z [M+H]+ 480.

Example 13

Production of 7-(cyclopropylmethyl)-2-{[4-(4-methylpiperazin-1-yl)phenyl]amino}pyrimido[4',5':4,5]pyrimido[1,2-b]indazol-5(7H)-one

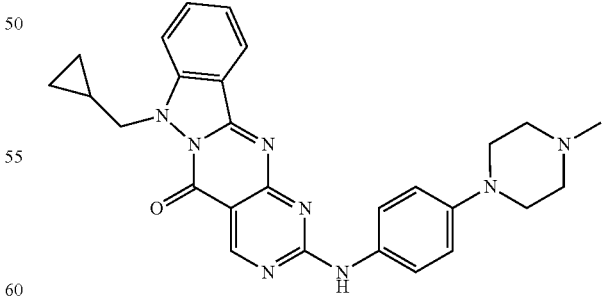

The title compound was produced as a yellow solid in the same manner as in Example 1, for which, however, 7-(cyclopropylmethyl)-2-(methylthio)pyrimido[4',5':4,5]pyrimido[1,2-b]indazol-5(7H)-one obtained in Production Example 8 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

¹H-NMR (400 MHz, CDCl₃) δ: 9.37 (1H, s), 8.30 (1H, d, J=6.8 Hz), 7.76 (1H, t, J=7.8 Hz), 7.62 (1H, s), 7.52 (1H, s), 7.45 (1H, d, J=8.8 Hz), 7.40 (1H, t, J=7.6 Hz), 6.98 (2H, d, J=8.8 Hz), 4.53 (2H, d, J=7.3 Hz), 3.28-3.21 (4H, m), 2.69-2.61 (4H, m), 2.40 (3H, s), 0.68-0.61 (1H, m), 0.29-0.16 (4H, m).

ESI-MS Found: m/z [M+H]+ 481.

Example 14

Production of 7-(2,2-difluoroethyl)-2-{[4-(4-methylpiperazin-1-yl)phenyl]amino}pyrimido[4',5':4,5]pyrimido[1,2-b]indazol-5(7H)-one

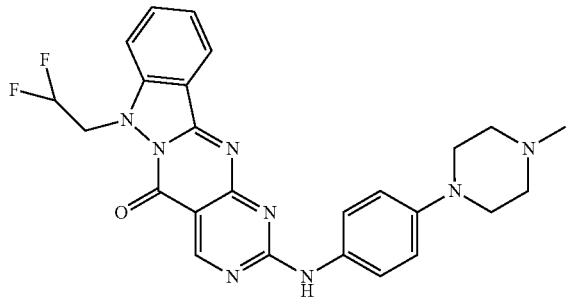

The title compound was produced as a yellow solid in the same manner as in Example 1, for which, however, 7-(2,2-difluoroethyl)-2-(methylthio)pyrimido[4',5':4,5]pyrimido[1,2-b]indazol-5(7H)-one obtained in Production Example 9 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

¹H-NMR (400 MHz, DMSO-d₆) δ: 10.08 (1H, s), 9.21 (1H, s), 8.31 (1H, s), 8.22 (1H, d, J=8.0 Hz), 7.89 (1H, t, J=7.8 Hz), 7.80 (1H, d, J=7.8 Hz), 7.72 (1H, s), 7.47 (1H, t, J=7.6 Hz), 6.96 (1H, d, J=8.6 Hz), 6.47 (1H, dt, J=54.1, 26.6 Hz), 5.05 (2H, dt, J=26.6, 7.2 Hz), 3.11 (4H, t, J=4.8 Hz), 2.48-2.44 (4H, m), 2.22 (3H, s).

ESI-MS Found: m/z [M+H]+ 491.

Example 15

Production of 7-benzyl-2-{[3-methyl-4-(4-methylpiperazin-1-yl)phenyl]amino}pyrimido[4',5':4,5]pyrimido[1,2-b]indazol-5(7H)-one

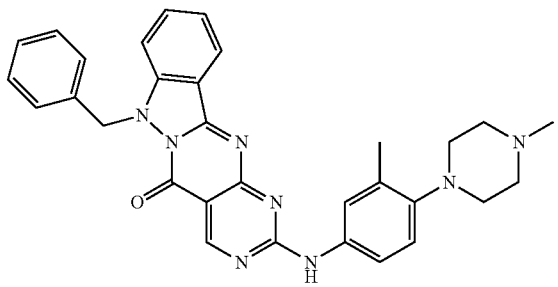

The title compound was produced as a yellow solid in the same manner as in Example 1, for which, however, 7-benzyl-2-(methylthio)pyrimido[4',5':4,5]pyrimido[1,2-b]indazol-5(7H)-one obtained in Production Example 10 was used in place of 7-methyl-2-(methylthio)pyrimido[4',5':4,5]pyrimido[1,2-b]indazol-5(7H)-one used in Example 1.

¹H-NMR (400 MHz, CDCl₃) δ: 9.38 (1H, s), 8.21 (1H, d, J=7.6 Hz), 7.79 (1H, t, J=7.4 Hz), 7.61-7.35 (5H, m), 7.19-6.99 (6H, m), 5.71 (2H, s), 3.00-2.93 (4H, m), 2.77-2.48 (4H, m), 2.40 (3H, s), 2.33 (3H, s).

ESI-MS Found: m/z [M+H]+ 531.

Example 16

Production of 7-(2-hydroxyethyl)-2-{[3-methyl-4-(4-methylpiperazin-1-yl)phenyl]amino}pyrimido[4',5':4,5]pyrimido[1,2-b]indazol-5(7H)-one

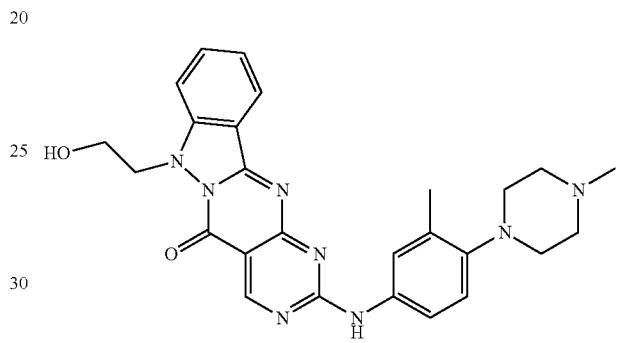

1) Production of 7-(2-{[tert-butyl(dimethyl)silyl]oxy}ethyl)-2-{[3-methyl-4-(4-methylpiperazin-1-yl)phenyl]amino}pyrimido[4',5':4,5]pyrimido[1,2-b]indazol-5(7H)-one The title compound was produced as a yellow solid (15 mg) in the same manner as in Example 1, for which, however, 7-(2-{[tert-butyl(dimethyl)silyl]oxy}ethyl)-2-(methylthio)pyrimido[4',5':4,5]pyrimido[1,2-b]indazol-5(7H)-one obtained in Production Example 11 was used in place of 7-methyl-2-(methylthio)pyrimido[4',5':4,5]pyrimido[1,2-b]indazol-5(7H)-one used in Example 1.

ESI-MS Found: m/z [M+H]+ 598.

2) Production of 7-(2-hydroxyethyl)-2-{[3-methyl-4-(4-methylpiperazin-1-yl)phenyl]amino}pyrimido[4',5':4,5]pyrimido[1,2-b]indazol-5(7H)-one A tetrahydrofuran solution (0.1 mL) of 1.0 M tetrabutylammonium fluoride was added to a tetrahydrofuran (2 mL) solution of the compound (15 mg) obtained in Example 16-1, and stirred for 30 minutes. The reaction liquid was concentrated under reduced pressure, and the residue was purified through basic silica gel column chromatography (ethyl acetate) to give the above-mentioned compound as a yellow solid.

¹H-NMR (400 MHz, DMSO-d₆) δ: 10.03 (1H, s), 9.21 (1H, s), 8.16 (1H, d, J=8.0 Hz), 7.86-7.68 (3H, m), 7.52 (1H, s), 7.39 (1H, t, J=7.3 Hz), 7.04 (1H, d, J=8.8 Hz), 4.71 (2H, t, J=4.8 Hz), 4.57 (1H, t, J=4.8 Hz), 3.53 (2H, q, J=4.8 Hz), 2.86-2.79 (4H, m), 2.53-2.42 (4H, m), 2.26 (3H, s), 2.23 (3H, s).

ESI-MS Found: m/z [M+H]+ 485.

Example 17

Production of 7-(2-hydroxyethyl)-2-[(2-methyl-1,2,3,4-tetrahydroisoquinolin-6-yl)amino]pyrimido[4',5':4,5]pyrimido[1,2-b]indazol-5(7H)-one

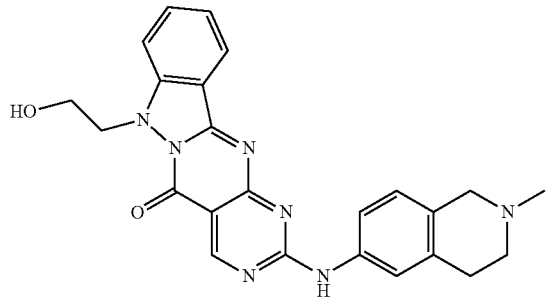

1) Production of 7-(2-{[tert-butyl(dimethyl)silyl]oxy}ethyl)-2-[(2-methyl-1,2,3,4-tetrahydroisoquinolin-6-yl)amino]pyrimido[4',5':4,5]pyrimido[1,2-b]indazol-5(7H)-one The title compound was produced as a yellow solid in the same manner as in Example 1, for which, however, 7-(2-{[tert-butyl(dimethyl)silyl]oxy}ethyl)-2-(methylthio)pyrimido[4',5':4,5]pyrimido[1,2-b]indazol-5(7H)-one obtained in Production Example 11 was used in place of 7-methyl-2-(methylthio)pyrimido[4',5':4,5]pyrimido[1,2-b]indazol-5(7H)-one used in Example 1, and 2-methyl-1,2,3,4-tetrahydroisoquinolin-6-amine was used in place of 3-methyl-4-(4-methyl-1-piperazinyl)aniline.

ESI-MS Found: m/z [M+H]+ 556.

2) Production of 7-(2-hydroxyethyl)-2-[(2-methyl-1,2,3,4-tetrahydroisoquinolin-6-yl)amino]pyrimido[4',5':4,5]pyrimido[1,2-b]indazol-5(7H)-one The title compound was produced as a yellow solid in the same manner as in Example 16-2, for which, however, 7-(2-{[tert-butyl(dimethyl)silyl]oxy}ethyl)-2-[(2-methyl-1,2,3,4-tetrahydroisoquinolin-6-yl)amino]pyrimido[4',5':4,5]pyrimido[1,2-b]indazol-5(7H)-one obtained in Example 17-1 was used in place of 7-(2-{[tert-butyl(dimethyl)silyl]oxy}ethyl)-2-{[3-methyl-4-(4-methylpiperazin-1-yl)phenyl]amino}pyrimido[4',5':4,5]pyrimido[1,2-b]indazol-5(7H)-one used in Example 16-2.

$^1$H-NMR (400 MHz, DMSO-$d_6$) δ: 10.12 (1H, s), 9.24 (1H, s), 8.18 (1H, d, J=8.2 Hz), 7.83 (1H, t, J=7.6 Hz), 7.77 (1H, d, J=8.6 Hz), 7.55 (1H, s), 7.40 (1H, t, J=7.4 Hz), 7.04 (1H, d, J=9.0 Hz), 4.72 (2H, t, J=4.9 Hz), 4.56 (1H, t, J=4.9 Hz), 3.53 (2H, q, J=4.92 Hz), 3.46 (2H, s), 2.83 (2H, t, J=5.5 Hz), 2.60 (2H, t, J=5.51 Hz), 2.34 (3H, s).

ESI-MS Found: m/z [M+H]+ 442.

Example 18

Production of 7-(2-hydroxyethyl)-2-[(3-methyl-2,3,4,5-tetrahydro-1H-3-benzazepin-7-yl)amino]pyrimido[4',5':4,5]pyrimido[1,2-b]indazol-5(7H)-one

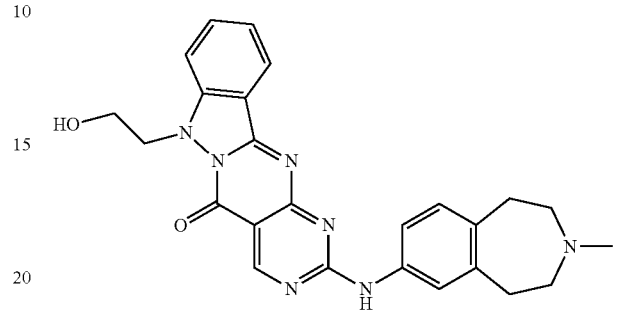

1) Production of 7-(2-{[tert-butyl(dimethyl)silyl]oxy}ethyl)-2-[(3-methyl-2,3,4,5-tetrahydro-1H-3-benzazepin-7-yl)amino]pyrimido[4',5':4,5]pyrimido[1,2-b]indazol-5(7H)-one The title compound was produced as a yellow solid in the same manner as in Example 1, for which, however, 7-(2-{[tert-butyl(dimethyl)silyl]oxy}ethyl)-2-(methylthio)pyrimido[4',5':4,5]pyrimido[1,2-b]indazol-5(7H)-one obtained in Production Example 11 was used in place of 7-methyl-2-(methylthio)pyrimido[4',5':4,5]pyrimido[1,2-b]indazol-5(7H)-one used in Example 1, and 3-methyl-2,3,4,5-tetrahydro-1H-3-benzazepin-7-amine was used in place of 3-methyl-4-(4-methyl-1-piperazinyl)aniline.

ESI-MS Found: m/z [M+H]+ 556.

2) Production of 7-(2-hydroxyethyl)-2-[(3-methyl-1,2,3,4-tetrahydroisoquinolin-7-yl)amino]pyrimido[4',5':4,5]pyrimido[1,2-b]indazol-5(7H)-one The title compound was produced as a yellow solid in the same manner as in Example 16-2, for which, however, 7-(2-{[tert-butyl(dimethyl)silyl]oxy}ethyl)-2-[(3-methyl-2,3,4,5-tetrahydro-1H-3-benzazepin-7-yl)amino]pyrimido[4',5':4,5]pyrimido[1,2-b]indazol-5(7H)-one obtained in Example 18-1 was used in place of 7-(2-{[tert-butyl(dimethyl)silyl]oxy}ethyl-2-{[3-methyl-4-(4-methylpiperazin-1-yl)phenyl]amino}pyrimido[4',5':4,5]pyrimido[1,2-b]indazol-5(7H)-one used in Example 16-2.

$^1$H-NMR (400 MHz, DMSO-$d_6$) δ: 10.11 (1H, s), 9.24 (1H, s), 8.18 (1H, d, J=8.2 Hz), 7.83 (1H, t, J=8.2 Hz), 7.77 (1H, d, J=8.6 Hz), 7.50 (1H, s), 7.40 (1H, t, J=7.4 Hz), 7.11 (1H, d, J=8.2 Hz), 4.72 (2H, t, J=5.2 Hz), 4.56 (1H, t, J=5.2 Hz), 3.53 (2H, q, J=5.2 Hz), 2.83 (4H, s), 3.60-4.40 (4H, m), 2.25 (3H, s).

ESI-MS Found: m/z [M+H]+ 456.

Example 19

Production of 7-(3-hydroxypropyl)-2-{[3-methyl-4-(4-methylpiperazin-1-yl)phenyl]amino}pyrimido[4',5':4,5]pyrimido[1,2-b]indazol-5(7H)-one

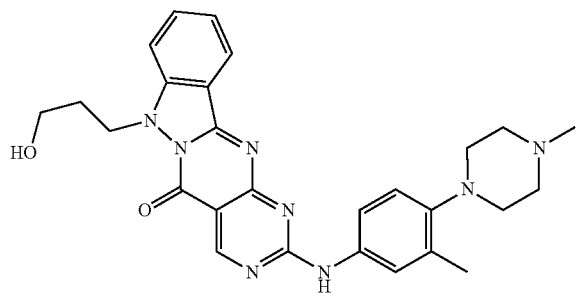

1) Production of 7-(3-{[tert-butyl(dimethyl)silyl]oxy}propyl)-2-{[3-methyl-4-(4-methylpiperazin-1-yl)phenyl]amino}pyrimido[4',5':4,5]pyrimido[1,2-b]indazol-5(7H)-one The title compound was produced as a yellow solid (15 mg) in the same manner as in Example 1, for which, however, 7-(3-{[tert-butyl(dimethyl)silyl]oxy}propyl)-2-(methylthio)pyrimido[4',5':4,5]pyrimido[1,2-b]indazol-5(7H)-one obtained in Production Example 12 was used in place of 7-methyl-2-(methylthio)pyrimido[4',5':4,5]pyrimido[1,2-b]indazol-5(7H)-one used in Example 1.

ESI-MS Found: m/z [M+H]+ 612.

2) Production of 7-(3-hydroxypropyl)-2-{[3-methyl-4-(4-methylpiperazin-1-yl)phenyl]amino}pyrimido[4',5':4,5]pyrimido[1,2-b]indazol-5(7H)-one The title compound was produced as a yellow solid in the same manner as in Example 16-2, for which, however, 7-(3-{[tert-butyl(dimethyl)silyl]oxy}propyl)-2-{[3-methyl-4-(4-methylpiperazin-1-yl)phenyl]amino}pyrimido[4',5':4,5]pyrimido[1,2-b]indazol-5(7H)-one obtained in Example 19-1 was used in place of 7-(2-{[tert-butyl(dimethyl)silyl]oxy}ethyl)-2-{[3-methyl-4-(4-methylpiperazin-1-yl)phenyl]amino}pyrimido[4',5':4,5]pyrimido[1,2-b]indazol-5(7H)-one used in Example 16-2.

$^1$H-NMR (400 MHz, DMSO-$d_6$) δ: 10.05 (1H, s), 9.22 (1H, s), 8.19 (1H, d, J=7.8 Hz), 7.87 (1H, ddd, J=8.3, 7.1, 1.2 Hz), 7.83-7.66 (1H, m), 7.78 (1H, d, J=8.5 Hz), 7.53 (1H, br s), 7.44 (1H, ddd, J=7.8, 7.1, 0.7 Hz), 7.04 (1H, d, J=8.5 Hz), 4.70 (2H, t, J=7.2 Hz), 4.48 (1H, t, J=5.0 Hz), 3.22 (2H, dt, J=5.0, 6.0 Hz), 2.85-2.80 (4H, m), 2.52-2.43 (4H, m), 2.26 (3H, s), 2.23 (3H, s), 1.43 (2H, tt, J=7.2, 6.0 Hz).

ESI-MS Found: m/z [M+H]+ 499.

Example 20

Production of 7-(2-methoxyethyl)-2-{[4-(4-methylpiperazin-1-yl)phenyl]amino}pyrimido[4',5':4,5]pyrimido[1,2-b]indazol-5(7H)-one

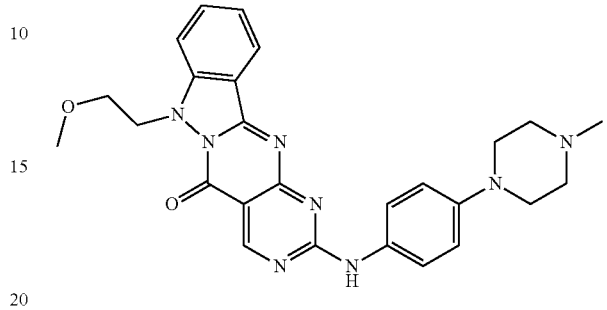

The title compound was produced as a yellow solid in the same manner as in Example 1, for which, however, 7-(2-methoxyethyl)-2-(methylthio)pyrimido[4',5':4,5]pyrimido[1,2-b]indazol-5(7H)-one obtained in Production Example 13 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

$^1$H-NMR (400 MHz, CDCl$_3$) δ: 9.35 (1H, s), 8.26 (1H, d, J=7.3 Hz), 7.74 (1H, t, J=7.8 Hz), 7.57 (2H, s), 7.47 (1H, d, J=8.8 Hz), 7.37 (1H, t, J=7.6 Hz), 6.98 (2H, d, J=8.8 Hz), 4.72 (2H, t, J=4.9 Hz), 3.65 (2H, t, J=4.9 Hz), 3.22 (4H, t, J=4.9 Hz), 3.12 (3H, s), 2.62 (4H, t, J=4.9 Hz), 2.38 (3H, s).

ESI-MS Found: m/z [M+H]+ 485.

Example 21

Production of 2-{[3-methyl-4-(4-methylpiperazin-1-yl)phenyl]amino}-7-(pyridin-2-yl)pyrimido[4',5':4,5]pyrimido[1,2-b]indazol-5(7H)-one

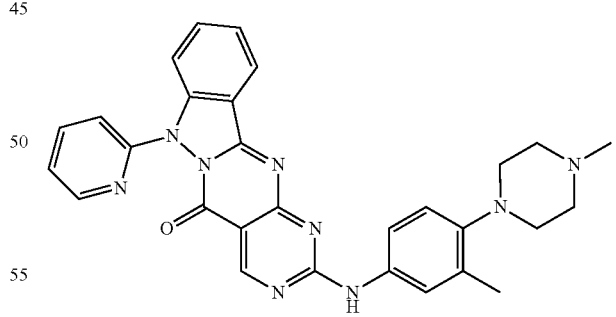

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1.

$^1$H-NMR (400 MHz, CDCl$_3$) δ: 9.30 (1H, s), 8.50 (1H, ddd, J=4.9, 1.7, 0.7 Hz), 8.35 (1H, d, J=7.8 Hz), 7.94 (1H, td, J=7.7, 1.7 Hz), 7.72 (1H, ddd, J=8.5, 7.3, 1.2 Hz), 7.66-7.32

(5H, m), 7.55 (1H, d, J=8.5 Hz), 7.35 (1H, ddd, J=7.7, 4.9, 0.7 Hz), 7.09 (1H, d, J=8.5 Hz), 2.99-2.94 (4H, m), 2.71-2.53 (4H, m), 2.39 (3H, s), 2.35 (3H, s).
ESI-MS Found: m/z [M+H]+ 518.

Example 22

Production of 2-{[3-(hydroxymethyl)-4-(4-methylpiperazin-1-yl)phenyl]amino}-7-(pyridin-2-yl)pyrimido[4',5':4,5]pyrimido[1,2-b]indazol-5(7H)-one

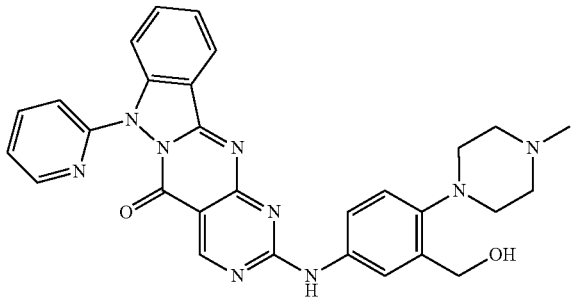

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and [5-amino-2-(4-methyl-1-piperazin-1-yl)phenyl]methanol was used in place of 3-methyl-4-(4-methyl-1-piperazinyl)aniline.
¹H-NMR (400 MHz, CDCl₃) δ: 9.30 (1H, s), 8.51-8.48 (1H, m), 8.34 (1H, d, J=8.0 Hz), 7.95 (1H, td, J=7.8, 1.9 Hz), 7.80-7.43 (7H, m), 7.36 (1H, dd, J=7.3, 4.9 Hz), 7.27 (1H, d, J=8.5 Hz), 4.85 (2H, s), 3.06-3.01 (4H, m), 2.83-2.45 (4H, m), 2.39 (3H, s).
ESI-MS Found: m/z [M+H]+ 534.

Example 23

Production of 2-{[4-(4-methylpiperazin-1-yl)phenyl]amino}-7-(pyridin-2-yl)pyrimido[4',5':4,5]pyrimido[1,2-b]indazol-5(7H)-one

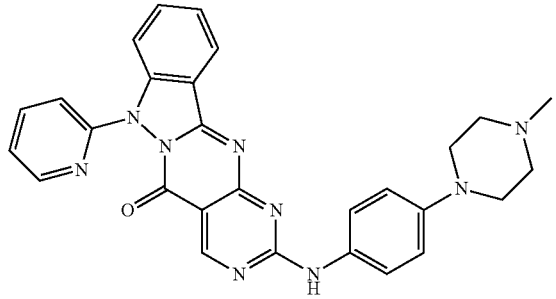

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

¹H-NMR (400 MHz, CDCl₃) δ: 9.28 (1H, s), 8.50 (1H, d, J=4.7 Hz), 8.34 (1H, d, J=7.1 Hz), 7.94 (1H, dt, J=1.5, 7.8 Hz), 7.80-7.40 (7H, m), 7.35 (1H, dd, J=6.8, 5.1 Hz), 6.98 (2H, d, J=8.5 Hz), 3.25-3.19 (4H, m), 2.65-2.58 (4H, m), 2.37 (3H, s).
ESI-MS Found: m/z [M+H]+ 504.

Example 24

Production of 2-{[3-methoxy-4-(4-methylpiperazin-1-yl)phenyl]amino}-7-(pyridin-2-yl)pyrimido[4',5':4,5]pyrimido[1,2-b]indazol-5(7H)-one

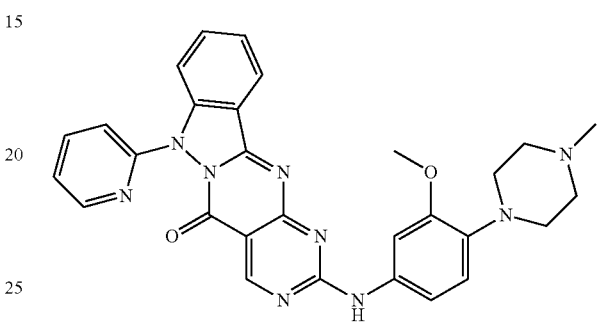

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 3-methoxy-4-(4-methyl-1-piperazinyl)aniline was used in place of 3-methyl-4-(4-methyl-1-piperazinyl)aniline.
¹H-NMR (400 MHz, CDCl₃) δ: 9.30 (1H, s), 8.49 (1H, d, J=4.6 Hz), 8.34 (1H, d, J=7.8 Hz), 7.95 (1H, td, J=7.7, 1.8 Hz), 7.74-7.69 (1H, m), 7.57-7.45 (4H, m), 7.40-7.21 (2H, m), 7.35 (1H, dd, J=7.1, 5.1 Hz), 6.98 (1H, d, J=8.3 Hz), 3.93 (3H, s), 3.22-3.02 (4H, m), 2.73-2.59 (4H, m), 2.38 (3H, s).
ESI-MS Found: m/z [M+H]+ 534.

Example 25

Production of 2-({4-[4-(2-hydroxyethyl)piperazin-1-yl]-3-methylphenyl}amino)-7-(pyridin-2-yl)pyrimido[4',5':4,5]pyrimido[1,2-b]indazol-5(7H)-one

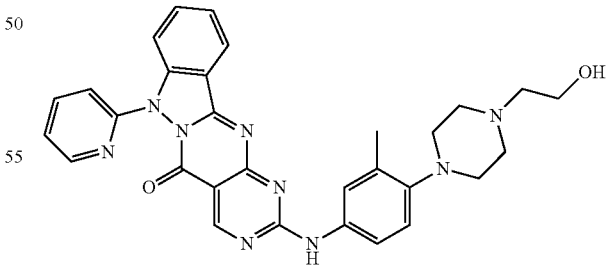

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 2-[4-(4-amino-2-methylphenyl)piperazin-1-yl]ethanol was used in place of 3-methyl-4-(4-methyl-1-piperazinyl)aniline.

$^1$H-NMR (400 MHz, DMSO-d$_6$) δ: 10.13 (1H, s), 9.14 (1H, s), 8.47 (1H, dd, J=5.0, 1.2 Hz), 8.29 (1H, d, J=7.8 Hz), 8.03 (1H, td, J=8.0, 1.8 Hz), 7.90-7.48 (2H, m), 7.84 (1H, ddd, J=8.3, 7.1, 1.2 Hz), 7.73 (1H, d, J=8.3 Hz), 7.69 (1H, d, J=8.0 Hz), 7.56 (1H, t, J=7.6 Hz), 7.44 (1H, dd, J=6.8, 5.1 Hz), 7.06 (1H, d, J=8.5 Hz), 4.42 (1H, t, J=6.0 Hz), 3.53 (2H, q, J=6.0 Hz), 2.87-2.79 (4H, m), 2.63-2.52 (4H, m), 2.45 (2H, t, J=6.0 Hz), 226 (3H, s).

ESI-MS Found: m/z [M+H]+ 548.

Example 26

Production of 2-{[4-(4-isopropylpiperazin-1-yl)phenyl]amino}-7-(pyridin-2-yl)pyrimido[4',5':4,5]pyrimido[1,2-b]indazol-5(7H)-one

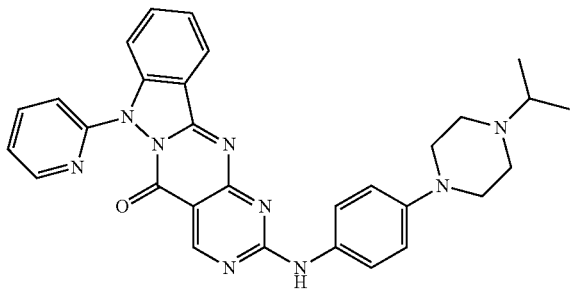

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 4-(4-isopropylpiperazin-1-yl)aniline was used in place of 3-methyl-4-(4-methyl-1-piperazinyl)aniline.

$^1$H-NMR (400 MHz, CDCl$_3$) δ: 9.29 (1H, s), 8.50 (1H, d, J=3.4 Hz), 8.35 (1H, d, J=7.8 Hz), 7.94 (1H, td, J=8.2, 3.1 Hz), 7.71 (1H, t, J=8.8 Hz), 7.60 (1H, s), 7.56 (2H, d, J=8.8 Hz), 7.49 (2H, t, J=8.5 Hz), 7.35 (1H, dd, J=7.1, 5.1 Hz), 6.98 (2H, d, J=9.3 Hz), 3.27-3.22 (4H, m), 2.80-2.71 (5H, m), 1.13 (6H, d, J=6.3 Hz).

ESI-MS Found: m/z [M+H]+ 532.

Example 27

Production of 2-{[4-(4-acetylpiperazin-1-yl)phenyl]amino}-7-(pyridin-2-yl)pyrimido[4',5':4,5]pyrimido[1,2-b]indazol-5(7H)-one

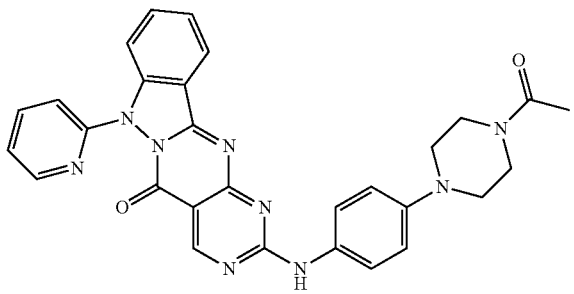

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 4-(4-acetylpiperazin-1-yl)aniline was used in place of 3-methyl-4-(4-methyl-1-piperazinyl)aniline.

$^1$H-NMR (400 MHz, CDCl$_3$) δ: 9.29 (1H, s), 8.50 (1H, dd, J=4.6, 1.7 Hz), 8.35 (1H, d, J=7.8 Hz), 7.95 (1H, td, J=7.8, 2.0 Hz), 7.74-7.70 (1H, m), 7.60 (1H, s), 7.55 (2H, d, J=8.3 Hz), 7.52 (2H, d, J=7.8 Hz), 7.48 (1H, t, J=7.6 Hz), 7.35 (1H, ddd, J=7.3, 4.9, 1.0 Hz), 6.99 (2H, d, J=8.8 Hz), 3.80 (2H, t, J=5.4 Hz), 3.65 (2H, t, J=5.1 Hz), 3.18 (2H, t, J=5.1 Hz), 3.14 (2H, t, J=5.1 Hz), 2.16 (3H, s).

ESI-MS Found: m/z [M+H]+ 532.

Example 28

Production of 2-{[4-(4-isobutyrylpiperazin-1-yl)phenyl]amino}-7-(pyridin-2-yl)pyrimido[4',5':4,5]pyrimido[1,2-b]indazol-5(7H)-one

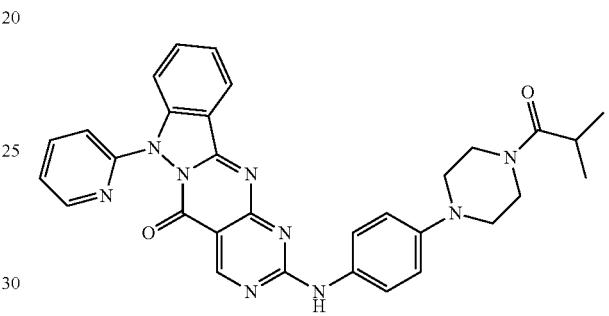

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 4-(4-isobutyrylpiperazin-1-yl)aniline was used in place of 3-methyl-4-(4-methyl-1-piperazinyl)aniline.

$^1$H-NMR (400 MHz, CDCl$_3$) δ: 9.29 (1H, s), 8.50 (1H, dd, J=4.6, 1.2 Hz), 8.35 (1H, d, J=7.8 Hz), 7.95 (1H, td, J=7.8, 2.0 Hz), 7.74-7.70 (1H, m), 7.64 (1H, s), 7.57-7.45 (4H, m), 7.35 (1H, dd, J=8.3, 5.4 Hz), 6.98 (2H, d, J=8.8 Hz), 3.81 (2H, t, J=5.4 Hz), 3.70 (2H, t, J=5.4 Hz), 3.16 (4H, t, J=5.4 Hz), 2.89-2.81 (1H, m), 1.17 (6H, d, J=6.8 Hz).

ESI-MS Found: m/z [M+H]+ 560.

Example 29

Production of 2-({4-[4-(2,2-dimethylpropanoyl)piperazin-1-yl]phenyl}amino)-7-(pyridin-2-yl)pyrimido[4',5':4,5]pyrimido[1,2-b]indazol-5(7H)-one

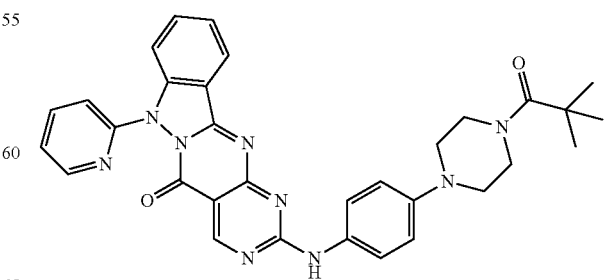

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 4-[4-(2,2-dimethylpropanoyl)piperazin-1-yl]aniline was used in place of 3-methyl-4-(4-methyl-1-piperazinyl)aniline.

$^1$H-NMR (400 MHz, CDCl$_3$) δ: 9.29 (1H, s), 8.50 (1H, d, J=4.3 Hz), 8.35 (1H, d, J=7.2 Hz), 7.95 (1H, t, J=7.5 Hz), 7.76-7.46 (2H, m), 7.72 (1H, t, J=7.8 Hz), 7.55 (1H, d, J=8.4 Hz), 7.50 (2H, t, J=10.0 Hz), 7.35 (1H, t, J=6.1 Hz), 6.99 (2H, d, J=8.4 Hz), 3.88-3.80 (4H, m), 3.19-3.14 (4H, m), 1.33 (9H, s).

ESI-MS Found: m/z [M+H]+ 574.

Example 30

Production of 2-({4-[4-(cyclopropylcarbonyl)piperazin-1-yl]phenyl}amino)-7-(pyridin-2-yl)pyrimido[4',5':4,5]pyrimido[1,2-b]indazol-5(7H)-one

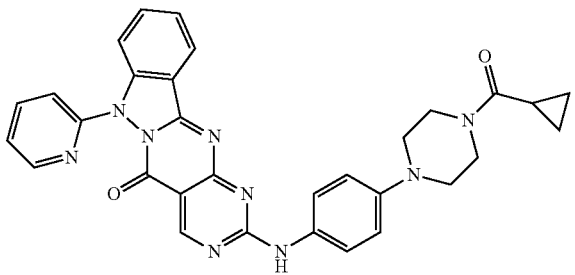

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 4-[4-(cyclopropylcarbonyl)piperazin-1-yl]aniline was used in place of 3-methyl-4-(4-methyl-1-piperazinyl)aniline.

$^1$H-NMR (400 MHz, CDCl$_3$) δ: 9.29 (1H, s), 8.50 (1H, dd, J=5.1, 1.7 Hz), 8.35 (1H, d, J=8.3 Hz), 7.95 (1H, td, J=7.8, 2.0 Hz), 7.72 (1H, t, J=7.8 Hz), 7.67-7.57 (2H, m), 7.55 (1H, d, J=8.3 Hz), 7.52 (1H, d, J=7.8 Hz), 7.48 (1H, t, J=7.6 Hz), 7.35 (1H, dd, J=7.3, 4.9 Hz), 6.99 (2H, d, J=8.8 Hz), 3.84 (4H, d, J=15.6 Hz), 3.19 (4H, d, J=15.6 Hz), 1.83-1.77 (1H, m), 1.03 (2H, dt, J=7.8, 3.4 Hz), 0.81 (2H, dt, J=11.5, 3.4 Hz).

ESI-MS Found: m/z [M+H]+ 558.

Example 31

Production of 2-({4-[4-(cyclobutylcarbonyl)piperazin-1-yl]phenyl}amino)-7-(pyridin-2-yl)pyrimido[4',5':4,5]pyrimido[1,2-b]indazol-5(7H)-one

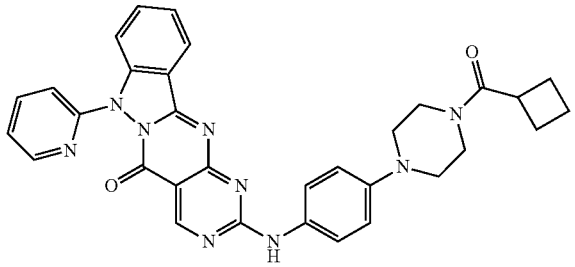

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 4-[4-(cyclobutylcarbonyl)piperazin-1-yl]aniline was used in place of 3-methyl-4-(4-methyl-1-piperazinyl)aniline.

$^1$H-NMR (400 MHz, CDCl$_3$) δ: 9.29 (1H, s), 8.50 (1H, dd, J=4.9, 2.0 Hz), 8.35 (1H, d, J=7.8 Hz), 7.95 (1H, td, J=7.8, 2.0 Hz), 7.74-7.70 (2H, m), 7.64 (1H, s), 7.54 (2H, dd, J=11.5, 8.0 Hz), 7.48 (1H, t, J=7.6 Hz), 7.36 (1H, ddd, J=7.3, 4.9, 1.0 Hz), 6.99 (2H, d, J=7.3 Hz), 3.80 (2H, t, J=4.9 Hz), 3.54 (2H, t, J=4.9 Hz), 3.36-3.27 (1H, m), 3.13 (4H, dd, J=10.7, 6.3 Hz), 2.39 (2H, tt, J=13.7, 5.1 Hz), 2.19 (2H, dt, J=17.6, 6.7 Hz), 2.03-1.95 (1H, m), 1.94-1.85 (1H, m).

ESI-MS Found: m/z [M+H]+ 572.

Example 32

Production of 2-({3-(hydroxymethyl)-4-[4-(methoxyacetyl)piperazin-1-yl]phenyl}amino)-7-(pyridin-2-yl)pyrimido[4',5':4,5]pyrimido[1,2-b]indazol-5(7H)-one

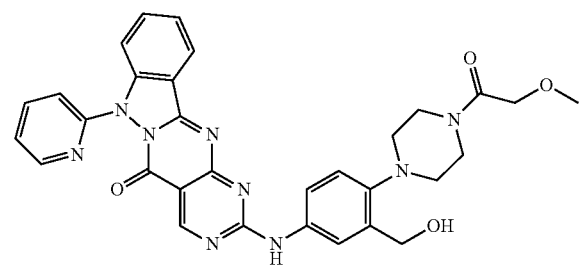

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 5-amino-2-[4-(methoxyacetyl)piperazin-1-yl]phenyl)methanol was used in place of 3-methyl-4-(4-methyl-1-piperazinyl)aniline.

$^1$H-NMR (400 MHz, CDCl$_3$) δ: 9.32 (1H, s), 8.51 (1H, dd, J=4.9, 1.9 Hz), 8.39 (1H, d, J=7.8 Hz), 8.10-7.10 (10H, m), 4.86 (2H, s), 4.17 (2H, s), 3.84-3.65 (4H, m), 3.42 (3H, s), 3.10-2.98 (4H, m).

ESI-MS Found: m/z [M+H]+ 592.

Example 33

Production of 2-({3-fluoro-4-[4-(methoxyacetyl)piperazin-1-yl]-phenyl}amino)-7-(pyridin-2-yl)pyrimido[4',5':4,5]pyrimido[1,2-b]indazol-5(7H)-one

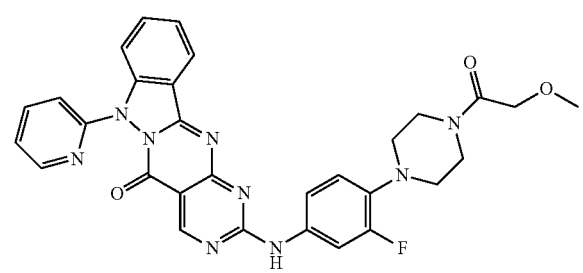

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 3-fluoro-4-[4-(methoxyacetyl)piperazin-1-yl]aniline was used in place of 3-methyl-4-(4-methyl-1-piperazinyl)aniline.

¹H-NMR (400 MHz, CDCl₃) δ: 9.31 (1H, s), 8.50 (1H, dd, J=4.9, 1.9 Hz), 8.36 (1H, d, J=7.8 Hz), 7.96 (1H, td, J=7.8, 1.9 Hz), 7.76-7.67 (3H, m), 7.54 (2H, d, J=8.3 Hz), 7.49 (1H, t, J=7.6 Hz), 7.36 (1H, ddd, J=7.3, 4.9, 1.0 Hz), 7.32 (1H, br s), 6.96 (1H, t, J=9.0 Hz), 4.17 (2H, s), 3.83-3.81 (2H, m), 3.70-3.68 (2H, m), 3.46 (3H, s), 3.09-3.06 (4H, m).

ESI-MS Found: m/z [M+H]+ 580.

Example 34

Production of 2-({3-chloro-4-[4-(methoxyacetyl)piperazin-1-yl]phenyl}amino)-7-(pyridin-2-yl)pyrimido[4',5':4,5]pyrimido[1,2-b]indazol-5(7H)-one

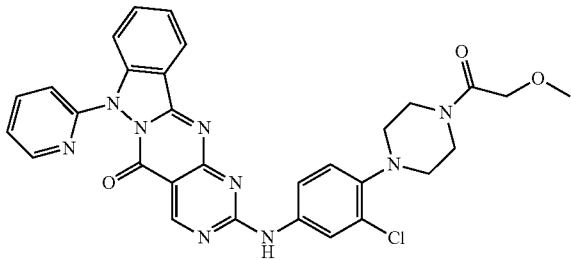

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 3-chloro-4-[4-(methoxyacetyl)piperazin-1-yl]aniline was used in place of 3-methyl-4-(4-methyl-1-piperazinyl)aniline.

¹H-NMR (400 MHz, CDCl₃) δ: 9.31 (1H, s), 8.49 (1H, dd, J=4.9, 2.0 Hz), 8.38-8.32 (1H, m), 7.96 (1H, td, J=7.8, 2.0 Hz), 7.81 (1H, d, J=2.4 Hz), 7.76-7.61 (2H, m), 7.55-7.47 (4H, m), 7.36 (1H, dd, J=7.8, 4.9 Hz), 7.05 (1H, d, J=8.3 Hz), 4.17 (2H, s), 3.85-3.79 (2H, m), 3.71-3.66 (2H, m), 3.46 (3H, s), 3.07-3.01 (4H, m).

ESI-MS Found: m/z [M+H]+ 597.

Example 35

Production of 2-{[4-(4-glycoloylpiperazin-1-yl)phenyl]amino}-7-(pyridin-2-yl)pyrimido[4',5':4,5]pyrimido[1,2-b]indazol-5(7H)-one

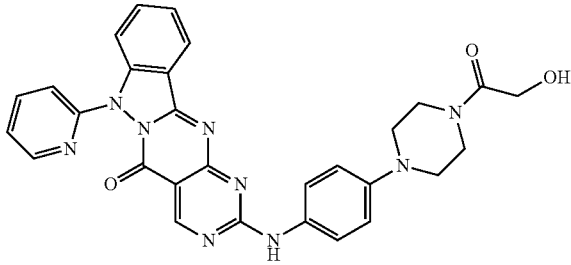

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 2-[4-(4-aminophenyl)piperazin-1-yl]-2-oxoethanol was used in place of 3-methyl-4-(4-methyl-1-piperazinyl)aniline.

¹H-NMR (400 MHz, CDCl₃) δ: 9.28 (1H, s), 8.49 (1H, d, J=4.9 Hz), 8.34 (1H, d, J=7.8 Hz), 7.95 (1H, td, J=7.7, 1.6 Hz), 7.81 (1H, s), 7.72 (1H, t, J=7.8 Hz), 7.67 (2H, s), 7.53 (1H, t, J=8.3 Hz), 7.47 (1H, t, J=7.8 Hz), 7.36 (1H, dd, J=6.8, 4.9 Hz), 6.98 (2H, d, J=8.8 Hz), 4.24 (2H, s), 3.85 (2H, t, J=5.1 Hz), 3.46 (2H, t, J=5.1 Hz), 3.18 (4H, q, J=4.6 Hz).

ESI-MS Found: m/z [M+H]+ 548.5.

Example 36

Production of 2-({4-[4-(2-hydroxy-2-methylpropanoyl)piperazin-1-yl]phenyl}amino)-7-(pyridin-2-yl)pyrimido[4',5':4,5]pyrimido[1,2-b]indazol-5(7H)-one

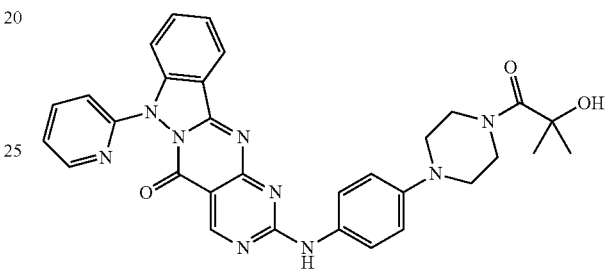

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 1-[4-(4-aminophenyl)piperazin-1-yl]-2-methyl-1-oxopropan-2-ol was used in place of 3-methyl-4-(4-methyl-1-piperazinyl)aniline.

¹H-NMR (400 MHz, CDCl₃) δ: 9.28 (1H, s), 8.49 (1H, t, J=3.9 Hz), 8.34 (1H, d, J=7.8 Hz), 7.95 (1H, td, J=7.8, 2.0 Hz), 7.72 (1H, t, J=7.8 Hz), 7.65 (2H, s), 7.53 (2H, t, J=9.3 Hz), 7.48 (1H, t, J=7.6 Hz), 7.35 (1H, ddd, J=7.3, 4.9, 1.0 Hz), 6.98 (2H, d, J=9.3 Hz), 3.88 (4H, t, J=5.1 Hz), 3.18 (4H, t, J=5.1 Hz), 1.55 (9H, s).

ESI-MS Found: m/z [M+H]+ 576.5.

Example 37

Production of 2-({-4-[4-(methoxyacetyl)piperazin-1-yl]-phenyl}amino)-7-(pyridin-2-yl)pyrimido[4',5':4,5]pyrimido[1,2-b]indazol-5(7H)-one

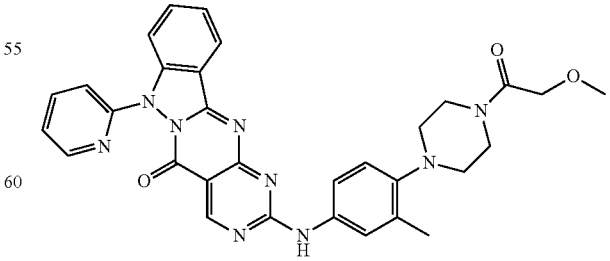

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 4-[4-(methoxyacetyl)piperazin-1-yl]-3-methylaniline was used in place of 3-methyl-4-(4-methyl-1-piperazinyl)aniline.

$^1$H-NMR (400 MHz, CDCl$_3$) δ: 9.30 (1H, s), 8.50 (1H, dq, J=4.9, 1.0 Hz), 8.35 (1H, d, J=7.8 Hz), 7.95 (1H, td, J=7.8, 2.0 Hz), 7.73 (1H, dd, J=7.3, 1.5 Hz), 7.71 (1H, dd, J=7.1, 1.2 Hz), 7.65 (1H, s), 7.54 (1H, dd, J=10.5, 8.0 Hz), 7.48 (1H, t, J=7.6 Hz), 7.44 (1H, s), 7.36 (1H, dd, J=4.9, 1.0 Hz), 7.35 (1H, dd, J=4.9, 1.0 Hz), 7.04 (1H, d, J=8.8 Hz), 4.17 (3H, s), 3.82-3.76 (2H, m), 3.67-3.62 (2H, m), 3.47 (2H, s), 2.93-2.88 (4H, m), 2.38 (3H, s).

ESI-MS Found: m/z [M+H]+ 576.5.

Example 38

Production of 2-{[4-(4-acetylpiperazin-1-yl)-3-methylphenyl]amino}-7-(pyridin-2-yl)pyrimido[4',5':4,5]pyrimido[1,2-b]indazol-5(7H)-one

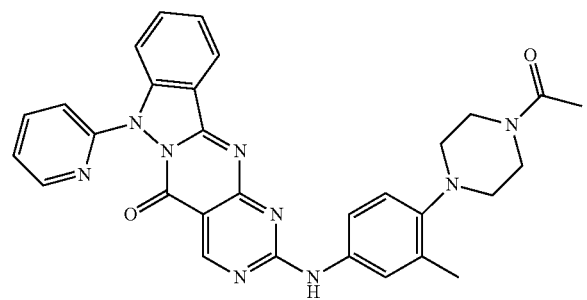

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 4-(4-acetylpiperazin-1-yl)-3-methylaniline was used in place of 3-methyl-4-(4-methyl-1-piperazinyl)aniline.

$^1$H-NMR (400 MHz, CDCl$_3$) δ: 9.30 (1H, s), 8.50 (1H, dd, J=4.9, 1.5 Hz), 8.34 (1H, d, J=7.8 Hz), 7.95 (1H, td, J=7.7, 1.6 Hz), 7.72 (1H, t, J=7.8 Hz), 7.63 (1H, s), 7.54 (1H, dd, J=10.5, 8.0 Hz), 7.48 (1H, t, J=7.6 Hz), 7.44 (2H, s), 7.36 (1H, dd, J=7.3, 4.9 Hz), 7.03 (1H, d, J=8.8 Hz), 3.77 (2H, t, J=4.9 Hz), 3.62 (2H, t, J=4.9 Hz), 2.91 (2H, t, J=4.9 Hz), 2.87 (2H, t, J=4.91 Hz), 2.37 (3H, s), 2.16 (3H, s).

ESI-MS Found: m/z [M+H]+ 546.

Example 39

Production of 2-{[4-(4-cyclopropylpiperazin-1-yl)-3-methylphenyl]amino}-7-(pyridin-2-yl)pyrimido[4',5':4,5]pyrimido[1,2-b]indazol-5(7H)-one

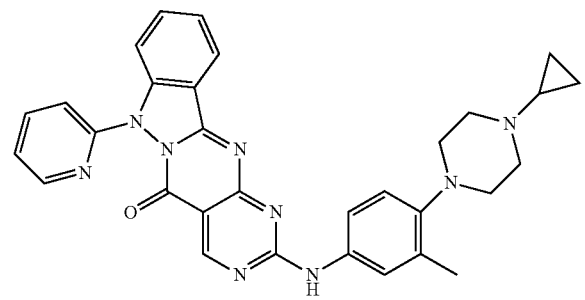

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 4-(4-cyclopropylpiperazin-1-yl)-3-methylaniline was used in place of 3-methyl-4-(4-methyl-1-piperazinyl)aniline.

$^1$H-NMR (400 MHz, CDCl$_3$) δ: 9.30 (1H, s), 8.50 (1H, d, J=4.2 Hz), 8.35 (1H, d, J=7.8 Hz), 7.94 (1H, t, J=7.1 Hz), 7.77-7.22 (8H, m), 7.07 (1H, d, J=8.5 Hz), 3.00-2.71 (8H, m), 2.36 (3H, s), 1.76-1.57 (1H, m), 0.56-0.42 (4H, m).

ESI-MS Found: m/z [M+H]+ 544.

Example 40

Production of 2-({4-[(4-methylpiperazin-1-yl)methyl]phenyl}amino)-7-(pyridin-2-yl)pyrimido[4',5':4,5]pyrimido[1,2-b]indazol-5(7H)-one

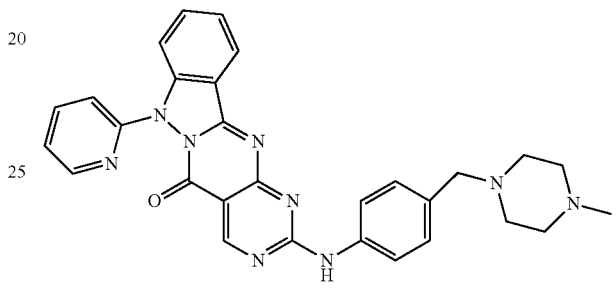

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 4-[(4-methylpiperazin-1-yl)methyl]aniline was used in place of 3-methyl-4-(4-methyl-1-piperazinyl)aniline.

$^1$H-NMR (400 MHz, DMSO-d$_6$) δ: 10.31 (1H, s), 9.18 (1H, s), 8.48 (1H, dd, J=4.9, 1.8 Hz), 8.31 (1H, d, J=7.0 Hz), 8.04 (1H, td, J=7.8, 1.8 Hz), 7.86 (1H, dd, J=7.0, 1.1 Hz), 7.84 (1H, dd, J=7.0, 1.2 Hz), 7.74 (1H, d, J=8.2 Hz), 7.70 (1H, d, J=8.2 Hz), 7.57 (1H, t, J=7.4 Hz), 7.44 (1H, dd, J=7.2, 4.9 Hz), 7.28 (2H, d, J=8.6 Hz), 3.43 (2H, s), 2.55-2.19 (8H, m), 2.15 (3H, s).

ESI-MS Found: m/z [M+H]+ 518.

Example 41

Production of 2-({4-[(4-isobutyrylpiperazin-1-yl)methyl]phenyl}amino)-7-(pyridin-2-yl)pyrimido[4',5':4,5]pyrimido[1,2-b]indazol-5(7H)-one

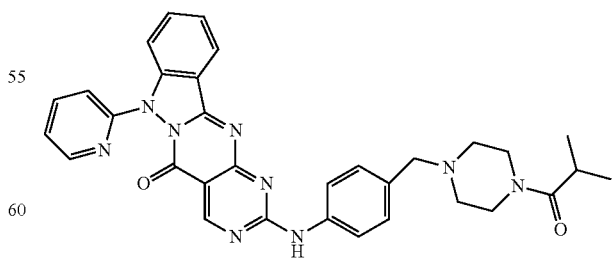

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]

pyrimido[1,2-b]indazol-5(7H)-one used in Example 1, and 4-[(4-isobutyrylpiperazin-1-yl)methyl]aniline was used in place of 3-methyl-4-(4-methyl-1-piperazinyl)aniline.

¹H-NMR (400 MHz, CDCl₃) δ: 9.33 (1H, s), 8.50 (1H, dd, J=4.9, 1.0 Hz), 8.37 (1H, d, J=7.8 Hz), 7.96 (1H, td, J=7.8, 2.0 Hz), 7.7.5-7.69 (3H, m), 7.66 (1H, s), 7.54 (2H, t, J=7.6 Hz), 7.49 (1H, t, J=8.0 Hz), 7.38-7.33 (2H, m), 3.68-3.63 (2H, m), 3.55-3.50 (4H, m), 2.83-2.75 (1H, m), 2.47-2.42 (4H, m), 1.13 (6H, d, J=6.8 Hz).

ESI-MS Found: m/z [M+H]+ 574.

Example 42

Production of 2-[(4-{[4-(2,2-dimethylpropanoyl)piperazin-1-yl]methyl}phenyl)amino]-7-(pyridin-2-yl)pyrimido[4',5':4,5]pyrimido[1,2-b]indazol-5(7H)-one

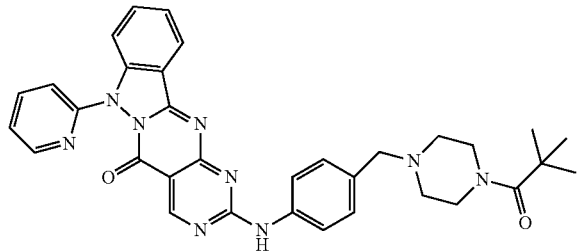

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 4-{[4-(2,2-dimethylpropanoyl)piperazin-1-yl]methyl}aniline was used in place of 3-methyl-4-(4-methyl-1-piperazinyl)aniline.

¹H-NMR (400 MHz, CDCl₃) δ: 9.32 (1H, s), 8.50 (1H, dd, J=4.6, 1.2 Hz), 8.36 (1H, d, J=7.8 Hz), 7.96 (1H, td, J=7.8, 2.0 Hz), 7.76-7.67 (4H, m), 7.54 (1H, t, J=7.6 Hz), 7.48 (1H, t, J=7.6 Hz), 7.38-7.32 (3H, m), 3.66 (4H, t, J=4.6 Hz), 3.51 (2H, s), 2.45 (4H, t, J=4.9 Hz), 1.28 (9H, s).

ESI-MS Found: m/z [M+H]+ 588.

Example 43

Production of 2-[(2-methyl-1,2,3,4-tetrahydroisoquinolin-6-yl)amino]-7-(pyridin-2-yl)pyrimido[4',5':4,5]pyrimido[1,2-b]indazol-5(7H)-one

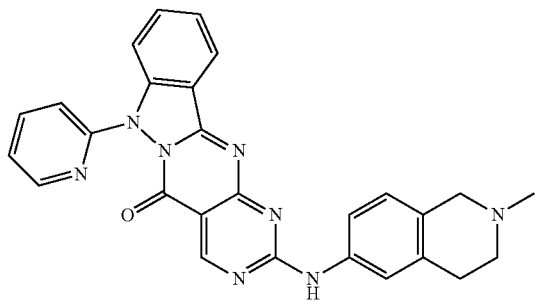

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]

pyrimido[1,2-b]indazol-5(7H)-one used in Example 1, and 2-methyl-1,2,3,4-tetrahydroisoquinolin-6-amine was used in place of 3-methyl-4-(4-methyl-1-piperazinyl)aniline.

¹H-NMR (400 MHz, DMSO-d₆) δ: 10.21 (1H, s), 9.16 (1H, s), 8.48 (1H, ddd, J=4.9, 1.8, 0.7 Hz), 8.30 (1H, d, J=7.8 Hz), 8.04 (1H, ddd, J=8.0, 7.6, 1.8 Hz), 7.84 (1H, ddd, J=8.5, 7.3, 1.2 Hz), 7.79-7.66 (3H, m), 7.60-7.53 (2H, m), 7.44 (1H, ddd, J=7.6, 4.9, 1.0 Hz), 7.05 (1H, d, J=8.3 Hz), 3.46 (2H, s), 2.84 (2H, t, J=5.8 Hz), 2.59 (2H, t, J=5.8 Hz), 2.34 (3H, s).

ESI-MS Found: m/z [M+H]+ 475.

Example 44

Production of 2-[(2-methyl-1,2,3,4-tetrahydroisoquinolin-7-yl)amino]-7-(pyridin-2-yl)pyrimido[4',5':4,5]pyrimido[1,2-b]indazol-5(7H)-one

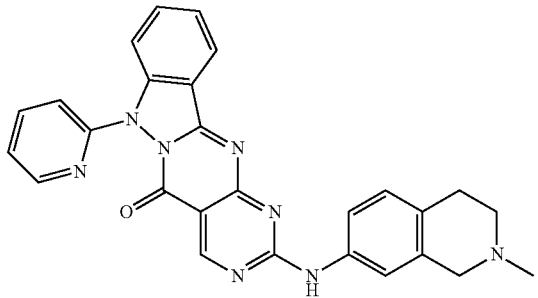

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and 2-methyl-1,2,3,4-tetrahydroisoquinolin-7-amine was used in place of 3-methyl-4-(4-methyl-1-piperazinyl)aniline.

¹H-NMR (400 MHz, DMSO-d₆) δ: 10.21 (1H, s), 9.16 (1H, s), 8.48 (1H, ddd, J=4.9, 1.8, 0.7 Hz), 8.30 (1H, d, J=7.8 Hz), 8.04 (1H, ddd, J=8.0, 7.6, 1.8 Hz), 7.84 (1H, ddd, J=8.5, 7.3, 1.2 Hz), 7.79-7.66 (3H, m), 7.60-7.53 (2H, m), 7.44 (1H, ddd, J=7.6, 4.9, 1.0 Hz), 7.05 (1H, d, J=8.3 Hz), 3.46 (2H, s), 2.84 (2H, t, J=5.8 Hz), 2.59 (2H, t, J=5.8 Hz), 2.34 (3H, s).

ESI-MS Found: m/z [M+H]+ 475.

Example 45

Production of 2-{[4-(diethylamino)phenyl]amino}-7-(pyridin-2-yl)pyrimido[4',5':4,5]pyrimido[1,2-b]indazol-5(7H)-one

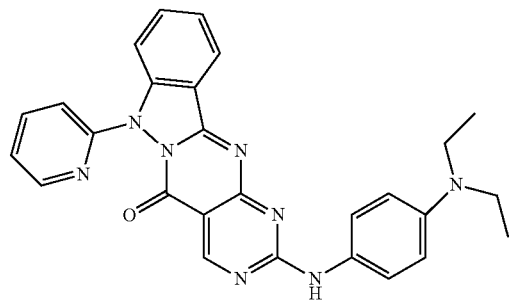

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]

pyrimido[1,2-b]indazol-5(7H)-one used in Example 1, and N,N-diethylbenzene-1,4-diamine was used in place of 3-methyl-4-(4-methyl-1-piperazinyl)aniline.

¹H-NMR (400 MHz, DMSO-d₆) δ: 9.98 (1H, s), 9.08 (1H, s), 8.47 (1H, dd, J=5.3, 1.6 Hz), 8.28 (1H, d, J=7.8 Hz), 8.03 (1H, td, J=7.8, 1.6 Hz), 7.83 (1H, t, J=7.8 Hz), 7.72 (1H, d, J=8.2 Hz), 7.68 (1H, d, J=7.8 Hz), 7.68-7.62 (2H, m), 7.56 (1H, t, J=7.8 Hz), 7.44 (1H, dd, J=7.2, 5.3 Hz), 6.70 (2H, d, J=8.2 Hz), 3.33 (2H, q, J=7.0 Hz), 1.09 (3H, t, J=7.0 Hz).

ESI-MS Found: m/z [M+H]+ 477.

Example 46

Production of 2-anilino-7-(pyridin-2-yl)pyrimido[4',5':4,5]pyrimido[1,2-b]indazol-5(7H)-one

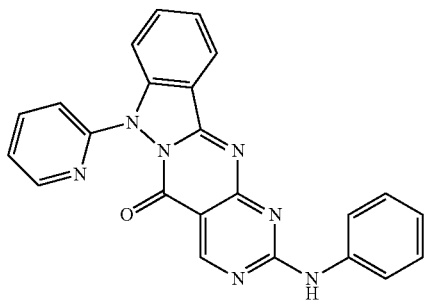

The title compound was produced as a yellow solid in the same manner as in Example 1, for which, however, 2-(methylthio)-7-pyridin-2-ylpyrimido[4',5':4,5]pyrimido[1,2-b]indazol-5(7H)-one obtained in Production Example 14 was used in place of 7-methyl-2-(methylthio)pyrimido[4',5':4,5]pyrimido[1,2-b]indazol-5(7H)-one used in Example 1, and aniline was used in place of 3-methyl-4-(4-methyl-1-piperazinyl)aniline.

¹H-NMR (400 MHz, DMSO-d₆) δ: 10.34 (1H, s), 9.19 (1H, s), 8.48 (1H, dd, J=5.1, 1.6 Hz), 8.32 (1H, d, J=7.8 Hz), 8.04 (1H, td, J=7.8, 2.0 Hz), 7.93 (2H, d, J=8.2 Hz), 7.83-7.87 (1H, m), 7.74 (1H, d, J=8.6 Hz), 7.71 (1H, d, J=7.8 Hz), 7.57 (1H, t, J=7.4 Hz), 7.45 (1H, dd, J=7.0, 5.1 Hz), 7.39 (2H, t, J=7.8 Hz), 7.08 (1H, t, J=7.2 Hz).

ESI-MS Found: m/z [M+H]+ 406.

Example 47

Production of 2-{[3-methyl-4-(4-methylpiperazin-1-yl)phenyl]amino}-7-(6-methylpyridin-2-yl)pyrimido[4',5':4,5]pyrimido[1,2-b]indazol-5(7H)-one

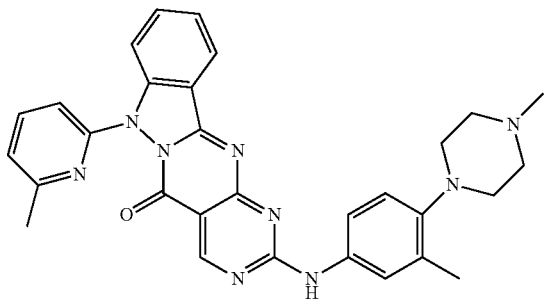

The title compound was produced as a yellow solid in the same manner as in Example 1, for which, however, 7-(6-methylpyridin-2-yl)-2-(methylthio)pyrimido[4',5':4,5]pyrimido[1,2-b]indazol-5(7H)-one obtained in Production Example 15 was used in place of 7-methyl-2-(methylthio)pyrimido[4',5':4,5]pyrimido[1,2-b]indazol-5(7H)-one used in Example 1.

¹H-NMR (400 MHz, CDCl₃) δ: 9.30 (1H, s), 8.34 (1H, d, J=8.0 Hz), 7.79 (1H, t, J=7.7 Hz), 7.71 (1H, ddd, J=8.5, 7.1, 1.2 Hz), 7.65-7.35 (4H, m), 7.57 (1H, d, J=8.5 Hz), 7.23 (1H, d, J=7.7 Hz), 7.18 (1H, d, J=7.7 Hz), 7.09 (1H, d, J=8.5 Hz), 3.00-2.93 (4H, m), 2.73-2.48 (4H, m), 2.51 (3H, s), 2.39 (3H, s), 2.35 (3H, s).

ESI-MS Found: m/z [M+H]+ 532.

Example 48

Production of 2-{[3-methyl-4-(4-methylpiperazin-1-yl)phenyl]amino}-7-(5-methylpyridin-2-yl)pyrimido[4',5':4,5]pyrimido[1,2-b]indazol-5(7H)-one

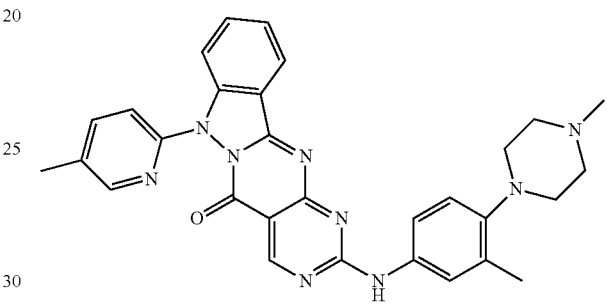

The title compound was produced as a yellow solid in the same manner as in Example 1, for which, however, 7-(5-methylpyridin-2-yl)-2-(methylthio)pyrimido[4',5':4,5]pyrimido[1,2-b]indazol-5(7H)-one obtained in Production Example 16 was used in place of 7-methyl-2-(methylthio)pyrimido[4',5':4,5]pyrimido[1,2-b]indazol-5(7H)-one used in Example 1.

¹H-NMR (400 MHz, CDCl₃) δ: 9.29 (1H, s), 8.34 (1H, d, J=7.8 Hz), 8.30-8.28 (1H, m), 7.75 (1H, ddd, J=8.0, 2.4, 0.7 Hz), 7.70 (1H, dt, J=1.2, 7.8 Hz), 7.65-7.36 (6H, m), 7.09 (1H, d, J=8.5 Hz), 3.01-2.94 (4H, m), 2.78-2.52 (4H, m), 2.41 (3H, s), 2.40 (3H, s), 2.35 (3H, s).

ESI-MS Found: m/z [M+H]+ 532.

Example 49

Production of 2-{[3-methyl-4-(4-methylpiperazin-1-yl)phenyl]amino}-7-(4-methylpyridin-2-yl)pyrimido[4',5':4,5]pyrimido[1,2-b]indazol-5(7H)-one

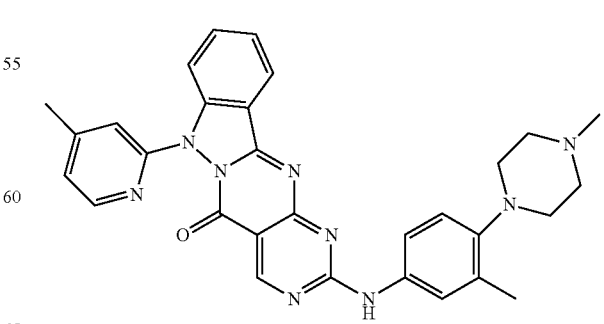

The title compound was produced as a yellow solid in the same manner as in Example 1, for which, however, 7-(4- methylpyridin-2-yl)-2-(methylthio)pyrimido[4',5':4,5]pyrimido[1,2-b]indazol-5(7H)-one obtained in Production Example 17 was used in place of 7-methyl-2-(methylthio)pyrimido[4',5':4,5]pyrimido[1,2-b]indazol-5(7H)-one used in Example 1.

$^1$H-NMR (400 MHz, CDCl$_3$) δ: 9.30 (1H, s), 8.37-8.31 (2H, m), 7.70 (1H, ddd, J=8.3, 7.1, 1.2 Hz), 7.66-7.37 (5H, m), 7.35 (1H, s), 7.16 (1H, d, J=4.9 Hz), 7.10 (1H, d, J=8.5 Hz), 3.02-2.95 (4H, m), 2.80-2.55 (4H, m), 2.51 (3H, s), 2.42 (3H, s), 2.35 (3H, s).

ESI-MS Found: m/z [M+H]+ 532.

Example 50

Production of N,N-dimethyl-6-[2-{[3-methyl-4-(4-methylpiperazin-1-yl)phenyl]amino}-5-oxopyrimido[4',5':4,5]pyrimido[1,2-b]indazol-7(5H)-yl]pyridine-2-carboxamide

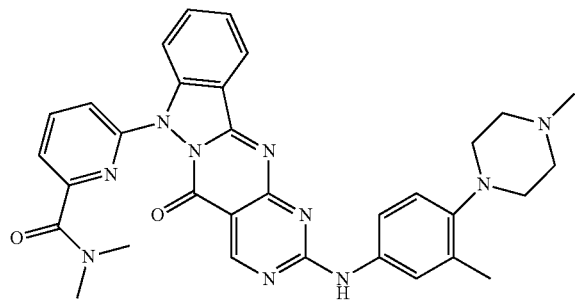

The title compound was produced as a yellow solid in the same manner as in Example 1, for which, however, N,N-dimethyl-6-[2-(methylthio)-5-oxopyrimido[4',5':4,5]pyrimido[1,2-b]indazol-7(5H)-yl]pyridine-2-carboxamide obtained in Production Example 18 was used in place of 7-methyl-2-(methylthio)pyrimido[4',5':4,5]pyrimido[1,2-b]indazol-5(7H)-one used in Example 1.

$^1$H-NMR (400 MHz, CDCl$_3$) δ: 9.24 (1H, s), 8.34 (1H, d, J=7.6 Hz), 8.07 (1H, t, J=7.8 Hz), 7.75-7.66 (2H, m), 7.62 (1H, d, J=8.0 Hz), 7.60-7.36 (5H, m), 7.10 (1H, d, J=8.5 Hz), 3.03 (3H, s), 2.99-2.94 (4H, m), 2.93 (3H, s), 2.74-2.50 (4H, m), 2.39 (3H, s), 2.36 (3H, s).

ESI-MS Found: m/z [M+H]+ 589.

Example 51

Production of N,N-dimethyl-6-[2-{[3-methyl-4-(4-methylpiperazin-1-yl)phenyl]amino}-5-oxopyrimido[4',5':4,5]pyrimido[1,2-b]indazol-7(5H)-yl]pyridine-3-carboxamide

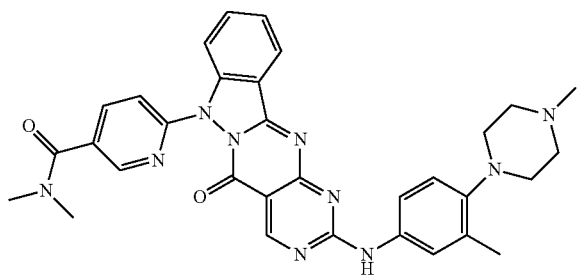

The title compound was produced as a yellow solid in the same manner as in Example 1, for which, however, N,N-dimethyl-6-[2-(methylthio)-5-oxopyrimido[4',5':4,5]pyrimido[1,2-b]indazol-7(5H)-yl]nicotinamide obtained in Production Example 19 was used in place of 7-methyl-2-(methylthio)pyrimido[4',5':4,5]pyrimido[1,2-b]indazol-5(7H)-one used in Example 1.

$^1$H-NMR (400 MHz, CDCl$_3$) δ: 9.31 (1H, br s), 8.57 (1H, dd, J=2.3, 0.6 Hz), 8.35 (1H, d, J=8.0 Hz), 7.99 (1H, dd, J=8.3, 2.3 Hz), 7.74 (1H, ddd, J=8.3, 7.1, 1.0 Hz), 7.68 (1H, d, J=8.3 Hz), 7.65-7.35 (3H, m), 7.50 (1H, ddd, J=8.3, 7.1, 1.0 Hz), 7.44 (1H, dd, J=8.3, 1.0 Hz), 7.10 (1H, d, J=8.3 Hz), 3.15 (3H, s), 3.10 (3H, s), 3.01-2.92 (4H, m), 2.75-2.49 (4H, m), 2.39 (3H, s), 2.35 (3H, s).

ESI-MS Found: m/z [M+H]+ 589.

Example 52

Production of 7-(6-methoxypyridin-2-yl)-2-{[3-methyl-4-(4-methylpiperazin-1-yl)phenyl]amino}pyrimido[4',5':4,5]pyrimido[1,2-b]indazol-5(7H)-one

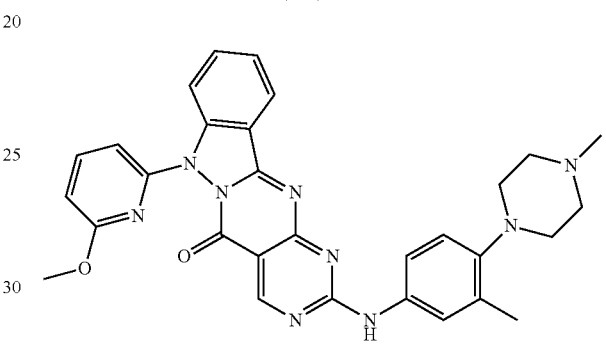

The title compound was produced as a yellow solid in the same manner as in Example 1, for which, however, 7-(6-methoxypyridin-2-yl)-2-(methylthio)pyrimido[4',5':4,5]pyrimido[1,2-b]indazol-5(7H)-one obtained in Production Example 20 was used in place of 7-methyl-2-(methylthio)pyrimido[4',5':4,5]pyrimido[1,2-b]indazol-5(7H)-one used in Example 1.

$^1$H-NMR (400 MHz, CDCl$_3$) δ: 9.31 (1H, s), 8.34 (1H, d, J=7.5 Hz), 7.77 (1H, dd, J=8.3, 7.5 Hz), 7.72 (1H, ddd, J=8.3, 7.1, 1.2 Hz), 7.64-7.39 (3H, m), 7.60 (1H, d, J=8.3 Hz), 7.48 (1H, ddd, J=7.7, 7.1, 0.7 Hz), 7.09 (1H, d, J=8.5 Hz), 7.03 (1H, dd, J=7.7, 0.5 Hz), 6.76 (1H, dd, J=8.3, 0.7 Hz), 3.76 (3H, s), 3.01-2.93 (4H, m), 2.76-2.49 (4H, m), 2.40 (3H, s), 2.35 (3H, s).

ESI-MS Found: m/z [M+H]+ 548.

Example 53

Production of 2-{[3-methyl-4-(4-methylpiperazin-1-yl)phenyl]amino}-7-(6-nitropyridin-2-yl)pyrimido[4',5':4,5]pyrimido[1,2-b]indazol-5(7H)-one

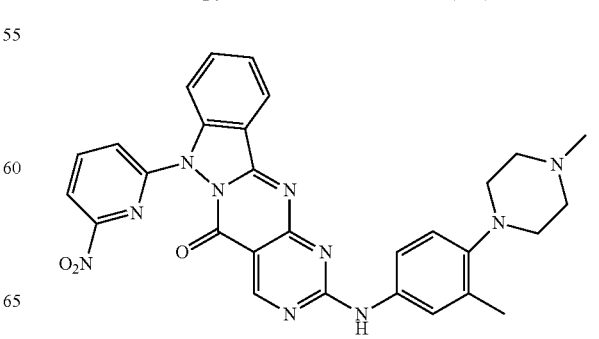

The title compound was produced as a yellow solid in the same manner as in Example 1, for which, however, 7-(6-nitropyridin-2-yl)-2-(methylthio)pyrimido[4',5':4,5]pyrimido[1,2-b]indazol-5(7H)-one obtained in Production Example 21 was used in place of 7-methyl-2-(methylthio)pyrimido[4',5':4,5]pyrimido[1,2-b]indazol-5(7H)-one used in Example 1.

$^1$H-NMR (400 MHz, CDCl$_3$) δ: 9.20 (1H, s), 8.64 (1H, dd, J=4.6, 1.7 Hz), 8.54 (1H, dd, J=8.0, 1.7 Hz), 8.39 (1H, d, J=8.0 Hz), 7.76 (1H, ddd, J=8.2, 7.3, 1.0 Hz), 7.72-7.25 (3H, m), 7.62 (1H, dd, J=8.0, 4.6 Hz), 7.53 (1H, ddd, J=8.2, 7.3, 1.0 Hz), 7.39 (1H, d, J=8.2 Hz), 7.09 (1H, d, J=8.5 Hz), 3.01-2.94 (4H, m), 2.79-2.52 (4H, m), 2.41 (3H, s), 2.35 (3H, s).

ESI-MS Found: m/z [M+H]+ 563.

Example 54

Production of 7-[6-(hydroxyamino)pyridin-2-yl]-2-{[3-methyl-4-(4-methylpiperazin-1-yl)phenyl]amino}pyrimido[4',5':4,5]pyrimido[1,2-b]indazol-5(7H)-one

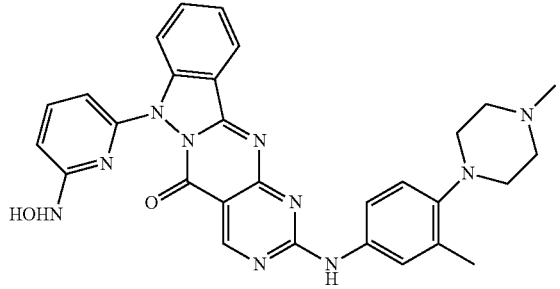

The title compound was produced as a yellow solid in the same manner as in Example 1, for which, however, 7-[6-(hydroxyamino)pyridin-2-yl]-2-(methylthio)pyrimido[4',5':4,5]pyrimido[1,2-b]indazol-5(7H)-one obtained in Production Example 22 was used in place of 7-methyl-2-(methylthio)pyrimido[4',5':4,5]pyrimido[1,2-b]indazol-5(7H)-one used in Example 1.

$^1$H-NMR (400 MHz, DMSO-d$_6$) δ: 10.13 (1H, s), 9.11 (1H, s), 9.06 (1H, s), 8.97 (1H, d, J=1.5 Hz), 8.29 (1H, d, J=7.8 Hz), 7.85-7.67 (3H, m), 7.81 (1H, ddd, J=8.3, 7.3, 1.2 Hz), 7.60-7.49 (2H, m), 7.39 (1H, dd, J=7.9, 4.8 Hz), 7.19 (1H, d, J=8.5 Hz), 7.05 (1H, d, J=8.5 Hz), 2.88-2.79 (4H, m), 2.46 (4H, d, J=2.0 Hz), 2.27 (3H, s), 2.25 (3H, s).

ESI-MS Found: m/z [M+H]+ 549.

Example 55

Production of 2-{[3-methyl-4-(4-methylpiperazin-1-yl)phenyl]amino}-7-(3-thienyl)pyrimido[4',5':4,5]pyrimido[1,2-b]indazol-5(7H)-one

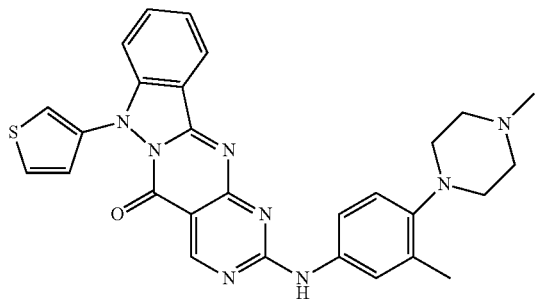

The title compound was produced as a yellow solid in the same manner as in Example 1, for which, however, 2-(methylthio)-7-(3-thienyl)pyrimido[4',5':4,5]pyrimido[1,2-b]indazol-5(7H)-one obtained in Production Example 23 was used in place of 7-methyl-2-(methylthio)pyrimido[4',5':4,5]pyrimido[1,2-b]indazol-5(7H)-one used in Example 1.

$^1$H-NMR (400 MHz, CDCl$_3$) δ: 9.28 (1H, s), 8.33 (1H, d, J=8.3 Hz), 7.70 (1H, t, J=7.3 Hz), 7.59 (1H, s), 7.52 (1H, s), 7.48 (1H, d, J=3.4 Hz), 7.42-7.39 (2H, m), 7.22 (1H, d, J=8.4 Hz), 7.04 (1H, d, J=8.4 Hz), 7.03 (1H, d, J=3.4 Hz), 2.98 (4H, t, J=4.9 Hz), 2.70-2.64 (4H, m), 2.40 (3H, s), 2.37 (3H, s).

ESI-MS Found: m/z [M+H]+ 524.

Example 56

Production of 7-[4-(hydroxymethyl)phenyl]-2-{[4-(4-methylpiperazin-1-yl)phenyl]amino}pyrimido[4',5':4,5]pyrimido[1,2-b]indazol-5(7H)-one

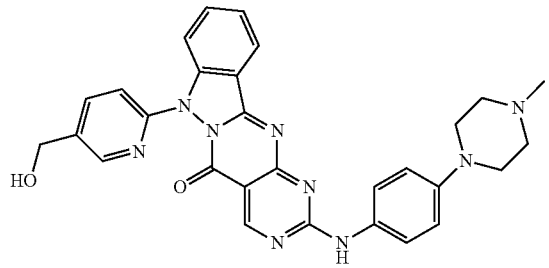

The title compound was produced as a yellow solid in the same manner as in Example 1, for which, however, 7-[4-(hydroxymethyl)phenyl]-2-(methylthio)pyrimido[4',5':4,5]pyrimido[1,2-b]indazol-5(7H)-one obtained in Production Example 24 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

$^1$H-NMR (400 MHz, CDCl$_3$) δ: 9.24 (1H, s), 8.34 (1H, d, J=8.3 Hz), 7.68 (1H, t, J=7.3 Hz), 7.51 (3H, d, J=8.3 Hz), 7.43 (2H, t, J=7.3 Hz), 7.37 (2H, d, J=8.3 Hz), 7.19 (1H, d, J=8.3 Hz), 6.98 (2H, d, J=8.8 Hz), 4.78 (2H, s), 3.22 (4H, t, J=5.4 Hz), 2.62 (4H, t, J=5.4 Hz), 2.38 (3H, s).

ESI-MS Found: m/z [M+H]+ 533.

Example 57

Production of 2-{[3-methyl-4-(4-methylpiperazin-1-yl)phenyl]amino}-7-(3-methylpyridin-2-yl)pyrimido[4',5':4,5]pyrimido[1,2-b]indazol-5(7H)-one

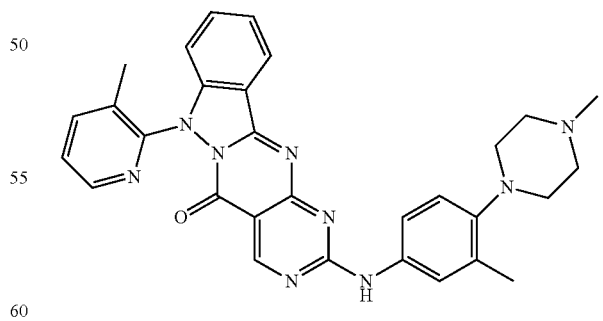

The title compound was produced as a yellow solid in the same manner as in Example 1, for which, however, 7-(3-methylpyridin-2-yl)-2-(methylthio)pyrimido[4',5':4,5]pyrimido[1,2-b]indazol-5(7H)-one obtained in Production Example 25 was used in place of 7-methyl-2-(methylthio)pyrimido[4',5':4,5]pyrimido[1,2-b]indazol-5(7H)-one used in Example 1.

¹H-NMR (400 MHz, CDCl₃) δ: 9.24 (1H, s), 8.37 (1H, d, J=8.0 Hz), 8.24 (1H, dd, J=4.6, 1.3 Hz), 7.85 (1H, dd, J=7.8, 1.3 Hz), 7.76-7.23 (3H, m), 7.68 (1H, ddd, J=8.5, 7.3, 1.0 Hz), 7.45 (1H, ddd, J=8.5, 7.3, 1.0 Hz), 7.32 (1H, dd, J=7.8, 4.6 Hz), 7.09 (1H, d, J=8.5 Hz), 6.99 (1H, d, J=8.5 Hz), 2.99-2.92 (4H, m), 2.79-2.50 (4H, m), 2.73 (3H, s), 2.39 (3H, s), 2.35 (3H, s).

ESI-MS Found: m/z [M+H]+ 532.

Example 58

Production of 2-{[3-methyl-4-(4-methylpiperazin-1-yl)phenyl]amino}-7-(pyridin-3-yl)pyrimido[4',5':4,5]pyrimido[1,2-b]indazol-5(7H)-one

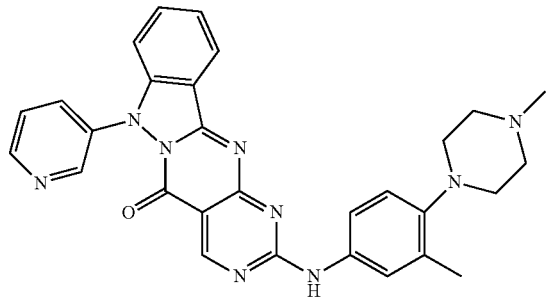

The title compound was produced as a yellow solid in the same manner as in Example 1, for which, however, 2-(methylthio)-7-pyridin-3-yl-pyrimido[4',5':4,5]pyrimido[1,2-b]indazol-5(7H)-one obtained in Production Example 26 was used in place of 7-methyl-2-(methylthio)pyrimido[4',5':4,5]pyrimido[1,2-b]indazol-5(7H)-one used in Example 1.

¹H-NMR (400 MHz, CDCl₃) δ: 9.25 (1H, s), 8.76 (1H, dd, J=2.7, 0.5 Hz), 8.71 (1H, dd, J=4.6, 1.5 Hz), 8.36 (1H, d, J=7.8 Hz), 7.78-7.35 (5H, m), 7.73 (1H, ddd, J=8.5, 7.3, 1.2 Hz), 7.67 (1H, ddd, J=8.3, 2.7, 1.5 Hz), 7.20 (1H, d, J=8.5 Hz), 7.09 (1H, d, J=8.5 Hz), 2.99-2.93 (4H, m), 2.76-2.49 (4H, m), 2.39 (3H, s), 2.35 (3H, s).

ESI-MS Found: m/z [M+H]+ 518.

Example 59

Production of 2-{[3-methyl-4-(4-methylpiperazin-1-yl)phenyl]amino}-7-(pyridin-4-yl)pyrimido[4',5':4,5]pyrimido[1,2-b]indazol-5(7H)-one

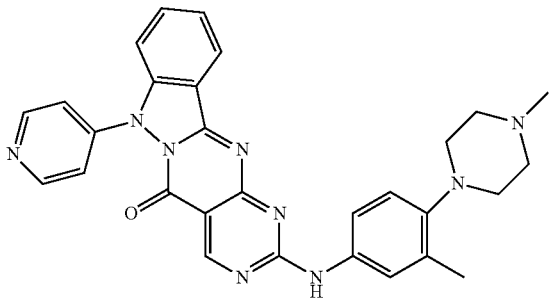

The title compound was produced as a yellow solid in the same manner as in Example 1, for which, however, 2-(methylthio)-7-pyridin-4-yl-pyrimido[4',5':4,5]pyrimido[1,2-b]indazol-5(7H)-one obtained in Production Example 27 was used in place of 7-methyl-2-(methylthio)pyrimido[4',5':4,5]pyrimido[1,2-b]indazol-5(7H)-one used in Example 1.

¹H-NMR (400 MHz, CDCl₃) δ: 9.30 (1H, br s), 8.79-8.76 (2H, m), 8.36 (1H, d, J=7.8 Hz), 7.80-7.24 (3H, m), 7.75 (1H, ddd, J=8.5, 7.3, 1.2 Hz), 7.51 (1H, ddd, J=8.5, 7.3, 1.2 Hz), 7.39 (1H, d, J=8.5 Hz), 7.30-7.27 (2H, m), 7.10 (1H, d, J=8.5 Hz), 3.01-2.95 (4H, m), 2.83-2.49 (4H, m), 2.41 (3H, s), 2.36 (3H, s).

ESI-MS Found: m/z [M+H]+ 518.

Example 60

Production of 2-{[3-methyl-4-(4-methylpiperazin-1-yl)phenyl]amino}-7-(pyrimidin-5-yl)pyrimido[4',5':4,5]pyrimido[1,2-b]indazol-5(7H)-one

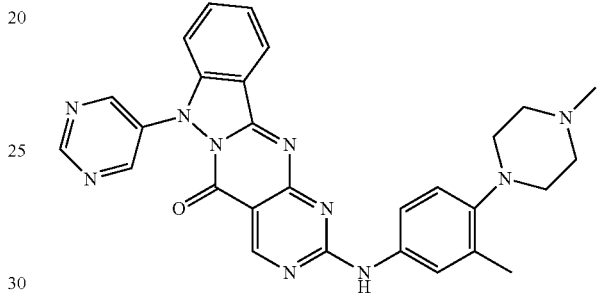

The title compound was produced as a yellow solid in the same manner as in Example 1, for which, however, 2-(methylthio)-7-pyrimidin-5-yl-pyrimido[4',5':4,5]pyrimido[1,2-b]indazol-5(7H)-one obtained in Production Example 28 was used in place of 7-methyl-2-(methylthio)pyrimido[4',5':4,5]pyrimido[1,2-b]indazol-5(7H)-one used in Example 1.

¹H-NMR (400 MHz, CDCl₃) δ: 9.29 (1H, s), 9.26 (1H, br s), 8.84 (2H, s), 8.38 (1H, d, J=8.0 Hz), 7.77 (1H, ddd, J=8.3, 7.3, 1.2 Hz), 7.74-7.34 (4H, m), 7.21 (1H, d, J=8.5 Hz), 7.09 (1H, d, J=8.5 Hz), 3.00-2.94 (4H, m), 2.77-2.48 (4H, m), 2.40 (3H, s), 2.35 (3H, s).

ESI-MS Found: m/z [M+H]+ 519.

Example 61

Production of 2-{[3-methyl-4-(4-methylpiperazin-1-yl)phenyl]amino}-7-(pyrimidin-2-yl)pyrimido[4',5':4,5]pyrimido[1,2-b]indazol-5(7H)-one

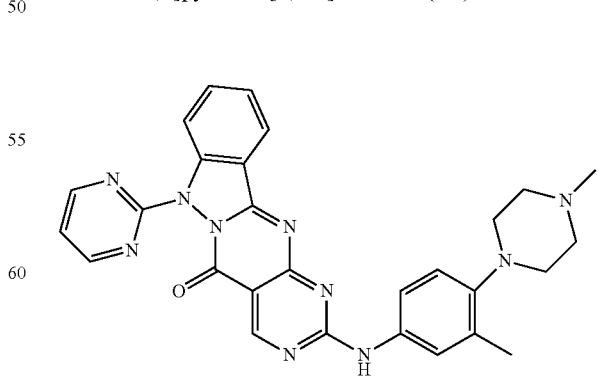

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1.

¹H-NMR (400 MHz, CDCl₃) δ: 9.35 (1H, s), 8.77 (2H, d, J=4.9 Hz), 8.33 (1H, d, J=7.8 Hz), 8.27 (1H, d, J=8.5 Hz), 7.78 (1H, ddd, J=8.5, 7.3, 1.2 Hz), 7.71-7.36 (4H, m), 7.25 (1H, t, J=4.9 Hz), 7.10 (1H, d, J=8.5 Hz), 3.01-2.95 (4H, m), 2.80-2.50 (4H, m), 2.41 (3H, s), 2.35 (3H, s).

ESI-MS Found: m/z [M+H]+ 519.

Example 62

Production of 2-{[4-(4-methylpiperazin-1-yl)phenyl]amino}-7-(pyrimidin-2-yl)pyrimido[4',5':4,5]pyrimido[1,2-b]indazol-5(7H)-one

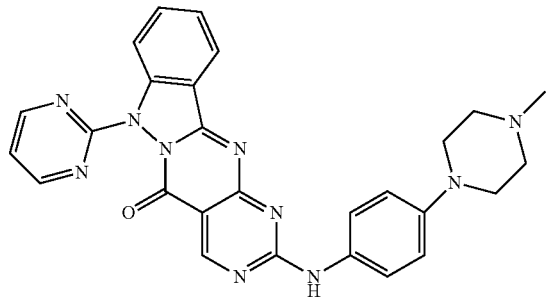

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

¹H-NMR (400 MHz, CDCl₃) δ: 9.33 (1H, s), 8.77 (2H, d, J=4.9 Hz), 8.32 (1H, d, J=8.2 Hz), 8.26 (1H, d, J=8.3 Hz), 7.77 (1H, ddd, J=8.3, 7.3, 1.2 Hz), 7.52-7.52 (3H, m), 7.52 (1H, ddd, J=8.2, 7.3, 0.7 Hz), 7.25 (1H, t, J=4.9 Hz), 6.98 (2H, d, J=9.0 Hz), 3.27-3.21 (4H, m), 2.67-2.60 (4H, m), 2.39 (3H, s).

ESI-MS Found: m/z [M+H]+ 505.

Example 63

Production of 2-[{4-(4-isopropylpiperazin-1-yl)phenyl}amino]-7-(pyrimidin-2-yl)pyrimido[4',5':4,5]pyrimido[1,2-b]indazol-5(7H)-one

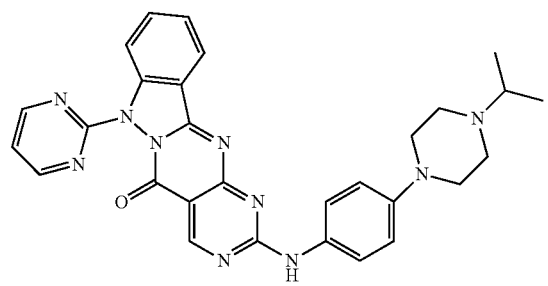

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-(4-isopropylpiperazin-1-yl)aniline was used in place of 3-methyl-4-(4-methyl-1-piperazinyl)aniline.

¹H-NMR (400 MHz, CDCl₃) δ: 9.34 (1H, s), 8.77 (2H, d, J=4.9 Hz), 8.33 (1H, d, J=8.1 Hz), 8.27 (1H, d, J=8.4 Hz), 7.77 (1H, ddd, J=8.4, 7.3, 1.2 Hz), 7.72-7.39 (3H, m), 7.52 (1H, ddd, J=8.1, 7.3, 1.0 Hz), 7.25 (1H, t, J=4.9 Hz), 6.99 (2H, d, J=9.0 Hz), 3.32-3.18 (4H, m), 2.86-2.67 (5H, m), 1.14 (6H, d, J=6.1 Hz).

ESI-MS Found: m/z [M+H]+ 533.

Example 64

Production of 2-{[4-(4-cyclopropylpiperazin-4-yl)-3-methylphenyl]amino}-7-(pyrimidin-2-yl)pyrimido[4',5':4,5]pyrimido[1,2-b]indazol-5(7H)-one

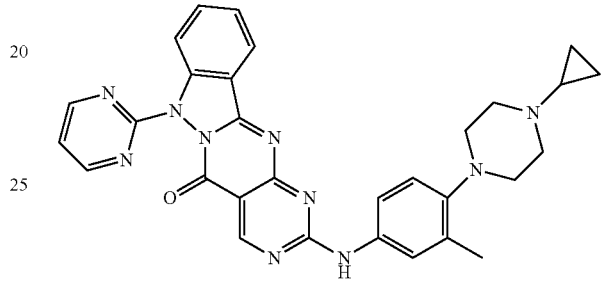

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-(4-cyclopropylpiperazin-1-yl)-3-methylaniline was used in place of 3-methyl-4-(4-methyl-1-piperazinyl)aniline.

¹H-NMR (400 MHz, CDCl₃) δ: 9.26 (1H, s), 8.51 (1H, dd, J=5.1, 1.7 Hz), 8.33 (1H, d, J=8.3 Hz), 7.92 (1H, td, J=7.8, 2.0 Hz), 7.72 (1H, t, J=7.8 Hz), 7.67-7.57 (2H, m), 7.55 (1H, d, J=8.3 Hz), 7.52 (1H, d, J=7.8 Hz), 7.48 (1H, t, J=7.6 Hz), 7.35 (1H, dd, J=7.3, 4.9 Hz), 6.99 (2H, d, J=8.8 Hz), 3.84 (4H, d, J=15.6 Hz), 3.19 (4H, d, J=15.6 Hz), 2.35 (3H, s), 1.83-1.77 (1H, m), 1.03 (2H, dt, J=7.8, 3.4 Hz), 0.81 (2H, dt, J=11.5, 3.4 Hz).

ESI-MS Found: m/z [M+H]+ 545.

Example 65

Production of 2-({4-[4-(2-methoxyethyl)piperazin-1-yl]-3-methylphenyl}amino)-7-(pyrimidin-2-yl)pyrimido[4',5':4,5]pyri=mido[1,2-b]indazol-5(7H)-one

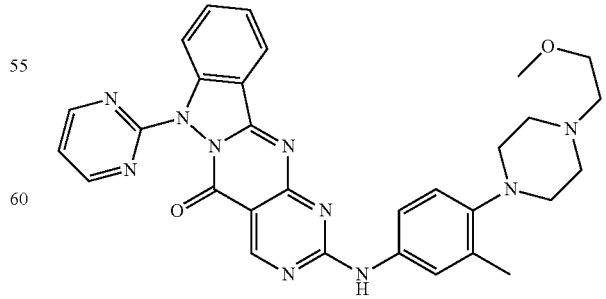

The title compound was produced as a yellow solid in the same manner as in Example 1, for which, however, 2-(methylthio)-7-pyrimidin-2-yl-pyrimido[4',5':4,5]pyrimido[1,2-b]

indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-[4-(2-methoxyethyl)piperazin-1-yl]-3-methylaniline was used in place of 3-methyl-4-(4-methyl-1-piperazinyl)aniline.

$^1$H-NMR (400 MHz, CDCl$_3$) δ: 9.35 (1H, s), 8.77 (2H, d, J=4.9 Hz), 8.33 (1H, d, J=8.3 Hz), 8.27 (1H, d, J=8.3 Hz), 7.78 (1H, dt, J=11.1, 3.8 Hz), 7.52 (1H, t, J=7.6 Hz), 7.45 (1H, s), 7.39 (1H, s), 7.25 (1H, t, J=4.9 Hz), 7.09 (1H, d, J=8.8 Hz), 3.58 (2H, t, J=5.6 Hz), 3.39 (3H, s), 2.98 (4H, t, J=5.9 Hz), 2.75-2.65 (6H, m), 2.35 (3H, s).

ESI-MS Found: m/z [M+H]+ 563.

Example 66

Production of 2-{[3-(hydroxymethyl)-4-(4-methylpiperazin-1-yl)phenyl]amino}-7-(pyrimidin-2-yl)pyrimido[4',5':4,5]pyrimido[1,2-b]indazol-5(7H)-one

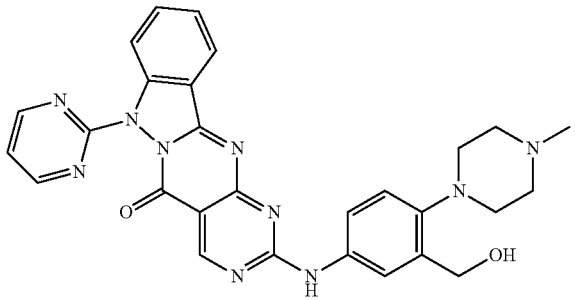

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and [5-amino-2-(4-methylpiperazin-1-yl)phenyl]methanol was used in place of 3-methyl-4-(4-methyl-1-piperazinyl)aniline.

$^1$H-NMR (400 MHz, CDCl$_3$) δ: 9.35 (1H, s), 8.77 (2H, d, J=4.9 Hz), 8.33 (1H, d, J=7.8 Hz), 8.27 (1H, d, J=8.5 Hz), 7.78 (1H, ddd, J=8.5, 7.3, 1.2 Hz), 7.71-7.36 (4H, m), 7.25 (1H, t, J=4.9 Hz), 7.10 (1H, d, J=8.5 Hz), 3.01-2.95 (4H; m), 2.80-2.50 (4H, m), 2.41 (3H, s), 2.35 (3H, s).

ESI-MS Found: m/z [M+H]+ 535.

Example 67

Production of 2-{[3-fluoro-4-(4-methylpiperazin-1-yl)phenyl]amino}-7-(pyrimidin-2-yl)pyrimido[4',5':4,5]pyrimido[1,2-b]indazol-5(7H)-one

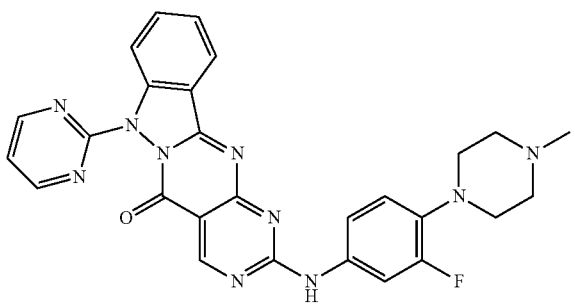

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 3-fluoro-4-(4-methyl-1-piperazinyl)aniline was used in place of 3-methyl-4-(4-methyl-1-piperazinyl)aniline.

$^1$H-NMR (400 MHz, CDCl$_3$) δ: 9.36 (1H, s), 8.78 (2H, d, J=4.9 Hz), 8.34 (1H, d, J=7.8 Hz), 8.28 (1H, d, J=8.3 Hz), 7.79 (1H, dd, J=11.5, 4.1 Hz), 7.68 (1H, d, J=13.7 Hz), 7.53 (2H, t, J=7.3 Hz), 7.36-7.24 (1H, m), 6.99 (1H, t, J=9.0 Hz), 3.14 (4H, t, J=4.6 Hz), 2.64 (4H, t, J=6.3 Hz), 2.38 (3H, s).

ESI-MS Found: m/z [M+H]+ 523.

Example 68

Production of 2-{[3-(1-hydroxyethyl)-4-(4-methylpiperazin-1-yl)phenyl]amino}-7-(pyrimidin-2-yl)pyrimido[4',5':4,5]pyrimido[1,2-b]indazol-5(7H)-one

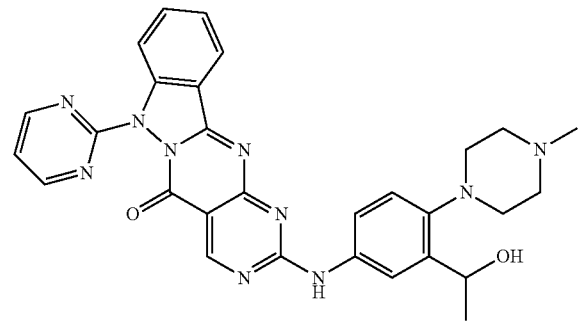

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 1-[5-amino-2-(4-methylpiperazin-1-yl)phenyl]ethanol was used in place of 3-methyl-4-(4-methyl-1-piperazinyl)aniline.

$^1$H-NMR (400 MHz, CDCl$_3$) δ: 9.36 (1H, s), 8.77 (2H, d, J=4.9 Hz), 8.33 (1H, d, J=8.3 Hz), 8.27 (1H, d, J=8.3 Hz), 7.84 (1H, s), 7.78 (1H, t, J=7.3 Hz), 7.63 (1H, s), 7.53 (1H, t, J=7.3 Hz), 7.36 (1H, dd, J=5.6, 3.2 Hz), 7.26-7.24 (1H, m), 5.11 (1H, d, J=7.6 Hz), 3.10-2.96 (4H, m), 2.75-2.50 (4H, m), 2.38 (3H, s), 1.57 (3H, d, J=7.6 Hz).

ESI-MS Found: m/z [M+H]+ 549.

Example 69

Production of N,N-dimethyl-2-[(4-methylpiperazin-1-yl)-5-[(5-oxo-7-(pyrimidin-2-yl)-5,7-dihydropyrimido[4',5':4,5]pyrimido[1,2-b]indazol-2-yl)amino]benzamide

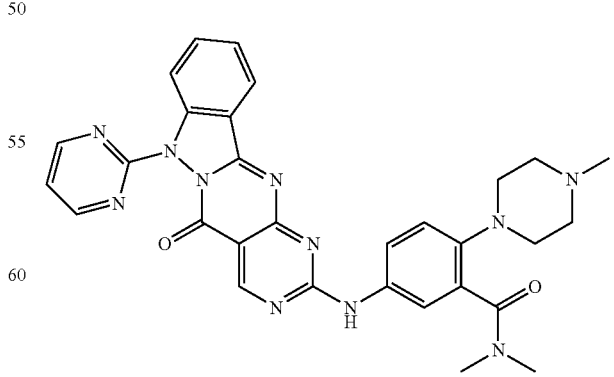

The title compound was produced as a yellow solid in the same manner as in Example 1, for which, however, 2-(methylthio)-7-pyrimidin-2-yl-pyrimido[4',5':4,5]pyrimido[1,2-b]

indazol-5(7H)-one obtained in Production Example 29 was used in place of 7-methyl-2-(methylthio)pyrimido[4',5':4,5]pyrimido[1,2-b]indazol-5(7H)-one used in Example 1, and 5-amino-N,N-dimethyl-2-(4-methylpiperazin-1-yl)benzamide was used in place of 3-methyl-4-(4-methyl-1-piperazinyl)aniline.

$^1$H-NMR (400 MHz, CDCl$_3$) δ: 9.35 (1H, s), 8.78 (2H, d, J=4.9 Hz), 8.34 (1H, d, J=7.8 Hz), 8.27 (1H, d, J=8.3 Hz), 7.93 (1H, s), 7.78 (1H, t, J=8.5 Hz), 7.57 (1H, s), 7.53 (1H, t, J=7.3 Hz), 7.45 (1H, d, J=2.9 Hz), 7.28-7.23 (1H, m), 7.10 (1H, d, J=8.8 Hz), 3.15 (3H, s), 2.91 (6H, s), 2.61-2.52 (4H, m), 2.39 (4H, s).

ESI-MS Found: m/z [M+H]+ 576.

Example 70

Production of 2-({4-[(2R)-2,4-dimethylpiperazin-1-yl]phenyl}amino)-7-(pyrimidin-2-yl)pyrimido[4',5':4,5]pyrimido[1,2-b]indazol-5(7H)-one

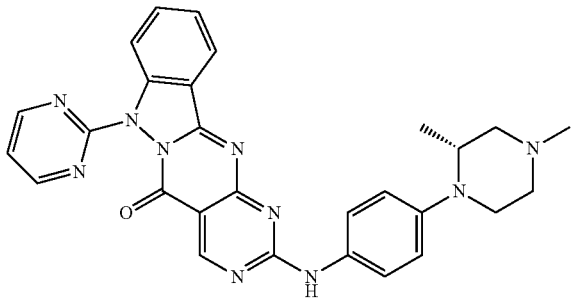

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-[(2R)-2,4-dimethylpiperazin-1-yl]aniline was used in place of 3-methyl-4-(4-methyl-1-piperazinyl)aniline.

$^1$H-NMR (400 MHz, CDCl$_3$) δ: 9.34 (1H, s), 8.77 (2H, d, J=4.9 Hz), 8.34 (1H, d, J=7.8 Hz), 8.27 (1H, d, J=8.3 Hz), 7.80-7.75 (1H, m), 7.62 (1H, s), 7.52 (1H, td, J=7.6, 1.0 Hz), 7.47 (1H, s), 7.27-7.23 (1H, m), 7.01 (2H, d, J=9.3 Hz), 3.75-3.68 (1H, m), 3.19-3.13 (2H, m), 2.76-2.69 (1H, m), 2.62-2.55 (1H, m), 2.53-2.47 (1H, m), 2.47-2.39 (1H, m), 2.34 (3H, s), 1.07 (3H, d, J=6.8 Hz).

ESI-MS Found: m/z [M+H]+ 519.

Example 71

Production of 2-({4-[(2S)-2,4-dimethylpiperazin-1-yl]phenyl}amino)-7-(pyrimidin-2-yl)pyrimido[4',5':4,5]pyrimido[1,2-b]indazol-5(7H)-one

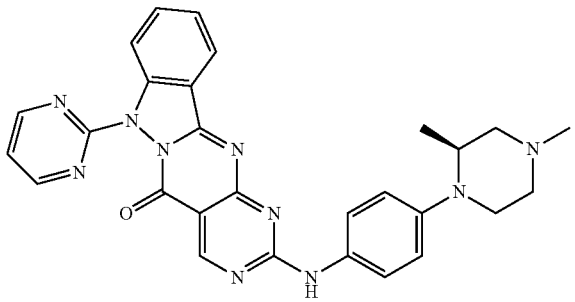

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-[(2S)-2,4-dimethylpiperazin-1-yl]aniline was used in place of 3-methyl-4-(4-methyl-1-piperazinyl)aniline.

$^1$H-NMR (400 MHz, CDCl$_3$) δ: 9.34 (1H, s), 8.77 (2H, d, J=4.9 Hz), 8.34 (1H, d, J=7.8 Hz), 827 (1H, d, J=8.3 Hz), 7.80-7.75 (1H, m), 7.62 (1H, s), 7.52 (1H, td, J=7.6, 1.0 Hz), 7.47 (1H, s), 7.27-7.23 (1H, m), 7.01 (2H, d, J=9.3 Hz), 3.75-3.68 (1H, m), 3.19-3.13 (2H, m), 2.76-2.69 (1H, m), 2.62-2.55 (1H, m), 2.53-2.47 (1H, m), 2.47-2.39 (1H, m), 2.34 (3H, s), 1.07 (3H, d, J=6.8 Hz).

ESI-MS Found: m/z [M+H]+ 519.

Example 72

Production of 2-({4-[(3S)-3,4-dimethylpiperazin-1-yl]phenyl}amino)-7-(pyrimidin-2-yl)pyrimido[4',5':4,5]pyrimido[1,2-b]indazol-5(7H)-one

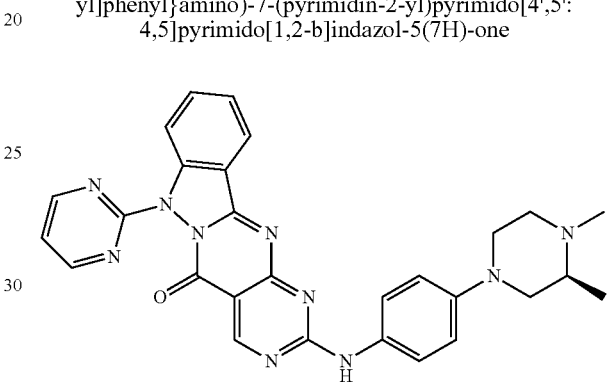

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-[(3S)-3,4-dimethylpiperazin-1-yl]aniline was used in place of 3-methyl-4-(4-methyl-1-piperazinyl)aniline.

$^1$H-NMR (400 MHz, CDCl$_3$) δ: 9.33 (1H, s), 8.77 (2H, d, J=4.9 Hz), 8.32 (1H, d, J=8.2 Hz), 8.26 (1H, d, J=8.4 Hz), 7.77 (1H, t, J=7.7 Hz), 7.56 (2H, s), 7.52 (1H, t, J=7.7 Hz), 7.25 (1H, t, J=5.3 Hz), 6.97 (2H, d, J=9.0 Hz), 3.51 (1H, d, J=11.3 Hz), 3.44 (1H, d, J=11.3 Hz), 2.97-2.89 (2H, m), 2.55 (1H, t, J=10.9 Hz), 2.46 (1H, td, J=11.2, 3.3 Hz), 2.36 (3H, s), 2.33-2.24 (1H, m), 1.15 (3H, d, J=6.3 Hz).

ESI-MS Found: m/z [M+H]+ 519.

Example 73

Production of 2-({4-[(3R)-3,4-dimethylpiperazin-1-yl]phenyl}amino)-7-(pyrimidin-2-yl)pyrimido[4',5':4,5]pyrimido[1,2-b]indazol-5(7H)-one

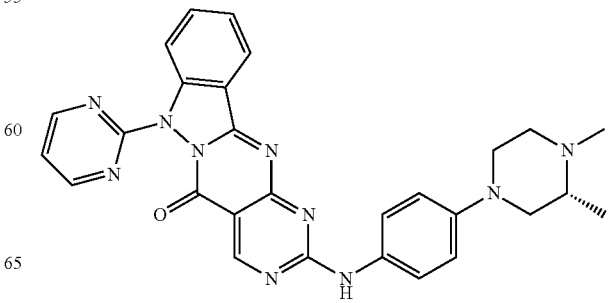

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-[(3R)-3,4-dimethylpiperazin-1-yl]aniline was used in place of 3-methyl-4-(4-methyl-1-piperazinyl)aniline.

$^1$H-NMR (400 MHz, CDCl$_3$) δ: 9.33 (1H, s), 8.77 (2H, d, J=4.9 Hz), 8.32 (1H, d, J=8.2 Hz), 8.26 (1H, d, J=8.4 Hz), 7.77 (1H, t, J=7.7 Hz), 7.56 (2H, s), 7.52 (1H, t, J=7.7 Hz), 7.25 (1H, t, J=5.3 Hz), 6.97 (2H, d, J=9.0 Hz), 3.51 (1H, d, J=11.3 Hz), 3.44 (1H, d, J=11.3 Hz), 2.97-2.89 (2H, m), 2.55 (1H, t, J=10.9 Hz), 2.46 (1H, td, J=11.2, 3.3 Hz), 2.36 (3H, s), 2.33-2.24 (1H, m), 1.15 (3H, d, J=6.3 Hz).

ESI-MS Found: m/z [M+H]+ 519.

Example 74

Production of 2-({4-[(3S)-3-isopropyl-4-methylpiperazin-1-yl]phenyl}amino)-7-(pyrimidin-2-yl)pyrimido[4',5':4,5]pyrimido[1,2-b]indazol-5(7H)-one

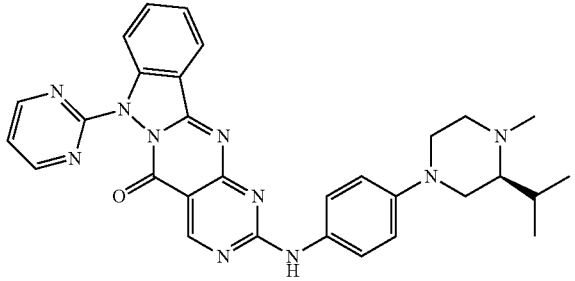

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-[(3S)-3-isopropyl-4-methylpiperazin-1-yl]aniline was used in place of 3-methyl-4-(4-methyl-1-piperazinyl)aniline.

$^1$H-NMR (400 MHz, CDCl$_3$) δ: 9.33 (1H, s), 8.77 (2H, d, J=4.9 Hz), 8.33 (1H, d, J=7.3 Hz), 8.26 (1H, d, J=8.3 Hz), 7.77 (1H, t, J=7.1 Hz), 7.59 (1H, s), 7.52 (1H, t, J=7.6 Hz), 7.49 (1H, s), 7.25 (1H, t, J=5.4 Hz), 6.98 (2H, d, J=8.8 Hz), 3.48 (2H, d, J=11.2 Hz), 2.96 (1H, d, J=11.7 Hz), 2.89 (1H, td, J=11.8, 3.3 Hz), 2.59 (1H, t, J=11.2 Hz), 2.49 (1H, td, J=11.7, 2.9 Hz), 2.32 (3H, s), 2.23-2.15 (1H, m), 2.09 (1H, d, J=10.2 Hz), 1.03 (3H, d, J=6.8 Hz), 0.95 (3H, d, J=6.8 Hz).

ESI-MS Found: m/z [M+H]+ 547.

Example 75

Production of 2-({4-[(3R)-3-isopropyl-4-methylpiperazin-1-yl]phenyl}amino)-7-(pyrimidin-2-yl)pyrimido[4',5':4,5]pyrimido[1,2-b]indazol-5(7H)-one

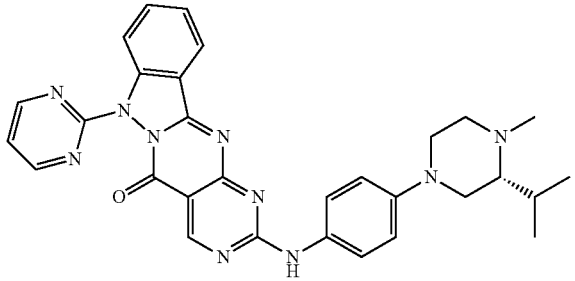

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-[(3R)-3-isopropyl-4-methylpiperazin-1-yl]aniline was used in place of 3-methyl-4-(4-methyl-1-piperazinyl)aniline.

$^1$H-NMR (400 MHz, CDCl$_3$) δ: 9.33 (1H, s), 8.77 (2H, d, J=4.9 Hz), 8.33 (1H, d, J=7.3 Hz), 8.26 (1H, d, J=8.3 Hz), 7.77 (1H, t, J=7.1 Hz), 7.59 (1H, s), 7.52 (1H, t, J=7.6 Hz), 7.49 (1H, s), 7.25 (1H, t, J=5.4 Hz), 6.98 (2H, d, J=8.8 Hz), 3.48 (2H, d, J=11.2 Hz), 2.96 (1H, d, J=11.7 Hz), 2.89 (1H, td, J=11.8, 3.3 Hz), 2.59 (1H, t, J=11.2 Hz), 2.49 (1H, td, J=11.7, 2.9 Hz), 2.32 (3H, s), 2.23-2.15 (1H, m), 2.09 (1H, d, J=10.2 Hz), 1.03 (3H, d, J=6.8 Hz), 0.95 (3H, d, J=6.8 Hz).

ESI-MS Found: m/z [M+H]+ 547.

Example 76

Production of N,N,1-trimethyl-4-{4-[5-oxo-7-(pyrimidin-2-yl)-5,7-dihydropyrimido[4',5':4,5]pyrimido[1,2-b]indazol-2-yl)amino]phenyl}piperazine-2-carboxamide

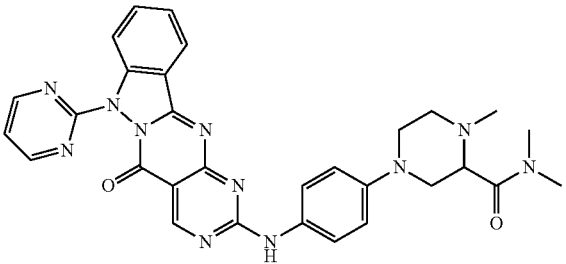

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-(4-aminophenyl-N,N,1-trimethylpiperazine-2-carboxamide was used in place of 3-methyl-4-(4-methyl-1-piperazinyl)aniline.

$^1$H-NMR (400 MHz, CDCl$_3$) δ: 9.33 (1H, s), 8.77 (2H, d, J=4.9 Hz), 8.32 (1H, d, J=7.8 Hz), 8.27 (1H, d, J=8.3 Hz), 7.77 (1H, t, J=7.3 Hz), 7.62 (1H, s), 7.52 (2H, t, J=7.3 Hz), 7.25 (1H, t, J=4.9 Hz), 6.97 (2H, d, J=8.8 Hz), 3.52 (2H, d, J=10.7 Hz), 3.34 (1H, dd, J=11.0, 3.2 Hz), 3.24 (3H, s), 3.11-2.96 (3H, m), 3.04 (3H, s), 2.48 (1H, td, J=11.7, 3.3 Hz), 2.30 (3H, s).

ESI-MS Found: m/z [M+H]+ 576.

Example 77

Production of N,N,1-trimethyl-4-{2-methyl-4-[(5-oxo-7-(pyrimidin-2-yl)-5,7-dihydropyrimido[4',5':4,5]pyrimido[1,2-b]indazol-2-yl)amino]phenyl}piperazine-2-carboxamide

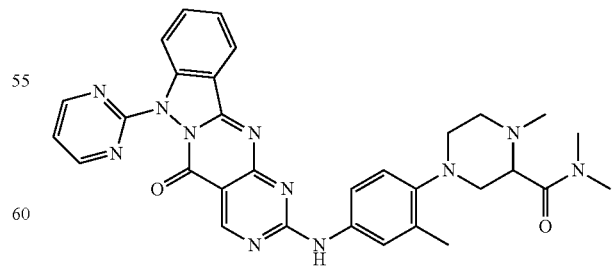

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]

pyrimido[1,2-b]indazol-5(7H)-one used in Example 1, and 4-(4-amino-2-methylphenyl)-N,N,1-trimethylpiperazine-2-carboxamide was used in place of 3-methyl-4-(4-methyl-1-piperazinyl)aniline.

$^1$H-NMR (400 MHz, CDCl$_3$) δ: 9.33 (1H, s), 8.77 (2H, d, J=4.9 Hz), 8.32 (1H, d, J=7.8 Hz), 8.27 (1H, d, J=8.3 Hz), 7.77 (1H, t, J=7.3 Hz), 7.62 (1H, s), 7.52 (1H, t, J=7.3 Hz), 7.25 (1H, t, J=4.9 Hz), 6.97 (2H, d, J=8.8 Hz), 3.52 (2H, d, J=10.7 Hz), 3.34 (1H, dd, J=11.0, 3.2 Hz), 3.24 (3H, s), 3.11-2.96 (3H, m), 3.04 (3H, s), 2.48 (1H, td, J=11.7, 3.3 Hz), 2.30 (3H, s), 2.16 (3H, s).

ESI-MS Found: m/z [M+H]+ 590.

Example 78

Production of 2-({4-[(3R)-3-(dimethylamino)pyrrolidin-1-yl]phenyl}amino)-7-(pyrimidin-2-yl)pyrimido[4',5':4,5]pyrimido[1,2-b]indazol-5(7H)-one

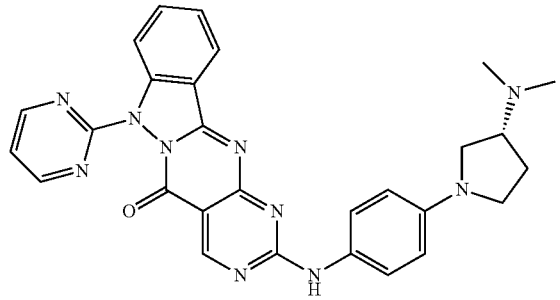

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and (3R)-1-(4-aminophenyl)-N,N-dimethylpyrrolidine-3-amine was used in place of 3-methyl-4-(4-methyl-1-piperazinyl)aniline.

$^1$H-NMR (400 MHz, DMSO-d$_6$) δ: 10.03 (1H, s), 9.12 (1H, s), 8.92 (1H, s), 8.91 (1H, s), 8.28 (1H, s), 8.12 (1H, d, J=8.6 Hz), 7.90 (1H, td, J=7.8, 1.0 Hz), 7.67 (1H, s), 7.61 (1H, t, J=7.8 Hz), 7.52 (1H, t, J=4.9 Hz), 6.58 (2H, d, J=6.3 Hz), 3.44 (1H, t, J=8.0 Hz), 3.36 (1H, t, J=9.0 Hz), 3.25 (1H, d, J=7.4 Hz), 3.05 (1H, t, J=8.4 Hz), 2.80 (1H, t, J=7.2 Hz), 2.21 (6H, s), 2.19-2.12 (1H, m), 1.81 (1H, t, J=9.8 Hz).

ESI-MS Found: m/z [M+H]+ 519.

Example 79

Production of 2-({4-[(3S)-3-(dimethylamino)pyrolidin-1-yl]phenyl}amino)-7-(pyrimidin-2-yl)pyrimido[4',5':4,5]pyrimido[1,2-b]indazol-5(7H)-one

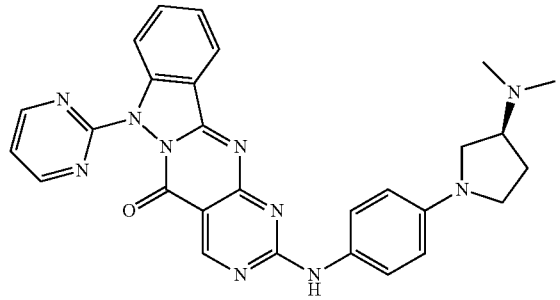

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and (3S)-1-(4-aminophenyl)-N,N-dimethylpyrrolidine-3-amine was used in place of 3-methyl-4-(4-methyl-1-piperazinyl)aniline.

$^1$H-NMR (400 MHz, DMSO-d$_6$) δ: 10.03 (1H, s), 9.12 (1H, s), 8.92 (1H, s), 8.91 (1H, s), 8.28 (1H, s), 8.12 (1H, d, J=8.6 Hz), 7.90 (1H, td, J=7.8, 1.0 Hz), 7.67 (1H, s), 7.61 (1H, t, J=7.8 Hz), 7.52 (1H, t, J=4.9 Hz), 6.58 (2H, d, J=6.3 Hz), 3.44 (1H, t, J=8.0 Hz), 3.36 (1H, t, J=9.0 Hz), 3.25 (1H, d, J=7.4 Hz), 3.05 (1H, t, J=8.4 Hz), 2.80 (1H, t, J=7.2 Hz), 2.21 (6H, s), 2.19-2.12 (1H, m), 1.81 (1H, t, J=9.8 Hz).

ESI-MS Found: m/z [M+H]+ 519.

Example 80

Production of 2-({4-[3-(dimethylamino)pyrrolidin-1-yl]-3-fluorophenyl}amino)-7-(pyrimidin-2-yl)pyrimido[4',5':4,5]pyrimido[1,2-b]indazol-5(7H)-one

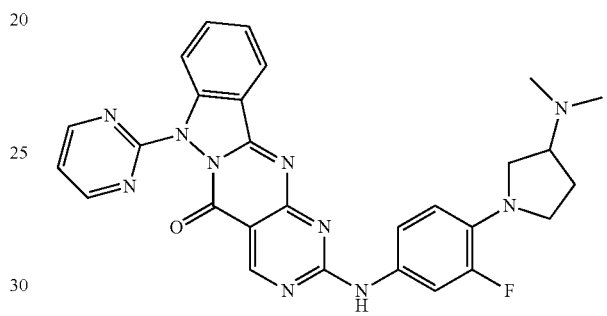

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 1-(4-amino-2-fluorophenyl)-N,N-dimethylpyrrolidine-3-amine was used in place of 3-methyl-4-(4-methyl-1-piperazinyl)aniline.

$^1$H-NMR (400 MHz, CDCl$_3$) δ: 9.33 (1H, s), 8.78 (2H, d, J=4.9 Hz), 8.34 (1H, d, J=7.8 Hz), 8.27 (1H, d, J=8.8 Hz), 7.78 (1H, t, J=8.5 Hz), 7.53 (2H, t, J=7.6 Hz), 7.38 (1H, s), 7.30-7.23 (1H, m), 6.69 (1H, t, J=9.0 Hz), 3.57-3.43 (3H, m), 3.32 (1H, td, J=8.0, 2.4 Hz), 2.89-2.81 (1H, m), 2.33 (3H, s), 2.21-2.13 (1H, m), 1.95-1.84 (1H, m).

ESI-MS Found: m/z [M+H]+ 537.

Example 81

Production of 2-{[4-(1-methylpiperidin-4-yl)phenyl]amino}-7-(pyrimidin-2-yl)pyrimido[4',5':4,5]pyrimido[1,2-b]indazol-5(7H)-one

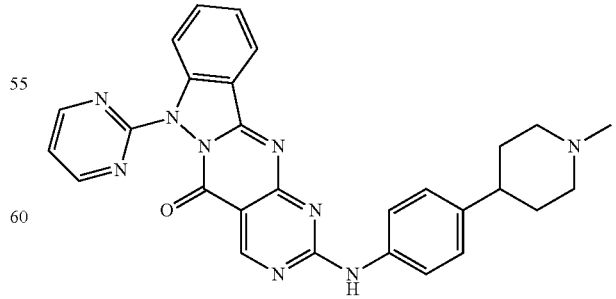

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-(1-methylpiperidin-4-yl)aniline was used in place of 3-methyl-4-(4-methyl-1-piperazinyl)aniline.

$^1$H-NMR (400 MHz, CDCl$_3$) δ: 9.36 (1H, s), 8.78 (2H, d, J=4.9 Hz), 8.34 (1H, d, J=7.4 Hz), 8.27 (1H, d, J=8.6 Hz), 7.78 (1H, t, J=7.2 Hz), 7.74-7.65 (2H, m), 7.62 (1H, s), 7.53 (2H, t, J=7.5 Hz), 7.30-7.23 (1H, m), 3.18 (2H, d, J=10.8 Hz), 2.46 (3H, s), 2.28 (2H, t, J=11.4 Hz), 2.00-1.88 (1H, m), 1.47-1.23 (2H, m), 0.95-0.86 (2H, m).

ESI-MS Found: m/z [M+H]+ 504

Example 82

Production of tert-butyl 2-{4-[(5-oxo-7-(pyrimidin-2-yl)-5,7-dihydropyrimido[4',5':4,5]pyrimido[1,2-b]indazol-2-yl)amino]phenyl}piperidine-1-carboxylate

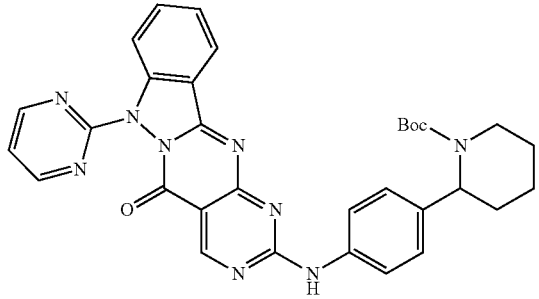

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and tert-butyl 2-(4-aminophenyl)piperidine-1-carboxylate was used in place of 3-methyl-4-(4-methyl-1-piperazinyl)aniline.

$^1$H-NMR (400 MHz, CDCl$_3$) δ: 9.38 (1H, s), 8.78 (2H, d, J=4.9 Hz), 8.34 (1H, d, J=7.8 Hz), 8.28 (1H, d, J=7.8 Hz), 7.78 (1H, t, J=7.9 Hz), 7.74 (1H, d, J=6.3 Hz), 7.65 (1H, s), 7.53 (1H, J=7.5 Hz), 7.30-7.24 (3H, m), 5.45 (1H, s), 4.06 (1H, d, J=12.3 Hz), 2.83-2.75 (1H, m), 2.62 (1H, s), 2.32 (1H, d, J=12.1 Hz), 1.95-1.86 (1H, m), 1.60-1.42 (3H, m), 1.49 (97H, s).

ESI-MS Found: m/z [M+H]+ 590.

Example 83

Production of 2-[{4-(piperidin-2-yl)phenyl}amino]-7-(pyrimidin-2-yl)pyrimido[4',5':4,5]pyrimido[1,2-b]indazol-5(7H)-one

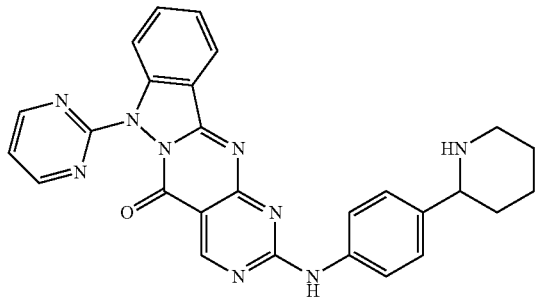

The compound (20 mg) obtained in Example 82 was dissolved in trifluoroacetic acid (1 mL), and stirred at room temperature for 1 hour. The reaction liquid was concentrated under reduced pressure, and the residue was purified through basic silica gel chromatography (ethyl acetate) to give the title compound as a yellow solid.

$^1$H-NMR (400 MHz, CDCl$_3$) δ: 9.37 (1H, s), 8.77 (2H, d, J=4.9 Hz), 8.34 (1H, d, J=8.0 Hz), 8.27 (1H, d, J=8.4 Hz), 7.78 (1H, t, J=7.8 Hz), 7.72-7.64 (2H, m), 7.57 (1H, s), 7.53 (2H, t, J=7.6 Hz), 7.40 (1H, d, J=8.4 Hz), 3.61 (1H, d, J=8.2 Hz), 3.22 (1H, d, J=10.2 Hz), 2.82 (1H, t, J=10.2 Hz), 1.93-1.57 (5H, m), 1.52 (1H, t, J=9.1 Hz).

ESI-MS Found: m/z [M+H]+ 490.

Example 84

Production of 2-({4-[3-(dimethylamino)azetidin-1-yl]phenyl}amino)-7-(pyrimidin-2-yl)pyrimido[4',5':4,5]pyrimido[1,2-b]indazol-5(7H)-one

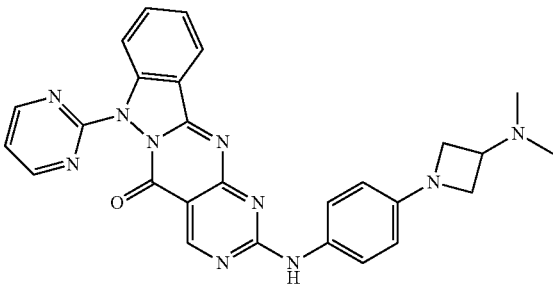

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 1-(4-aminophenyl)-N,N-dimethylazetidin-3-amine was used in place of 3-methyl-4-(4-methyl-1-piperazinyl)aniline.

$^1$H-NMR (400 MHz, DMSO-d$_6$) δ: 10.92 (1H, s), 10.15 (1H, s), 9.15 (1H, s), 8.91 (2H, d, J=4.9 Hz), 8.29 (1H, d, J=7.8 Hz), 8.12 (1H, d, J=8.6 Hz), 7.90 (1H, t, J=7.8 Hz), 7.75 (1H, s), 7.62 (1H, t, J=7.5 Hz), 7.52 (1H, t, J=4.8 Hz), 6.56 (2H, d, J=8.0 Hz), 4.19 (1H, s), 4.10 (2H, t, J=7.9 Hz), 3.97 (2H, dd, J=7.8, 5.3 Hz), 2.78 (6H, s).

ESI-MS Found: m/z [M+H]+ 505.

Example 85

Production of 2-{[1-(1-methylpiperidin-4-yl)-1H-pyrazol-4-yl]amino}-7-(pyrimidin-2-yl)pyrimido[4',5':4,5]pyrimido[1,2-b]indazol-5(7H)-one

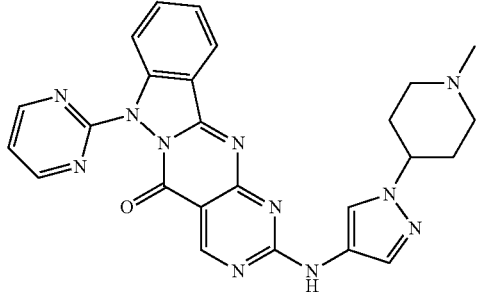

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 1-(1-methylpiperidin-4-yl)-1H-pyrazol-4-amine was used in place of 3-methyl-4-(4-methyl-1-piperazinyl)aniline.

¹H-NMR (400 MHz, DMSO-d₆) δ: 10.29 (1H, s), 9.13 (1H, s), 8.91 (2H, d, J=4.9 Hz), 8.32 (1H, d, J=7.8 Hz), 8.16 (1H, s), 8.13 (1H, d, J=8.8 Hz), 7.90 (1H, t, J=7.8 Hz), 7.69 (1H, s), 7.62 (1H, t, J=7.6 Hz), 7.53 (1H, t, J=4.9 Hz), 4.22-4.12 (1H, m), 2.90-2.82 (2H, m), 2.21 (3H, s), 2.09-1.90 (6H, m).
ESI-MS Found: m/z [M+H]+ 494.

Example 86

Production of 2-({4-[(1-methylpyrrolidin-3-yl)oxy]phenyl}amino)-7-(pyrimidin-2-yl)pyrimido[4',5':4,5]pyrimido[1,2-b]indazol-5(7H)-one

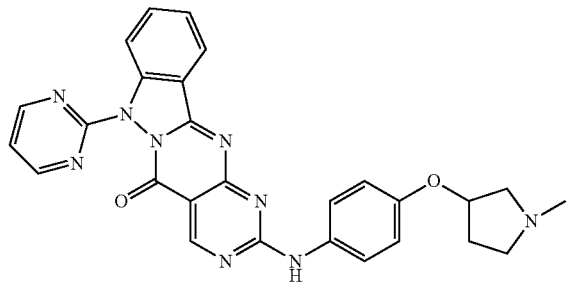

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-[(1-methylpyrrolidin-3-yl)oxy]aniline was used in place of 3-methyl-4-(4-methyl-1-piperazinyl)aniline.
¹H-NMR (400 MHz, CDCl₃) δ: 9.34 (1H, s), 8.78 (2H, d, J=4.9 Hz), 8.32 (1H, d, J=8.0 Hz), 8.27 (1H, d, J=8.4 Hz), 7.78 (1H, t, J=7.7 Hz), 7.66 (2H, s), 7.53 (1H, t, J=7.6 Hz), 7.28-7.25 (1H, m), 6.90 (2H, d, J=8.8 Hz), 5.03-4.97 (1H, m), 3.71-3.61 (1H, m), 3.06 (2H, t, J=11.0 Hz), 2.76 (3H, s), 2.49-2.34 (2H, m), 2.34-2.24 (1H, m).
ESI-MS Found: m/z [M+H]+ 506.

Example 87

Production of 2-({4-[(3-hydroxypyrrolidin-1-yl)methyl]phenyl}amino)-7-(pyrimidin-2-yl)pyrimido[4',5':4,5]pyrimido[1,2-b]indazol-5(7H)-one

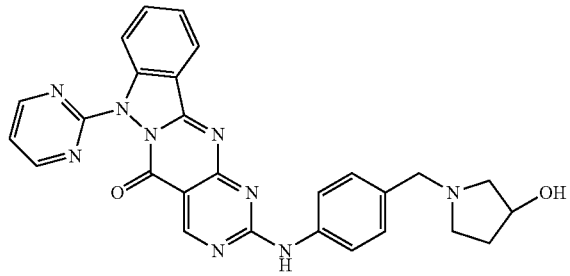

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 1-(4-aminobenzyl)pyrrolidin-3-ol was used in place of 3-methyl-4-(4-methyl-1-piperazinyl)aniline.
¹H-NMR (400 MHz, CDCl₃) δ: 9.34 (1H, s), 8.78 (2H, d, J=4.9 Hz), 8.32 (1H, d, J=8.0 Hz), 8.27 (1H, d, J=8.4 Hz), 7.78 (1H, t, J=7.7 Hz), 7.66 (2H, s), 7.53 (1H, t, J=7.6 Hz), 7.28-7.25 (1H, m), 6.90 (2H, d, J=8.8 Hz), 5.03-4.97 (1H, m), 3.71-3.61 (1H, m), 3.51 (2H, s), 3.06 (2H, t, J=11.0 Hz), 2.49-2.34 (2H, m), 2.34-2.24 (1H, m).
ESI-MS Found: m/z [M+H]+ 506.

Example 88

Production of 2-{[4-(1,4-dimethylpiperidin-4-yl)phenyl]amino}-7-(pyrimidin-2-yl)pyrimido[4',5':4,5]pyrimido[1,2-b]indazol-5(7H)-one

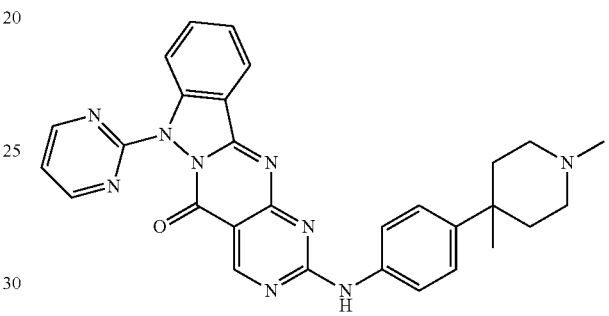

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-(1,4-dimethylpiperidin-4-yl)aniline was used in place of 3-methyl-4-(4-methyl-1-piperazinyl)aniline.
¹H-NMR (400 MHz, CDCl₃) δ: 9.37 (1H, s), 8.78 (2H, d, J=4.9 Hz), 8.35 (1H, d, J=7.8 Hz), 8.28 (1H, d, J=8.3 Hz), 7.79 (1H, t, J=7.8 Hz), 7.74-7.65 (2H, m), 7.56-7.51 (2H, m), 7.39 (2H, d, J=8.8 Hz), 2.56-2.48 (1H, m), 2.48-2.39 (1H, m), 2.29 (2H, s), 2.23-2.15 (2H, m), 1.85-1.77 (2H, m), 1.61 (3H, s), 1.25 (3H, s).
ESI-MS Found: m/z [M+H]+ 518.

Example 89

Production of 2-({4-[2-(diethylamino)ethoxy]phenyl}amino)-7-(pyrimidin-2-yl)pyrimido[4',5':4,5]pyrimido[1,2-b]indazol-5(7H)-one

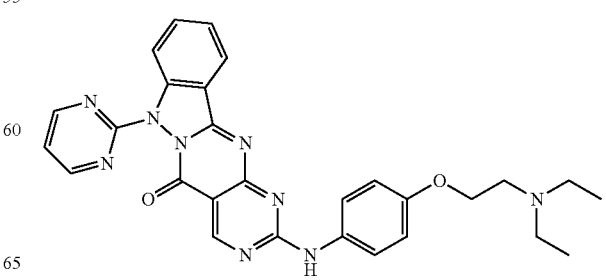

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-[2-(diethylamino)ethoxy]aniline was used in place of 3-methyl-4-(4-methyl-1-piperazinyl)aniline.

¹H-NMR (400 MHz, CDCl₃) δ: 9.36 (1H, s), 8.75 (2H, d, J=4.9 Hz), 8.31 (1H, d, J=7.3 Hz), 8.27 (2H, d, J=8.3 Hz), 7.77 (1H, t, J=8.5 Hz), 7.53 (1H, t, J=7.6 Hz), 7.46 (1H, s), 7.35 (1H, s), 7.25 (1H, t, J=5.4 Hz), 6.83 (1H, d, J=8.8 Hz), 4.16 (2H, t, J=5.9 Hz), 2.85 (2H, t, J=5.9 Hz), 2.38 (6H, s).

ESI-MS Found: m/z [M+H]+ 522.

Example 90

Production of 2-({4-[2-(dimethylamino)ethoxy]-3-methylphenyl}amino)-7-(pyrimidin-2-yl)pyrimido[4',5':4,5]pyrimido[1,2-b]indazol-5(7H)-one

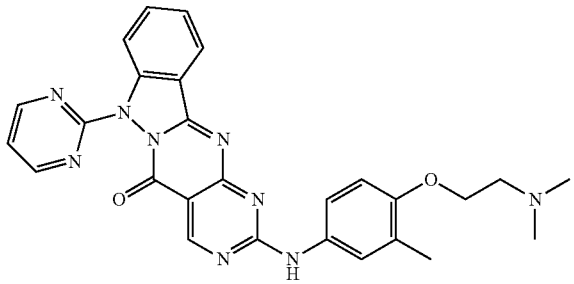

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-[2-(dimethylamino)ethoxy]-3-methylaniline was used in place of 3-methyl-4-(4-methyl-1-piperazinyl)aniline.

¹H-NMR (400 MHz, CDCl₃) δ: 9.34 (1H, s), 8.77 (2H, d, J=4.9 Hz), 8.32 (1H, d, J=7.3 Hz), 8.27 (1H, d, J=8.3 Hz), 7.77 (1H, t, J=8.5 Hz), 7.52 (1H, t, J=7.6 Hz), 7.46 (1H, s), 7.35 (1H, s), 7.25 (1H, t, J=5.4 Hz), 6.87 (1H, d, J=8.8 Hz), 4.11 (2H, t, J=5.9 Hz), 2.80 (2H, t, J=5.9 Hz), 2.38 (6H, s), 2.28 (3H, s).

ESI-MS Found: m/z [M+H]+ 508.

Example 91

Production of 2-({-4-[(dimethylamino)methyl]phenyl}amino)-7-(pyrimidin-2-yl)pyrimido[4',5':4,5]pyrimido[1,2-b]indazol-5(7H)-one

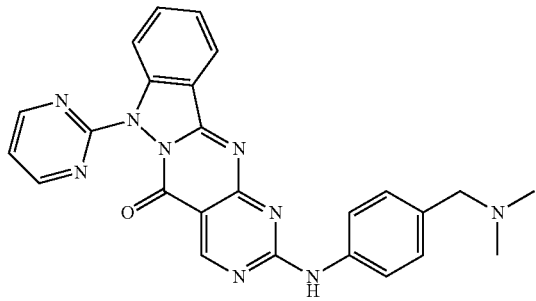

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-[dimethylamino)methyl]aniline was used in place of 3-methyl-4-(4-methyl-1-piperazinyl)aniline.

¹H-NMR (400 MHz, CDCl₃) δ: 9.38 (1H, s), 8.78 (1H, s), 8.77 (1H, s), 8.35 (1H, d, J=7.8 Hz), 8.28 (1H, d, J=8.8 Hz), 7.81-7.76 (1H, m), 7.72 (1H, d, J=7.8 Hz), 7.62 (1H, s), 7.55-7.51 (1H, m), 7.34 (2H, d, J=8.3 Hz), 7.26 (1H, t, J=4.9 Hz), 3.44 (2H, s), 2.27 (6H, s).

ESI-MS Found: m/z [M+H]+ 464.

Example 92

Production of 2-({4-[2-(dimethylamino)ethyl]phenyl}amino)-7-(pyrimidin-2-yl)pyrimido[4',5':4,5]pyrimido[1,2-b]indazol-5(7H)-one

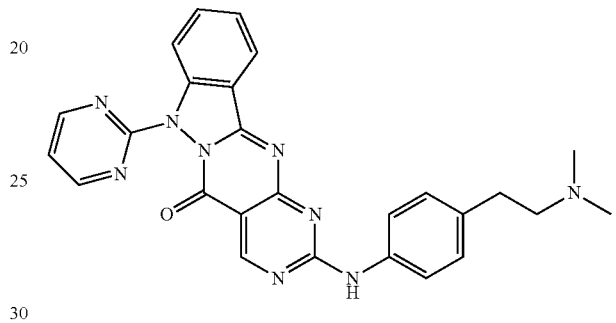

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 4-[2-(dimethylamino)ethyl]aniline was used in place of 3-methyl-4-(4-methyl-1-piperazinyl)aniline.

¹H-NMR (400 MHz, CDCl₃) δ: 9.36 (1H, s), 8.78 (1H, s), 8.77 (1H, s), 8.33 (1H, d, J=7.8 Hz), 8.27 (1H, d, J=8.3 Hz), 7.78 (1H, t, J=8.3 Hz), 7.64 (2H, s), 7.53 (1H, t, J=7.8 Hz), 7.27-7.23 (3H, m), 2.81 (2H, t, J=8.0 Hz), 2.57 (2H, t, J=8.0 Hz), 2.33 (6H, s).

ESI-MS Found: m/z [M+H]+ 478.

Example 93

Production of 2-[(1-ethyl-1H-indol-5-yl)amino]-7-(pyrimidin-2-yl)pyrimido[4',5':4,5]pyrimido[1,2-b]indazol-5(7H)-one

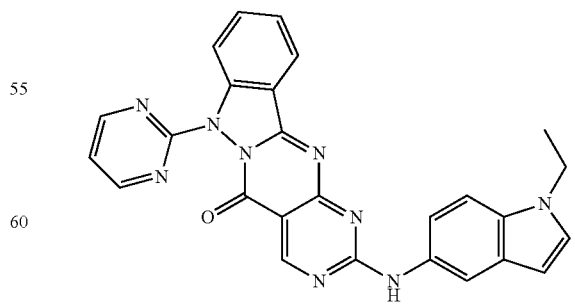

The title compound was produced as a yellow solid in the same manner as in Example 1, for which, however, 2-(methylthio)-7-pyrimidin-2-yl-pyrimido[4',5':4,5]pyrimido[1,2-b]

indazol-5(7H)-one obtained in Production Example 29 was used in place of 7-methyl-2-(methylthio)pyrimido[4',5':4,5]pyrimido[1,2-b]indazol-5(7H)-one used in Example 1, and 1-ethyl-1H-indol-5-amine was used in place of 3-methyl-4-(4-methyl-1-piperazinyl)aniline.

¹H-NMR (400 MHz, DMSO-d₆) δ: 10.19 (1H, s), 9.17 (1H, s), 8.92 (2H, d, J=4.9 Hz), 8.37-8.07 (2H, m), 8.13 (1H, d, J=8.5 Hz), 7.90 (1H, ddd, J=8.5, 7.3, 1.2 Hz), 7.61 (1H, ddd, J=8.0, 7.3, 0.7 Hz), 7.57-7.44 (2H, m), 7.53 (1H, t, J=4.9 Hz), 7.39 (1H, d, J=3.2 Hz), 6.45 (1H, d, J=2.4 Hz), 4.21 (2H, q, J=7.2 Hz), 1.38 (3H, t, J=7.2 Hz).

ESI-MS Found: m/z [M+H]+ 474.

Example 94

Production of 2-({1-[2-(dimethylamino)ethyl]-1H-indol-5-yl}amino)-7-(pyrimidin-2-yl)pyrimido[4',5':4,5]pyrimido[1,2-b]indazol-5(7H)-one

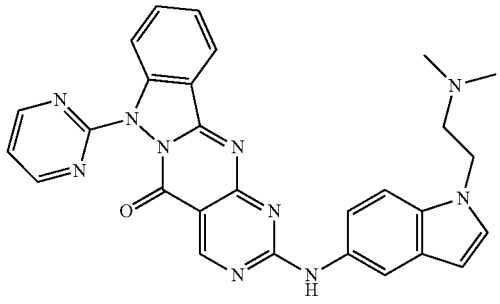

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 1-[2-(dimethylamino)ethyl]-1H-indol-5-amine was used in place of 3-methyl-4-(4-methyl-1-piperazinyl)aniline.

¹H-NMR (400 MHz, CDCl₃) δ: 9.35 (1H, s), 8.77 (2H, d, J=4.9 Hz), 8.32 (1H, d, J=7.6 Hz), 8.26 (1H, d, J=8.5 Hz), 8.16-7.80 (1H, m), 7.55-7.34 (1H, m), 7.76 (1H, ddd, J=8.5, 7.3, 1.2 Hz), 7.69-7.58 (1H, m), 7.51 (1H, ddd, J=7.8, 7.3, 0.7 Hz), 7.36 (1H, d, J=8.5 Hz), 7.24 (1H, t, J=4.9 Hz), 7.16 (1H, d, J=3.2 Hz), 6.52 (1H, d, J=2.9 Hz), 4.24 (2H, t, J=7.2 Hz), 2.71 (2H, t, J=7.2 Hz), 2.31 (6H, s).

ESI-MS Found: m/z [M+H]+ 517.

Example 95

Production of 7-(pyrimidin-2-yl)-2-({1-[2-(pyrrolidin-1-yl)ethyl]-1H-indol-5-yl}amino)pyrimido[4',5':4,5]pyrimido[1,2-b]indazol-5(7H)-one

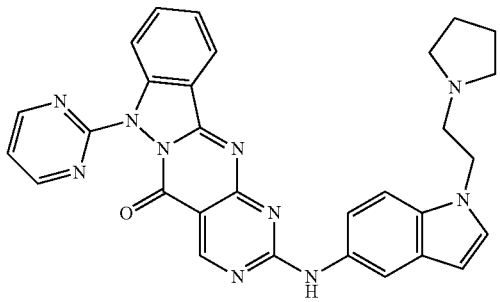

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 1-[2-(pyrrolidin-1-yl)ethyl]-1H-indol-5-amine was used in place of 3-methyl-4-(4-methyl-1-piperazinyl)aniline.

¹H-NMR (400 MHz, CDCl₃) δ: 9.35 (1H, s), 8.77 (2H, d, J=4.9 Hz), 8.33 (1H, d, J=7.8 Hz), 8.26 (1H, d, J=8.5 Hz), 8.18-7.72 (1H, m), 7.77 (1H, ddd, J=8.5, 7.1, 1.2 Hz), 7.67-7.56 (1H, m), 7.55-7.35 (1H, m), 7.51 (1H, ddd, J=8.0, 7.3, 0.7 Hz), 7.38 (1H, d, J=8.3 Hz), 7.24 (1H, t, J=4.9 Hz), 7.17 (1H, d, J=3.2 Hz), 6.52 (1H, d, J=3.2 Hz), 4.29 (2H, t, J=7.3 Hz), 2.91 (2H, t, J=7.3 Hz), 2.63-2.53 (4H, m), 1.86-1.76 (4H, m).

ESI-MS Found: m/z [M+H]+ 543.

Example 96

Production of 2-[(2-ethyl-2H-indazol-6-yl)amino]-7-(pyrimidin-2-yl)pyrimido[4',5':4,5]pyrimido[1,2-b]indazol-5(7H)-one

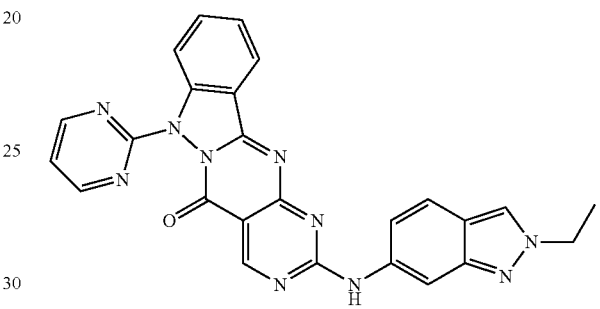

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 2-ethyl-2H-indazol-6-amine was used in place of 3-methyl-4-(4-methyl-1-piperazinyl)aniline.

¹H-NMR (400 MHz, DMSO-d₆) δ: 10.41 (1H, s), 9.25 (1H, s), 8.92 (2H, d, J=4.9 Hz), 8.77-8.35 (2H, m), 8.30 (1H, s), 8.14 (1H, d, J=8.5 Hz), 7.91 (1H, ddd, J=8.5, 7.3, 1.2 Hz), 7.68-7.59 (2H, m), 7.54 (1H, t, J=4.9 Hz), 7.31 (1H, dd, J=9.0, 1.7 Hz), 4.43 (2H, q, J=7.2 Hz), 1.52 (3H, t, J=7.3 Hz).

ESI-MS Found: m/z [M+H]+ 475.

Example 97

Production of 2-[(1-ethyl-1H-indazol-6-yl)amino]-7-(pyrimidin-2-yl)pyrimido[4',5':4,5]pyrimido[1,2-b]indazol-5(7H)-one

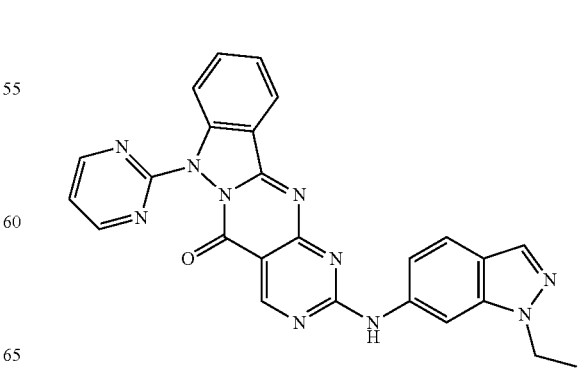

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 1-ethyl-1H-indazol-6-amine was used in place of 3-methyl-4-(4-methyl-1-piperazinyl)aniline.

$^1$H-NMR (400 MHz, DMSO-d$_6$) δ: 10.85 (1H, s), 9.59 (1H, s), 9.25 (2H, d, J=4.9 Hz), 8.62 (2H, d, J=7.8 Hz), 8.46 (1H, d, J=8.5 Hz), 8.31 (1H, s), 8.23 (1H, ddd, J=8.5, 7.3, 1.0 Hz), 8.05 (1H, d, J=8.5 Hz), 7.99-7.82 (3H, m), 4.73 (2H, q, J=7.2 Hz), 1.78 (3H, t, J=7.2 Hz).

ESI-MS Found: m/z [M+H]+ 475.

Example 98

Production of 2-[(2-ethyl-2H-indazol-5-yl)amino]-7-(pyrimidin-2-yl)pyrimido[4',5':4,5]pyrimido[1,2-b]indazol-5(7H)-one

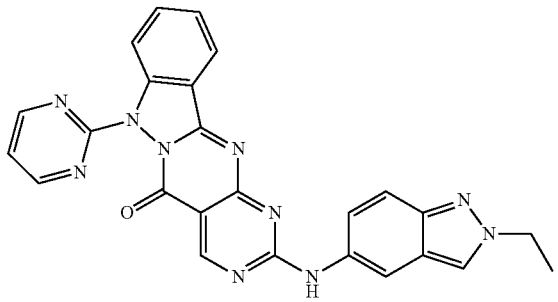

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 2-ethyl-2H-indazol-5-amine was used in place of 3-methyl-4-(4-methyl-1-piperazinyl)aniline.

$^1$H-NMR (400 MHz, DMSO-d$_6$) δ: 10.32 (1H, s), 9.22 (1H, s), 8.92 (2H, d, J=4.9 Hz), 8.35 (3H, t, J=16.7 Hz), 8.14 (1H, d, J=8.3 Hz), 7.91 (1H, ddd, J=8.3, 7.3, 1.0 Hz), 7.69-7.48 (4H, m), 4.44 (2H, q, J=7.2 Hz), 1.52 (3H, t, J=7.3 Hz).

ESI-MS Found: m/z [M+H]+ 475.

Example 99

Production of 2-[(1-ethyl-1H-indazol-5-yl)amino]-7-(pyrimidin-2-yl)pyrimido[4',5':4,5]pyrimido[1,2-b]indazol-5(7H)-one

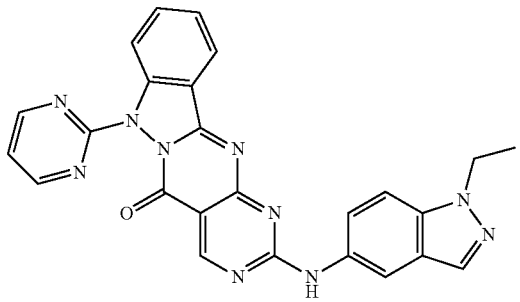

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 1-ethyl-1H-indazol-5-amine was used in place of 3-methyl-4-(4-methyl-1-piperazinyl)aniline.

$^1$H-NMR (400 MHz, DMSO-d$_6$) δ: 10.38 (1H, s), 9.22 (1H, s), 8.92 (2H, d, J=4.9 Hz), 8.53-8.25 (2H, m), 8.13 (1H, d, J=8.5 Hz), 8.08 (1H, s), 7.91 (1H, ddd, J=8.5, 7.3, 1.2 Hz), 7.81-7.59 (3H, m), 7.53 (1H, t, J=4.9 Hz), 4.44 (2H, q, J=7.2 Hz), 1.41 (3H, t, J=7.2 Hz).

ESI-MS Found: m/z [M+H]+ 475.

Example 100

Production of 2-[(2-methyl-1,2,3,4-tetrahydroisoquinolin-6-yl)amino]-7-(pyrimidin-2-yl)pyrimido[4',5':4,5]pyrimido[1,2-b]indazol-5(7H)-one

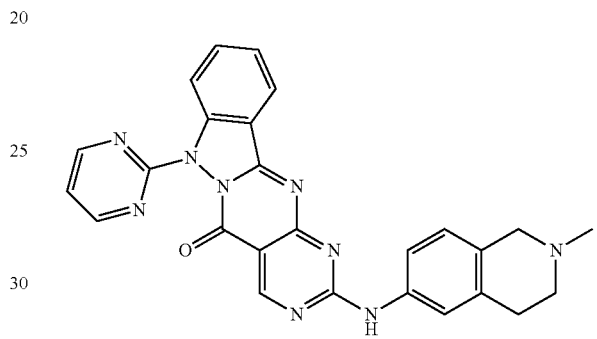

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 2-methyl-1,2,3,4-tetrahydroisoquinolin-6-amine was used in place of 3-methyl-4-(4-methyl-1-piperazinyl)aniline.

$^1$H-NMR (400 MHz, CDCl$_3$) δ: 9.36 (1H, s), 8.78 (2H, d, J=4.9 Hz), 8.34 (1H, d, J=7.8 Hz), 8.27 (1H, d, J=8.5 Hz), 7.78 (1H, ddd, J=8.5, 7.1, 1.2 Hz), 7.62-7.39 (4H, m), 7.25 (1H, d, J=4.9 Hz), 7.06 (1H, d, J=8.3 Hz), 3.59 (2H, s), 2.99 (2H, t, J=5.9 Hz), 2.71 (2H, t, J=5.9 Hz), 2.48 (3H, s).

ESI-MS Found: m/z [M+H]+ 476.

Example 101

Production of 2-[(2-methyl-1,2,3,4-tetrahydroisoquinolin-7-yl)amino]-7-(pyrimidin-2-yl)pyrimido[4',5':4,5]pyrimido[1,2-b]indazol-5(7H)-one

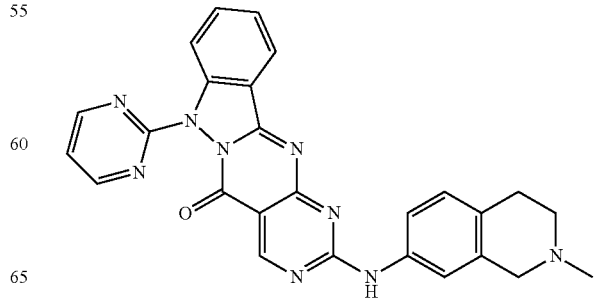

Example 102

Production of 2-[(2-methyl-2,3-dihydro-1H-isoindol-5-yl)amino]-7-(pyrimidin-2-yl)pyrimido[4',5':4,5]pyrimido[1,2-b]indazol-5(7H)-one

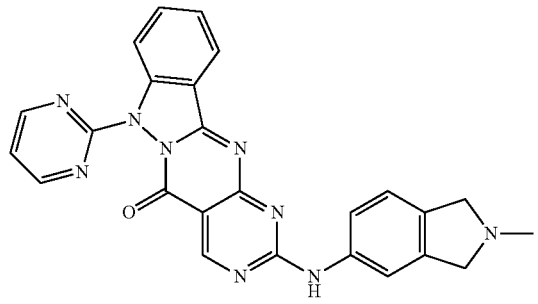

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 2-methylisoindolin-5-amine was used in place of 3-methyl-4-(4-methyl-1-piperazinyl)aniline.

¹H-NMR (400 MHz, DMSO-d₆) δ: 10.35 (1H, s), 9.22 (1H, s), 8.92 (2H, d, J=4.9 Hz), 8.31 (1H, d, J=8.0 Hz), 8.14 (1H, d, J=8.5 Hz), 7.91 (1H, ddd, J=8.5, 7.3, 1.2 Hz), 7.85-7.68 (2H, m), 7.62 (1H, ddd, J=8.0, 7.3, 0.7 Hz), 7.53 (1H, t, J=4.9 Hz), 7.24 (1H, d, J=8.3 Hz), 3.92 (2H, s), 3.86 (2H, s), 2.54 (3H, s).

ESI-MS Found: m/z [M+H]+ 462.

Example 103

Production of 7-(pyrimidin-2-yl)-2-[(1,1,2-trimethyl-1,2,3,4-tetrahydroisoquinolin-6-yl)amino]pyrimido[4',5':4,5]pyrimido[1,2-b]indazol-5(7H)-one

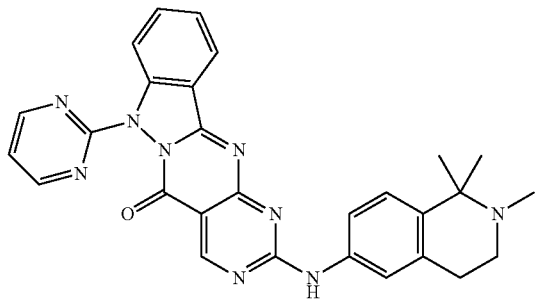

The title compound was produced as a yellow solid in the same manner as in Example 1, for which, however, 2-(methylthio)-7-pyrimidin-2-yl-pyrimido[4',5':4,5]pyrimido[1,2-b]indazol-5(7H)-one obtained in Production Example 29 was used in place of 7-methyl-2-(methylthio)pyrimido[4',5':4,5]pyrimido[1,2-b]indazol-5(7H)-one used in Example 1, and 1,1,2-trimethyl-1,2,3,4-tetrahydroisoquinolin-6-amine was used in place of 3-methyl-4-(4-methyl-1-piperazinyl)aniline.

¹H-NMR (400 MHz, DMSO-d₆) δ: 10.23 (1H, br s), 9.20 (1H, s), 8.92 (2H, d, J=4.9 Hz), 8.30 (1H, d, J=7.8 Hz), 8.13 (1H, dt, J=8.5, 0.7 Hz), 7.91 (1H, ddd, J=8.5, 7.3, 1.2 Hz), 7.81-7.66 (1H, m), 7.62 (1H, ddd, J=7.8, 7.3, 0.7 Hz), 7.53 (1H, t, J=4.9 Hz), 7.45 (1H, br s), 7.33 (1H, d, J=8.5 Hz), 2.80-2.72 (4H, m), 2.34 (3H, s), 1.33 (6H, s).

ESI-MS Found: m/z [M+H]+ 504.

Example 104

Production of 2-{[3-methyl-4-(4-methylpiperazin-1-yl)phenyl]amino}-7-(pyrazin-2-yl)pyrimido[4',5':4,5]pyrimido[1,2-b]indazol-5(7H)-one

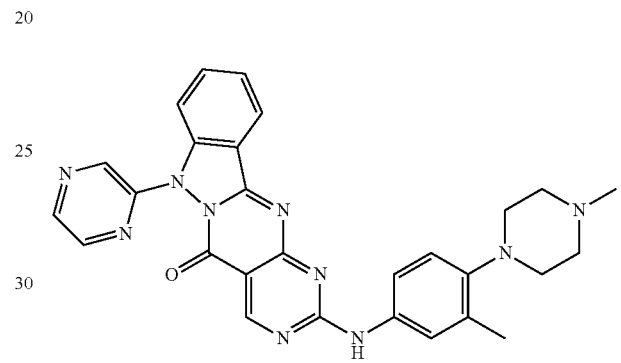

The title compound was produced as a yellow solid in the same manner as in Example 1, for which, however, 2-(methylthio)-7-pyrazin-2-yl-pyrimido[4',5':4,5]pyrimido[1,2-b]indazol-5(7H)-one obtained in Production Example 30 was used in place of 7-methyl-2-(methylthio)pyrimido[4',5':4,5]pyrimido[1,2-b]indazol-5(7H)-one used in Example 1.

¹H-NMR (400 MHz, CDCl₃) δ: 9.30 (1H, s), 8.85 (1H, d, J=1.4 Hz), 8.62 (1H, d, J=2.5 Hz), 8.48 (1H, dd, J=2.5, 1.4 Hz), 8.37 (1H, d, J=7.8 Hz), 7.76 (1H, ddd, J=8.5, 7.3, 1.2 Hz), 7.69-7.35 (4H, m), 7.63 (1H, d, J=8.5 Hz), 7.10 (1H, d, J=8.8 Hz), 2.99-2.93 (4H, m), 2.76-2.47 (4H, m), 2.39 (3H, s), 2.35 (3H, s).

ESI-MS Found: m/z [M+H]+ 519.

Example 105

Production of 2-{[4-(4-methylpiperazin-1-yl)phenyl]amino}-7-(1,3-thiazol-2-yl)pyrimido[4',5':4,5]pyrimido[1,2-b]indazol-5(7H)-one

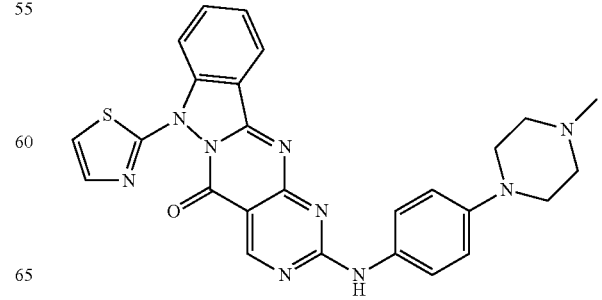

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

$^1$H-NMR (400 MHz, CDCl$_3$) δ: 9.29 (1H, br s), 8.38-8.24 (1H, m), 7.77 (1H, ddd, J=8.3, 7.3, 1.0 Hz), 7.73-7.45 (3H, m), 7.70 (1H, d, J=3.5 Hz), 7.63 (1H, d, J=8.3 Hz), 7.52 (1H, t, J=8.0 Hz), 7.40 (1H, d, J=3.5 Hz), 6.98 (2H, d, J=9.0 Hz), 3.25-3.17 (4H, m), 2.64-2.56 (4H, m), 2.37 (3H, s).

ESI-MS Found: m/z [M+H]+ 510.

Example 105

Production of 2-{[3-(hydroxymethyl)-4-(4-methylpiperazin-1-yl)phenyl]amino}-7-(1,3-thiazol-2-yl)pyrimido[4',5':4,5]pyrimido[1,2-b]indazol-5(7H)-one

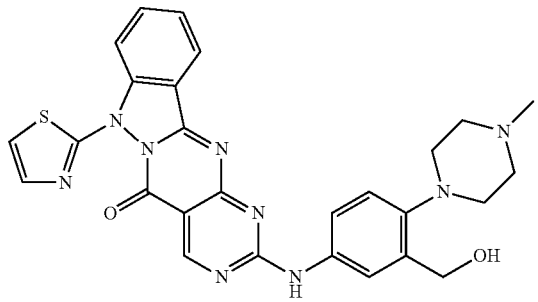

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and [5-amino-2-(4-methyl-1-piperazin-1-yl)phenyl]methanol was used in place of 3-methyl-4-(4-methyl-1-piperazinyl)aniline.

$^1$H-NMR (400 MHz, CDCl$_3$) δ: 9.31 (1H, s), 8.33 (1H, d, J=7.8 Hz), 7.78 (1H, t, J=7.8 Hz), 7.71 (1H, d, J=3.4 Hz), 7.65 (1H, s), 7.62 (1H, d, J=8.3 Hz), 7.53 (1H, t, J=7.6 Hz), 7.47 (1H, s), 7.42 (1H, d, J=3.4 Hz), 7.28 (1H, d, J=8.8 Hz), 4.85 (2H, s), 3.03 (4H, t, J=4.6 Hz), 2.62 (4H, s), 2.38 (3H, s).

ESI-MS Found: m/z [M+H]+ 540.

Example 106

Production of 2-[(4-{4-(2-hydroxyethyl)piperazin-1-yl}phenyl)amino]-7-(1,3-thiazol-2-yl)pyrimido[4',5':4,5]pyrimido[1,2-b]indazol-5(7H)-one

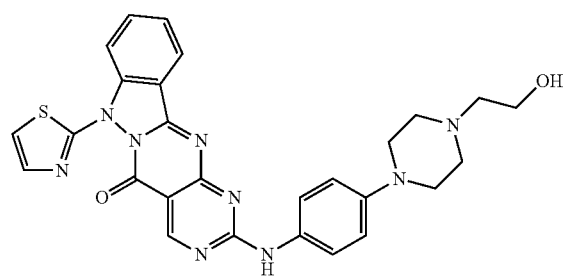

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 2-[4-(4-aminophenyl)piperazin-1-yl]ethanol was used in place of 3-methyl-4-(4-methyl-1-piperazinyl)aniline.

$^1$H-NMR (400 MHz, CDCl$_3$) δ: 9.30 (1H, s), 8.34 (1H, d, J=8.3 Hz), 7.78 (1H, t, J=7.8 Hz), 7.71 (1H, d, J=3.4 Hz), 7.63 (1H, d, J=8.3 Hz), 7.55-7.43 (2H, m), 7.53 (1H, t, J=7.6 Hz), 7.41 (1H, d, J=3.4 Hz), 6.98 (2H, d, J=9.3 Hz), 3.68 (2H, t, J=5.4 Hz), 3.22 (4H, t, J=4.9 Hz), 2.71 (4H, t, J=4.9 Hz), 2.63 (2H, t, J=5.4 Hz).

ESI-MS Found: m/z [M+H]+ 540.

Example 107

Production of 2-[(4-{4-[(dimethylamino)acetyl]piperazin-1-yl}phenyl)amino]-7-(1,3-thiazol-2-yl)pyrimido[4',5':4,5]pyrimido[1,2-b]indazol-5(7H)-one

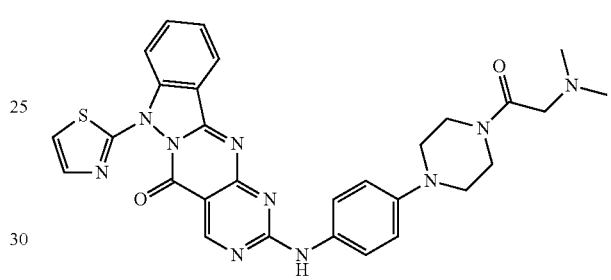

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-{4-[(dimethylamino)acetyl]piperazin-1-yl}aniline was used in place of 3-methyl-4-(4-methyl-1-piperazinyl)aniline.

$^1$H-NMR (400 MHz, CDCl$_3$) δ: 9.30 (1H, s), 8.33 (1H, d, J=8.0 Hz), 7.78 (1H, ddd, J=8.5, 7.5, 1.0 Hz), 7.71 (1H, d, J=3.4 Hz), 7.65-7.50 (2H, m), 7.63 (2H, d, J=8.5 Hz), 7.53 (1H, ddd, J=8.0, 7.5, 1.0 Hz), 7.41 (1H, d, J=3.4 Hz), 6.98 (2H, d, J=9.0 Hz), 3.84-3.76 (4H, br m), 3.21-3.12 (4H, br m), 3.17 (2H, s), 2.30 (6H, s).

ESI-MS Found: m/z [M+H]+ 581.

Example 108

Production of 2-({4-[(3R)-3,4-dimethylpiperazin-1-yl)phenyl]amino}-7-(1,3-thiazol-2-yl)pyrimido[4',5':4,5]pyrimido[1,2-b]indazol-5(7H)-one

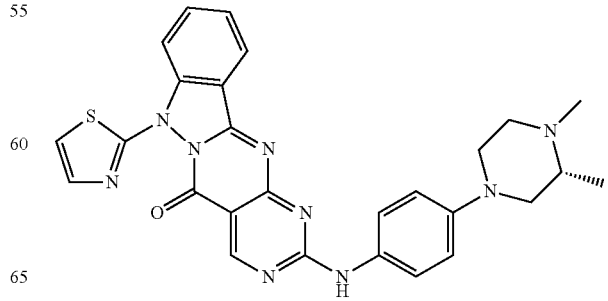

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-[(3R)-3,4-dimethylpiperazin-1-yl]aniline was used in place of 3-methyl-4-(4-methyl-1-piperazinyl)aniline.

$^1$H-NMR (400 MHz, CDCl$_3$) δ: 9.29 (1H, s), 8.32 (1H, d, J=6.8 Hz), 7.77 (1H, t, J=7.8 Hz), 7.70 (1H, d, J=3.4 Hz), 7.63 (1H, d, J=8.3 Hz), 7.52 (3H, t, J=7.6 Hz), 7.40 (1H, d, J=3.4 Hz), 6.97 (2H, d, J=8.8 Hz), 3.51 (1H, dt, J=11.9, 2.9 Hz), 3.45 (1H, dt, J=11.9, 2.9 Hz), 2.93 (2H, t, J=10.7 Hz), 2.55 (1H, t, J=10.7 Hz), 2.45 (1H, td, J=12.3, 4.1 Hz), 2.36 (3H, s), 2.31-2.25 (1H, m), 1.15 (3H, d, J=6.3 Hz).

ESI-MS Found: m/z [M+H]+ 524.

Example 109

Production of 2-({4-[3-(hydroxymethyl)-4-methylpiperazin-1-yl]phenyl}amino)-7-(1,3-thiazol-2-yl)pyrimido[4',5':4,5]pyrimido[1,2-b]indazol-5(7H)-one

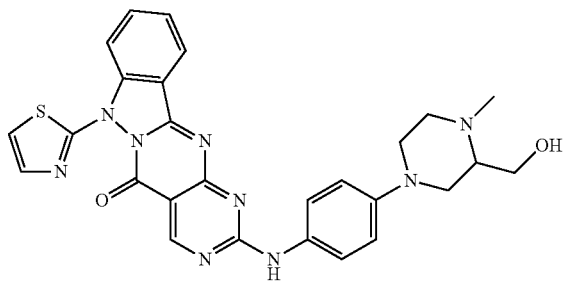

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and [4-(4-aminophenyl)-1-methylpiperazin-2-yl]methanol was used in place of 3-methyl-4-(4-methyl-1-piperazinyl)aniline.

$^1$H-NMR (400 MHz, CDCl$_3$) δ: 9.29 (1H, s), 8.33 (1H, d, J=7.8 Hz), 7.80-7.75 (1H, m), 7.71 (1H, d, J=3.4 Hz), 7.63 (2H, d, J=8.3 Hz), 7.55-7.51 (2H, m), 7.41 (1H, d, J=3.4 Hz), 6.99 (2H, d, J=8.3 Hz), 3.95 (1H, dd, J=11.5, 4.4 Hz), 3.59 (1H, dd, J=11.3, 1.8 Hz), 3.52-3.48 (2H, m), 3.02-2.86 (3H, m), 2.59 (1H, td, J=11.3, 3.2 Hz), 2.43-2.35 (1H, m), 2.42 (3H, s).

ESI-MS Found: m/z [M+H]+ 540.

Example 110

Production of N,N,1-trimethyl-4-(4-{[5-oxo-7-(1,3-thiazol-2-yl)-5,7-dihydropyrimido[4',5':4,5]pyrimido[1,2-b]indazol-2-yl]amino}phenyl)piperazine-2-carboxamide

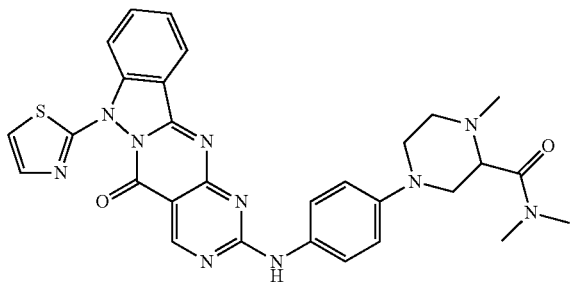

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-(4-aminophenyl)-N,N,1-trimethylpiperazine-2-carboxamide was used in place of 3-methyl-4-(4-methyl-1-piperazinyl)aniline.

$^1$H-NMR (400 MHz, CDCl$_3$) δ: 9.29 (1H, s), 8.35-8.27 (1H, m), 7.80-7.74 (1H, m), 7.70 (1H, d, J=3.5 Hz), 7.63 (2H, d, J=8.6 Hz), 7.52 (2H, t, J=7.5 Hz), 7.41 (1H, d, J=3.5 Hz), 6.96 (2H, d, J=8.6 Hz), 3.52 (2H, d, J=11.2 Hz), 3.36-3.31 (1H, m), 3.24 (3H, s), 3.11-2.95 (2H, m), 3.03 (3H, s), 2.53-2.44 (1H, m), 2.30 (3H, s).

ESI-MS Found: m/z [M+H]+ 581.

Example 111

Production of 2-({4-[(2S)-2-(hydroxymethyl)-4-methylpiperazin-1-yl]phenyl}amino)-7-(1,3-thiazol-2-yl)pyrimido[4',5':4,5]pyrimido[1,2-b]indazol-5(7H)-one

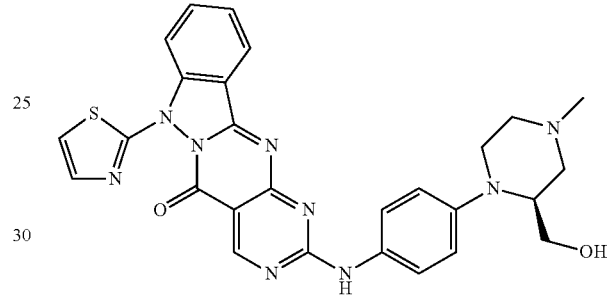

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and [(2S)-1-(4-aminophenyl)-4-methylpiperazin-2-yl]methanol was used in place of 3-methyl-4-(4-methyl-1-piperazinyl)aniline.

$^1$H-NMR (400 MHz, CDCl$_3$) δ: 9.29 (1H, s), 8.33 (1H, d, J=7.4 Hz), 7.79-7.75 (1H, m), 7.70 (1H, d, J=3.5 Hz), 7.63 (2H, d, J=8.6 Hz), 7.56-7.48 (1H, m), 7.52 (1H, t, J=7.5 Hz), 7.40 (1H, d, J=3.5 Hz), 6.96 (2H, d, J=8.6 Hz), 3.98-3.90 (1H, m), 3.86-3.80 (2H, m), 3.55 (1H, td, J=11.5, 3.7 Hz), 3.35 (1H, dt, J=11.6, 3.4 Hz), 3.08 (1H, dt, J=11.3, 2.2 Hz), 2.94-2.87 (1H, m), 2.63-2.58 (1H, m), 2.43-2.29 (1H, m), 2.35 (3H, s).

ESI-MS Found: m/z [M+H]+ 540.

Example 112

Production of 2-({4-[(2R)-2-(hydroxymethyl)-4-methylpiperazin-1-yl]phenyl}amino)-7-(1,3-thiazol-2-yl)pyrimido[4',5':4,5]pyrimido[1,2-b]indazol-5(7H)-one

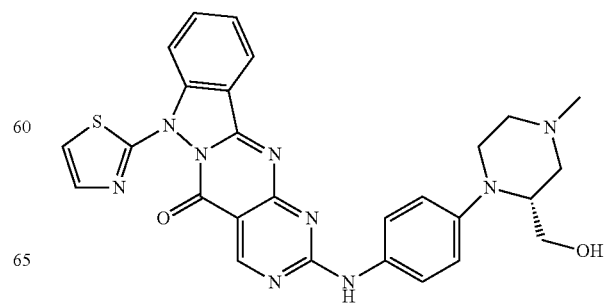

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and [(2R)-1-(4-aminophenyl)-4-methylpiperazin-2-yl]methanol was used in place of 3-methyl-4-(4-methyl-1-piperazinyl)aniline.

¹H-NMR (400 MHz, CDCl₃) δ: 9.29 (1H, s), 8.33 (1H, d, J=7.4 Hz), 7.79-7.75 (1H, m), 7.70 (1H, d, J=3.5 Hz), 7.63 (2H, d, J=8.6 Hz), 7.56-7.48 (1H, m), 7.52 (1H, t, J=7.5 Hz), 7.40 (1H, d, J=3.5 Hz), 6.96 (2H, d, J=8.6 Hz), 3.98-3.90 (1H, m), 3.86-3.80 (2H, m), 3.55 (1H, td, J=11.5, 3.7 Hz), 3.35 (1H, dt, J=11.6, 3.4 Hz), 3.08 (1H, dt, J=11.3, 2.2 Hz), 2.94-2.87 (1H, m), 2.63-2.58 (1H, m), 2.43-2.29 (1H, m), 2.35 (3H, s).

ESI-MS Found: m/z [M+H]+ 540

Example 113

Production of 2-({4-[(2R)-2-(methoxymethyl)-4-methylpiperazin-1-yl]phenyl}amino)-7-(1,3-thiazol-2-yl)pyrimido[4',5':4,5]pyrimido[1,2-b]indazol-5(7H)-one

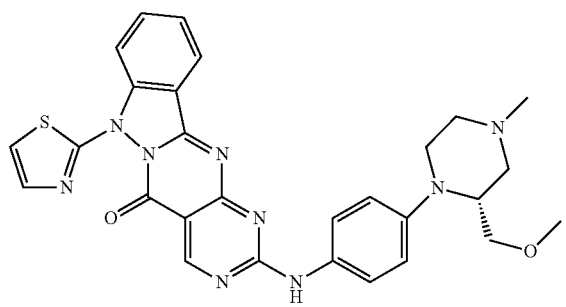

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-[(2R)-2-(methoxymethyl)-4-methylpiperazin-2-yl]aniline was used in place of 3-methyl-4-(4-methyl-1-piperazinyl)aniline.

¹H-NMR (400 MHz, CDCl₃) δ: 9.30 (1H, s), 8.33 (1H, d, J=7.6 Hz), 7.80-7.75 (1H, m), 7.71 (1H, d, J=3.7 Hz), 7.66-7.47 (2H, m), 7.63 (1H, d, J=8.3 Hz), 7.55-7.51 (1H, m), 7.41 (1H, d, J=3.7 Hz), 6.98 (2H, d, J=8.5 Hz), 3.87-3.79 (1H, m), 3.73-3.64 (1H, m), 3.36-3.26 (2H, m), 3.31 (3H, s), 3.17-3.08 (1H, m), 2.99-2.91 (1H, m), 2.85-2.76 (1H, m), 2.43-2.23 (2H, m), 2.35 (3H, s).

ESI-MS Found: m/z [M+H]+ 554

Example 114

Production of 2-{[4-(4-methylpiperazin-2-yl)phenyl]amino}-7-(1,3-thiazol-2-yl)pyrimido[4',5':4,5]pyrimido[1,2-b]indazol-5(7H)-one

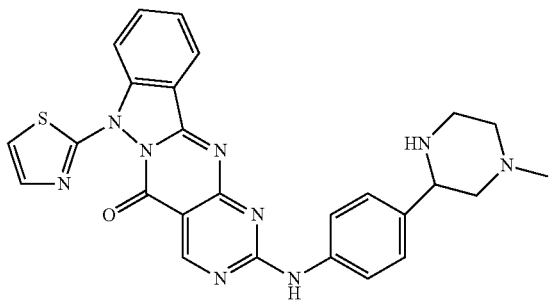

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-(4-methylpiperazin-2-yl)aniline was used in place of 3-methyl-4-(4-methyl-1-piperazinyl)aniline.

¹H-NMR (400 MHz, DMSO-d₆) δ: 10.37 (1H, s), 9.21 (1H, s), 8.34-7.54 (8H, m), 7.40 (2H, dd, J=15.9, 8.5 Hz), 3.92-3.84 (1H, m), 3.46-3.21 (2H, m), 3.05-2.74 (4H, m), 2.23 (3H, s), 2.18-1.96 (1H, m).

ESI-MS Found: m/z [M+H]+ 510.

Example 115

Production of 2-{[4-(4-methyl-1,4-diazepan-1-yl)phenyl]amino}-7-(1,3-thiazol-2-yl)pyrimido[4',5':4,5]pyrimido[1,2-b]indazol-5(7H)-one

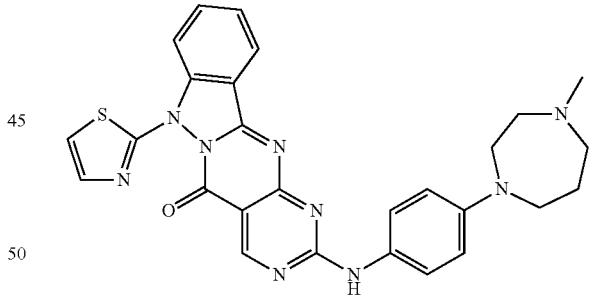

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-(4-methyl-1,4-diazepan-1-yl)aniline was used in place of 3-methyl-4-(4-methyl-1-piperazinyl)aniline.

¹H-NMR (400 MHz, CDCl₃) δ: 9.27 (1H, s), 8.33 (1H, d, J=7.4 Hz), 7.77 (1H, t, J=7.4 Hz), 7.70 (1H, d, J=3.7 Hz), 7.63 (1H, d, J=7.4 Hz), 7.60-7.32 (2H, m), 7.52 (1H, t, J=7.4 Hz), 7.40 (1H, d, J=3.7 Hz), 6.72 (2H, d, J=8.8 Hz), 3.63-3.57 (2H, m), 3.54-3.48 (2H, m), 2.75-2.70 (2H, m), 2.61-2.54 (2H, m), 2.39 (3H, s), 2.08-1.98 (2H, m).

ESI-MS Found: m/z [M+H]+ 524.

Example 116

Production of 2-{[4-(4-methyl-5-oxo-1,4-diazepan-1-yl)phenyl]amino}-7-(1,3-thiazol-2-yl)pyrimido[4',5':4,5]pyrimido[1,2-b]indazol-5(7H)-one

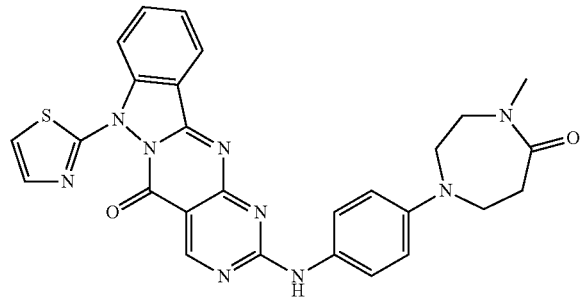

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 1-(4-aminophenyl)-4-methyl-1,4-diazepan-5-one was used in place of 3-methyl-4-(4-methyl-1-piperazinyl)aniline.

$^1$H-NMR (400 MHz, CDCl$_3$) δ: 9.30 (1H, s), 8.33 (1H, d, J=7.4 Hz), 7.78 (1H, t, J=7.4 Hz), 7.71 (1H, d, J=3.5 Hz), 7.66-7.50 (2H, m), 7.63 (1H, d, J=7.4 Hz), 7.53 (1H, t, J=7.4 Hz), 7.41 (1H, d, J=3.5 Hz), 6.93 (2H, d, J=8.6 Hz), 3.60-3.55 (1H, m), 3.50-3.45 (4H, m), 3.05 (3H, s), 2.85-2.80 (2H, m).
ESI-MS Found: m/z [M+H]+ 537.

Example 117

Production of 2-{[4-(4-hydroxypiperidin-1-yl)-3-methylphenyl]amino}-7-(1,3-thiazol-2-yl)pyrimido[4',5':4,5]pyrimido[1,2-b]indazol-5(7H)-one

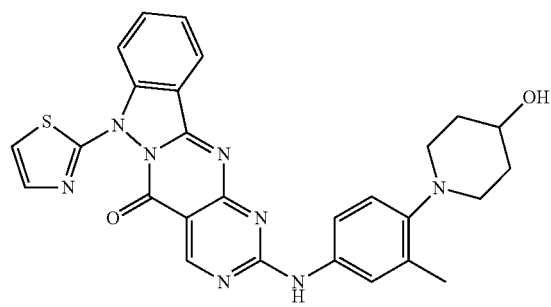

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 1-(4-amino-2-methylphenyl)piperidin-4-ol was used in place of 3-methyl-4-(4-methyl-1-piperazinyl)aniline.

$^1$H-NMR (400 MHz, DMSO-d$_6$) δ: 10.18 (1H, s), 9.16 (1H, s), 8.29 (1H, d, J=8.5 Hz), 7.89 (1H, ddd, J=8.5, 7.2, 1.2 Hz), 7.82-7.66 (1H, m), 7.81 (1H, d, J=3.4 Hz), 7.76 (1H, d, J=3.4 Hz), 7.69 (1H, dt, J=8.5, 0.7 Hz), 7.62 (1H, ddd, J=7.8, 7.2, 0.7 Hz), 7.52 (1H, br s), 7.04 (1H, d, J=8.5 Hz), 4.67 (1H, d, J=4.3 Hz), 3.66-3.54 (1H, m), 3.03-2.92 (2H, m), 2.63 (2H, t, J=9.8 Hz), 2.26 (3H, s), 1.91-1.78 (2H, m), 1.62-1.49 (2H, m).
ESI-MS Found: m/z [M+H]+ 525.

Example 118

Production of 2-{[4-(3-hydroxyazetidin-1-yl)-3-methylphenyl]amino}-7-(1,3-thiazol-2-yl)pyrimido[4',5':4,5]pyrimido[1,2-b]indazol-5(7H)-one

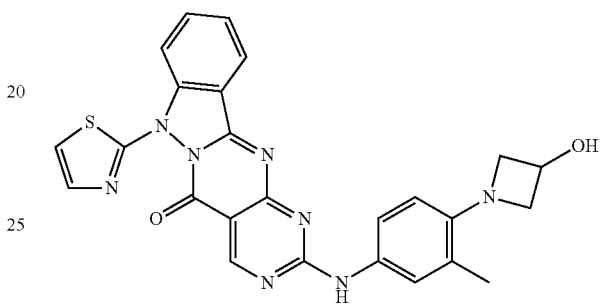

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 1-(4-amino-2-methylphenyl)azetidin-3-ol was used in place of 3-methyl-4-(4-methyl-1-piperazinyl)aniline.

$^1$H-NMR (400 MHz, DMSO-d$_6$) δ: 10.07 (1H, s), 9.12 (1H, s), 8.29 (1H, d, J=7.6 Hz), 7.89 (1H, ddd, J=8.5, 7.6, 1.0 Hz), 7.80 (1H, d, J=3.5 Hz), 7.75 (1H, d, J=3.5 Hz), 7.72-7.56 (1H, m), 7.69 (1H, d, J=8.5 Hz), 7.61 (1H, t, J=7.6 Hz), 7.36 (1H, s), 6.51 (1H, d, J=8.5 Hz), 5.52 (1H, d, =6.3 Hz), 4.49 (1H, dtt, J=6.3, 6.3, 6.3 Hz), 4.09 (2H, t, J=6.3 Hz), 3.50 (2H, t, J=6.3 Hz), 2.15 (3H, s).
ESI-MS Found: m/z [M+H]+ 497.

Example 119

Production of 2-({4-[(1-methylpiperidin-4-yl)oxy]phenyl}amino)-7-(1,3-thiazol-2-yl)pyrimido[4',5':4,5]pyrimido[1,2-b]indazol-5(7H)-one

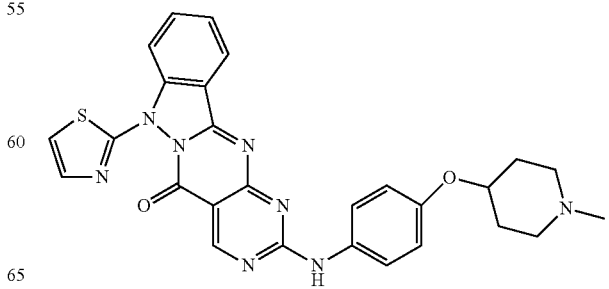

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-[(1-methylpiperidin-4-yl)oxy]aniline was used in place of 3-methyl-4-(4-methyl-1-piperazinyl)aniline.

$^{1}$H-NMR (400 MHz, CDCl$_3$) δ: 9.30 (1H, br s), 8.33 (1H, d, J=8.0 Hz), 7.78 (1H, ddd, J=8.5, 7.2, 1.2 Hz), 7.74-7.48 (3H, m), 7.71 (1H, d, J=3.5 Hz), 7.63 (1H, d, J=8.5 Hz), 7.53 (1H, ddd, J=8.0, 7.2, 0.7 Hz), 7.41 (1H, d, J=3.5 Hz), 6.96 (2H, d, J=9.0 Hz), 4.38-4.28 (1H, m), 2.80-2.69 (2H, m), 2.43-2.28 (2H, m), 2.35 (3H, s), 2.11-1.99 (2H, m), 1.97-1.84 (2H, m).

ESI-MS Found: m/z [M+H]+ 525.

Example 120

Production of 2-({4-[hydroxy(1-methylpiperidin-4-yl)methyl]phenyl}amino)-7-(1,3-thiazol-2-yl)pyrimido[4',5':4,5]pyrimido[1,2-b]indazol-5(7H)-one

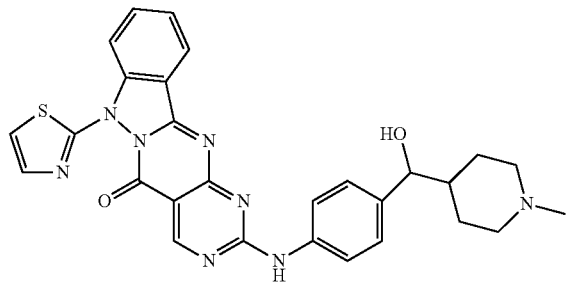

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and (4-aminophenyl)(1-methylpiperidin-4-yl)methanol was used in place of 3-methyl-4-(4-methyl-1-piperazinyl)aniline.

$^{1}$H-NMR (400 MHz, CDCl$_3$) δ: 9.32 (1H, s), 8.34 (1H, d, J=7.8 Hz), 7.78 (1H, t, J=7.8 Hz), 7.71 (4H, d, J=3.9 Hz), 7.62 (1H, d, J=8.3 Hz), 7.53 (1H, t, J=7.3 Hz), 7.42 (1H, d, J=3.4 Hz), 7.34 (1H, d, J=8.8 Hz), 4.36 (1H, d, J=7.8 Hz), 2.93 (1H, d, J=11.7 Hz), 2.79 (1H, d, J=11.7 Hz), 2.25 (3H, s), 2.06 (1H, dd, J=12.7, 3.4 Hz), 1.92 (1H, td, J=11.8, 3.1 Hz), 1.85-1.77 (1H, m), 1.62-1.53 (1H, m), 1.51-1.37 (1H, m), 1.31-1.23 (3H, m).

ESI-MS Found: m/z [M+H]+ 539.

Example 121

Production of 2-({4-[3-(dimethylamino)propoxy]phenyl}amino)-7-(1,3-thiazol-2-yl)pyrimido[4',5':4,5]pyrimido[1,2-b]indazol-5(7H)-one

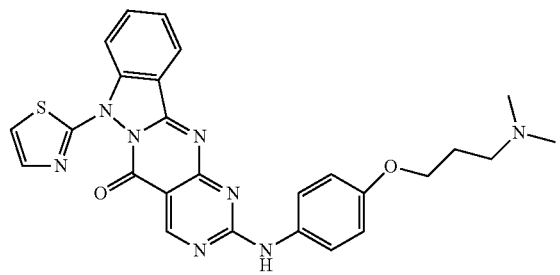

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-[3-(dimethylamino)propoxy]aniline was used in place of 3-methyl-4-(4-methyl-1-piperazinyl)aniline.

$^{1}$H-NMR (400 MHz, CDCl$_3$) δ: 9.30 (1H, s), 8.33 (1H, d, J=7.8 Hz), 7.78 (1H, t, J=7.8 Hz), 7.71 (1H, d, J=3.5 Hz), 7.63 (1H, d, J=8.2 Hz), 7.59-7.48 (1H, m), 7.52 (2H, t, J=7.4 Hz), 7.41 (1H, d, J=3.5 Hz), 6.95 (2H, d, J=9.0 Hz), 4.04 (2H, t, J=6.5 Hz), 2.47 (2H, t, J=7.4 Hz), 2.27 (6H, s), 2.01-1.94 (2H, m).

ESI-MS Found: m/z [M+H]+ 513.

Example 122

Production of 2-[(4-{2-[isopropyl(methyl)amino]ethoxy}phenyl)amino]-7-(1,3-thiazol-2-yl)pyrimido[4',5':4,5]pyrimido[1,2-b]indazol-5(7H)-one

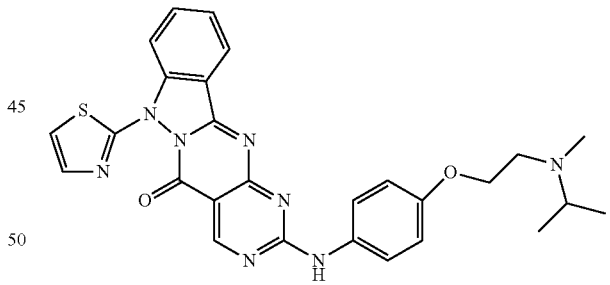

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-{2-[isopropyl(methyl)amino]ethoxy}aniline was used in place of 3-methyl-4-(4-methyl-1-piperazinyl)aniline.

$^{1}$H-NMR (400 MHz, CDCl$_3$) δ: 9.30 (1H, s), 8.34 (1H, d, J=8.3 Hz), 7.78 (1H, t, J=7.8 Hz), 7.71 (1H, d, J=3.9 Hz), 7.67-7.57 (1H, m), 7.63 (1H, d, J=8.3 Hz), 7.53 (2H, t, J=7.6 Hz), 7.41 (1H, d, J=3.4 Hz), 6.96 (2H, d, J=8.8 Hz), 4.07 (2H, t, J=6.3 Hz), 2.95-2.88 (1H, m), 2.82 (2H, t, J=6.3 Hz), 2.35 (3H, s), 1.06 (6H, d, J=6.3 Hz).

ESI-MS Found: m/z [M+H]+ 527

Example 123

Production of 2-({4-[3-(dimethylamino)-2-hydroxypropoxy]phenyl}amino)-7-(1,3-thiazol-2-yl)pyrimido[4',5':4,5]pyrimido[1,2-b]indazol-5(7H)-one

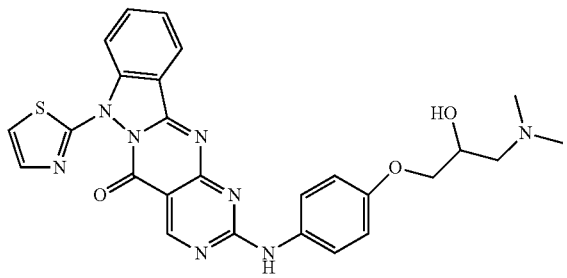

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 1-(4-aminophenoxy)-3-(dimethylamino)propan-2-ol was used in place of 3-methyl-4-(4-methyl-1-piperazinyl)aniline.

$^1$H-NMR (400 MHz, CDCl$_3$) δ: 9.30 (1H, s), 8.33 (1H, d, J=8.3 Hz), 7.77 (1H, t, J=7.8 Hz), 7.71 (1H, d, J=3.4 Hz), 7.63 (1H, d, J=8.3 Hz), 7.56-7.45 (1H, m), 7.53 (1H, t, J=7.6 Hz), 7.41 (1H, d, J=3.4 Hz), 7.35 (1H, s), 6.88 (1H, d, J=8.8 Hz), 4.14-3.96 (3H, m), 2.59 (1H, dd, J=12.2, 9.5 Hz), 2.45 (1H, dd, J=12.2, 3.9 Hz), 2.35 (6H, s), 2.29 (3H, s).

ESI-MS Found: m/z [M+H]+ 543.

Example 124

Production of 2-({4-[2-dimethylamino)-1-methylethoxy]phenyl}amino)-7-(1,3-thiazol-2-yl)pyrimido[4',5':4,5]pyrimido[1,2-b]indazol-5(7H)-one

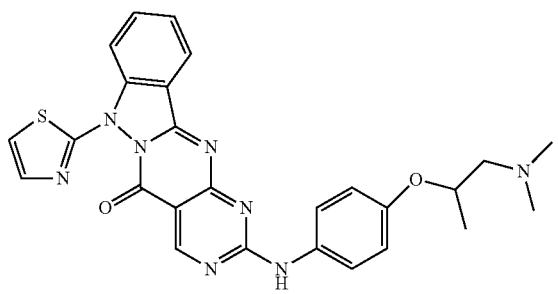

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-[2-(dimethylamino)-1-methylethoxy]aniline was used in place of 3-methyl-4-(4-methyl-1-piperazinyl)aniline.

$^1$H-NMR (400 MHz, CDCl$_3$) δ: 9.30 (1H, s), 8.33 (1H, d, J=7.3 Hz), 7.77 (1H, t, J=7.8 Hz), 7.71 (1H, d, J=3.4 Hz), 7.63 (1H, d, J=8.3 Hz), 7.57 (2H, s), 7.52 (1H, t, J=8.0 Hz), 7.41 (1H, d, J=3.4 Hz), 6.97 (3H, d, J=8.8 Hz), 4.51 (1H, m), 2.66 (1H, dd, J=12.9, 6.6 Hz), 2.43 (1H, dd, J=12.9, 5.1 Hz), 2.32 (6H, s), 1.32 (3H, d, J=6.3 Hz).

ESI-MS Found: m/z [M+H]+ 513.

Example 125

Production of 2-({4-[2-(dimethylamino)propoxy]phenyl}amino)-7-(1,3-thiazol-2-yl)pyrimido[4',5':4,5]pyrimido[1,2-b]indazol-5(7H)-one

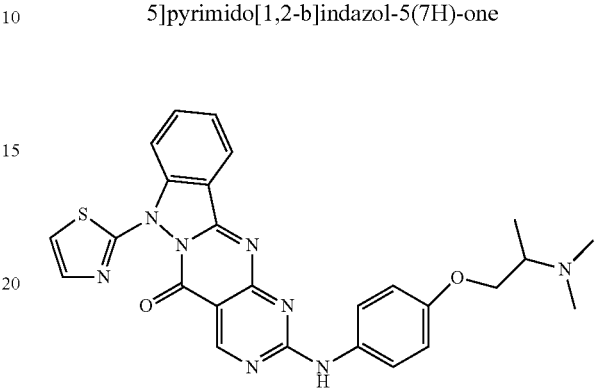

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-[2-(dimethylamino)propoxy]aniline was used in place of 3-methyl-4-(4-methyl-1-piperazinyl)aniline.

$^1$H-NMR (400 MHz, CDCl$_3$) δ: 9.30 (1H, s), 8.33 (1H, d, J=6.3 Hz), 7.77 (1H, t, J=7.8 Hz), 7.71 (1H, d, J=3.4 Hz), 7.63 (1H, d, J=8.8 Hz), 7.61-7.55 (2H, m), 7.52 (1H, t, J=7.6 Hz), 7.41 (1H, d, J=3.9 Hz), 6.97 (2H, d, J=8.8 Hz), 4.06 (1H, dd, J=9.5, 5.6 Hz), 3.86 (1H, dd, J=9.5, 5.9 Hz), 2.98 (1H, m), 2.37 (6H, s), 1.15 (3H, d, J=6.8 Hz).

ESI-MS Found: m/z [M+H]+ 513.

Example 126

Production of 2-({4-[3-(dimethylamino)-1-hydroxypropyl]phenyl}amino)-7-(1,3-thiazol-2-yl)pyrimido[4',5':4,5]pyrimido[1,2-b]indazol-5(7H)-one

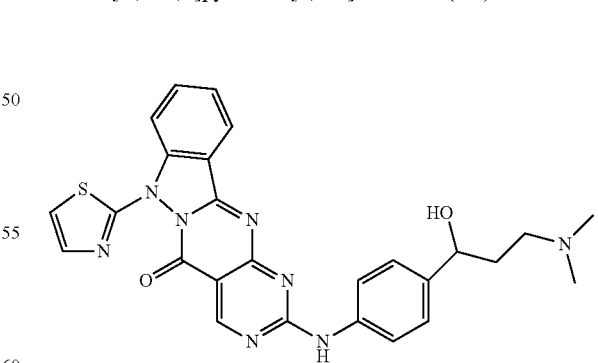

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 1-(4-aminophenyl)-3-(dimethylamino)propanol was used in place of 3-methyl-4-(4-methyl-1-piperazinyl)aniline.

$^1$H-NMR (400 MHz, CDCl$_3$) δ: 9.33 (1H, s), 8.33 (1H, d, J=7.8 Hz), 7.78 (2H, td, J=7.8, 1.3 Hz), 7.71 (3H, d, J=3.4 Hz), 7.63 (1H, d, J=8.3 Hz), 7.53 (1H, td, J=7.6, 1.3 Hz), 7.44-7.40 (2H, m), 4.96 (1H, dd, J=7.6, 3.7 Hz), 2.71-2.64 (1H, m), 2.51 (1H, dq, J=12.4, 2.9 Hz), 2.32 (6H, s), 1.87-1.82 (2H, m).

ESI-MS Found: m/z [M+H]+ 513.

Example 127

Production of 2-({3-[3-dimethylamino)propoxy]phenyl}amino)-7-(1,3-thiazol-2-yl)pyrimido[4',5':4,5]pyrimido[1,2-b]indazol-5(7H)-one

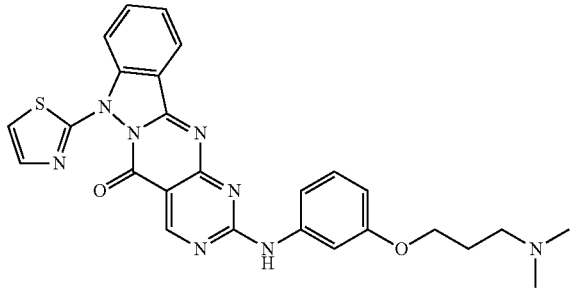

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 3-[3-(dimethylamino)propoxy]aniline was used in place of 3-methyl-4-(4-methyl-1-piperazinyl)aniline.

$^1$H-NMR (400 MHz, CDCl$_3$) δ: 9.31 (1H, s), 8.30 (1H, d, J=7.8 Hz), 7.75 (1H, t, J=8.0 Hz), 7.67 (1H, d, J=3.5 Hz), 7.61 (1H, s), 7.60 (1H, d, J=8.6 Hz), 7.50 (1H, t, J=7.8 Hz), 7.38 (1H, d, J=3.5 Hz), 7.32 (1H, s), 7.26 (1H, d, J=7.8 Hz), 6.67 (1H, dd, J=9.2, 2.5 Hz), 4.03 (2H, t, J=6.5 Hz), 2.45 (2H, t, J=7.2 Hz), 2.24 (6H, s), 1.99-1.92 (2H, m).

ESI-MS Found: m/z [M+H]+ 513.

Example 128

Production of 2-({3-[3-(dimethylamino)propoxy]-4-methoxyphenyl}amino)-7-(1,3-thiazol-2-yl)pyrimido[4',5':4,5]pyrimido[1,2-b]indazol-5(7H)-one

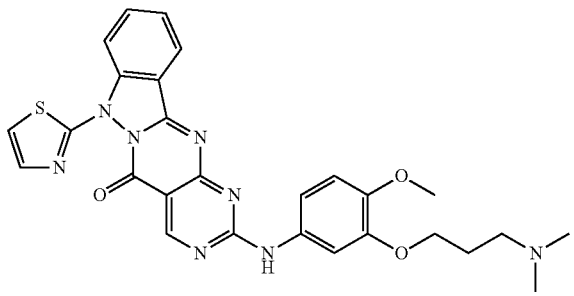

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 3-[3-(dimethylamino)propoxy]-4-methoxyaniline was used in place of 3-methyl-4-(4-methyl-1-piperazinyl)aniline.

$^1$H-NMR (400 MHz, CDCl$_3$) δ: 9.31 (1H, s), 8.32 (1H, d, J=8.3 Hz), 7.78 (1H, t, J=7.8 Hz), 7.71 (1H, d, J=3.9 Hz), 7.63 (1H, d, J=8.3 Hz), 7.61-7.49 (3H, m), 7.53 (1H, t, J=7.3 Hz), 7.41 (1H, d, J=3.9 Hz), 6.91 (1H, d, J=8.8 Hz), 4.14 (2H, t, J=6.6 Hz), 3.89 (3H, s), 2.50 (2H, t, J=7.3 Hz), 2.26 (6H, s), 2.09-2.03 (2H, m).

ESI-MS Found: m/z [M+H]+ 543.

Example 129

Production of 2-({4-[3-(dimethylamino)propoxy]-3-methoxyphenyl}amino)-7-(1,3-thiazol-2-yl)pyrimido[4',5':4,5]pyrimido[1,2-b]indazol-5(7H)-one

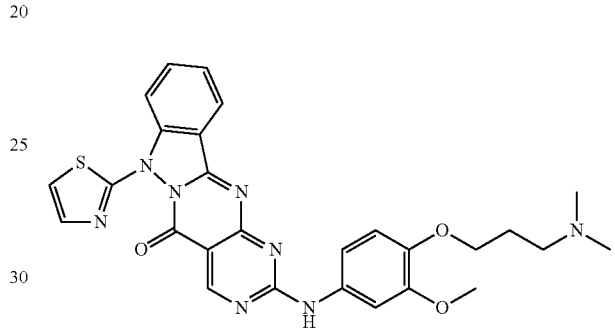

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-[3-(dimethylamino)propoxy]-3-methoxyaniline was used in place of 3-methyl-4-(4-methyl-1-piperazinyl)aniline.

$^1$H-NMR (400 MHz, CDCl$_3$) δ: 9.30 (1H, s), 8.33 (1H, d, J=7.8 Hz), 7.78 (1H, t, J=7.8 Hz), 7.71 (1H, d, J=3.5 Hz), 7.63 (1H, d, J=8.2 Hz), 7.59-7.48 (1H, m), 7.52 (2H, t, J=7.4 Hz), 7.41 (1H, d, J=3.5 Hz), 6.95 (2H, d, J=9.0 Hz), 4.04 (2H, t, J=6.5 Hz), 3.92 (3H, s), 2.47 (2H, t, J=7.4 Hz), 2.27 (6H, s), 2.01-1.94 (2H, m).

ESI-MS Found: m/z [M+H]+ 543.

Example 130

Production of 2-({4-[2-(dimethylamino)ethoxy]phenyl}amino)-7-(1,3-thiazol-2-yl)pyrimido[4',5':4,5]pyrimido[1,2-b]indazol-5(7H)-one

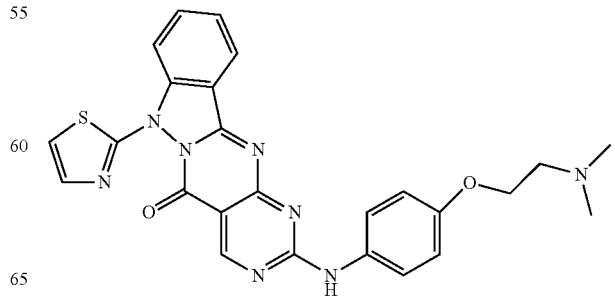

Example 131

Production of 2-({4-[3-(dimethylamino)-2-methyl-propoxy]phenyl}amino)-7-(1,3-thiazol-2-yl)pyrimido[4',5':4,5]pyrimido[1,2-b]indazol-5(7H)-one

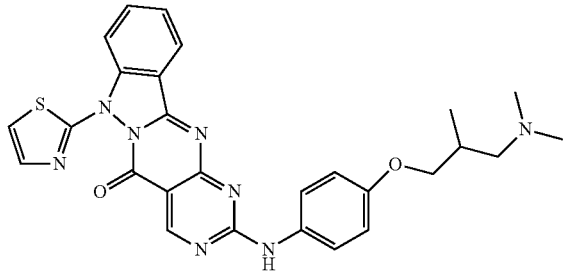

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-[3-(dimethylamino)-2-methylpropoxy]aniline was used in place of 3-methyl-4-(4-methyl-1-piperazinyl)aniline.

$^1$H-NMR (400 MHz, CDCl$_3$) δ: 9.34 (1H, s), 8.34 (1H, d, J=7.8 Hz), 7.78 (1H, t, J=7.8 Hz), 7.71 (1H, d, J=3.5 Hz), 7.63 (1H, d, J=8.2 Hz), 7.53 (1H, t, J=7.4 Hz), 7.41 (1H, d, J=3.5 Hz), 7.33 (1H, s), 7.30 (1H, d, J=7.8 Hz), 6.72 (1H, dd, J=9.8, 3.1 Hz), 4.02 (1H, dd, J=9.0, 4.7 Hz), 3.83 (1H, dd, J=9.0, 5.9 Hz), 2.48-2.39 (1H, m), 2.28 (6H, s), 2.26-2.15 (2H, m).

ESI-MS Found: m/z [M+H]+ 527.

Example 132

Production of 2-({3-[3-(dimethylamino)propoxy]-4-methylphenyl}amino)-7-(1,3-thiazol-2-yl)pyrimido[4',5':4,5]pyrimido[1,2-b]indazol-5(7H)-one

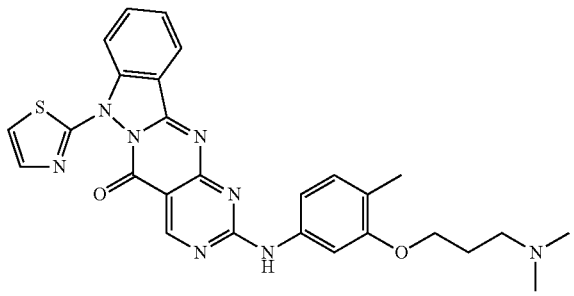

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 3-[3-(dimethylamino)propoxy]-4-methylaniline was used in place of 3-methyl-4-(4-methyl-1-piperazinyl)aniline.

$^1$H-NMR (400 MHz, CDCl$_3$) δ: 9.32 (1H, s), 8.33 (1H, d, J=7.4 Hz), 7.78 (1H, dt, J=10.7, 4.0 Hz), 7.71 (1H, d, J=3.5 Hz), 7.63 (1H, d, J=8.2 Hz), 7.63-7.57 (1H, m), 7.53 (1H, t, J=7.4 Hz), 7.41 (1H, d, J=3.9 Hz), 7.23 (1H, s), 7.13 (1H, d, J=7.4 Hz), 4.09 (2H, t, J=6.1 Hz), 2.54 (2H, t, J=7.4 Hz), 2.30 (6H, s), 2.22 (3H, s), 2.06-1.99 (2H, m).

ESI-MS Found: m/z [M+H]+ 527.

Example 133

Production of methyl 4-(4-{[5-oxo-7-(1,3-thiazol-2-yl)-5,7-dihydropyrimido[4',5':4,5]pyrimido[1,2-b]indazol-2-yl]amino}phenoxy)butanoate

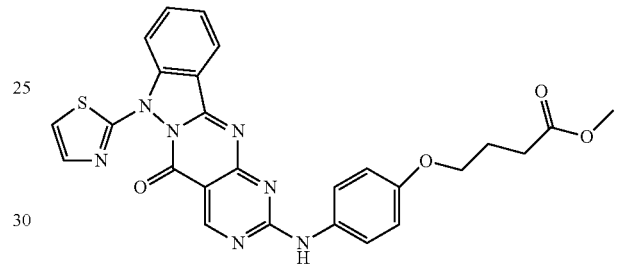

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and methyl 4-(4-aminophenoxy)butanoate was used in place of 3-methyl-4-(4-methyl-1-piperazinyl)aniline.

$^1$H-NMR (400 MHz, CDCl$_3$) δ: 9.30 (1H, s), 8.32 (1H, d, J=8.2 Hz), 7.77 (1H, t, J=7.8 Hz), 7.71 (1H, d, J=3.5 Hz), 7.66-7.57 (2H, m), 7.63 (1H, d, J=8.6 Hz), 7.52 (1H, t, J=7.6 Hz), 7.41 (1H, d, J=3.5 Hz), 6.93 (2H, d, J=8.6 Hz), 4.16 (2H, q, J=7.2 Hz), 4.03 (2H, t, J=6.1 Hz), 2.53 (2H, t, J=7.4 Hz), 2.16-2.09 (2H, m), 1.28 (3H, t, J=7.2 Hz).

ESI-MS Found: m/z [M+H]+ 542.

Example 134

Production of 2-({4-[(dimethylamino)methyl]phenyl}amino)-7-(1,3-thiazol-2-yl)pyrimido[4',5':4,5]pyrimido[1,2-b]indazol-5(7H)-one

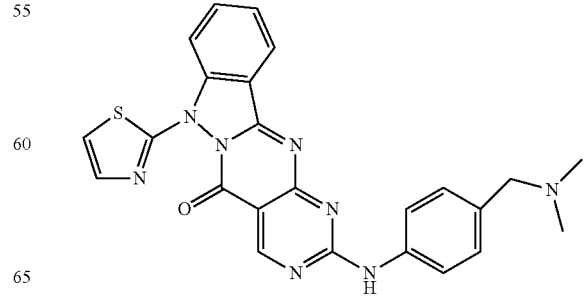

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-[(dimethylamino)methyl]aniline was used in place of 3-methyl-4-(4-methyl-1-piperazinyl)aniline.

$^1$H-NMR (400 MHz, CDCl$_3$) δ: 9.34 (1H, s), 8.35 (1H, d, J=7.8 Hz), 7.81-7.76 (1H, m), 7.72-7.57 (2H, m), 7.71 (1H, d, J=3.4 Hz), 7.64 (1H, d, J=8.3 Hz), 7.56-7.51 (1H, m), 7.42 (1H, d, J=3.4 Hz), 7.35 (2H, d, J=8.3 Hz), 3.44 (2H, s), 2.26 (6H, s).

ESI-MS Found: m/z [M+H]+ 469.

Example 135

Production of 2-[(4-{5-[(dimethylamino)methyl]-1,2,4-oxadiazol-3-yl}phenyl)amino]-7-(1,3-thiazol-2-yl)pyrimido[4',5':4,5]pyrimido[1,2-b]indazol-5(7H)-one

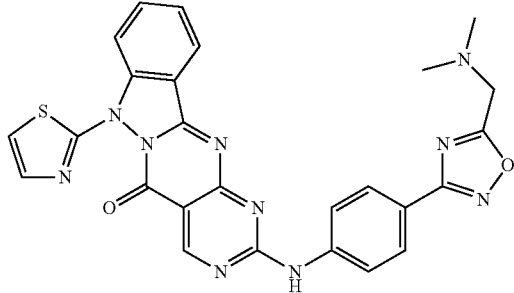

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-{5-[(dimethylamino)methyl]-1,2,4-oxadiazol-3-yl}aniline was used in place of 3-methyl-4-(4-methyl-1-piperazinyl)aniline.

$^1$H-NMR (400 MHz, CDCl$_3$) δ: 9.38 (1H, s), 8.38 (1H, d, J=8.0 Hz), 8.17 (2H, d, J=8.8 Hz), 7.96-7.90 (2H, m), 7.84-7.78 (1H, m), 7.75 (1H, s), 7.72 (1H, d, J=3.4 Hz), 7.64 (1H, d, J=8.3 Hz), 7.59-7.51 (1H, m), 7.43 (1H, d, J=3.4 Hz), 3.88 (2H, s), 2.45 (6H, s).

ESI-MS Found: m/z [M+H]+ 537.

Example 136

Production of 2-[(2-methyl-1,2,3,4-tetrahydroisoquinolin-6-yl)amino]-7-(1,3-thiazol-2-yl)pyrimido[4',5':4,5]pyrimido[1,2-b]indazol-5(7H)-one

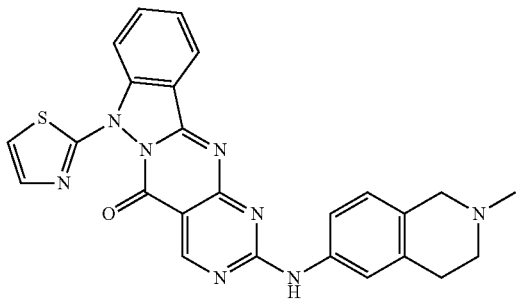

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 2-methyl-1,2,3,4-tetrahydroisoquinolin-6-amine was used in place of 3-methyl-4-(4-methyl-1-piperazinyl)aniline.

$^1$H-NMR (400 MHz, CDCl$_3$) δ: 9.32 (1H, s), 8.33 (1H, d, J=7.8 Hz), 7.78 (1H, t, J=7.8 Hz), 7.71 (1H, d, J=3.4 Hz), 7.63 (1H, d, J=8.3 Hz), 7.59 (1H, s), 7.53 (1H, t, J=7.6 Hz), 7.43 (1H, s), 7.41 (1H, d, J=3.4 Hz), 7.06 (1H, d, J=8.3 Hz), 3.59 (2H, s), 2.98 (2H, t, J=5.9 Hz), 2.70 (2H, t, J=5.9 Hz), 2.47 (3H, s).

ESI-MS Found: m/z [M+H]+ 481.

Example 137

Production of 2-[(2-methyl-1,2,3,4-tetrahydroisoquinolin-7-yl)amino]-7-(1,3-thiazol-2-yl)pyrimido[4',5':4,5]pyrimido[1,2-b]indazol-5(7H)-one

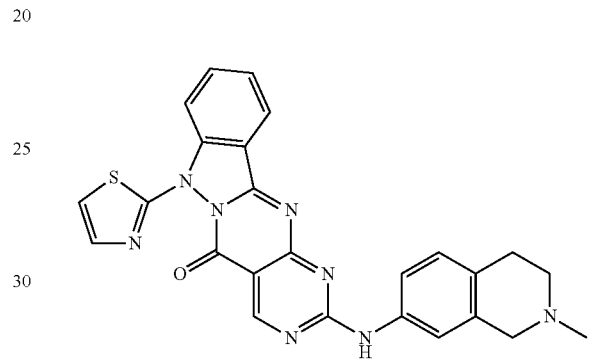

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 2-methyl-1,2,3,4-tetrahydroisoquinolin-7-amine was used in place of 3-methyl-4-(4-methyl-1-piperazinyl)aniline.

$^1$H-NMR (400 MHz, CDCl$_3$) δ: 9.31 (1H, s), 8.33 (1H, d, J=7.3 Hz), 7.79-7.75 (1H, m), 7.70 (1H, d, J=3.4 Hz), 7.63 (2H, d, J=8.3 Hz), 7.52 (1H, t, J=7.6 Hz), 7.41 (2H, d, J=3.4 Hz), 7.14 (1H, d, J=7.8 Hz), 3.64 (2H, s), 2.92 (2H, t, J=5.9 Hz), 2.70 (2H, t, J=5.9 Hz), 2.47 (3H, s).

ESI-MS Found: m/z [M+H]+ 481.

Example 138

Production of 2-{[2-(2-hydroxyethyl)-1,2,3,4-tetrahydroisoquinolin-7-yl]amino}-7-(1,3-thiazol-2-yl)pyrimido[4',5':4,5]pyrimido[1,2-b]indazol-5(7H)-one

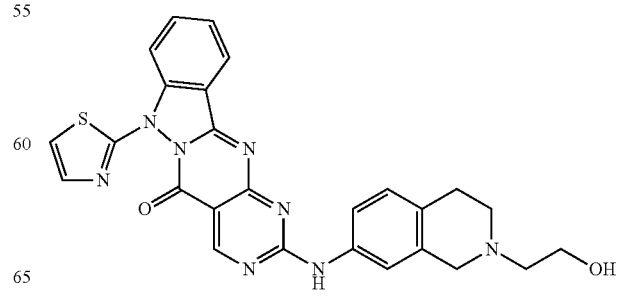

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 2-(7-amino-3,4-dihydroisoquinolin-2(1H)ethanol was used in place of 3-methyl-4-(4-methyl-1-piperazinyl)aniline.

$^1$H-NMR (400 MHz, CDCl$_3$) δ: 9.31 (1H, s), 8.33 (1H, d, J=8.6 Hz), 7.78 (1H, t, J=7.8 Hz), 7.73 (1H, s), 7.71 (1H, d, J=3.5 Hz), 7.63 (1H, d, J=8.2 Hz), 7.53 (1H, t, J=7.4 Hz), 7.44 (1H, s), 7.41 (1H, J=3.5 Hz), 7.13 (1H, d, J=7.8 Hz), 3.77 (2H, s), 3.74 (2H, t, J=5.3 Hz), 2.91 (2H, t, J=5.5 Hz), 2.84 (2H, t, J=5.5 Hz), 2.75 (2H, t, J=5.5 Hz).

ESI-MS Found: m/z [M+H]+ 511.

Example 139

Production of 2-[(6-methyl-5,6,7,8-tetrahydro-1,6-naphthyridin-3-yl)amino]-7-(1,3-thiazol-2-yl)pyrimido[4',5':4,5]pyrimido[1,2-b]indazol-5(7H)-one

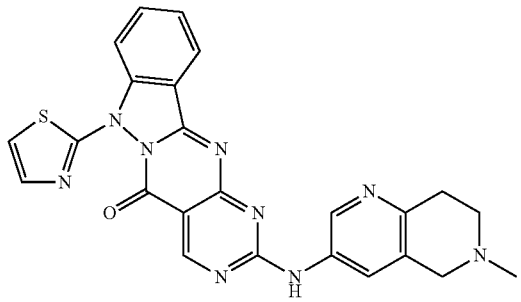

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 6-methyl-5,6,7,8-tetrahydro-1,6-naphthylpyridin-3-amine was used in place of 3-methyl-4-(4-methyl-1-piperazinyl)aniline.

$^1$H-NMR (400 MHz, CDCl$_3$) δ: 9.34 (1H, s), 8.51 (1H, s), 8.33 (1H, d, J=8.0 Hz), 8.11 (1H, s), 7.82-7.77 (1H, m), 7.72-7.71 (2H, m), 7.63 (1H, d, J=8.5 Hz), 7.54 (1H, t, J=7.6 Hz), 7.44-7.42 (1H, m), 3.71 (2H, s), 3.07 (2H, t, J=5.9 Hz), 2.83 (2H, t, J=5.9 Hz), 2.52 (3H, s).

ESI-MS Found: m/z [M+H]+ 482.

Example 140

Production of 2-[(3-methyl-2,3,4,5-tetrahydro-1H-3-benzazepin-7-yl)amino]-7-(1,3-thiazol-2-yl)pyrimido[4',5':4,5]pyrimido[1,2-b]indazol-5(7H)-one

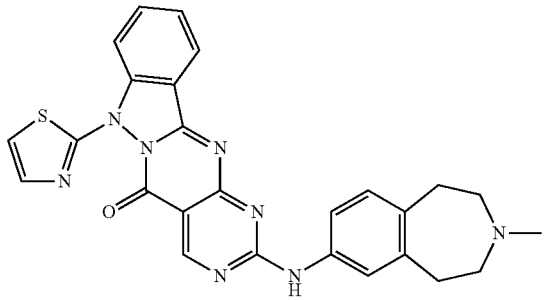

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 3-methyl-2,3,4,5-tetrahydro-1H-3-benzazepin-7-amine was used in place of 3-methyl-4-(4-methyl-1-piperazinyl)aniline.

$^1$H-NMR (400 MHz, DMSO-d$_6$) δ: 10.11 (1H, s), 9.24 (1H, s), 8.18 (1H, d, J=8.2 Hz), 7.83 (1H, t, J=8.2 Hz), 7.77 (1H, d, J=8.6 Hz), 7.50 (1H, s), 7.40 (1H, t, J=7.4 Hz), 7.11 (1H, d, J=8.2 Hz), 4.72 (2H, t, J=5.2 Hz), 4.56 (1H, t, J=5.2 Hz), 3.53 (2H, q, J=5.2 Hz), 2.83 (4H, s), 3.60-4.40 (4H, m), 2.25 (3H, s).

ESI-MS Found: m/z [M+H]+ 495.

Example 141

Production of 2-[(2-methyl-1,2,3,4-tetrahydro-1H-2-benzazepin-7-yl)amino]-7-(1,3-thiazol-2-yl)pyrimido[4',5':4,5]pyrimido[1,2-b]indazol-5(7H)-one

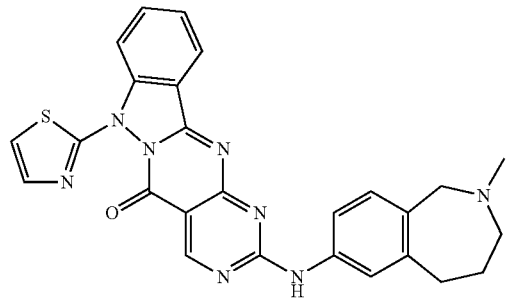

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 2-methyl-2,3,4,5-tetrahydro-1H-2-benzazepin-7-amine was used in place of 3-methyl-4-(4-methyl-1-piperazinyl)aniline.

$^1$H-NMR (400 MHz, CDCl$_3$) δ: 9.32 (1H, s), 8.35 (1H, d, J=7.8 Hz), 7.78 (1H, t, J=7.3 Hz), 7.71 (1H, d, J=3.9 Hz), 7.64 (1H, d, J=8.8 Hz), 7.53 (2H, t, J=7.6 Hz), 7.41 (1H, d, J=3.4 Hz), 7.35 (1H, s), 7.17 (1H, d, J=7.8 Hz), 3.86 (2H, s), 3.05 (2H, t, J=5.1 Hz), 2.89 (2H, t, J=5.1 Hz), 2.35 (3H, s), 1.82-1.74 (2H, m).

ESI-MS Found: m/z [M+H]+ 495.

Example 142

Production of 2-({4-[2-(dimethylamino)ethyl]-3-oxo-3,4-dihydro-2H-1,4-benzoxazin-7-yl}amino)-7-(1,3-thiazol-2-yl)pyrimido[4',5':4,5]pyrimido[1,2-b]indazol-5(7H)-one

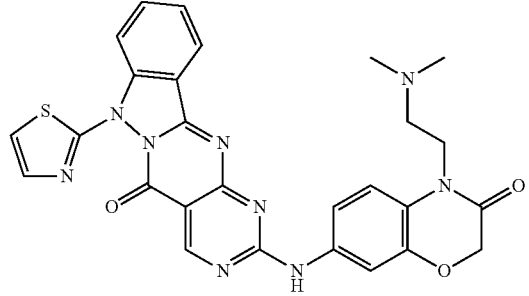

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 7-amino-4-[2-(dimethylamino)ethyl]-2H-1,4-benzoxazin-3(4H)-one was used in place of 3-methyl-4-(4-methyl-1-piperazinyl)aniline.

$^1$H-NMR (400 MHz, CDCl$_3$) δ: 9.32 (1H, s), 8.34 (1H, d, J=8.0 Hz), 7.79 (1H, ddd, J=8.4, 7.3, 1.2 Hz), 7.71 (1H, d, J=3.7 Hz), 7.67 (1H, br s), 7.62 (1H, d, J=8.4 Hz), 7.56-7.50 (1H, m), 7.54 (1H, ddd, J=8.0, 7.3, 0.7 Hz), 7.45-7.36 (1H, m), 7.43 (1H, d, J=3.7 Hz), 7.06 (1H, d, J=8.8 Hz), 4.64 (2H, s), 4.11-4.04 (2H, m), 2.62-2.54 (2H, m), 2.35 (6H, s).

ESI-MS Found: m/z [M+H]+ 554.

Example 143

Production of 2-({4-[2-(dimethylamino)ethyl]-3,4-dihydro-2H-1,4-benzoxazin-7-yl}amino)-7-(1,3-thiazol-2-yl)pyrimido[4',5':4,5]pyrimido[1,2-b]indazol-5(7H)-one

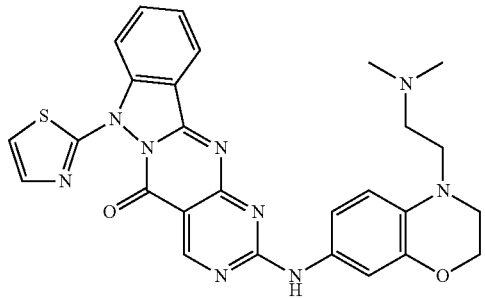

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 4-[2-(dimethylamino)ethyl]-3,4-dihydro-2H-1,4-benzoxazin-7-amine was used in place of 3-methyl-4-(4-methyl-1-piperazinyl)aniline.

$^1$H-NMR (400 MHz, DMSO-d$_6$) δ: 10.08 (1H, br s), 9.11 (1H, s), 8.39-8.29 (1H, m), 7.91 (7H, s), 7.91 (1H, s), 7.89 (1H, ddd, J=8.5, 7.3, 1.2 Hz), 7.80 (1H, d, J=3.7 Hz), 7.75 (1H, d, J=3.7 Hz), 7.69 (1H, d, J=8.5 Hz), 7.61 (1H, ddd, J=7.8, 7.3, 0.7 Hz), 6.70 (1H, d, J=8.5 Hz), 4.22-4.13 (2H, m), 3.38-3.28 (2H, m), 2.45-2.39 (2H, m), 2.17 (6H, d, J=18.0 Hz).

ESI-MS Found: m/z [M+H]+ 541.

Example 144

Production of 2-({1-[2-(dimethylamino)ethyl]-2,3-dihydro-1H-indol-5-yl}amino)-7-(1,3-thiazol-2-yl)pyrimido[4',5':4,5]pyrimido[1,2-b]indazol-5(7H)-one

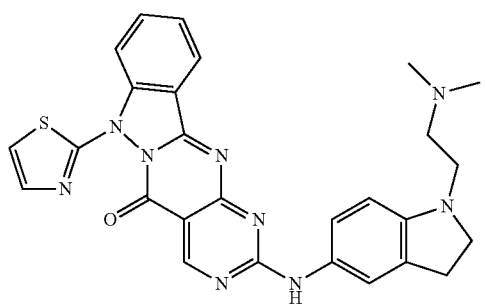

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 1-[2-(dimethylamino)ethyl]indolin-5-amine was used in place of 3-methyl-4-(4-methyl-1-piperazinyl)aniline.

$^1$H-NMR (400 MHz, DMSO-d$_6$) δ: 10.05 (1H, br s), 9.10 (1H, s), 8.35-8.20 (1H, m), 7.89 (1H, ddd, J=8.5, 7.3, 1.2 Hz), 7.80 (1H, d, J=3.4 Hz), 7.75 (1H, d, J=3.4 Hz), 7.69 (1H, d, J=8.5 Hz), 7.61 (1H, ddd, J=7.8, 7.3, 0.7 Hz), 7.56-7.43 (2H, m), 6.53 (1H, d, J=7.8 Hz), 3.39-3.28 (2H, m), 3.17-3.10 (2H, m), 2.96-2.86 (2H, m), 2.48-2.42 (2H, m), 2.20 (6H, s).

ESI-MS Found: m/z [M+H]+ 524.

Example 145

Production of 2-({1-[2-(dimethylamino)ethyl]-2-oxo-2,3-dihydro-1H-indol-5-yl}amino)-7-(1,3-thiazol-2-yl)pyrimido[4',5':4,5]pyrimido[1,2-b]indazol-5(7H)-one

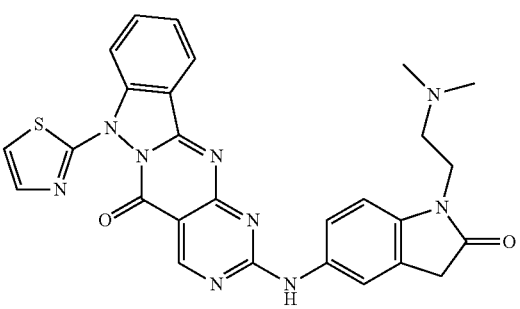

The title compound was produced as a yellow solid in the same manner as in Example 1, for which, however, 2-(methylthio)-7-(1,3-thiazol-2-yl)pyrimido[4',5':4,5]pyrimido[1,2-b]indazol-5(7H)-one obtained in Production Example 31 was used in place of 7-methyl-2-(methylthio)pyrimido[4',5':4,5]pyrimido[1,2-b]indazol-5(7H)-one used in Example 1, and 5-amino-1-[2-(dimethylamino)ethyl]-1,3-dihydro-2H-indol-2-one was used in place of 3-methyl-4-(4-methyl-1-piperazinyl)aniline.

$^1$H-NMR (400 MHz, CDCl$_3$) δ: 9.30 (1H, s), 8.33 (1H, d, J=8.0 Hz), 7.84-7.67 (1H, m), 7.79 (1H, ddd, J=8.5, 7.3, 1.2 Hz), 7.71 (1H, d, J=3.5 Hz), 7.66-7.44 (2H, m), 7.62 (1H, d, J=8.3 Hz), 7.53 (1H, ddd, J=8.0, 7.3, 0.7 Hz), 7.42 (1H, d, J=3.5 Hz), 6.88 (1H, d, J=8.5 Hz), 3.89-3.82 (2H, m), 3.61 (2H, s), 2.61-2.53 (2H, m), 2.33 (6H, s).

ESI-MS Found: m/z [M+H]+ 538.

Example 146

Production of 2-{[4-(4-methylpiperazin-1-yl)phenyl]amino}-7-(1,3-thiazol-4-yl)pyrimido[4',5':4,5]pyrimido[1,2-b]indazol-5(7H)-one

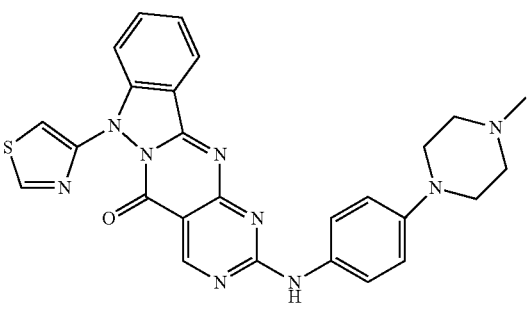

The title compound was produced as a yellow solid in the same manner as in Example 1, for which, however, 2-(methylthio)-7-(1,3-thiazol-4-yl)pyrimido[4',5':4,5]pyrimido[1,2-b]indazol-5(7H)-one obtained in Production Example 32 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

$^1$H-NMR (400 MHz, CDCl$_3$) δ: 9.26 (1H, s), 8.75 (1H, d, J=2.0 Hz), 8.33 (1H, d, J=7.3 Hz), 7.71 (1H, td, J=7.9, 1.1 Hz), 7.67 (1H, d, J=2.0 Hz), 7.60 (1H, s), 7.47 (1H, t, J=7.6 Hz), 7.38-7.31 (1H, m), 7.31 (1H, d, J=8.3 Hz), 6.97 (2H, d, J=8.8 Hz), 3.22 (4H, t, J=5.1 Hz), 2.62 (4H, t, J=4.9 Hz), 2.38 (3H, s).

ESI-MS Found: m/z [M+H]+ 510.

Example 147

Production of 7-(furan-3-yl)-2-{[4-(4-methylpiperazin-1-yl)phenyl]amino}pyrimido[4',5':4,5]pyrimido[1,2-b]indazol-5(7H)-one

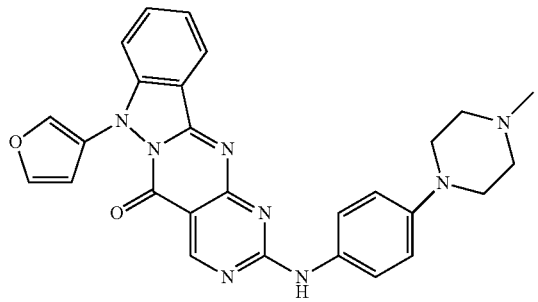

The title compound was produced as a yellow solid in the same manner as in Example 1, for which, however, 7-(3-furyl)-2-(methylthio)pyrimido[4',5':4,5]pyrimido[1,2-b]indazol-5(7H)-one obtained in Production Example 33 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

$^1$H-NMR (400 MHz, CDCl$_3$) δ: 9.27 (1H, s), 8.32 (1H, d, J=8.0 Hz), 7.94 (1H, dd, J=1.6, 0.9 Hz), 7.75-7.71 (1H, m), 7.66-7.36 (5H, m), 7.24 (2H, d, J=9.0 Hz), 6.98 (2H, d, J=9.0 Hz), 6.35 (1H, dd, J=2.1, 0.9 Hz), 3.22 (4H, t, J=5.1 Hz), 2.61 (4H, t, J=5.1 Hz), 2.37 (3H, s).

ESI-MS Found: m/z [M+H]+ 493.

Example 148

Production of 7-(1-methyl-1H-imidazol-2-yl)-2-{[4-(4-methylpiperazin-1-yl)phenyl]amino}pyrimido[4',5':4,5]pyrimido[1,2-b]indazol-5(7H)-one

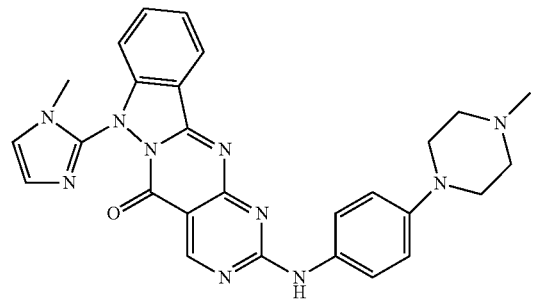

The title compound was produced as a yellow solid in the same manner as in Example 1, for which, however, 7-(1-methyl-1H-imidazol-2-yl)-2-(methylthio)pyrimido[4',5':4,5]pyrimido[1,2-b]indazol-5(7H)-one obtained in Production Example 34 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

$^1$H-NMR (400 MHz, CDCl$_3$) δ: 9.22 (1H, s), 8.33 (1H, d, J=8.0 Hz), 7.76-7.37 (3H, m), 7.72 (1H, ddd, J=8.5, 7.3, 1.2 Hz), 7.48 (1H, ddd, J=8.0, 7.3, 0.7 Hz), 7.10-7.03 (3H, m), 6.97 (2H, d, J=8.8 Hz), 4.00 (3H, s), 3.24-3.18 (4H, m), 2.63-2.57 (4H, m), 2.37 (3H, s).

ESI-MS Found: m/z [M+H]+ 507.

Example 149

Production of 7-cyclopropyl-2-{[3-methyl-(4-methylpiperazin-1-yl)phenyl]amino}pyrimido[4',5':4,5]pyrimido[1,2-b]indazol-5(7H)-one

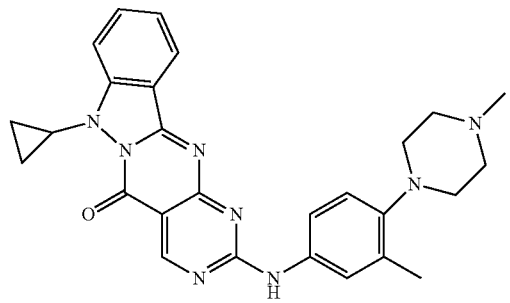

The title compound was produced as a yellow solid in the same manner as in Example 1, for which, however, 7-(1-methyl-1H-imidazol-2-yl)-2-(methylthio)pyrimido[4',5':4,5]pyrimido[1,2-b]indazol-5(7H)-one obtained in Production Example 35 was used in place of 7-methyl-2-(methylthio)pyrimido[4',5':4,5]pyrimido[1,2-b]indazol-5(7H)-one used in Example 1.

$^1$H-NMR (400 MHz, CDCl$_3$) δ: 9.34 (1H, s), 8.26 (1H, d, J=7.3 Hz), 7.80 (1H, t, J=7.3 Hz), 7.72-7.54 (3H, m), 7.58 (1H, d, J=8.8 Hz), 7.13 (1H, d, J=8.8 Hz), 3.41-3.32 (4H, m), 3.28-3.18 (4H, m), 2.82 (3H, s), 2.37 (3H, s), 1.34-1.15 (4H, m), 0.96-0.81 (1H, m).

ESI-MS Found: m/z [M+H]+ 481.

Example 150

Production of 9-hydroxy-2-{[4-(4-methylpiperazin-1-yl)phenyl]amino}-7-(pyridin-2-yl)pyrimido[4',5':4,5]pyrimido[1,2-b]indazol-5(7H)-one trifluoroacetate

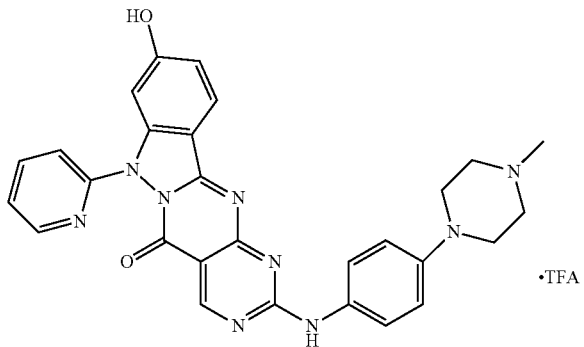

A crude product of the title compound was produced in the same manner as in Example 1, for which, however, 9-hydroxy-2-(methylthio)-7-pyridin-2-yl-pyrimido[4',5':4,5]pyrimido[1,2-b]indazol-5(7H)-one obtained in Production Example 36 was used in place of 7-methyl-2-(methylthio) pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline; and this was purified through preparative reversed-phase liquid chromatography to give the title compound.

¹H-NMR (400 MHz, DMSO-$d_6$) δ: 11.00 (1H, s), 10.11 (1H, s), 9.67 (1H, br s), 9.07 (1H, s), 8.48 (1H, ddd, J=4.9, 2.0, 0.8 Hz), 8.08 (1H, d, J=8.5 Hz), 8.02 (1H, td, J=7.8, 2.0 Hz), 7.87-7.70 (2H, m), 7.61 (1H, dt, J=7.8, 0.8 Hz), 7.43 (1H, ddd, J=7.8, 4.9, 0.8 Hz), 7.04 (2H, d, J=8.8 Hz), 7.02 (1H, d, J=2.0 Hz), 6.98 (1H, dd, J=8.5, 2.0 Hz), 3.99-2.74 (8H, m), 2.86 (3H, s).

ESI-MS Found: m/z [M+H]+ 520.

Example 151

Production of 10-hydroxy-2-{[4-(4-methylpiperazin-1-yl)phenyl]amino}-7-(pyridin-2-yl)pyrimido[4',5':4,5]pyrimido[1,2-b]indazol-5(7H)-one trifluoroacetate

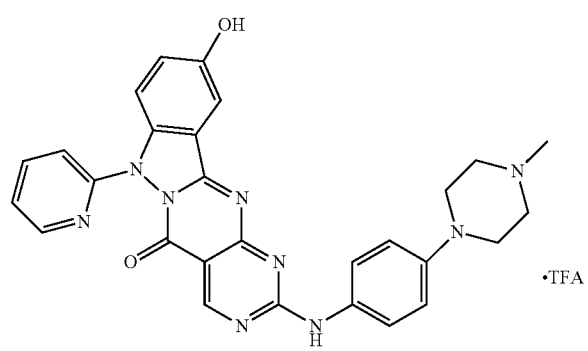

The title compound was produced as a yellow solid in the same manner as in Example 1, for which, however, 10-hydroxy-2-(methylthio)-7-pyridin-2-yl-pyrimido[4',5':4,5]pyrimido[1,2-b]indazol-5(7H)-one obtained in Production Example 37 was used in place of 7-methyl-2-(methylthio) pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

¹H-NMR (400 MHz, DMSO-$d_6$) δ: 10.17 (2H, br s), 9.66 (1H, br s), 9.12 (1H, br s), 8.43 (1H, ddd, J=4.9, 1.8, 0.7 Hz), 8.01 (1H, td, J=7.8, 1.8 Hz), 7.88-7.69 (2H, m), 7.63 (1H, dt, J=7.8, 0.7 Hz), 7.58 (1H, d, J=9.0 Hz), 7.45 (1H, d, J=2.4 Hz), 7.41 (1H, ddd, J=7.8, 4.9, 0.7 Hz), 7.29 (1H, dd, J=9.0, 2.4 Hz), 7.06 (2H, d, J=8.3 Hz), 3.86-3.77 (2H, m), 3.58-3.50 (2H, m), 3.26-3.13 (2H, m), 2.99-2.90 (2H, m), 2.87 (3H, d, J=3.7 Hz).

ESI-MS Found: m/z [M+H]+ 520.

Example 152

Production of 11-hydroxy-2-{[4-(4-methylpiperazin-1-yl)phenyl]amino}-7-(pyridin-2-yl)pyrimido[4',5':4,5]pyrimido[1,2-b]indazol-5(7H)-one trifluoroacetate

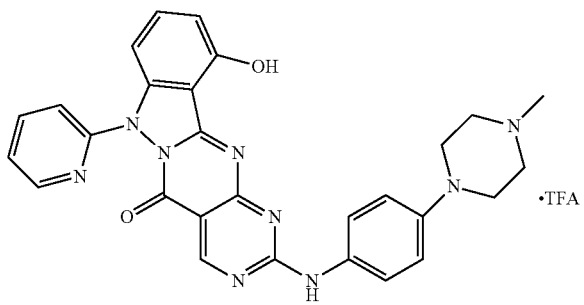

The title compound was produced as a yellow solid in the same manner as in Example 1, for which, however, 11-hydroxy-2-(methylthio)-7-pyridin-2-yl-pyrimido[4',5':4,5]pyrimido[1,2-b]indazol-5(7H)-one obtained in Production Example 38 was used in place of 7-methyl-2-(methylthio) pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

¹H-NMR (400 MHz, DMSO-$d_6$) δ: 11.21 (1H, br s), 10.12 (1H, br s), 9.68 (1H, br s), 9.09 (1H, s), 8.44 (1H, ddd, J=4.9, 1.8, 0.9 Hz), 8.02 (1H, ddd, J=8.0, 7.4, 1.8 Hz), 7.87-7.69 (2H, m), 7.65 (1H, dt, J=8.0, 0.9 Hz), 7.56 (1H, t, J=8.2 Hz), 7.42 (1H, ddd, J=7.4, 4.9, 0.9 Hz), 7.07 (2H, d, J=8.8 Hz), 7.02 (1H, d, J=8.2 Hz), 6.87 (1H, d, J=8.2 Hz), 3.88-3.75 (2H, m), 3.63-3.35 (2H, m), 3.26-3.11 (2H, m), 3.02-2.90 (2H, m), 2.87 (3H, s).

ESI-MS Found: m/z [M+H]+ 520.

Example 153

Production of 9-(2-hydroxyethoxy)-2-{[3-methyl-4-(4-methylpiperazin-1-yl)phenyl]amino}-7-(pyridin-2-yl)pyrimido[4',5':4,5]pyrimido[1,2-b]indazol-5(7H)-one

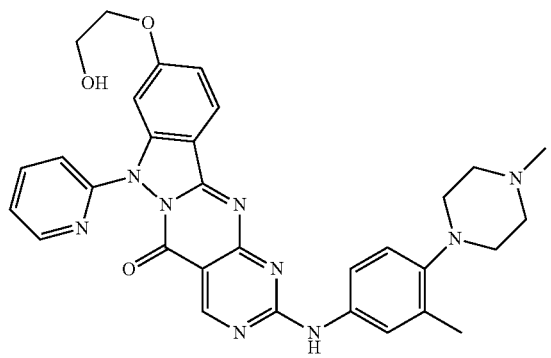

1) Production of 2-{[3-methyl-4-(4-methylpiperazin-1-yl)phenyl]amino}-7-(pyridin-2-yl)-9-[2-(tetrahydro-2H-pyran-2-yloxy)ethoxy]pyrimido[4',5':4,5]pyrimido[1,2-b]indazol-5(7H)-one The title compound was produced as a yellow solid in the same manner as in Example 1, for which, however, 2-(methylthio)-7-pyridin-2-yl-9-[2-(tetrahydro-2H-pyran-2-yloxy)ethoxy]pyrimido[4',5':4,5]pyrimido[1,2-b]indazol-5(7H)-one obtained in Production Example 39 was used in place of 7-methyl-2-(methylthio)pyrimido[4',5':4,5]pyrimido[1,2-b]indazol-5(7H)-one used in Example 1.

2) Production of 9-(2-hydroxyethoxy)-2-{[3-methyl-4-(4-methylpiperazin-1-yl)phenyl]amino}-7-(pyridin-2-yl)pyrimido[4',5':4,5]pyrimido[1,2-b]indazol-5(7H)-one 4 N hydrochloric acid/methanol solution (1 mL) was added to a chloroform (1 mL) solution of the compound obtained in Example 153-1, and stirred at room temperature for 30 minutes. The reaction liquid was concentrated under reduced pressure, and the residue was purified through basic silica gel chromatography to give the title compound as a yellow solid.
$^1$H-NMR (400 MHz, CDCl$_3$) δ: 9.26 (1H, s), 8.53 (1H, ddd, J=4.9, 1.8, 0.9 Hz), 8.21 (1H, d, J=8.5 Hz), 7.92 (1H, td, J=7.7, 1.8 Hz), 7.67-7.32 (4H, m), 7.35 (1H, ddd, J=7.7, 4.9, 0.9 Hz), 7.10-7.03 (3H, m), 4.19-4.14 (2H, m), 4.04-3.97 (2H, m), 3.06-2.94 (4H, m), 2.83-2.57 (4H, m), 2.44 (3H, s), 2.34 (3H, s), 2.13 (1H, br s).
ESI-MS Found: m/z [M+H]+ 564.

Example 154

Production of 10-(2-hydroxyethoxy)-2-{[4-(4-methylpiperazin-1-yl)phenyl]amino}-7-(pyridin-2-yl)pyrimido[4',5':4,5]pyrimido[1,2-b]indazol-5(7H)-one

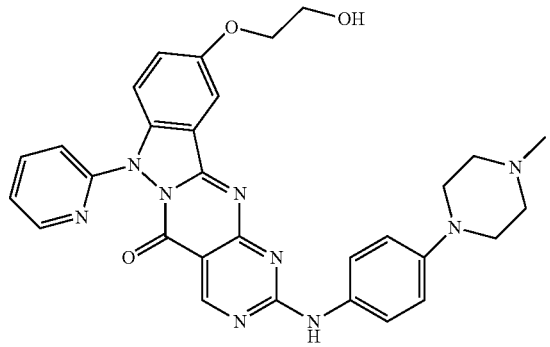

1) Production of 2-{[4-(4-methylpiperazin-1-yl)phenyl]amino}-7-(pyridin-2-yl)-10-[2-(tetrahydro-2H-pyran-2-yloxy)ethoxy]pyrimido[4',5':4,5]pyrimido[1,2-b]indazol-5(7H)-one The title compound was produced as a yellow solid in the same manner as in Example 1, for which, however, 2-(methylthio)-7-pyridin-2-yl-10-[2-(tetrahydro-2H-pyran-2-yloxy)ethoxy]pyrimido[4',5':4,5]pyrimido[1,2-b]indazol-5(7H)-one obtained in Production Example 40 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

2) Production of 10-(2-hydroxyethoxy)-2-{[4-(4-methylpiperazin-1-yl)phenyl]amino}-7-(pyridin-2-yl)pyrimido[4',5':4,5]pyrimido[1,2-b]indazol-5(7H)-one 4 N hydrochloric acid/methanol solution (1 mL) was added to a chloroform (1 mL) solution of the compound obtained in Example 154-1, and stirred at room temperature for 30 minutes. The reaction liquid was concentrated under reduced pressure, and the residue was purified through basic silica gel chromatography to give the title compound as a yellow solid.
$^1$H-NMR (400 MHz, DMSO-d$_6$) δ: 10.11 (1H, br s), 9.11 (1H, s), 8.45 (1H, ddd, J=4.6, 1.8, 0.7 Hz), 8.01 (1H, dt, J=1.8, 7.8 Hz), 7.83-7.59 (5H, m), 7.47-7.39 (2H, m), 6.96 (2H, d, J=9.0 Hz), 4.94 (1H, t, J=5.5 Hz), 4.15 (2H, t, J=4.8 Hz), 3.76 (2H, dt, J=5.5, 4.8 Hz), 3.15-3.07 (4H, m), 2.52-2.44 (4H, m), 2.22 (3H, s).
ESI-MS Found: m/z [M+H]+ 564.

Example 155

Production of 11-(2-hydroxyethoxy)-2-{[4-(4-methylpiperazin-1-yl)phenyl]amino}-7-(pyridin-2-yl)pyrimido[4',5':4,5]pyrimido[1,2-b]indazol-5(7H)-one

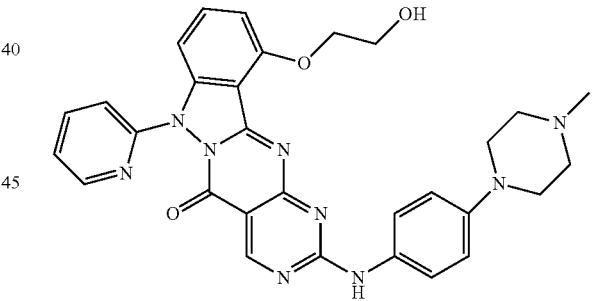

1) Production of 2-{[4-(4-methylpiperazin-1-yl)phenyl]amino}-7-(pyridin-2-yl)-11-[2-(tetrahydro-2H-pyran-2-yloxy)ethoxy]pyrimido[4',5':4,5]pyrimido[1,2-b]indazol-5(7H)-one The title compound was produced as a yellow solid in the same manner as in Example 1, for which, however, 2-(methylthio)-7-pyridin-2-yl-11-[2-(tetrahydro-2H-pyran-2-yloxy)ethoxy]pyrimido[4',5':4,5]pyrimido[1,2-b]indazol-5(7H)-one obtained in Production Example 41 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

2) Production of 11-(2-hydroxyethoxy)-2-{[4-(4-methylpiperazin-1-yl)phenyl]amino}-7-(pyridin-2-yl)pyrimido[4',5':4,5]pyrimido[1,2-b]indazol-5(7H)-one 4 N hydrochloric acid/methanol solution (1 mL) was added to a chloroform (1 mL) solution of the compound obtained in Example 155-1, and stirred at room temperature for 30 minutes. The reaction liquid was concentrated under reduced pressure, and the residue was purified through basic silica gel chromatography to give the title compound as a yellow solid.

$^1$H-NMR (400 MHz, DMSO-$d_6$) δ: 10.11 (1H, br s), 9.09 (1H, s), 8.46 (1H, ddd, J=4.8, 1.8, 0.7 Hz), 8.02 (1H, ddd, J=8.0, 7.4, 1.8 Hz), 7.76-7.52 (4H, m), 7.43 (1H, ddd, J=7.4, 4.8, 0.7 Hz), 7.17 (1H, d, J=8.2 Hz), 7.09 (1H, d, J=8.2 Hz), 6.94 (2H, d, J=8.5 Hz), 5.03 (1H, br s), 4.44-4.26 (2H, m), 3.85 (2H, q, J=5.2 Hz), 3.15-3.04 (4H, m), 2.47-2.42 (4H, m), 2.22 (3H, s).

ESI-MS Found: m/z [M+H]+ 564.

Example 156

Production of methyl {[2-{[4-(4-methylpiperazin-1-yl)phenyl]amino}-5-oxo-7-(pyridin-2-yl)-5,7-dihydropyrimido[4',5':4,5]pyrimido[1,2-b]indazol-9-yl]oxy}acetate

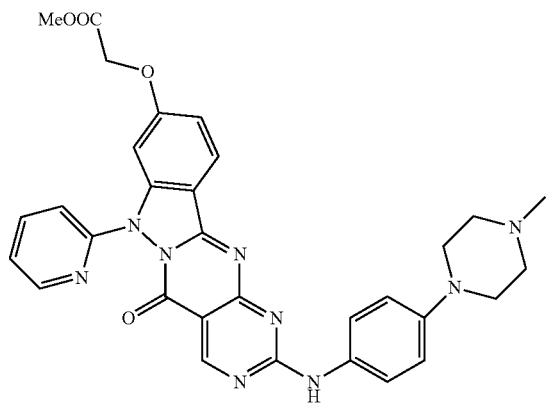

The title compound was produced as a yellow solid in the same manner as in Example 1, for which, however, methyl {[2-(methylthio)-5-oxo-7-pyridin-2-yl-5,7-dihydropyrimido[4',5':4,5]pyrimido[1,2-b]indazol-9-yl]oxy}acetate obtained in Production Example 47 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

$^1$H-NMR (400 MHz, CDCl$_3$) δ: 9.26 (1H, s), 8.52 (1H, ddd, J=4.9, 1.9, 0.7 Hz), 8.24 (1H, d, J=8.8 Hz), 7.91 (1H, td, J=7.8, 1.9 Hz), 7.74-7.31 (5H, m), 7.09 (1H, d, J=2.2 Hz), 7.05 (1H, dd, J=8.8, 2.2 Hz), 6.98 (2H, d, J=9.0 Hz), 4.72 (2H, s), 3.80 (3H, s), 3.36-3.25 (4H, m), 2.86-2.64 (4H, m), 2.47 (3H, br s).

ESI-MS Found: m/z [M+H]+ 592.

Example 157

Production of 2-{[2-{[4-(4-methylpiperazin-1-yl)phenyl]amino}-5-oxo-7-(pyridin-2-yl)-5,7-dihydropyrimido[4',5':4,5]pyrimido[1,2-b]indazol-9-yl]oxy}acetic acid trifluoroacetate

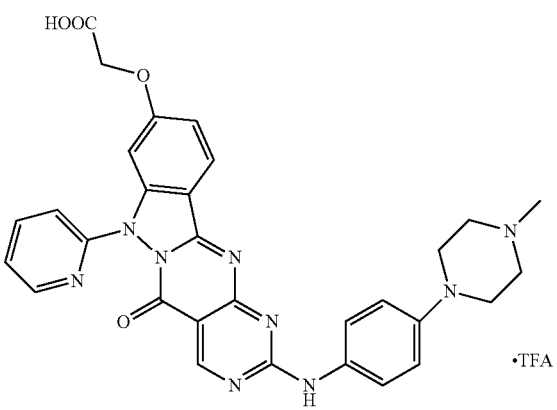

A trifluoroacetic acid (5 mL) solution of the compound (50 mg) obtained in Example 156 was stirred at 60° C. for 5 hours. The reaction solution was evaporated under reduced pressure to give the title compound as a yellow solid (20 mg).

$^1$H-NMR (400 MHz, DMSO-$d_6$) δ: 10.15 (1H, br s), 9.64 (1H, br s), 9.09 (1H, s), 8.47 (1H, ddd, J=4.9, 2.0, 1.0 Hz), 8.18 (1H, d, J=8.5 Hz), 8.03 (1H, ddd, J=8.0, 7.5, 2.0 Hz), 7.88-7.70 (2H, m), 7.67 (1H, d, J=8.0 Hz), 7.44 (1H, ddd, J=7.5, 4.9, 1.0 Hz), 7.18-7.12 (2H, m), 7.05 (2H, d, J=8.8 Hz), 4.87 (2H, s), 3.89-3.11 (6H, m), 3.01-2.82 (2H, m), 2.87 (3H, s).

ESI-MS Found: m/z [M+H]+ 578.

Example 158

Production of 2-{[2-{[4-(4-methylpiperazin-1-yl)phenyl]amino}-5-oxo-7-(pyridin-2-yl)-5,7-dihydropyrimido[4',5':4,5]pyrimido[1,2-b]indazol-9-yl]oxy}acetamide

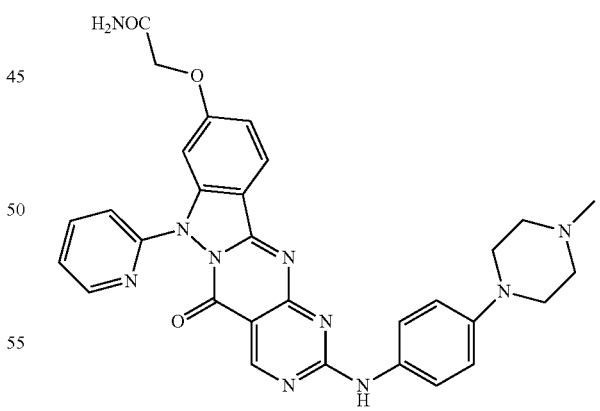

An N,N-dimethylformamide (1 mL) solution of the compound (10 mg) obtained in Example 157, ammonium chloride (5 mg), 1-(3-dimethylaminopropyl)-3-ethylcarbodiimide hydrochloride (10 mg), 1-hydroxybenzotriazole monohydrate (7 mg) and triethylamine (0.05 mL) was stirred for 16 hours. The reaction liquid was concentrated under reduced pressure, and the precipitated solid was collected through filtration, washed with distilled water and ethyl acetate in that order, and dried to give the title compound as a yellow solid (4.2 mg).

$^1$H-NMR (400 MHz, DMSO-d$_6$) δ: 10.07 (1H, s), 9.07 (1H, s), 8.48 (1H, ddd, J=4.9, 1.8, 0.7 Hz), 8.21 (1H, d, J=7.8 Hz), 8.02 (1H, td, J=7.8, 1.8 Hz), 7.84-7.58 (4H, m), 7.48-7.40 (2H, m), 7.21 (1H, d, J=2.0 Hz), 7.17 (1H, dd, J=8.8, 2.0 Hz), 6.96 (2H, d, J=8.8 Hz), 4.59 (2H, s), 3.16-3.06 (4H, m), 2.52-2.43 (4H, m), 2.23 (3H, s).

ESI-MS Found: m/z [M+H]+ 577.

Example 159

Production of 2-{[2-{[4-(4-methylpiperazin-1-yl)phenyl]amino}-5-oxo-7-(pyridin-2-yl)-5,7-dihydropyrimido[4',5':4,5]pyrimido[1,2-b]indazol-10-yl]oxy}acetic acid hydrochloride

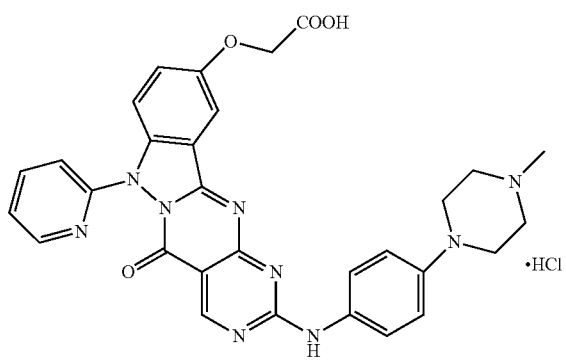

4 N hydrochloric acid/methanol solution (2 mL) was added to the compound (50 mg) obtained in Example 166-2, and stirred at room temperature for 5 hours. The reaction solution was evaporated under reduced pressure to give the title compound as a yellow solid (38 mg).

$^1$H-NMR (400 MHz, DMSO-d$_6$) δ: 10.84 (1H, br s), 10.21 (1H, br s), 9.13 (1H, s), 8.45 (1H, ddd, J=4.9, 2.0, 0.7 Hz), 8.02 (1H, td, J=7.7, 2.0 Hz), 7.92-7.61 (5H, m), 7.48 (1H, dd, J=9.1, 2.6 Hz), 7.43 (1H, ddd, J=7.7, 4.9, 0.7 Hz), 7.06 (2H, d, J=8.8 Hz), 4.91 (2H, s), 3.83-3.75 (2H, m), 3.54-3.45 (2H, m), 3.24-3.03 (4H, m), 2.81 (3H, d, J=4.4 Hz).

ESI-MS Found: m/z [M+H]+ 578.

Example 160

Production of 2-{[2-{[4-(4-methylpiperazin-1-yl)phenyl]amino}-5-oxo-7-(pyridin-2-yl)-5,7-dihydropyrimido[4',5':4,5]pyrimido[1,2-b]indazol-10-yl]oxy}acetamide

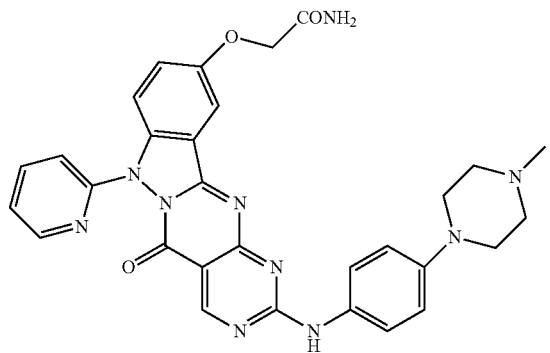

The title compound was produced as a yellow solid in the same manner as in Example 158, for which, however, 2-{[2-{[4-(4-methylpiperazin-1-yl)phenyl]amino}-5-oxo-7-(pyridin-2-yl)-5,7-dihydropyrimido[4',5':4,5]pyrimido[1,2-b]indazol-10-yl]oxy}acetic acid hydrochloride obtained in Example 159 was used in place of 2-{[2-{[4-(4-methylpiperazin-1-yl)phenyl]amino}-5-oxo-7-(pyridin-2-yl)-5,7-dihydropyrimido[4',5':4,5]pyrimido[1,2-b]indazol-9-yl]oxy}acetic acid trifluoroacetate used in Example 158.

$^1$H-NMR (400 MHz, DMSO-d$_6$) δ: 10.12 (1H, br s), 9.11 (1H, s), 8.45 (1H, ddd, J=4.9, 1.8, 0.7 Hz), 8.02 (1H, td, J=7.8, 1.8 Hz), 7.83-7.59 (6H, m), 7.51 (1H, dd, J=9.1, 2.6 Hz), 7.47-7.39 (2H, m), 6.97 (2H, d, J=8.5 Hz), 4.63 (2H, s), 3.17-3.06 (4H, m), 2.53-2.44 (4H, m), 2.22 (3H, s).

ESI-MS Found: m/z [M+H]+ 577.

Example 161

Production of 2-{[2-{[4-(4-methylpiperazin-1-yl)phenyl]amino}-5-oxo-7-(pyridin-2-yl)-5,7-dihydropyrimido[4',5':4,5]pyrimido[1,2-b]indazol-11-yl]oxy}acetic acid hydrochloride

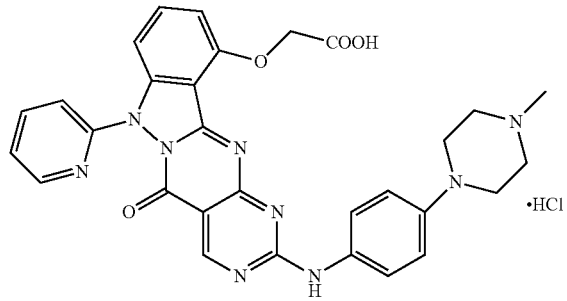

The title compound was produced as a yellow solid in the same manner as in Example 157, for which, however, tert-butyl [(2-{[4-(4-methylpiperazin-1-yl)phenyl]amino}-5-oxo-7-(pyridin-2-yl)-5,7-dihydropyrimido[4',5':4,5]pyrimido[1,2-b]indazol-11-yl)oxy]acetate obtained in Example 167 was used in place of tert-butyl [(2-{[4-(4-methylpiperazin-1-yl)phenyl]amino)-5-oxo-7-(pyridin-2-yl)-5,7-dihydropyrimido[4',5':4,5]pyrimido[1,2-b]indazol-9-yl]oxy}acetate used in Example 157.

$^1$H-NMR (400 MHz, DMSO-d$_6$) δ: 11.21 (1H, br s), 10.49 (1H, s), 9.44 (1H, s), 8.79 (1H, ddd, J=4.9, 2.0, 0.7 Hz), 8.37 (1H, td, J=7.8, 2.0 Hz), 8.13-7.96 (4H, m), 7.77 (1H, ddd, J=7.8, 4.9, 0.7 Hz), 7.53 (1H, d, J=8.3 Hz), 7.38 (2H, d, J=9.0 Hz), 7.23 (1H, d, J=8.3 Hz), 5.41 (2H, s), 4.15-4.06 (2H, m), 3.87-3.77 (2H, m), 3.57-3.36 (4H, m), 3.14 (3H, d, J=4.4 Hz).

ESI-MS Found: m/z [M+H]+ 578.

Example 162

Production of 2-{[2-{[4-(4-methylpiperazin-1-yl)phenyl]amino}-5-oxo-7-(pyridin-2-yl)-5,7-dihydropyrimido[4',5':4,5]pyrimido[1,2-b]indazol-11-yl]oxy}acetamide

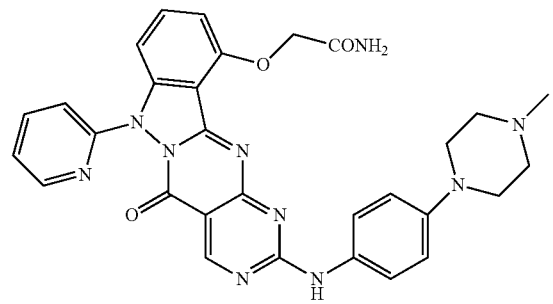

The title compound was produced as a yellow solid in the same manner as in Example 158, for which, however, 2-{[2-{[4-(4-methylpiperazin-1-yl)phenyl]amino}-5-oxo-7-(pyridin-2-yl)-5,7-dihydropyrimido[4',5':4,5]pyrimido[1,2-b]indazol-11-yl]oxy}acetic acid hydrochloride obtained in Example 161 was used in place of 2-{[2-{[4-(4-methylpiperazin-1-yl)phenyl]amino}-5-oxo-7-(pyridin-2-yl)-5,7-dihydropyrimido[4',5':4,5]pyrimido[1,2-b]indazol-9-yl]oxy}acetic acid trifluoroacetate used in Example 158.

¹H-NMR (400 MHz, DMSO-d₆) δ: 10.12 (1H, br s), 9.10 (1H, s), 8.47 (1H, ddd, J=4.6, 1.7, 0.7 Hz), 8.03 (1H, td, J=7.8, 1.8 Hz), 7.99-7.63 (6H, m), 7.44 (1H, ddd, J=7.4, 4.6, 0.7 Hz), 7.24 (1H, d, J=8.3 Hz), 7.09-6.93 (3H, m), 4.79 (2H, s), 3.16-3.06 (4H, m), 2.56-2.41 (4H, m), 2.22 (3H, s).

ESI-MS Found: m/z [M+H]+ 577.

Example 163

Production of 9-methoxy-2-{[4-(4-methylpiperazin-1-yl)phenyl]amino}-7-(pyridin-2-yl)pyrimido[4',5':4,5]pyrimido[1,2-b]indazol-5(7H)-one

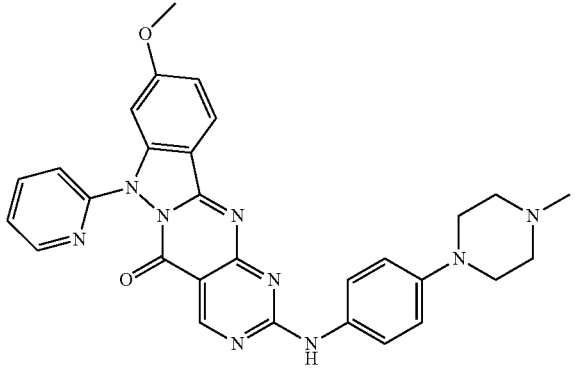

The title compound was produced as a yellow solid in the same manner as in Example 1, for which, however, 9-methoxy-2-(methylthio)-7-pyridin-2-yl-pyrimido[4',5':4,5]pyrimido[1,2-b]indazol-5(7H)-one obtained in Production Example 43 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

¹H-NMR (400 MHz, CDCl₃) δ: 9.25 (1H, s), 8.54 (1H, dd, J=4.9, 2.0 Hz), 8.20 (1H, d, J=9.3 Hz), 7.92 (1H, td, J=7.8, 2.0 Hz), 7.75-7.46 (3H, br m), 7.39 (1H, d, J=8.3 Hz), 7.34 (1H, ddd, J=7.3, 4.9, 1.0 Hz), 7.04-7.01 (2H, m), 6.97 (2H, d, J=9.3 Hz), 3.89 (3H, s), 3.23-3.20 (4H, m), 2.63-2.60 (4H, m), 2.37 (3H, s).

ESI-MS Found: m/z [M+H]+ 534.

Example 164

Production of 9-fluoro-2-{[4-(4-methylpiperazin-1-yl)phenyl]amino}-7-(pyridin-2-yl)pyrimido[4',5':4,5]pyrimido[1,2-b]indazol-5(7H)-one

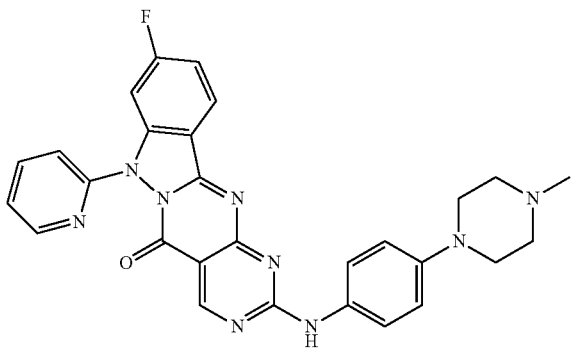

The title compound was produced as a yellow solid in the same manner as in Example 1, for which, however, 9-fluoro-2-(methylthio)-7-pyridin-2-yl-pyrimido[4',5':4,5]pyrimido[1,2-b]indazol-5(7H)-one obtained in Production Example 44 was used in place of 7-methyl-2-(methylthio)pyrimido[4',5':4,5]pyrimido[1,2-b]indazol-5(7H)-one used in Example 1, and 4-(4-methyl-1-piperazinyl)aniline was used in place of 3-methyl-4-(4-methyl-1-piperazinyl)aniline.

¹H-NMR (400 MHz, CDCl₃) δ: 9.27 (1H, s), 8.53 (1H, ddd, J=4.9, 2.0, 1.0 Hz), 8.35-8.29 (1H, m), 7.94 (1H, td, J=7.8, 2.0 Hz), 7.68-7.46 (3H, br m), 7.43 (1H, d, J=8.3 Hz), 7.37 (1H, ddd, J=7.3, 4.9, 1.0 Hz), 7.30 (1H, dd, J=8.8, 2.0 Hz), 7.19 (1H, td, J=8.8, 2.0 Hz), 6.98 (2H, d, J=9.3 Hz), 3.24-3.21 (4H, m), 2.63-2.60 (4H, m), 2.38 (3H, s).

ESI-MS Found: m/z [M+J]+ 522.

Example 165

Production of 2-anilino-9-hydroxy-7-(pyridin-2-yl)pyrimido[4',5':4,5]pyrimido[1,2-b]indazol-5(7H)-one

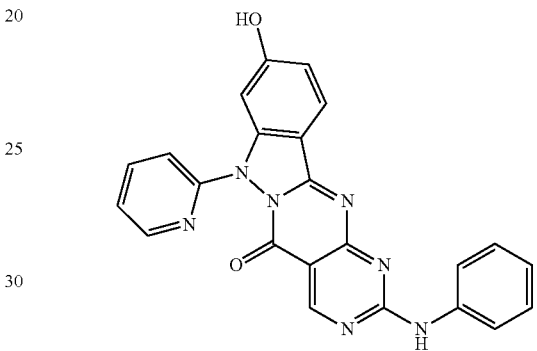

The title compound was produced as a yellow solid in the same manner as in Example 1, for which, however, 9-hydroxy-2-(methylthio)-7-pyridin-2-yl-pyrimido[4',5':4,5]pyrimido[1,2-b]indazol-5(7H)-one obtained in Production Example 36 was used in place of 7-methyl-2-(methylthio)pyrimido[4',5':4,5]pyrimido[1,2-b]indazol-5(7H)-one used in Example 1, and aniline was used in place of 3-methyl-4-(4-methyl-1-piperazinyl)aniline.

¹H-NMR (400 MHz, DMSO-d₆) δ: 10.32 (1H, s), 9.16 (1H, s), 8.48 (1H, dd, J=5.1, 1.6 Hz), 8.32 (1H, d, J=7.8 Hz), 8.04 (1H, td, J=7.8, 2.0 Hz), 7.93 (2H, d, J=8.2 Hz), 7.83-7.87 (1H, m), 7.74 (1H, s), 7.71 (1H, d, J=7.8 Hz), 7.45 (1H, dd, J=7.0, 5.1 Hz), 7.39 (2H, t, J=7.8 Hz), 7.08 (1H, t, J=7.2 Hz).

ESI-MS Found: m/z [M+H]+ 422.

Example 166

Production of tert-butyl [(2-{[4-(4-methylpiperazin-1-yl)phenyl]amino}-5-oxo-7-(pyridin-2-yl)-5,7-dihydropyrimido[4',5':4,5]pyrimido[1,2-b]indazol-10-yl]oxy}acetate

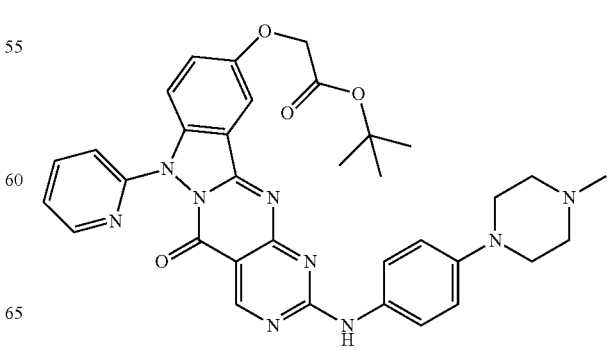

The title compound was produced as a yellow solid in the same manner as in Example 180, for which, however, tert-butyl {[2-(methylthio)-5-oxo-7-(pyridin-2-yl)-5,7-dihydropyrimido[4',5':4,5]pyrimido[1,2-b]indazol-10-yl]oxy}acetate was used in place of tert-butyl {[2-(methylthio)-5-oxo-7-(pyridin-2-yl)-5,7-dihydropyrimido[4',5':4,5]pyrimido[1,2-b]indazol-9-yl]oxy}acetate used in Example 180.

$^1$H-NMR (400 MHz, CDCl$_3$) δ: 9.28 (1H, br s), 8.48 (1H, ddd, J=4.9, 1.8, 0.8 Hz), 7.92 (1H, td, J=7.7, 1.8 Hz), 7.75-7.36 (7H, m), 7.33 (1H, ddd, J=7.7, 4.9, 0.8 Hz), 6.98 (2H, d, J=9.0 Hz), 4.62 (2H, s), 3.27-3.20 (4H, m), 2.68-2.60 (4H, m), 2.40 (3H, s), 1.52 (9H, s).

ESI-MS Found: m/z [M+H]+ 634.

Example 167

Production of tert-butyl [(2-{[4-(4-methylpiperazin-1-yl)phenyl]amino}-5-oxo-7-(pyridin-2-yl)-5,7-dihydropyrimido[4',5':4,5]pyrimido[1,2-b]indazol-11-yl]oxy}acetate

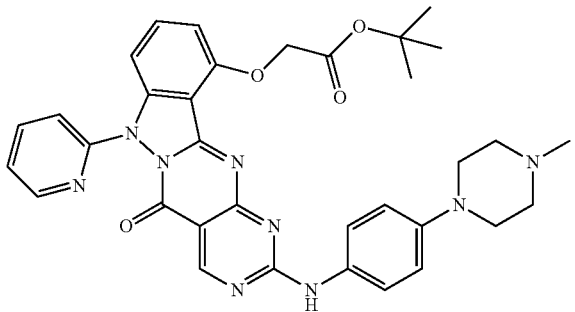

The title compound was produced as a yellow solid in the same manner as in Example 180, for which, however, tert-butyl {[2-(methylthio)-5-oxo-7-(pyridin-2-yl)-5,7-dihydropyrimido[4',5':4,5]pyrimido[1,2-b]indazol-11-yl]oxy}acetate was used in place of tert-butyl {[2-(methylthio)-5-oxo-7-(pyridin-2-yl)-5,7-dihydropyrimido[4',5':4,5]pyrimido[1,2-b]indazol-9-yl]oxy}acetate used in Example 180.

$^1$H-NMR (400 MHz, CDCl$_3$) δ: 9.27 (1H, br s), 8.50 (1H, ddd, J=4.9, 2.0, 0.8 Hz), 7.92 (1H, td, J=7.8, 2.0 Hz), 7.77-7.41 (4H, m), 7.56 (1H, t, J=8.3 Hz), 7.34 (1H, ddd, J=7.8, 4.9, 0.8 Hz), 7.11 (1H, d, J=8.3 Hz), 6.97 (2H, d, J=9.0 Hz), 6.65 (1H, d, J=8.3 Hz), 4.89 (2H, s), 3.26-3.20 (4H, m), 2.67-2.59 (4H, m), 2.39 (3H, s), 1.48 (9H, s).

ESI-MS Found: m/z [M+H]+ 634.

Example 168

Production of methyl 2-{[4-(4-methylpiperazin-1-yl)phenyl]amino}-5-oxo-7-(pyridin-2-yl)-5,7-dihydropyrimido[4',5':4,5]pyrimido[1,2-b]indazole-9-carboxylate

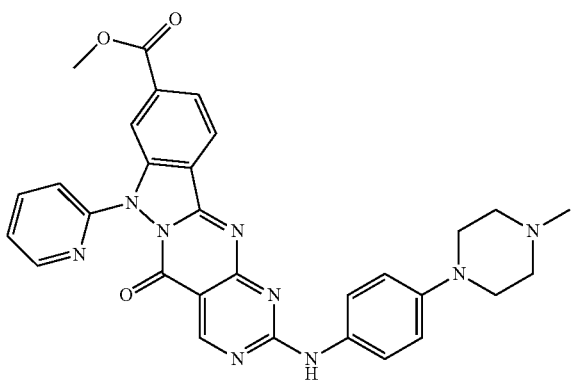

1) Production of methyl 2-(methylsulfinyl)-5-oxo-7-(pyridin-2-yl)-5,7-dihydropyrimido[4',5':4,5]pyrimido[1,2-b]indazole-9-carboxylate At 0° C., m-chloroperbenzoic acid (119 mg) was added to a chloroform solution of the compound (174 mg) obtained in Production Example 47-2, and stirred for 30 minutes. Aqueous saturated sodium hydrogencarbonate solution was added to the reaction liquid, and extracted with chloroform/isopropanol (80/20). The organic layer was dried with anhydrous magnesium sulfate, and the solvent was evaporated away to give crude methyl 2-(methylsulfinyl)-5-oxo-7-(pyridin-2-yl)-5,7-dihydropyrimido[4',5':4,5]pyrimido[1,2-b]indazole-9-carboxylate.

2) Production of methyl 2-{[4-(4-methylpiperazin-1-yl)phenyl]amino}-5-oxo-7-(pyridin-2-yl)-5,7-dihydropyrimido[4',5':4,5]pyrimido[1,2-b]indazole-9-carboxylate 4-(4-Methyl-1-piperazinyl)aniline (30 mg) and N,N-diisopropylethylamine (0.2 mL) were added to a toluene solution of the crude product (50 mg) obtained in Example 168-1, and stirred at 70° C. for 12 hours. The solvent was evaporated away, and the residue was purified through basic silica gel column chromatography (ethyl acetate) to give the above-mentioned compound as a yellow solid (36 mg).

$^1$H-NMR (400 MHz, CDCl$_3$) δ: 8.96 (1H, br s), 8.16 (1H, ddd, J=4.9, 2.0, 0.9 Hz), 8.07 (1H, d, J=7.3 Hz), 7.83-7.77 (2H, m), 7.67 (1H, td, J=7.6, 2.0 Hz), 7.43-7.10 (4H, m), 7.06 (1H, ddd, J=7.6, 4.9, 0.9 Hz), 6.65 (2H, d, J=8.8 Hz), 3.63 (3H, s), 2.94-2.88 (4H, m), 2.35-2.27 (4H, m), 2.07 (3H, s).

ESI-MS Found: m/z [M+H]+ 562.

Example 169

Production of methyl 2-{[4-(4-methylpiperazin-1-yl)phenyl]amino}-5-oxo-7-(pyridin-2-yl)-5,7-dihydropyrimido[4',5':4,5]pyrimido[1,2-b]indazole-10-carboxylate

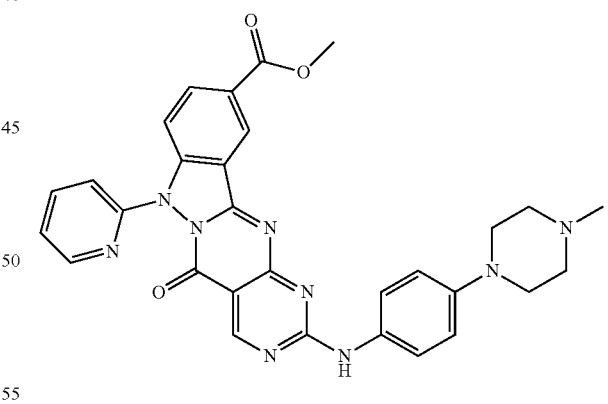

1) Production of methyl 2-(methylsulfinyl)-5-oxo-7-(pyridin-2-yl)-5,7-dihydropyrimido[4',5':4,5]pyrimido[1,2-b]indazole-10-carboxylate The title compound was produced as a yellow solid in the same manner as in Example 168-1, for which, however, methyl 2-(methylthio)-5-oxo-7-(pyridin-2-yl)-5,7-dihydropyrimido[4',5':4,5]pyrimido[1,2-b]indazole-10-carboxylate was used in place of methyl 2-(methylthio)-5-oxo-7-(pyridin-2-yl)-5,7-dihydropyrimido[4',5':4,5]pyrimido[1,2-b]indazole-9-carboxylate used in Example 168-1.

2) Production of methyl 2-{[4-(4-methylpiperazin-1-yl)phenyl]amino}-5-oxo-7-(pyridin-2-yl)-5,7-dihydropyrimido[4',5':4,5]pyrimido[1,2-b]indazole-10-carboxylate The title compound was produced as a yellow solid in the same manner as in Example 168-2, for which, however, methyl 2-(methylsulfinyl)-5-oxo-7-(pyridin-2-yl)-5,7-dihydropyrimido[4',5':4,5]pyrimido[1,2-b]indazole-10-carboxylate was used in place of methyl 2-(methylsulfinyl)-5-oxo-7-(pyridin-2-yl)-5,7-dihydropyrimido[4',5':4,5]pyrimido[1,2-b]indazole-9-carboxylate used in Example 168-2.

$^1$H-NMR (400 MHz, CDCl$_3$) δ: 9.28 (1H, br s), 9.08 (1H, br s), 8.52 (1H, ddd, J=4.9, 2.0, 1.0 Hz), 8.37 (1H, dd, J=8.8, 1.7 Hz), 7.97 (1H, td, J=7.7, 2.0 Hz), 7.78-7.42 (5H, m), 7.39 (1H, ddd, J=7.7, 4.9, 1.0 Hz), 6.99 (2H, d, J=8.5 Hz), 3.98 (3H, s), 3.27-3.21 (4H, m), 2.69-2.60 (4H, m), 2.40 (3H, s).
ESI-MS Found: m/z [M+H]+ 562.

Example 170

Production of methyl 2-{[4-(4-methylpiperazin-1-yl)phenyl]amino}-5-oxo-7-(pyridin-2-yl)-5,7-dihydropyrimido[4',5':4,5]pyrimido[1,2-b]indazole-11-carboxylate

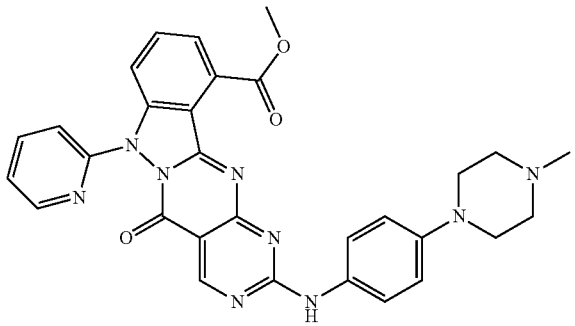

1) Production of methyl 2-(methylsulfinyl)-5-oxo-7-(pyridin-2-yl)-5,7-dihydropyrimido[4',5':4,5]pyrimido[1,2-b]indazole-11-carboxylate The title compound was produced as a yellow solid in the same manner as in Example 168-1, for which, however, methyl 2-(methylthio)-5-oxo-7-(pyridin-2-yl)-5,7-dihydropyrimido[4',5':4,5]pyrimido[1,2-b]indazole-11-carboxylate was used in place of methyl 2-(methylthio)-5-oxo-7-(pyridin-2-yl)-5,7-dihydropyrimido[4',5':4,5]pyrimido[1,2-b]indazole-9-carboxylate used in Example 168-1.

2) Production of methyl 2-{[4-(4-methylpiperazin-1-yl)phenyl]amino}-5-oxo-7-(pyridin-2-yl)-5,7-dihydropyrimido[4',5':4,5]pyrimido[1,2-b]indazole-11-carboxylate The title compound was produced as a yellow solid in the same manner as in Example 168-2, for which, however, methyl 2-(methylsulfinyl)-5-oxo-7-(pyridin-2-yl)-5,7-dihydropyrimido[4',5':4,5]pyrimido[1,2-b]indazole-11-carboxylate was used in place of methyl 2-(methylsulfinyl)-5-oxo-7-(pyridin-2-yl)-5,7-dihydropyrimido[4',5':4,5]pyrimido[1,2-b]indazole-9-carboxylate used in Example 168-2.

$^1$H-NMR (400 MHz, CDCl$_3$) δ: 9.28 (1H, br s), 8.51 (1H, ddd, J=4.9, 2.0, 0.8 Hz), 7.94 (1H, td, J=7.6, 2.0 Hz), 7.82-7.45 (7H, m), 7.37 (1H, ddd, J=7.6, 4.9, 0.8 Hz), 6.97 (2H, d, J=9.0 Hz), 4.18 (3H, s), 3.27-3.20 (4H, m), 2.71-2.58 (4H, m), 2.39 (3H, s).
ESI-MS Found: m/z [M+H]+ 562.

Example 171

Production of 2-{[4-(4-methylpiperazin-1-yl)phenyl]amino}-5-oxo-7-(pyridin-2-yl)-5,7-dihydropyrimido[4',5':4,5]pyrimido[1,2-b]indazole-9-carboxylic acid

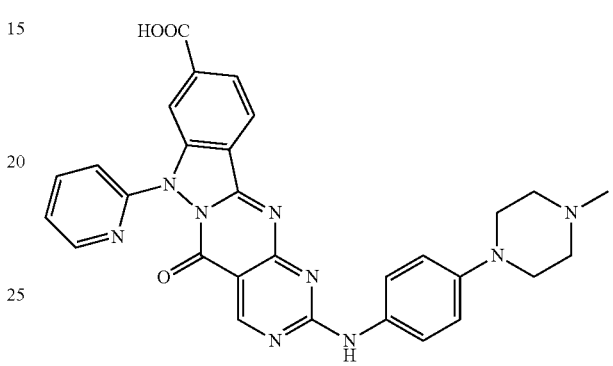

Lithium iodide (10 mg) was added to a pyridine (2 mL) solution of the compound (200 mg) obtained in Example 168-2, and stirred with heating under reflux for 15 hours. After cooled to room temperature, the reaction solution was evaporated under reduced pressure, water (5 mL) was added to the residue, and the precipitated solid was collected through filtration, washed with distilled water and ethyl acetate in that order and dried to give the title compound as a white solid (64 mg).

$^1$H-NMR (400 MHz, DMSO-d$_6$) δ: 10.10 (1H, s), 9.10 (1H, s), 8.48 (1H, ddd, J=4.9, 1.8, 0.7 Hz), 8.25-7.93 (4H, m), 7.87-7.57 (3H, m), 7.45 (1H, ddd, J=7.6, 4.9, 0.7 Hz), 6.97 (2H, d, J=8.5 Hz), 3.16-3.06 (4H, m), 2.53-2.41 (4H, m), 2.23 (3H, s).
ESI-MS Found: m/z [M+H]+ 548.

Example 172

Production of 2-{[4-(4-methylpiperazin-1-yl)phenyl]amino}-5-oxo-7-(pyridin-2-yl)-5,7-dihydropyrimido[4',5':4,5]pyrimido[1,2-b]indazole-9-carboxamide

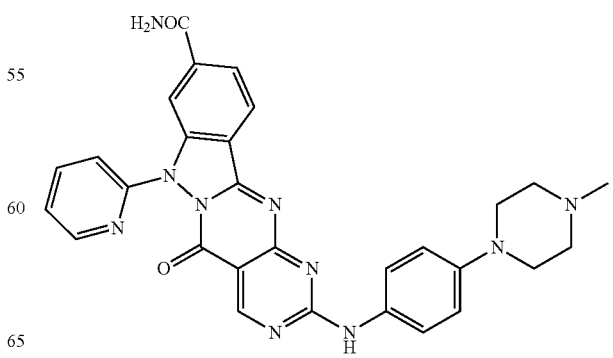

An N,N-dimethylformamide (3 mL) solution of the compound (30 mg) obtained in Example 171, ammonium chloride (10 mg), 1-(3-dimethylaminopropyl)-3-ethylcarbodiimide hydrochloride (20 mg), 1-hydroxybenzotriazole monohydrate (10 mg) and triethylamine (0.1 mL) was stirred for 16 hours. The reaction liquid was concentrated under reduced pressure, the precipitated solid was collected through filtration, washed with distilled water and ethyl acetate in that order, and dried to give the title compound as a yellow solid (15 mg).

$^1$H-NMR (400 MHz, DMSO-$d_6$) δ: 10.14 (1H, s), 9.13 (1H, s), 8.50 (1H, ddd, J=4.9, 2.0, 0.7 Hz), 8.45-8.24 (2H, m), 8.11 (1H, s), 8.06 (1H, td, J=7.8, 1.7 Hz), 7.99 (1H, dd, J=8.3, 1.0 Hz), 7.85-7.55 (4H, m), 7.47 (1H, ddd, J=7.8, 4.9, 0.7 Hz), 6.97 (2H, d, J=8.3 Hz), 3.17-3.07 (4H, m), 2.54-2.42 (4H, m), 2.22 (3H, s).

ESI-MS Found: m/z [M+H]+ 547.

Example 173

Production of N,N-dimethyl-2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-9-carboxamide

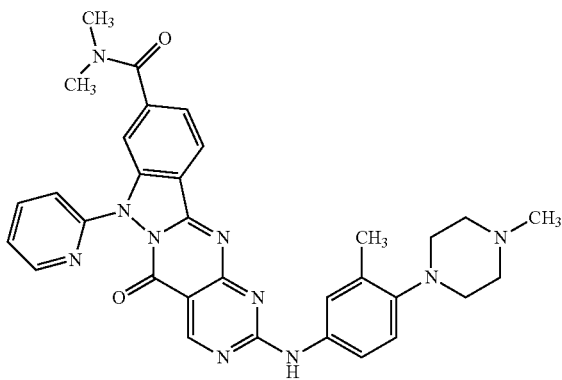

1) Production of methyl 2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-9-carboxylate The title compound was produced as a yellow solid in the same manner as in Example 168-2, for which, however, 3-methyl-4-(4-methyl-1-piperazinyl)aniline was used in place of 4-(4-methyl-1-piperazinyl)aniline used in Example 168-2.

2) Production of 2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-9-carboxylic acid The title compound was produced as a yellow solid in the same manner as in Example 171, for which, however, methyl 2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-9-carboxylate was used in place of methyl 2-{[4-(4-methylpiperazin-1-yl)phenyl]amino}-5-oxo-7-(pyridin-2-yl)-5,7-dihydropyrimido[4',5':4,5]pyrimido[1,2-b]indazole-9-carboxylate used in Example 171.

3) Production of N,N-dimethyl-2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-9-carboxamide An N,N-dimethylformamide (3 mL) solution of the compound (30 mg) obtained in Example 173-2, dimethylamine hydrochloride (10 mg), 1-(3-dimethylaminopropyl)-3-ethylcarbodiimide hydrochloride (20 mg), 1-hydroxybenzotriazole monohydrate (10 mg) and triethylamine (0.1 mL) was stirred for 16 hours. The reaction liquid was concentrated under reduced pressure, and the precipitated solid was collected through filtration, washed with distilled water and ethyl acetate in that order, and dried to give the title compound as a yellow solid (18 mg).

$^1$H-NMR (400 MHz, DMSO-$d_6$) δ: 9.15 (1H, s), 8.49 (1H, ddd, J=4.9, 2.0, 0.7 Hz), 8.33 (1H, d, J=8.0 Hz), 8.03 (1H, ddd, J=8.0, 7.5, 2.0 Hz), 7.85-7.66 (2H, m), 7.69 (1H, d, J=8.0 Hz), 7.58-7.50 (1H, m), 7.54 (1H, dd, J=8.0, 1.2 Hz), 7.45 (1H, ddd, J=7.5, 4.9, 0.7 Hz), 7.06 (1H, d, J=8.8 Hz), 3.00 (3H, br s), 2.89-2.80 (4H, m), 2.85 (3H, br s), 2.64-2.41 (4H, m), 2.29 (3H, br s), 2.27 (3H, br s).

ESI-MS Found: m/z [M+H]+ 575.

Example 174

Production of 2-{[4-(4-methylpiperazin-1-yl)phenyl]amino}-5-oxo-7-(pyridin-2-yl)-5,7-dihydropyrimido[4',5':4,5]pyrimido[1,2-b]indazole-10-carboxylic acid

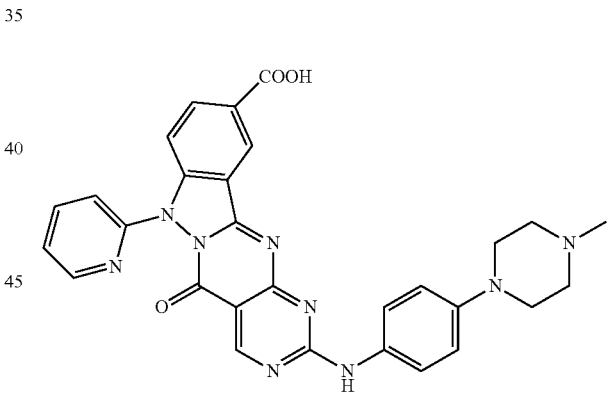

The title compound was produced as a yellow solid in the same manner as in Example 171, for which, however, methyl 2-{[4-(4-methylpiperazin-1-yl)phenyl]amino}-5-oxo-7-(pyridin-2-yl)-5,7-dihydropyrimido[4',5':4,5]pyrimido[1,2-b]indazole-10-carboxylate was used in place of methyl 2-{[4-(4-methylpiperazin-1-yl)phenyl]amino}-5-oxo-7-(pyridin-2-yl)-5,7-dihydropyrimido[4',5':4,5]pyrimido[1,2-b]indazole-9-carboxylate used in Example 171.

$^1$H-NMR (400 MHz, DMSO-$d_6$) δ: 10.17 (1H, s), 9.12 (1H, s), 8.70 (1H, s), 8.52 (1H, dd, J=4.8, 1.7 Hz), 8.33 (1H, dd, J=8.7, 1.5 Hz), 8.04 (1H, ddd, J=8.0, 7.1, 1.7 Hz), 7.85-7.64 (2H, m), 7.80 (1H, d, J=8.7 Hz), 7.68 (1H, d, J=8.0 Hz), 7.47 (1H, dd, J=7.1, 4.8 Hz), 6.98 (2H, d, J=7.3 Hz), 3.20-3.08 (4H, m), 2.62-2.52 (4H, m), 2.29 (3H, s).

ESI-MS Found: m/z [M+H]+ 548.

Example 175

Production of 2-{[4-(4-methylpiperazin-1-yl)phenyl]amino}-5-oxo-7-(pyridin-2-yl)-5,7-dihydropyrimido[4',5':4,5]pyrimido[1,2-b]indazole-10-carboxamide

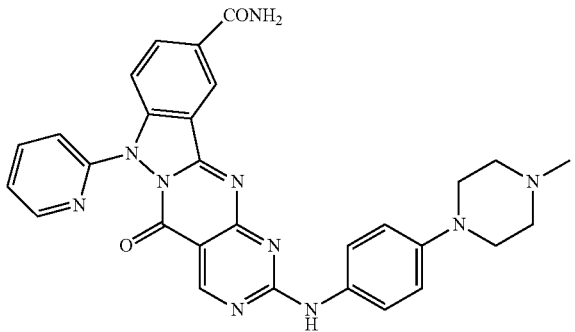

The title compound was produced as a yellow solid in the same manner as in Example 172, for which, however, 2-{[4-(4-methylpiperazin-1-yl)phenyl]amino}-5-oxo-7-(pyridin-2-yl)-5,7-dihydropyrimido[4',5':4,5]pyrimido[1,2-b]indazole-10-carboxylic acid was used in place of 2-{[4-(4-methylpiperazin-1-yl)phenyl]amino}-5-oxo-7-(pyridin-2-yl)-5,7-dihydropyrimido[4',5':4,5]pyrimido[1,2-b]indazole-9-carboxylic acid used in Example 172.

$^1$H-NMR (400 MHz, DMSO-d$_6$) δ: 10.16 (1H, s), 9.13 (1H, s), 8.94 (1H, br s), 8.51 (1H, ddd, J=4.9, 2.0, 0.7 Hz), 8.36-8.30 (2H, m), 8.04 (1H, td, J=7.8, 2.0 Hz), 7.86-7.66 (3H, m), 7.69 (1H, td, J=0.7, 7.8 Hz), 7.57 (1H, br s), 7.46 (1H, ddd, J=7.8, 4.9, 0.7 Hz), 6.97 (2H, d, J=8.5 Hz), 3.16-3.07 (4H, m), 2.54-2.41 (4H, m), 2.22 (3H, s).

ESI-MS Found: m/z [M+H]+ 547

Example 176

Production of N,N-dimethyl-2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-10-carboxamide

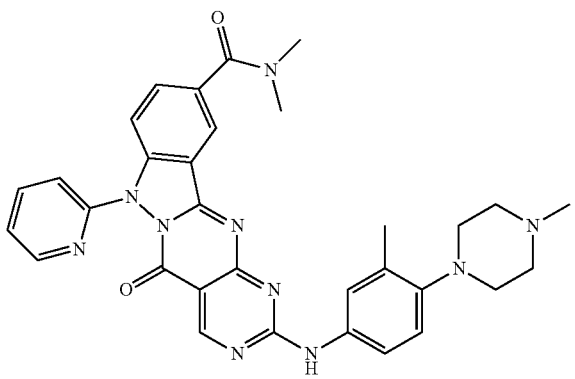

1) Production of methyl 2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-10-carboxylate The title compound was produced as a yellow solid in the same manner as in Example 168-2, for which, however, 3-methyl-4-(4-methyl-1-piperazinyl)aniline was used in place of 4-(4-methyl-1-piperazinyl)aniline used in Example 168-2.

2) Production of 2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-10-carboxylic acid The title compound was produced as a yellow solid in the same manner as in Example 171, for which, however, methyl 2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-10-carboxylate was used in place of methyl 2-{[4-(4-methylpiperazin-1-yl)phenyl]amino}-5-oxo-7-(pyridin-2-yl)-5,7-dihydropyrimido[4',5':4,5]pyrimido[1,2-b]indazole-9-carboxylate used in Example 171.

3) Production of N,N-dimethyl-2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-10-carboxamide The title compound was produced as a yellow solid in the same manner as in Example 173-3, for which, however, 2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-10-carboxylic acid was used in place of 2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-9-carboxylic acid used in Example 173-3.

$^1$H-NMR (400 MHz, DMSO-d$_6$) δ: 9.29 (1H, s), 8.51 (1H, ddd, J=4.9, 2.0, 0.9 Hz), 8.38 (1H, d, J=0.7 Hz), 7.96 (1H, td, J=7.6, 2.0 Hz), 7.87 (1H, dd, J=8.8, 1.7 Hz), 7.63-7.34 (3H, m), 7.59 (1H, d, J=8.8 Hz), 7.51 (1H, d, J=8.0 Hz), 7.37 (1H, ddd, J=7.6, 4.9, 0.9 Hz), 7.09 (1H, d, J=8.5 Hz), 3.16 (3H, br s), 3.09 (3H, br s), 2.99-2.91 (4H, m), 2.72-2.49 (4H, m), 2.38 (3H, s), 2.35 (3H, s).

ESI-MS Found: m/z [M+H]+ 575.

Example 177

Production of 2-{[4-(4-methylpiperazin-1-yl)phenyl]amino}-5-oxo-7-(pyridin-2-yl)-5,7-dihydropyrimido[4',5':4,5]pyrimido[1,2-b]indazole-11-carboxylic acid

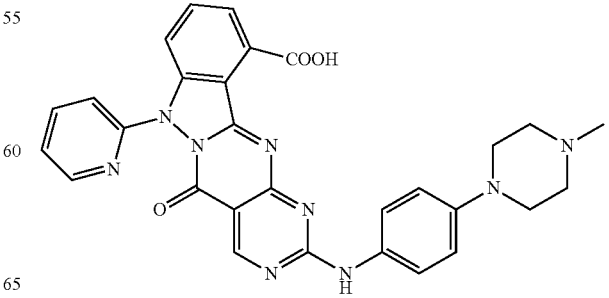

The title compound was produced as a yellow solid in the same manner as in Example 171, for which, however, methyl 2-{[4-(4-methylpiperazin-1-yl)phenyl]amino}-5-oxo-7-(pyridin-2-yl)-5,7-dihydropyrimido[4',5':4,5]pyrimido[1,2-b]indazole-11-carboxylate was used in place of methyl 2-{[4-(4-methylpiperazin-1-yl)phenyl]amino}-5-oxo-7-(pyridin-2-yl)-5,7-dihydropyrimido[4',5':4,5]pyrimido[1,2-b]indazole-9-carboxylate used in Example 171.

$^1$H-NMR (400 MHz, DMSO-d$_6$) δ: 10.28 (1H, br s), 9.15 (1H, s), 8.52 (1H, dd, J=4.9, 1.7 Hz), 8.11-7.84 (3H, m), 8.06 (1H, td, J=7.6, 1.7 Hz), 7.79-7.43 (3H, m), 7.49 (1H, dd, J=7.6, 4.9 Hz), 7.04-6.87 (2H, m), 3.61-2.98 (4H, m), 2.63-2.40 (4H, m), 2.28 (3H, br s).

ESI-MS Found: m/z [M+H]+ 548.

Example 178

Production of 2-{[4-(4-methylpiperazin-1-yl)phenyl]amino}-5-oxo-7-(pyridin-2-yl)-5,7-dihydropyrimido[4',5':4,5]pyrimido[1,2-b]indazole-11-carboxamide

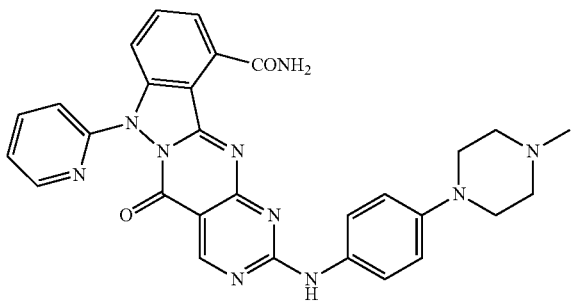

The title compound was produced as a yellow solid in the same manner as in Example 172, for which, however, 2-{[4-(4-methylpiperazin-1-yl)phenyl]amino}-5-oxo-7-(pyridin-2-yl)-5,7-dihydropyrimido[4',5':4,5]pyrimido[1,2-b]indazole-11-carboxylic acid was used in place of 2-{[4-(4-methylpiperazin-1-yl)phenyl]amino}-5-oxo-7-(pyridin-2-yl)-5,7-dihydropyrimido[4',5':4,5]pyrimido[1,2-b]indazole-9-carboxylic acid used in Example 172.

$^1$H-NMR (400 MHz, DMSO-d$_6$) δ: 11.10-10.71 (1H, m), 10.51-10.10 (1H, m), 9.15 (1H, s), 8.50 (1H, dd, J=4.9, 1.2 Hz), 8.32-8.10 (2H, m), 8.06 (1H, td, J=7.8, 1.7 Hz), 8.00-7.43 (2H, m), 7.92 (1H, t, J=8.0 Hz), 7.86 (1H, d, J=8.0 Hz), 7.48 (1H, dd, J=6.8, 4.9 Hz), 6.94 (2H, d, J=7.6 Hz), 3.16-3.03 (4H, m), 2.55-2.40 (4H, m), 2.22 (3H, s).

ESI-MS Found: m/z [M+H]+ 547

Example 179

Production of N,N-dimethyl-2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-11-carboxamide

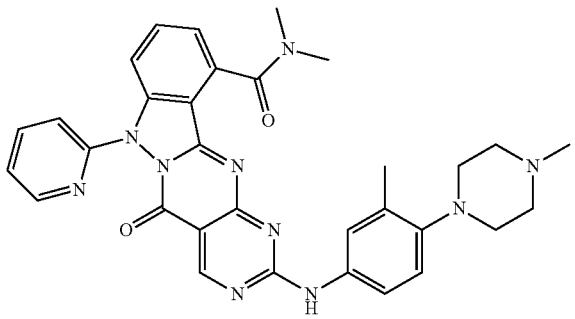

1) Production of methyl 2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-11-carboxylate The title compound was produced as a yellow solid in the same manner as in Example 168-2, for which, however, 3-methyl-4-(4-methyl-1-piperazinyl)aniline was used in place of 4-(4-methyl-1-piperazinyl)aniline used in Example 168-2.

2) Production of 2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-11-carboxylic acid The title compound was produced as a yellow solid in the same manner as in Example 171, for which, however, methyl 2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-11-carboxylate was used in place of methyl 2-{[4-(4-methylpiperazin-1-yl)phenyl]amino}-5-oxo-7-(pyridin-2-yl)-5,7-dihydropyrimido[1,2-b]indazole-9-carboxylate used in Example 171.

3) Production of N,N-dimethyl-2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-11-carboxamide The title compound was produced as a yellow solid in the same manner as in Example 173-3, for which, however, 2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-11-carboxylic acid was used in place of 2-{[3-methyl-4-(4-methylpiperazin-1-yl)phenyl]amino}-5-oxo-7-(pyridin-2-yl)-5,7-dihydropyrimido[4',5':4,5]pyrimido[1,2-b]indazole-9-carboxylic acid used in Example 173-3.

$^1$H-NMR (400 MHz, DMSO-d$_6$) δ: 9.27 (1H, br s), 8.51 (1H, ddd, J=4.9, 1.8, 0.7 Hz), 7.93 (1H, td, J=7.8, 1.8 Hz), 7.73 (1H, dd, J=8.3, 7.3 Hz), 7.59 (1H, d, J=8.3 Hz), 7.56-7.38 (2H, m), 7.46 (1H, d, J=7.8 Hz), 7.41 (1H, d, J=7.3 Hz), 7.36 (1H, ddd, J=7.8, 4.9, 0.7 Hz), 7.05 (1H, d, J=8.8 Hz), 3.39 (3H, s), 2.98-2.93 (4H, m), 2.95 (3H, s), 2.73-2.49 (4H, m), 2.38 (3H, s), 2.36 (3H, s).

ESI-MS Found: m/z [M+H]+ 575.

Example 180

Production of tert-butyl [(2-{[4-(4-methylpiperazin-1-yl)phenyl]amino}-5-oxo-7-(pyridin-2-yl)-5,7-dihydropyrimido[4',5':4,5]pyrimido[1,2-b]indazol-9-yl]oxy)acetate

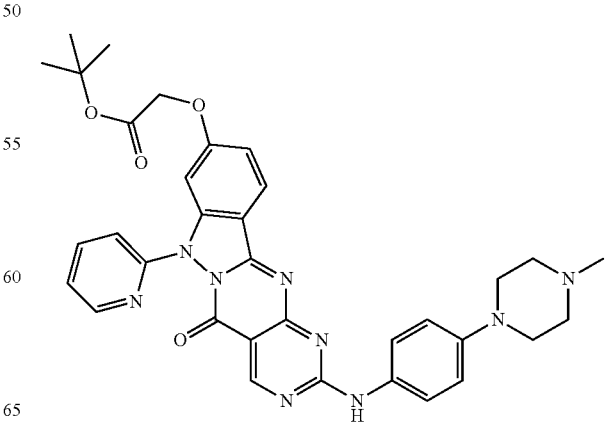

At 0° C., m-chloroperbenzoic acid (170 mg) was added to a toluene solution of the compound (294 mg) obtained in Production Example 42-1, and stirred for 30 minutes. 3-Methyl-4-(4-methyl-1-piperazinyl)aniline (100 mg) and N,N-diisopropylethylamine (0.5 mL) were added to the reaction liquid, and stirred at 70° C. for 15 hours. The solvent was evaporated away, and the residue was purified through basic silica gel column chromatography (ethyl acetate) to give the title compound as a yellow solid (280 mg).

ESI-MS Found: m/z [M+H]+ 634.

INDUSTRIAL APPLICABILITY

The compounds of the invention have an excellent Wee1-kinase-inhibitory effect, and are therefore useful in the field of medicine, especially in the field of various cancer treatments.

The invention claimed is:

1. A compound of formula (I), or its pharmaceutically-acceptable salt, ester or N-oxide derivative:

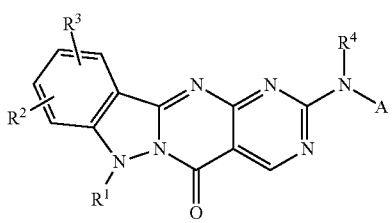
(I)

wherein,
a and b each independently mean 0 or 1;
A is an aryl or heteroaryl group, which is optionally substituted with a substituent selected from the group consisting of a halogen atom, a hydroxyl group, —(C=O)$_a$O$_b$(C1-C6)alkyl group and a group of -Q$^{1a}$-R$^{1a}$, wherein the alkyl group of the substituent may be substituted with a halogen atom or a hydroxyl group, or A is a group of a formula (a):

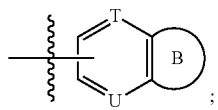
(a)

wherein the ring B is a 5-membered to 7-membered aliphatic ring condensed with the ring of a formula (b):

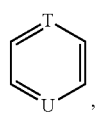
(b)

wherein one or two or more methylene groups constituting the ring B are each independently replaced by an oxygen atom, a sulfur atom, a sulfinyl group, a sulfonyl group, a carbonyl group or a group of —N(R$^{1b}$)—, and one or two or more methylene groups constituting the ring B are each independently optionally substituted with a halogen atom, a hydroxyl group, a —(C=O)$_a$O$_b$(C1-C6)alkyl group or a group of -Q$^{1b}$-N(R$^{2b}$)R$^{3b}$, wherein the alkyl group of the substituent is optionally substituted with a halogen atom or a hydroxyl group;

Q$^{1a}$, Q$^{1b}$, Q$^{2a}$ and Q$^{3a}$ are each independently a single bond or a (C1-C6)alkylene group, wherein one or two or more methylene groups constituting the (C1-C6)alkylene group are each independently optionally replaced by an oxygen atom, a sulfur atom, a sulfinyl group, a sulfonyl group, a carbonyl group or a group of —N(R$^{2a}$)—, and are each independently optionally substituted with a halogen atom, a hydroxyl group, a cyano group or a —(C=O)$_a$O$_b$(C1-C6)alkyl group;

R$^1$ is a —(C=O)$_a$O$_b$(C1-C6)alkyl group, a —(C=O)$_a$O$_b$(C2-C6)alkenyl group, a —(C=O)$_a$O$_b$(C3-C6)cycloalkyl group, an aryl group or a heteroaryl group, wherein the alkyl, alkenyl and cycloalkyl group are each independently optionally substituted with R$^{1c}$, and the aryl and heteroaryl group are each optionally independently substituted with R$^{1d}$;

R$^{1a}$ is a hydrogen atom, a hydroxyl group, a formyl group, a —(C=O)$_a$O$_b$(C1-C6)alkyl group or a group of —(C=O)$_a$N(R$^{3a}$)R$^{4a}$, wherein the alkyl group is optionally substituted with a halogen atom or a hydroxyl group, or R$^{1a}$ is a heterocyclic group which is optionally substituted with a substituent selected from the group consisting of a halogen atom, a hydroxyl group, an oxo group, a —(C=O)$_a$O$_b$(C1-C6)alkyl group, a —(C=O)$_a$O$_b$(C3-C6)cycloalkyl group and a group of -Q$^{2a}$-R$^{5a}$, wherein the alkyl and cycloalkyl group of the substituent are each independently optionally substituted with a halogen atom, a hydroxyl group, a —(C=O)$_a$O$_b$(C1-C6)alkyl group or a group of —(C=O)$_a$N(R$^{3a}$)R$^{4a}$;

R$^{1b}$ is a hydrogen atom or a —(C=O)$_a$O$_b$(C1-C6)alkyl group, wherein the alkyl group is substituted with a halogen atom, a hydroxyl group or a group of —(C=O)$_a$N(R$^{4b}$)R$^{5b}$;

R$^{1c}$ is a halogen atom, a hydroxyl group, a cyano group, a —(C=O)$_a$O$_b$(C1-C6)alkyl group, a —(C=O)$_a$O$_b$(C3-C6)cycloalkyl group, an aryl group or a heteroaryl group, wherein the alkyl and cycloalkyl group are each independently optionally substituted with a halogen atom or a hydroxyl group, and the aryl and heteroaryl group are each independently optionally substituted with a substituent selected from the group consisting of a nitro group, a hydroxyamino group, a —(C=O)$_a$O$_b$(C1-C6)alkyl group and a group of —(C=O)$_a$N(R$^{2c}$)R$^{3c}$, and the alkyl group of the substituent is substituted with a halogen atom or a hydroxyl group;

R$^{1d}$ is a nitro group, a hydroxyamino group, a —(C=O)$_a$O$_b$(C1-C6)alkyl group or a group of —(C=O)$_a$N(R$^{2d}$)R$^{3d}$, wherein the alkyl group is optionally substituted with a halogen atom or a hydroxyl group;

R$^{1e}$, R$^{2a}$, R$^{2b}$, R$^{2c}$, R$^{2d}$, R$^{2e}$, R$^{3a}$, R$^{3b}$, R$^{3c}$, R$^{3d}$, R$^{3e}$, R$^{4a}$, R$^{4b}$, R$^{4e}$ and R$^{5b}$ are each independently a hydrogen atom or a —(C=O)$_a$O$_b$(C1-C6)alkyl group, wherein the alkyl group is optionally substituted with a halogen atom or a hydroxyl group;

R$^2$ and R$^3$ are each independently a hydrogen atom, a halogen atom, a hydroxyl group, a carboxyl group, a —(C=O)$_a$O$_b$(C1-C6)alkyl group or a group of —(C=O)$_a$N(R$^{1e}$)R$^{2e}$, wherein the alkyl group is optionally substituted with a substituent selected from the group consisting of a halogen atom, a hydroxyl group, a carboxyl group, a —(C=O)$_a$O$_b$(C1-C6)alkyl group and a group of —(C=O)$_a$N(R$^{3e}$)R$^{4e}$;

R$^4$ is a hydrogen atom or a (C1-C6)alkyl group;

R$^{5a}$ is a hydrogen atom, a hydroxyl group, a formyl group, a —(C=O)$_a$O$_b$(C1-C6)alkyl group or a group of —(C=O)$_a$N(R$^{3a}$)R$^{4a}$, wherein the alkyl group is optionally substituted with a halogen atom or a hydroxyl group, or $R^{5a}$ is a heterocyclic group optionally substituted with a substituent selected from the group consisting of a halogen atom, a hydroxyl group, an oxo group, a —(C═O)$_a$O$_b$(C1-C6)alkyl group and a group of -Q$^{3a}$-R$^{6a}$, and the alkyl group of the substituent is optionally substituted with a halogen atom, a hydroxyl group or a —(C═O)$_a$O$_b$(C1-C6)alkyl group;

$R^{6a}$ is a hydrogen atom, a halogen atom, a hydroxyl group or a —(C═O)$_a$O$_b$(C1-C6)alkyl group, wherein the alkyl group is optionally substituted with a halogen atom or a hydroxyl group; and T and U are each independently a nitrogen atom, or a methine group optionally substituted with a halogen atom, a hydroxyl group, a cyano group or a —(C═O)$_a$O$_b$(C1-C6)alkyl group, wherein the alkyl group of the substituent is optionally substituted with a halogen atom or a hydroxyl group.

2. The compound or its pharmaceutically-acceptable salt, ester or N-oxide derivative of claim 1, wherein $R^1$ is an aryl or heteroaryl group, which is optionally substituted with $R^{1d}$.

3. The compound or its pharmaceutically-acceptable salt, ester or N-oxide derivative of claim 1, wherein $R^1$ is a phenyl, furyl, thienyl, imidazolyl, thiazolyl, pyridyl, pyrazinyl or pyrimidinyl group, which is optionally substituted with $R^{1d}$.

4. The compound or its pharmaceutically-acceptable salt or N-oxide derivative of claim 1, wherein $R^2$ and $R^3$ are each independently a hydrogen atom or a hydroxyl group.

5. The compound or its pharmaceutically-acceptable salt, ester or N-oxide derivative of claim 1, wherein A is a phenyl, pyrazolyl, indolyl or indazolyl group, which is optionally substituted with a substituent selected from the group consisting of a halogen atom, a hydroxyl group, a —(C═O)$_a$O$_b$(C1-C6)alkyl group and a group of -Q$^{1a}$-R$^{1a}$, and the alkyl group of the substituent is optionally substituted with a halogen atom or a hydroxyl group.

6. The compound or its pharmaceutically-acceptable salt, ester or N-oxide derivative of claim 1, wherein A is a group of the formula (a), and the group is selected from those of a formula (a-1);

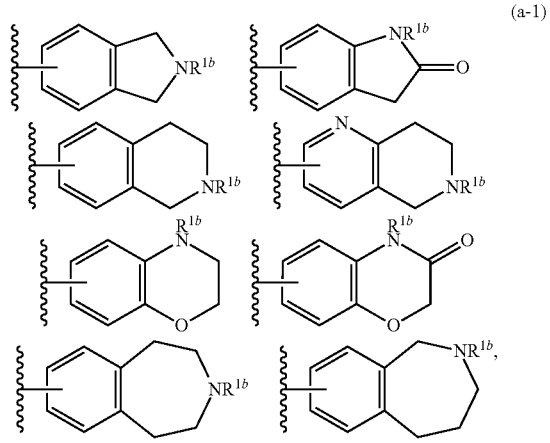

(a-1)

and one or two or more methylene groups constituting the aliphatic ring of the group are each independently substituted with a halogen atom, a hydroxyl group, a —(C═O)$_a$O$_b$(C1-C6)alkyl group or a group of -Q$^{1b}$-N(R$^{2b}$)R$^{3b}$, wherein the alkyl group of the substituent is optionally substituted with a halogen atom or a hydroxyl group.

7. The compound or its pharmaceutically-acceptable salt or N-oxide derivative of claim 1, wherein the compound is represented by a formula (I-1):

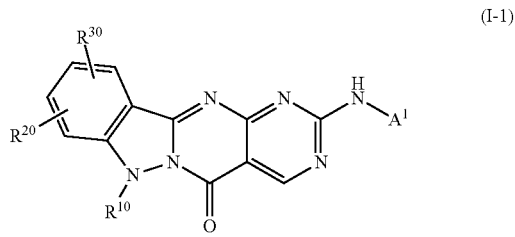

(I-1)

wherein
A$^1$ is a phenyl, pyrazolyl, indolyl or indazolyl group, which is optionally substituted with a substituent selected from the group consisting of a halogen atom, a hydroxyl group, a —(C═O)$_a$O$_b$(C1-C6)alkyl group and a group of -Q$^{1a}$-R$^{1a}$, wherein the alkyl group of the substituent is optionally substituted with a halogen atom or a hydroxyl group, or A$^1$ is a group selected from those of a formula (a-1):

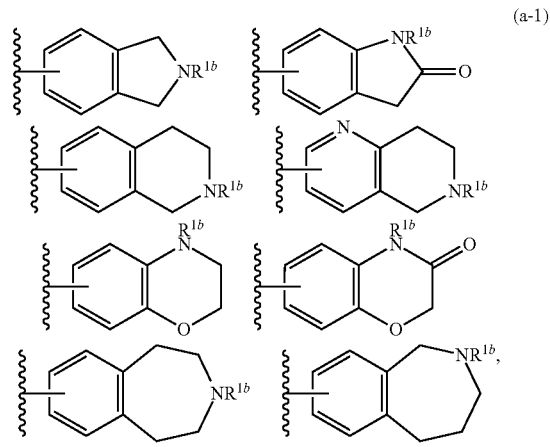

(a-1)

wherein one or two or more methylene groups constituting the aliphatic ring of the group are each independently optionally substituted with a halogen atom, a hydroxyl group, a —(C═O)$_a$O$_b$(C1-C6)alkyl group or a group of -Q$^{1b}$-N(R$^{2b}$)R$^{3b}$, and the alkyl group of the substituent is optionally substituted with a halogen atom or a hydroxyl group;

R$^{10}$ is an aryl or heteroaryl group, which is optionally substituted with R$^{1d}$; and R$^{20}$ and R$^{30}$ are each independently a hydrogen atom or a hydroxyl group.

8. The compound or its pharmaceutically-acceptable salt or N-oxide derivative of claim 1, wherein, in the group of -Q$^{1a}$R$^{1a}$, (i) Q$^{1a}$ is a (C1-C6)alkylene group, wherein one methylene group constituting the (C1-C6)alkylene group is optionally replaced by an oxygen atom, and one or two methylene groups constituting the (C1-C6)alkylene group are optionally substituted with a hydroxyl group or a —(C═O)$_a$O$_b$(C1-C6)alkyl group; and R$^{1a}$ is a group of —(C═O)$_a$N(R$^{3a}$)R$^{4a}$; or (ii) Q$^{1a}$ is a (C1-C6)alkylene group, wherein one methylene group constituting the (C1-C6)alkylene group is optionally replaced by an oxygen atom, and one or two methylene groups constituting the (C1-C6)alkylene group are optionally substituted with a hydroxyl group or a —(C=O)$_a$O$_b$(C1-C6)alkyl group; and R$^{1a}$ is a heterocyclic group optionally substituted with a —(C=O)$_a$O$_b$(C1-C6)alkyl group, wherein the alkyl group of the substituent is optionally substituted with a hydroxyl group or a —(C=O)$_a$O$_b$(C1-C6)alkyl group; or (iii) Q$^{1a}$ is a single bond; and R$^{1a}$ is a heterocyclic group optionally substituted with a substituent selected from the group consisting of a hydroxyl group, an oxo group and a —(C=O)$_a$O$_b$(C1-C6)alkyl group, wherein the alkyl group of the substituent is optionally substituted with a hydroxyl group, a —(C=O)$_a$O$_b$(C1-C6)alkyl group or a group of —(C=O)$_a$N(R$^{3a}$)R$^{4a}$.

9. The compound or its pharmaceutically-acceptable salt or N-oxide derivative of claim 1, wherein the heterocyclic group of R$^{1a}$ is an azetidinyl group, a piperidinyl group, a piperazinyl group or a perhydro-1,4-diazepinyl group.

10. The compound or its pharmaceutically-acceptable salt of claim 1, wherein the compound is selected from:
- 2-{[3-methyl-4-(4-methylpiperazin-1-yl)phenyl]amino}-7-(pyridin-2-yl)pyrimido[4',5':4,5]pyrimido[1,2-b]indazol-5(7H)-one;
- 2-{[4-(4-methylpiperazin-1-yl)phenyl]amino}-7-(pyridin-2-yl)pyrimido[4',5':4,5]pyrimido[1,2-b]indazol-5(7H)-one;
- 2-[(2-methyl-1,2,3,4-tetrahydroisoquinolin-6-yl)amino]-7-(pyridin-2-yl)pyrimido[4',5':4,5]pyrimido[1,2-b]indazol-5(7H)-one;
- 2-[(2-methyl-1,2,3,4-tetrahydroisoquinolin-7-yl)amino]-7-(pyridin-2-yl)pyrimido[4',5':4,5]pyrimido[1,2-b]indazol-5(7H)-one;
- 2-{[3-methyl-4-(4-methylpiperazin-1-yl)phenyl]amino}-7-(3-thienyl)pyrimido[4',5':4,5]pyrimido[1,2-b]indazol-5(7H)-one;
- 2-{[3-methyl-4-(4-methylpiperazin-1-yl)phenyl]amino}-7-(pyrimidin-2-yl)pyrimido[4',5':4,5]pyrimido[1,2-b]indazol-5(7H)-one;
- 2-{[4-(4-methylpiperazin-1-yl)phenyl]amino}-7-(pyrimidin-2-yl)pyrimido[4',5':4,5]pyrimido[1,2-b]indazol-5(7H)-one;
- 2-({4-[(3S)-3-(dimethylamino)pyrrolidin-1-yl]phenyl}amino)-7-(pyrimidin-2-yl)pyrimido[4',5':4,5]pyrimido[1,2-b]indazol-5(7H)-one;
- 2-{[4-(1,4-dimethylpiperidin-4-yl)phenyl]amino}-7-(pyrimidin-2-yl)pyrimido[4',5':4,5]pyrimido[1,2-b]indazol-5(7H)-one;
- 2-({4-[2-(dimethylamino)ethoxy]-3-methylphenyl}amino)-7-(pyrimidin-2-yl)pyrimido[4',5':4,5]pyrimido[1,2-b]indazol-5(7H)-one;
- 2-({4-[(dimethylamino)methyl]phenyl}amino)-7-(pyrimidin-2-yl)pyrimido[4',5':4,5]pyrimido[1,2-b]indazol-5(7H)-one;
- 2-({4-[2-(dimethylamino)ethyl]phenyl}amino)-7-(pyrimidin-2-yl)pyrimido[4',5':4,5]pyrimido[1,2-b]indazol-5(7H)-one;
- 2-[(2-methyl-1,2,3,4-tetrahydroisoquinolin-6-yl)amino]-7-(pyrimidin-2-yl)pyrimido[4',5':4,5]pyrimido[1,2-b]indazol-5(7H)-one;
- 2-[(2-methyl-1,2,3,4-tetrahydroisoquinolin-7-yl)amino]-7-(pyrimidin-2-yl)pyrimido[4',5':4,5]pyrimido[1,2-b]indazol-5(7H)-one;
- 2-[(2-methyl-2,3-dihydro-1H-isoindol-5-yl)amino]-7-(pyrimidin-2-yl)pyrimido[4',5':4,5]pyrimido[1,2-b]indazol-5(7H)-one;
- 7-(pyrimidin-2-yl)-2-[(1,1,2-trimethyl-1,2,3,4-tetrahydroisoquinolin-6-yl)amino]pyrimido[4',5':4,5]pyrimido[1,2-b]indazol-5(7H)-one;
- 2-{[4-(4-methylpiperazin-1-yl)phenyl]amino}-7-(1,3-thiazol-2-yl)pyrimido[4',5':4,5]pyrimido[1,2-b]indazol-5(7H)-one;
- 2-({4-[3-(dimethylamino)propoxy]phenyl}amino)-7-(1,3-thiazol-2-yl)pyrimido[4',5':4,5]pyrimido[1,2-b]indazol-5(7H)-one;
- 2-[(2-methyl-1,2,3,4-tetrahydroisoquinolin-6-yl)amino]-7-(1,3-thiazol-2-yl)pyrimido[4',5':4,5]pyrimido[1,2-b]indazol-5(7H)-one;
- 2-[(2-methyl-1,2,3,4-tetrahydroisoquinolin-7-yl)amino]-7-(1,3-thiazol-2-yl)pyrimido[4',5':4,5]pyrimido[1,2-b]indazol-5(7H)-one;
- 2-({4-[2-(dimethylamino)ethyl]-3,4-dihydro-2H-1,4-benzoxazin-7-yl}amino)-7-(1,3-thiazol-2-yl)pyrimido[4',5':4,5]pyrimido[1,2-b]indazol-5(7H)-one;
- 2-({1-[2-(dimethylamino)ethyl]-2,3-dihydro-1H-indol-5-yl}amino)-7-(1,3-thiazol-2-yl)pyrimido[4',5':4,5]pyrimido[1,2-b]indazol-5(7H)-one;
- 2-{[4-(4-methylpiperazin-1-yl)phenyl]amino}-thiazol-4-yl)pyrimido[4',5':4,5]pyrimido[1,2-b]indazol-5(7H)-one;
- 7-(furan-3-yl)-2-{[4-(4-methylpiperazin-1-yl)phenyl]amino}pyrimido[4',5':4,5]pyrimido[1,2-b]indazol-5(7H)-one; or
- 9-hydroxy-2-{[4-(4-methylpiperazin-1-yl)phenyl]amino}-7-(pyridin-2-yl)pyrimido[4',5':4,5]pyrimido[1,2-b]indazol-5(7H)-one.

11. A pharmaceutical composition comprising a therapeutically-effective amount of the compound of claim 1 or its pharmaceutically-acceptable salt or N-oxide derivative, and a pharmaceutically-acceptable carrier or diluent.

12. A method of treating a Wee1 kinase mediated cancer wherein the cancer is selected from the group consisting of breast cancer, lung cancer, pancreatic cancer, colon cancer, ovarian cancer, acute leukemia, chronic lymphatic leukemia, chronic myelocytic leukemia and Hodgkin's lymphoma with a therapeutically effective amount of the pharmaceutical composition of claim 11 to a mammal in need thereof.

13. A combined preparation for simultaneous, separate or successive administration in cancer therapy, comprising the following two separate preparations (a) and (b):
(a) a preparation comprising a compound of claim 1 or its pharmaceutically-acceptable salt or N-oxide derivative, together with a pharmaceutically-acceptable carrier or diluent, and
(b) a preparation comprising, together with a pharmaceutically-acceptable carrier or diluent, an anticancer agent selected from the group consisting of anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, interferons, biological response modifiers, and other anticancer agents, or its pharmaceutically acceptable salt or N-oxide derivative, wherein
the anticancer alkylating agents are nitrogen mustard N-oxide, cyclophosphamide, ifosfamide, melphalan, busulfan, mitobronitol, carboquone, thiotepa, ranimustine, nimustine, temozolomide, or carmustine;
the anticancer antimetabolites are methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine, or pemetrexed disodium;

the anticancer antibiotics are actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus, or valrubicin;

the plant-derived anticancer agents are vincristine, vinblastine, vindeshine, etoposide, sobuzoxane, docetaxel, paclitaxel, or vinorelbine;

the anticancer platinum coordination compounds are cisplatin, carboplatin, nedaplatin, or oxaliplatin;

the anticancer camptothecin derivatives are irinotecan, topotecan, or camptothecin;

the anticancer tyrosine kinase inhibitors are gefitinib, imatinib, or erlotinib;

the monoclonal antibodies are cetuximab, bevacizumab, rituximab, alemtuzumab, or trastuzumab;

the interferons are interferon α, interferon α-2a, interferon α-2b, interferon β, interferon γ-1a, or interferon γ-n1, the biological response modifiers are krestin, lentinan, sizofuran, picibanil, or ubenimex, and the other anticancer agents are mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, or goserelin.

14. A pharmaceutical composition comprising the compound of claim 1 or its pharmaceutically-acceptable salt or N-oxide derivative, and an anticancer agent selected from the group consisting of anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, biological response modifiers, and other anticancer agents wherein the anticancer alkylating agents are nitrogen mustard N-oxide, cyclophosphamide, ifosfamide, melphalan, busulfan, mitobronitol, carboquone, thiotepa, ranimustine, nimustine, temozolomide, or carmustine;

the anticancer antimetabolites are methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine, or pemetrexed disodium;

the anticancer antibiotics are actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus, or valrubicin;

the plant-derived anticancer agents are vincristine, vinblastine, vindeshine, etoposide, sobuzoxane, docetaxel, paclitaxel, or vinorelbine;

the anticancer platinum coordination compounds are cisplatin, carboplatin, nedaplatin, or oxaliplatin;

the anticancer camptothecin derivatives are irinotecan, topotecan, or camptothecin;

the anticancer tyrosine kinase inhibitors are gefitinib, imatinib, or erlotinib;

the monoclonal antibodies are cetuximab, bevacizumab, rituximab, alemtuzumab, or trastuzumab;

the interferons are interferon α, interferon α-2a, interferon α-2b, interferon β, interferon γ-1a, or interferon γ-n1, the biological response modifiers are krestin, lentinan, sizofuran, picibanil, or ubenimex, and the other anticancer agents are mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, or goserelin or its pharmaceutically-acceptable salt, together with a pharmaceutically-acceptable carrier or diluent.

15. A method of enhancing the effectiveness of radiation by administering the pharmaceutical composition of claim 11 in a mammal in need thereof.

16. The method of claim 15 which further comprises an anticancer agent selected from the group consisting of anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, biological response modifiers, and other anticancer agents wherein the anticancer alkylating agents are nitrogen mustard N-oxide, cyclophosphamide, ifosfamide, melphalan, busulfan, mitobronitol, carboquone, thiotepa, ranimustine, nimustine, temozolomide, or carmustine;

the anticancer antimetabolites are methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine, or pemetrexed disodium;

the anticancer antibiotics are actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus, or valrubicin;

the plant-derived anticancer agents are vincristine, vinblastine, vindeshine, etoposide, sobuzoxane, docetaxel, paclitaxel, or vinorelbine;

the anticancer platinum coordination compounds are cisplatin, carboplatin, nedaplatin, or oxaliplatin;

the anticancer camptothecin derivatives are irinotecan, topotecan, or camptothecin;

the anticancer tyrosine kinase inhibitors are gefitinib, imatinib, or erlotinib;

the monoclonal antibodies are cetuximab, bevacizumab, rituximab, alemtuzumab, or trastuzumab;

the interferons are interferon α, interferon α-2a, interferon α-2b, interferon β, interferon γ-1a, or interferon γ-n1, the biological response modifiers are krestin, lentinan, sizofuran, picibanil, or ubenimex, and the other anticancer agents are mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, or goserelin.

* * * * *